US008560968B1

(12) United States Patent
Nair

(10) Patent No.: US 8,560,968 B1
(45) Date of Patent: Oct. 15, 2013

(54) METHOD AND APPARATUS FOR EVALUATING A HEART PATIENT

(76) Inventor: Vinod Nair, Houma, LA (US)

( * ) Notice: Subject to any disclaimer, the term of this patent is extended or adjusted under 35 U.S.C. 154(b) by 766 days.

(21) Appl. No.: 12/730,560

(22) Filed: Mar. 24, 2010

Related U.S. Application Data

(60) Provisional application No. 61/163,620, filed on Mar. 26, 2009.

(51) Int. Cl.
*G06F 3/048* (2013.01)
(52) U.S. Cl.
USPC ............................ 715/839; 715/810; 715/835
(58) Field of Classification Search
USPC ......... 715/200, 202, 203, 209, 215, 221–226, 715/230–231, 233, 273, 277, 700, 704, 705, 715/707–709, 712–722, 730–732, 738, 739, 715/745, 747, 764–767, 771, 781, 783, 802, 715/810, 835, 839, 846, 847, 848, 866; 600/481, 483, 508–528, 407–480
See application file for complete search history.

(56) References Cited

U.S. PATENT DOCUMENTS

| | | | | | |
|---|---|---|---|---|---|
| 5,911,133 | A | * | 6/1999 | Soble | 705/3 |
| 5,987,345 | A | * | 11/1999 | Engelmann et al. | 600/407 |
| 6,346,124 | B1 | * | 2/2002 | Geiser et al. | 600/450 |
| 7,822,627 | B2 | * | 10/2010 | St. Martin | 705/3 |
| 2002/0082825 | A1 | * | 6/2002 | Rowlandson et al. | 704/9 |
| 2002/0131625 | A1 | * | 9/2002 | Vining et al. | 382/128 |
| 2008/0250070 | A1 | * | 10/2008 | Abdulla et al. | 707/104.1 |
| 2009/0132588 | A1 | * | 5/2009 | Mahesh et al. | 707/104.1 |
| 2009/0171225 | A1 | * | 7/2009 | Gadodia et al. | 600/508 |

* cited by examiner

*Primary Examiner* — Enrique Iturralde
(74) *Attorney, Agent, or Firm* — Garvey, Smith, Nehrbass & North, L.L.C.; Brett A. North; Charles C. Garvey, Jr.

(57) ABSTRACT

A method of clinical evaluation of a cardiology patient includes the providing of a computer having a database and a user interface that includes a display screen. One or more images are displayed on the display screen, each being an anatomical representation of a part of a human heart which are a portion of a human heart, there is displayed on the screen patient data that corresponds to the part that is displayed on the screen. Such data can be for example prior or present test data. One embodiment includes a graphical medical generation system for replacing the dictation and transcription process of a cardiology health care professionals. A graphical display is provided which processes user input in conjunction with pre-defined cardiology reporting options to generate user-defined cardiology reports. A method and apparatus 10 is described for controlling, via a relational databases, the selection of pre-defined character strings to be inserted into the generated cardiology report. An option is provided for the user to customize character strings for insertion into the cardiology report. Another option is provided for the method and apparatus 10 to include comparisons with earlier cardiology reports and data testing to assist the user in generating a conclusion.

5 Claims, 46 Drawing Sheets

Appointment Request

Last Name : Smith                              Request Confirmation No :26

First Name : John

DOB       : 1/12/1956               4560

| Requested Date | Study | Indication |
|---|---|---|
| 3/2/2010 | Myocardial Perfusion Imaging | Coronary Risk Factors |

4562

<u>XYX Cardiology Clinic</u> has received your request for appointment. Please give us one working day to contact you. If you do not hear from us within this time frame, please contact our office at physical address. Please have your request ID with you when you call us so that we can assist you efficiently.

FIG. 45

METHOD AND APPARATUS FOR EVALUATING A HEART PATIENT

CROSS-REFERENCE TO RELATED APPLICATIONS

U.S. Provisional Patent Application Ser. No. 61/163,620, filed Mar. 26, 2009, is incorporated herein by reference.

Priority of U.S. Provisional Patent Application Ser. No. 61/163,620, filed Mar. 26, 2009, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND

The present invention relates to cardiology and more particularly to a method of evaluating a heart patient wherein a computer has a database and a user interface connected thereto that includes a display screen.

Even more particularly, the present invention relates to a method of evaluating a heart patient that employs a computer and a display screen, the display screen having multiple images that are displayed to a user, each image being an anatomical representation of a portion of a human heart, wherein multiple of the images depict different portions of the human heart and the display screen simultaneously displays data next to one or more of the images, the data being specific to the patient in the display data relating to at least one of the portions of the human heart that is represented by the display.

Currently, the practice of cardiology in the United States uses disparate modalities and systems for documentation. This includes for example handwritten notes, scanned images, document management systems, and fully integrated electronic medical systems.

The current state of the practice of cardiology includes: (1) Era of increasing demand; (2) Time constraints; (3) More complex procedures; (4) Increased imaging requirements; (5) Decrease allotted time per patient visit; and (6) Decreased reimbursement. Cardiologists can average of 8-10 minutes per patient.

Traditionally, the practice of dictating and transcribing cardiology reports has been used by cardiologists. Cardiologists have been increasingly burdened by the need to quickly and accurately generate cardiology reports after reviewing the results of heart studies.

Additionally, cardiologists must fill out forms for submission to insurance companies and provide information to regulatory agencies. To gather and produce all of this information, cardiologists must spend a significant portion of their work day dictating the needed information. Additionally, cardiologists must maintain a staff to transcribe the information into reports and to fill out required forms.

A cardiologists typically dictates a report reviewing the results of a heart study, which, subsequently, must be typed by a transcriber. This process is time consuming and repetitive. Using traditional manual methods of record keeping, patient data is not readily available for fast and easy review. A patient's medical record cannot be easily combined with other studies and/or reports, and/or other patient data for analysis and reporting.

There is a need to automate the report generation process to free up more time in the practice of cardiologists.

SUMMARY

One embodiment provides an integrated software solution for cardiac procedures encompassing reporting, storing, data mining, retrieving and online analysis. For example, the method of the present invention enables capture of predefined data elements and cardiac testing modalities.

In one embodiment the method and apparatus automates the report generation process by providing a graphical user interface incorporating a relational database with user selectable reporting components in a graphical environment.

In one embodiment is provided a method of clinical evaluation of a cardiology patient. The method includes the providing of a computer having a database. A user interface is provided which is connected to the computer and which includes a display screen. As part of the method, one or more images are displayed on the display screen which are anatomical representations, each of a different portion of a human heart.

In one embodiment the display can include patient data that is displayed on the display screen. In one embodiment the patient data relates specifically to the anatomical representation of the portion of the human heart that is being viewed on the display screen.

In one embodiment, multiple images can be displayed as optional parts of the human heart. In one embodiment one or more of those optional portions can be selectively enlarged for more easy inspection by a physician or other operator.

In one embodiment, the method includes entering data that relates specifically to the displayed image.

In one embodiment the method can include an interpreting cardiologist reviewing the data as part of a medical evaluation of a patient.

In one embodiment, the multiple images can include images of human heart chambers.

In one embodiment, the data displayed includes test results.

In one embodiment, multiple images are displayed on the display screen including multiple small images simultaneously displayed, each small image depicting a different part of the human heart.

In one embodiment, multiple images are displayed on the display screen, and wherein some of the images displayed are smaller images and wherein one or more of the displayed images is a larger image.

In one embodiment, a physician or operator can selectively enlarge one image or another image and by switching (e.g. clicking with computer mouse, touch screen) from one small image to another. The enlarged image selection generates data on the display screen that corresponds to the selected and enlarged image.

In one embodiment, a physician or operator can change from one image displayed to another image displayed without typing on a keyboard.

In one embodiment the method and apparatus provides a graphical display where a user has access to a first plurality of reporting segments.

In one embodiment the plurality of reporting segments are a plurality of geographical portions of a human organ. In one embodiment the segments can be portions of a human heart.

In one embodiment, the multiple anatomical images/views of the human heart can be displayed including: parasternal long axis view, short axis of left ventricle view, short axis view at the level of the aortic valve, apical two chamber view, and four chamber view.

In one embodiment the average time from review of the testing results to generation of a report by the cardiologist is less than 15, 14, 13, 12, 11, 10, 9, 8, 7, 6, 5, 4, and 3 minutes. In various embodiments the average time is between about any to the above specified time limits. In one embodiment the cardiologist generates more than 10, 15, 20, 25, 30, 35, 40, 50, 60, 70, 80, 90, and 100 cardiology reports a day. In various embodiments the number of reports generated varies between about any to the above specified daily number of reports.

In various embodiments the report generation method and apparatus incorporates previously defined reporting text strings or components, and includes a graphical user interface for selecting phrases to be inserted in the template. Preferably, the system will further comprise a graphics engine for display of graphical expressions of selection analysis.

For instance, a heart study can be conducted which will contain many basic elements common to all patients, but examination data will vary for each patient. Examination data can contain any number of variable responses, and each variable within the input can offer any number of different options from which to choose. In addition, cardiologists can personalize the report to suit a particular situation.

In one embodiment the examination and/or report input is electronically stored for possible future use in data mining, reporting, and/or analysis.

One embodiment enables a report on a cardiology study to be generated from a single graphical input screen. In one embodiment is provided a graphical input display having images of various views of the human heart for data entry.

In one embodiment report text is generated by making selections on a graphical input screen. In one embodiment a set of a plurality of suggested cardiology report data string conclusions is indexed to possible selections made on the graphical input screen. In one embodiment a plurality of the suggested conclusions for the cardiology report based on input by cardiologist automatically show up based on the graphical selections made by the user of the method and apparatus.

One embodiment provides an interface with existing cardiology testing devices. One embodiment enables an interface with billing and hospital admit systems. Examples of reports and studies can include (as examples): (1) Transthoracic echocardiography; (2) Transesophagial echocardiography; (3) Exercise treadmill test; (4) Stress echocardiogram; (5) Chemical stress echocardiogram; (6) Exercise myocardial perfusion imaging; (7) Chemical myocardial perfusion imaging; (8) Holier monitoring; (9) Coronary angiography; (10) Peripheral angiography; (11) Coronary computerized tomographic angiography, and (12) Peripheral computerized tomographic angiography.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the device illustrated and in its operation may be made without departing in any way from the spirit of the present invention. No feature of the invention is critical or essential unless it is expressly stated as being "critical" or "essential."

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 7 is a screen shot showing the input screen for the left atrium primary reporting structure where the "Remarks" has been selected for inputting report information. Remarks section allow the user to input custom text in the findings section of the report for the specific Primary Reporting Property being reporting on.

FIGS. 37-40 show one embodiment in which method and apparatus 10 can enforce appropriateness guidelines in scheduling a study.

FIGS. 41-45 illustrate one embodiment of automatic scheduling and study notification.

DETAILED DESCRIPTION

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate system, structure or manner.

One embodiment provides an integrated software solution for cardiac procedures encompassing reporting, storing, data mining, retrieving and online analysis. For example, the method of the present invention enables capture of predefined data elements and cardiac testing modalities.

In one embodiment is provided a document generation system for enhancing or replacing the dictation and transcription process. More particularly, a computer-based documentation system is provided which processes document templates in conjunction with pre-defined character strings to generate cardiology reports.

FIGS. 1-36 go through one example of generating a report on testing data for a cardiology test (in this case an echocardiogram).

Figure 1:
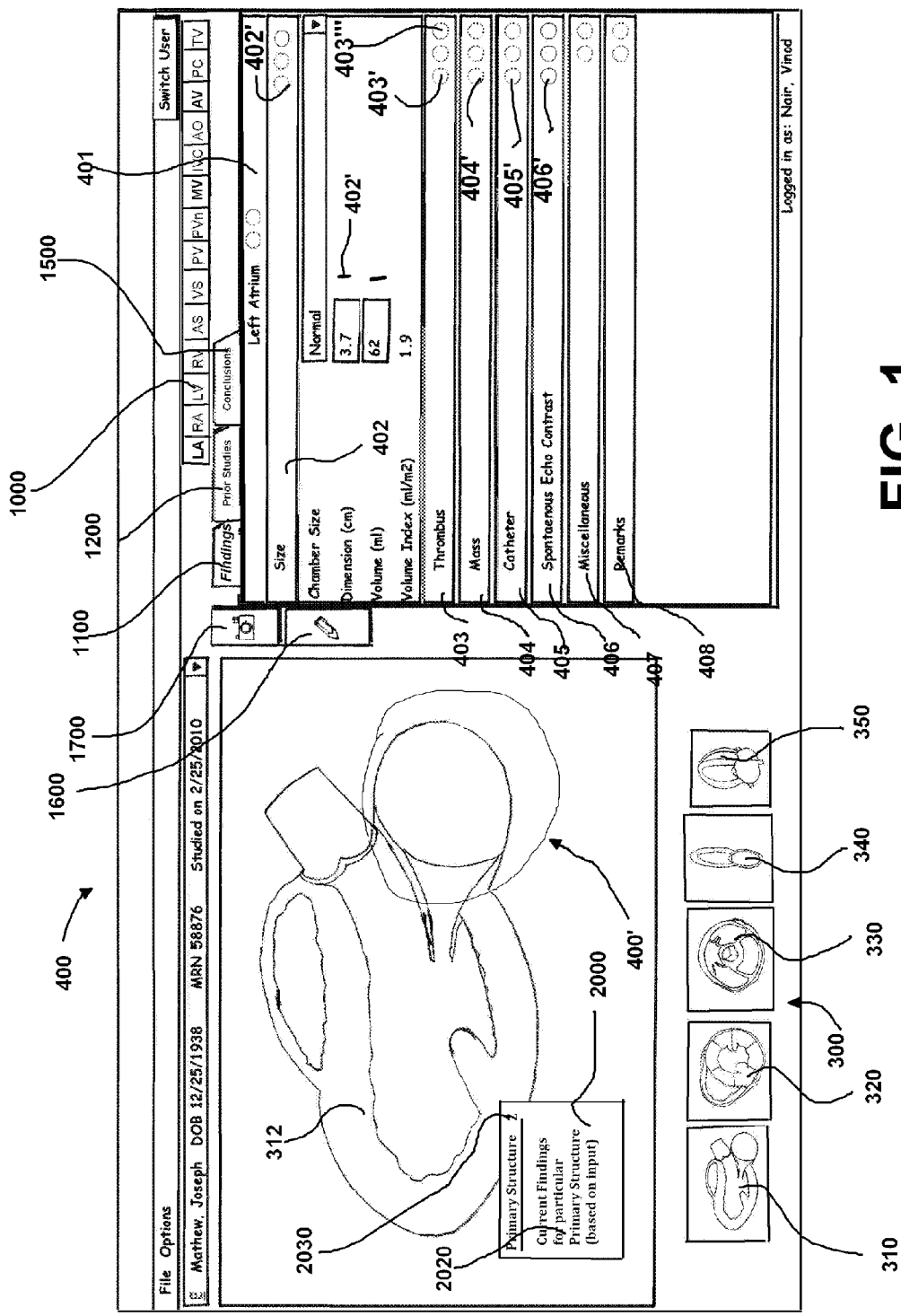
FIG. 1 is a screen shot showing a input display for generating a report on an echocardiogram, the display being used for reporting on one of the Primary Reporting Structures of an echocardiogram test (in this case the left Atrium), the display generally having a plurality of input sections for features or properties related to such Primary Reporting Structure.

FIG. 1 is a screen shot showing a input display 400 for generating a report 3010 on an echocardiogram, the display 100 being used for reporting on one of the Primary Reporting Structures of an echocardiogram test (in this case the left Atrium), the display generally having a plurality of input sections for features or properties related to such Primary Reporting Structure, and having the "Size" 402 property or attribute selected revealing a second tier of sections and/or information: Chamber size, Dimension, Volume, and Volume Index.

Figure 2:
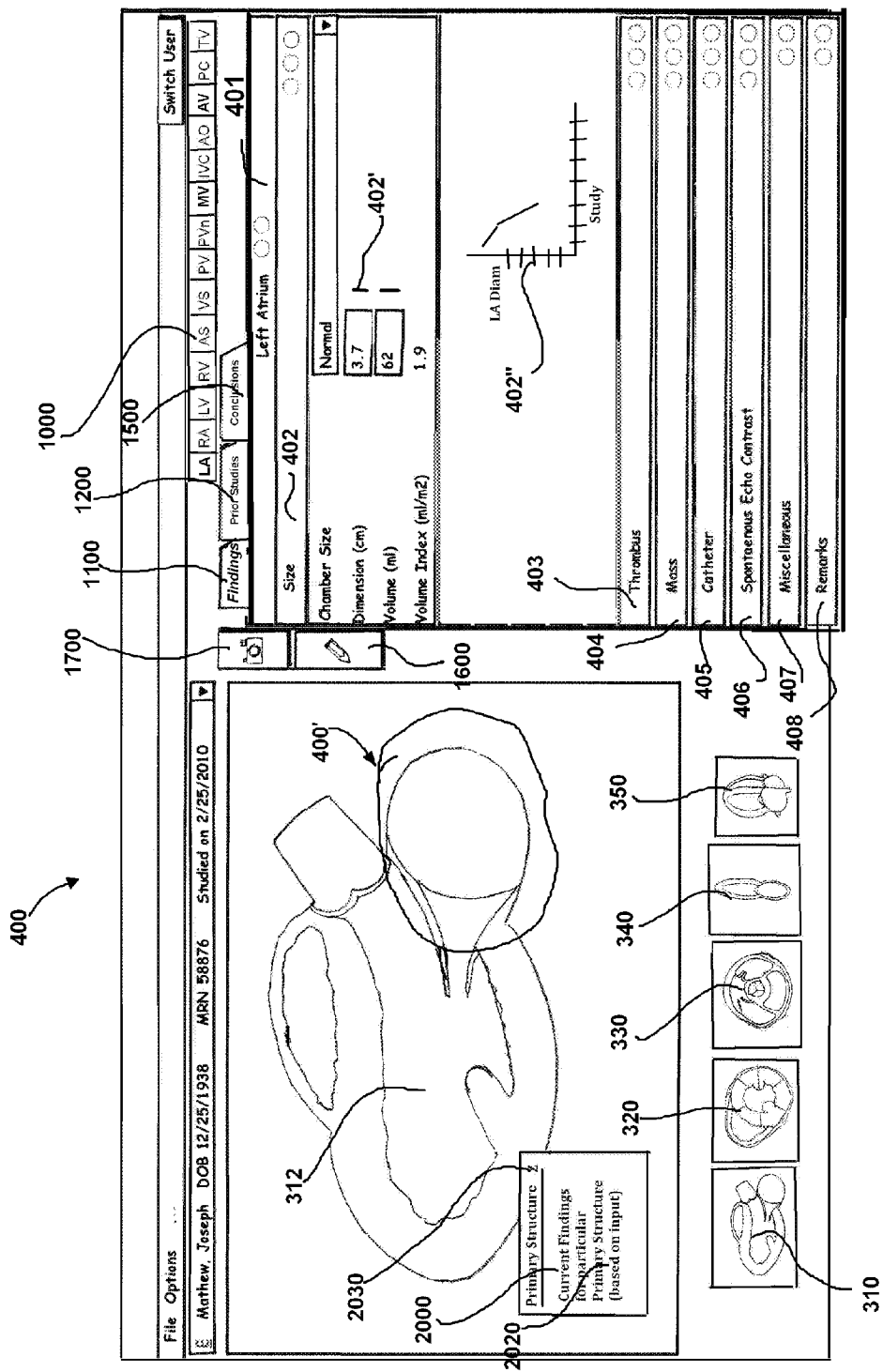
FIG. 2 is a screen shot showing the option of viewing pop up graphical comparison data for prior reports on the current report data. The pop up graph can be accessed by selecting the icon located next to the numerical data to be compared. Also in this figure is the current version of the text string for the findings on this primary reporting attribute which current version changes based on the input submitted in the display.

FIG. 2 is a screen shot showing the option of viewing pop up graphical comparison data 402" for prior reports on the current report data. The pop up graph can be accessed by selecting the icon 402' located next to the numerical data to be compared. Also in this figure is the current version 2020 of the text string for the findings on this primary reporting attribute which current version changes based on the input submitted in the display.

Figure 3:
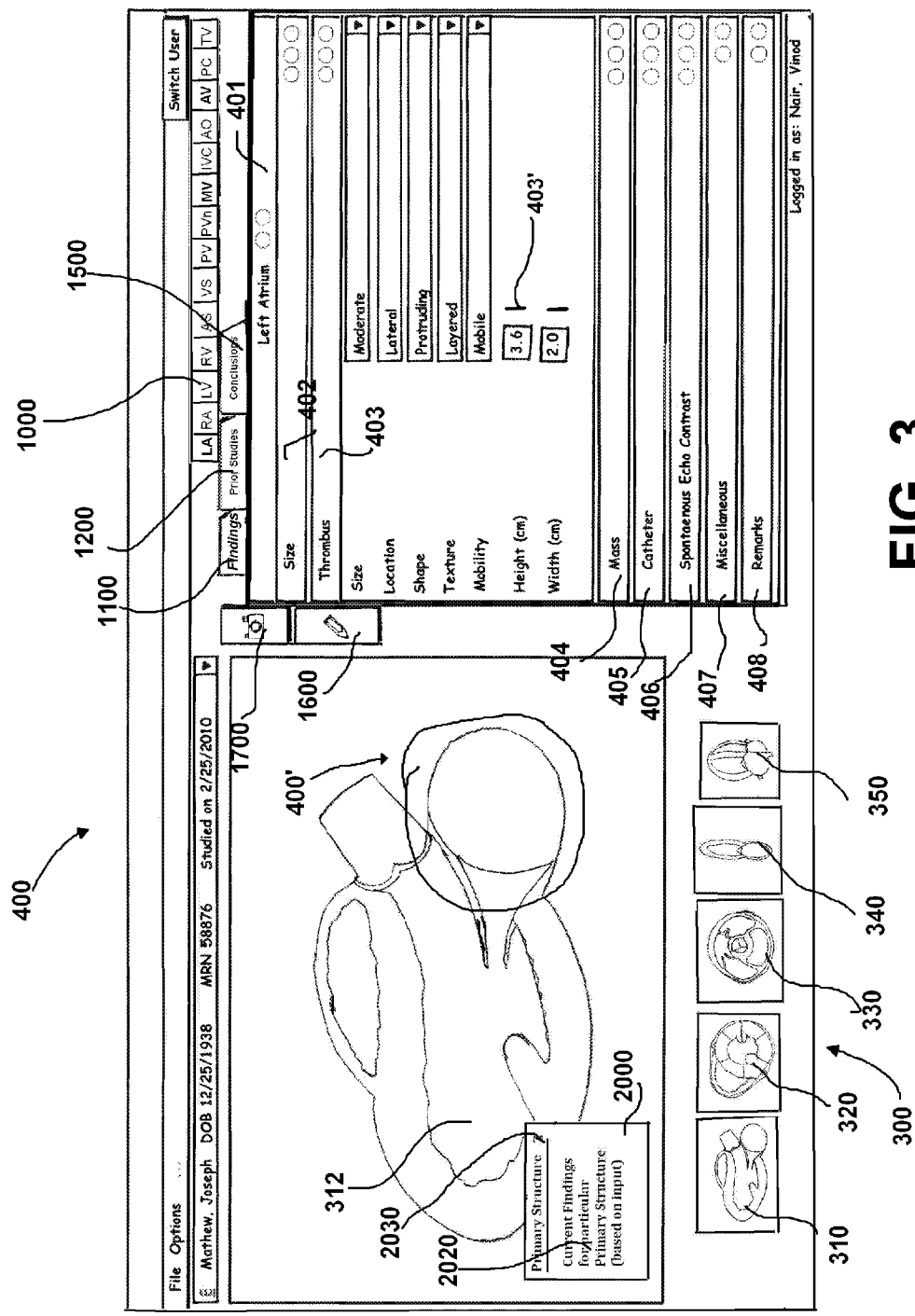
FIG. 3 is a screen shot showing the input screen for the left atrium primary reporting structure where the "Thrombus" property or attribute has been selected for inputting report information.

FIG. 3 is a screen shot showing the input screen 400 for the left atrium primary reporting structure where the "Thrombus" 403 property or attribute has been selected for inputting report information revealing a second tier of sections and/or information: Size, Location, Shape, Texture, Mobility, Height, and Width.

Figure 4:
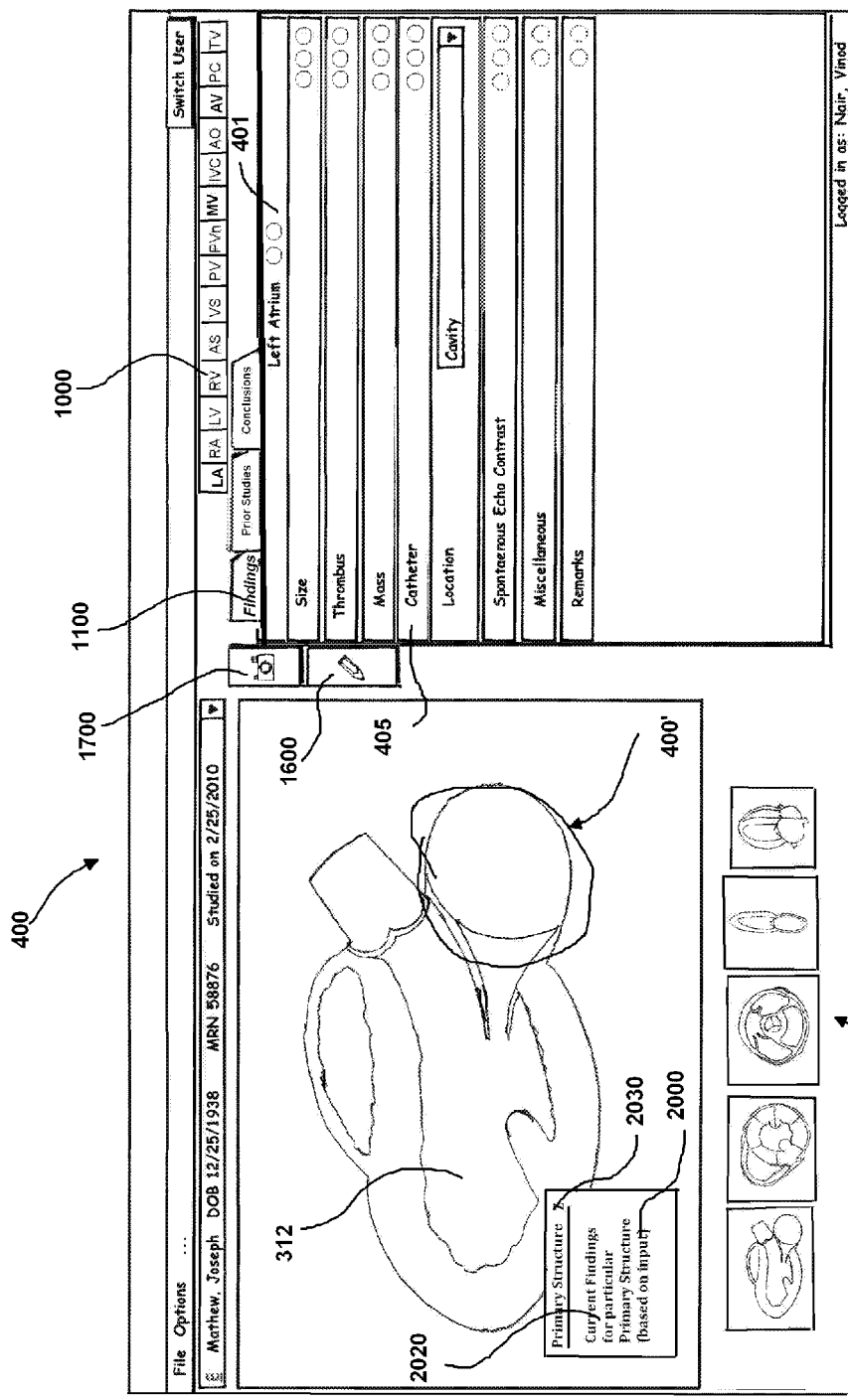
FIG. 4 is a screen shot showing the input screen for the left atrium primary reporting structure where the "Catheter" has been selected for inputting report information.

FIG. 4 is a screen shot showing the input screen 400 for the left atrium primary reporting structure where the "Catheter" has been selected for inputting report information revealing a second tier of sections and/or information: Location.

Figure 5:
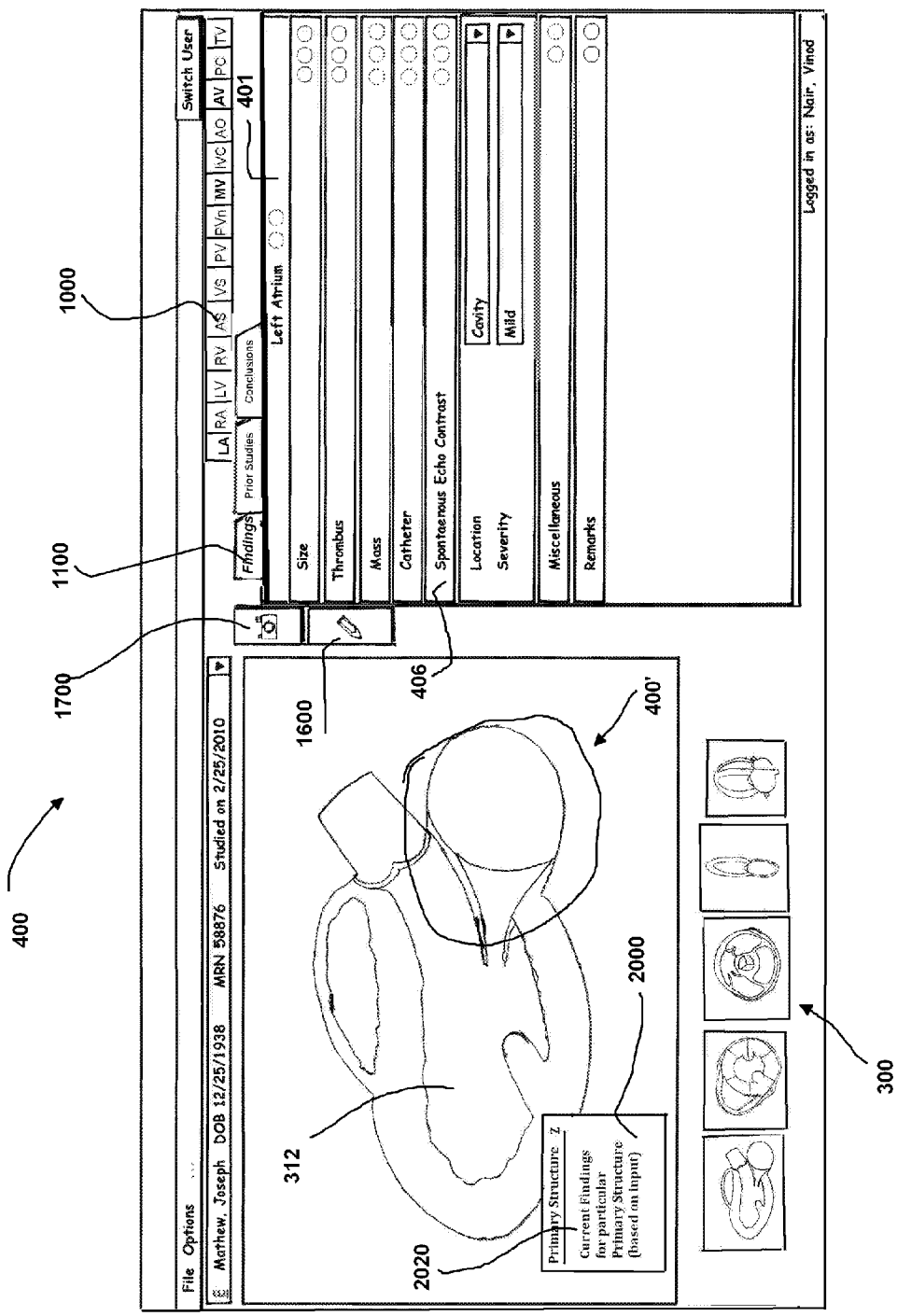
FIG. 5 is a screen shot showing the input screen for the left atrium primary reporting structure where the "Spontaneous Echo Contrast" has been selected for inputting report information.

FIG. 5 is a screen shot showing the input 400 screen for the left atrium primary reporting structure where the "Spontaneous Echo Contrast" has been selected for inputting report information revealing a second tier of sections and/or information: Location and Severity.

Figure 6:
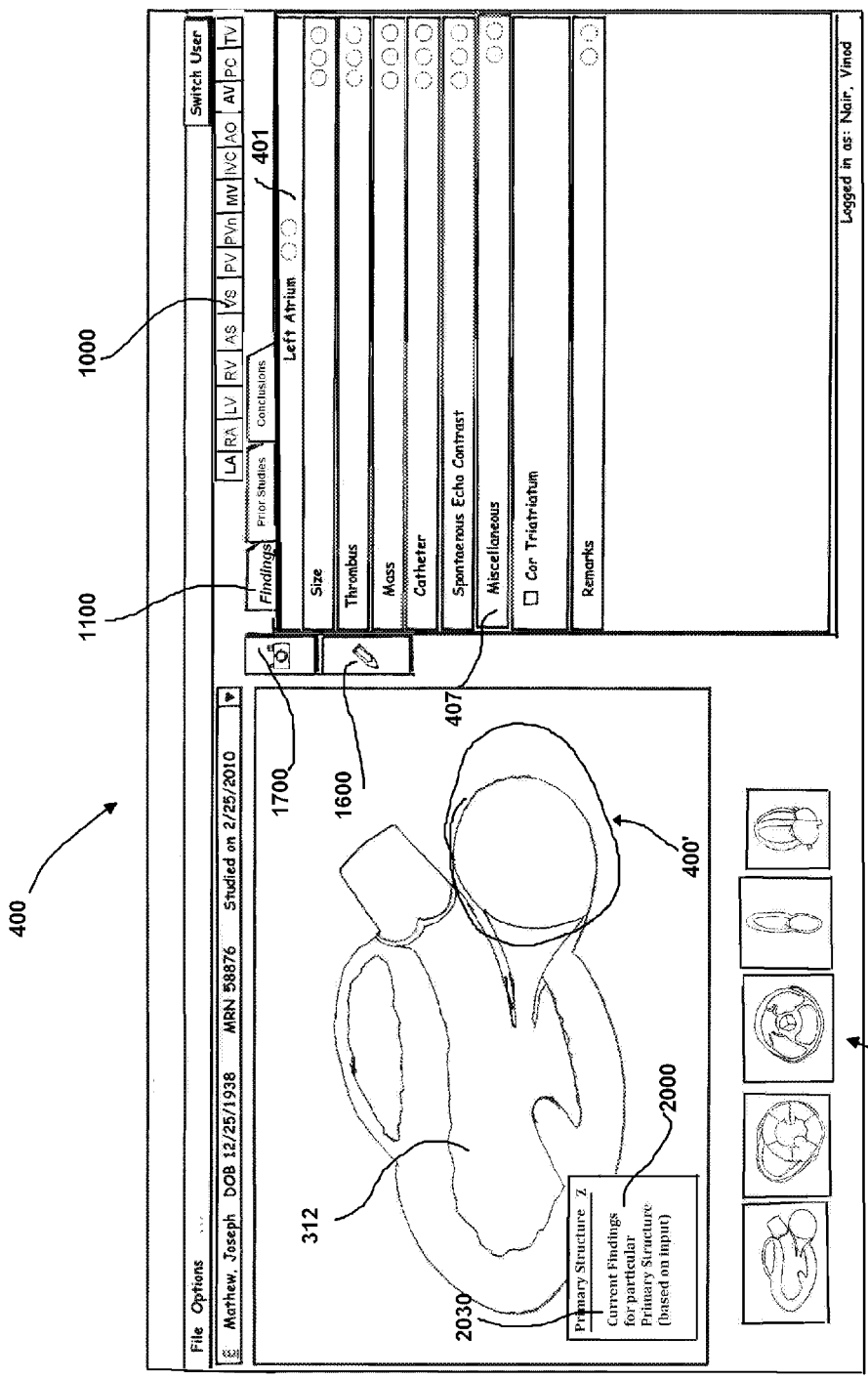
FIG. 6 is a screen shot showing the input screen for the left atrium primary reporting structure where the "Miscellaneous" has been selected for inputting report information.

FIG. 6 is a screen shot showing the input screen 400 for the left atrium primary reporting structure where the "Miscellaneous" has been selected for inputting report information revealing a second tier of sections and/or information: Cor Triatriatum.

Figure 7:
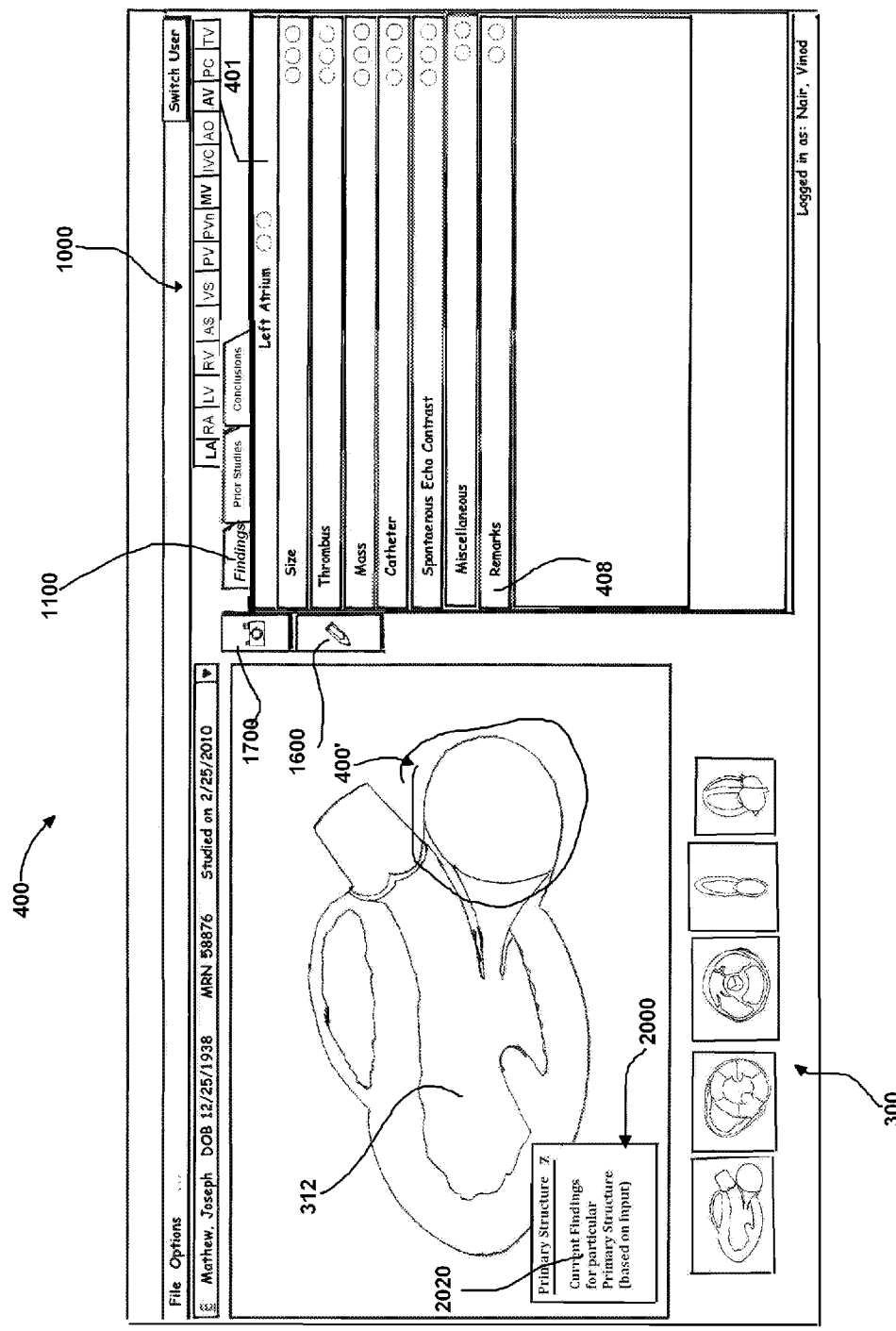

FIG. 7 is a screen shot showing the input screen 400 for the left atrium primary reporting structure where the "Remarks" has been selected for inputting report information. Remarks section allow the user 90 to add his own text to the text string inserted by the method and apparatus (based on the testing input) and include this user added text to the findings section of the report for the specific Primary Reporting Property being reporting on.

Figure 8:
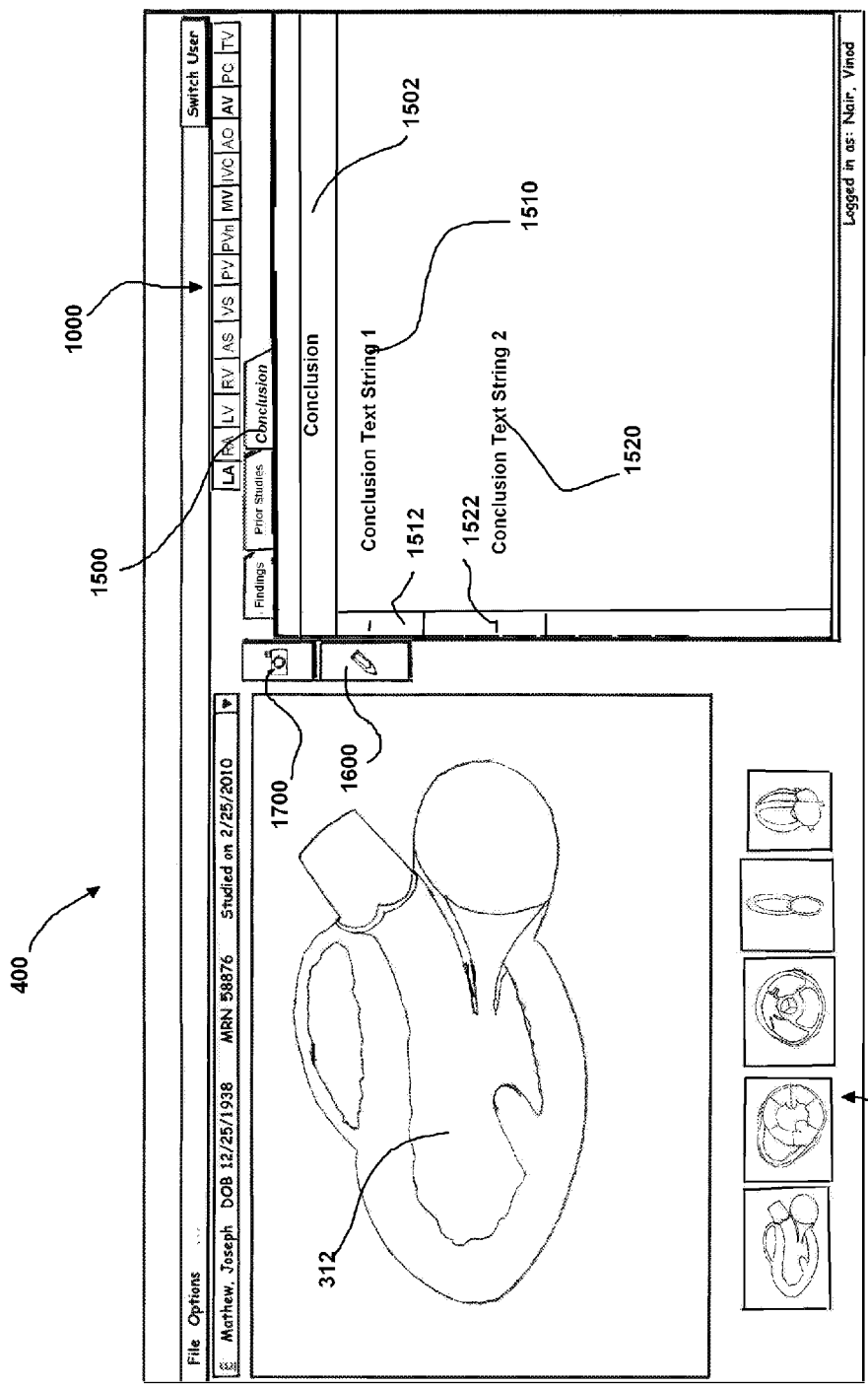
FIG. 8 is a screen shot showing a "Conclusion" input screen where conclusion text strings 1 and 2 are shown.

FIG. 8 is a screen shot showing a "Conclusion" input screen 400 where conclusion text strings 1 (item 1510) and 2 (item 1520) are shown.

Figure 9:
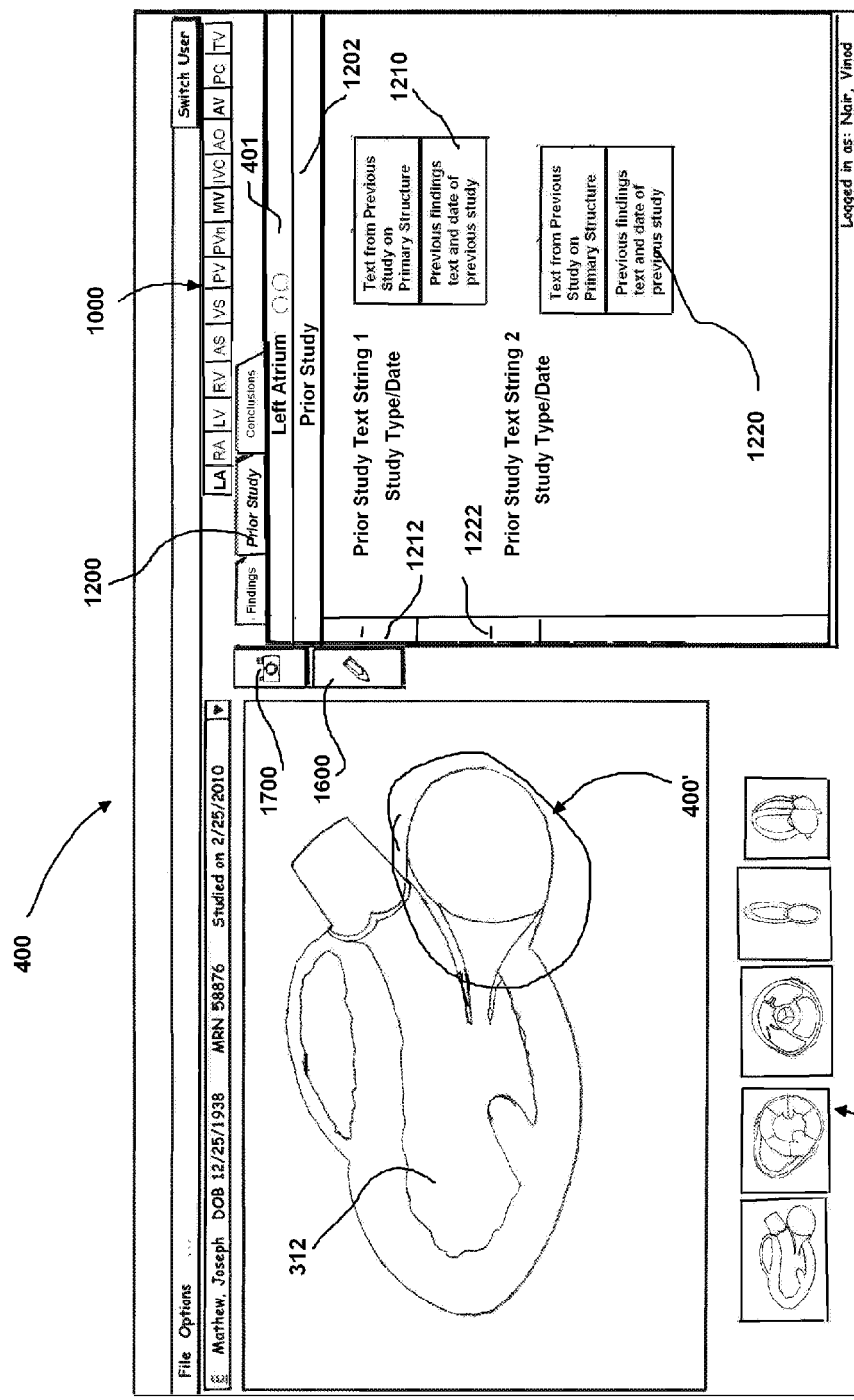
FIG. 9 is a screen shot showing the findings input screen for the left atrium primary reporting structure where the smaller image of the short axis left ventricle view has been selected thereby showing an enlarged image/view of this smaller image/view and also showing the various input areas for properties or attributes of this primary reporting structure.

FIG. 9 is a screen shot showing the findings input screen 400 for the left atrium primary reporting structure where the smaller image 310 of the short axis left ventricle view 310 has been selected thereby showing an enlarged image/view 312 of this smaller image/view and also showing the various input areas for properties or attributes of this primary reporting structure. In one embodiment prior findings for reports which have been previously entered or imported into method and apparatus 10 can be accessed. The prior findings can be accessed by selecting the prior study 1200 tab. In one embodiment prior findings are available for intramodality comparisons, and in one embodiment the only the prior findings for the particular prior reporting structure being reported upon are viewed. For example, in the Left Atrium 400 input screen prior findings for the left atrium of prior intra modality tests/reports can be reviewed. Similarly, when other primary reporting structures are being reported on (e.g., right atrium 410), prior findings from intra modalities from prior reports on intra modality tests can be viewed.

Figure 10:
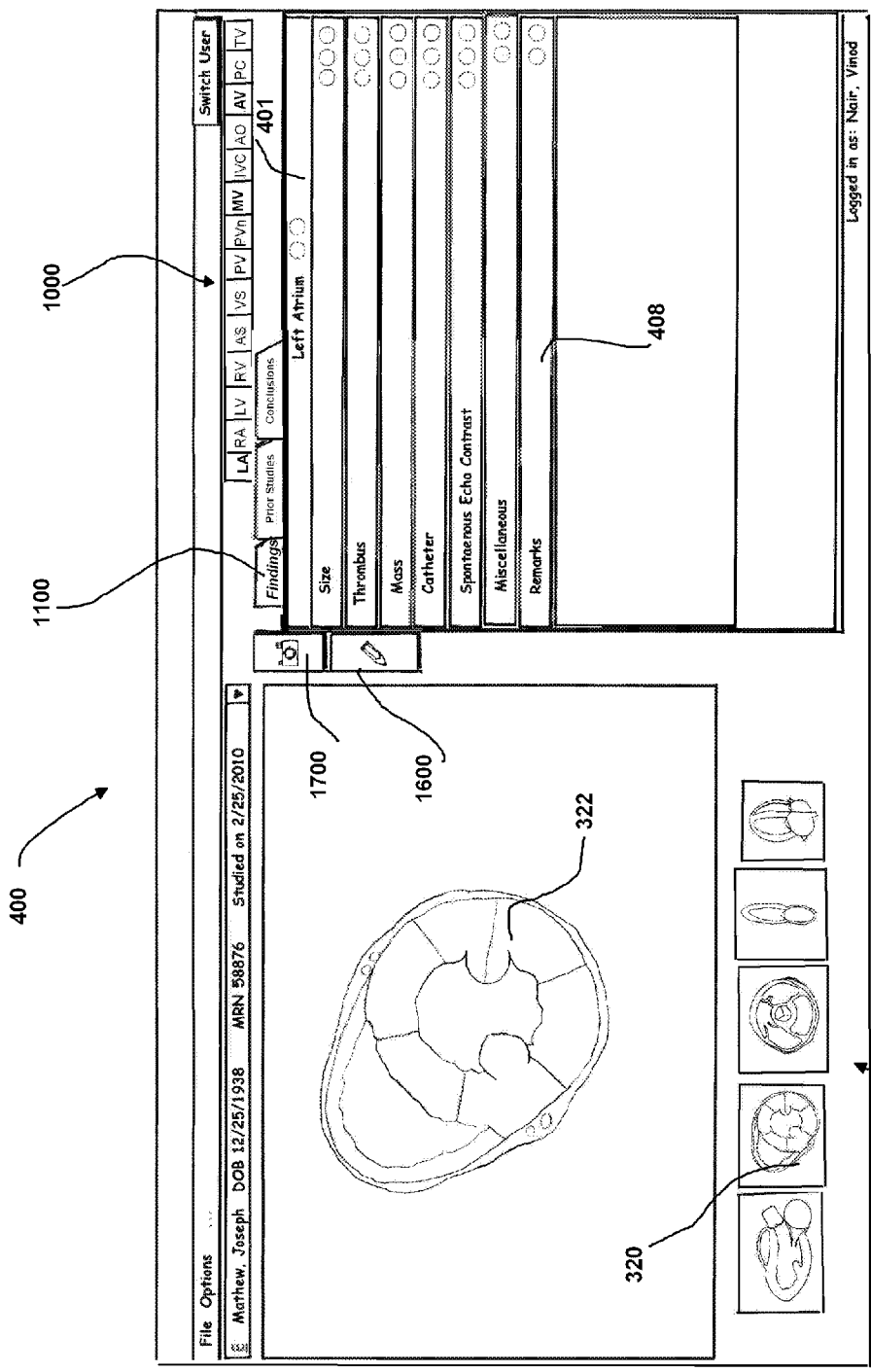
FIG. 10 is a screen shot showing the findings input screen for the left atrium primary reporting structure where the smaller image of the short axis left ventricle has been selected thereby showing an enlarged image/view of this smaller image/view and also showing the various input areas for properties or attributes of this primary reporting structure.

FIGS. 10-14 illustrate the ability to show different enlarged anatomical images or views of an organ on the input screen for the same primary reporting structure. FIG. 10 is a screen shot showing the findings input screen 400 for the left atrium primary reporting structure where the smaller image of the short axis left ventricle view 320 has been selected (from the plurality 300 of smaller anatomical images/views) thereby displaying an enlarged image/view 322 of this smaller image/view 320, and also showing the various input areas for properties or attributes of this primary reporting structure (items 401 through 408).

Figure 11:
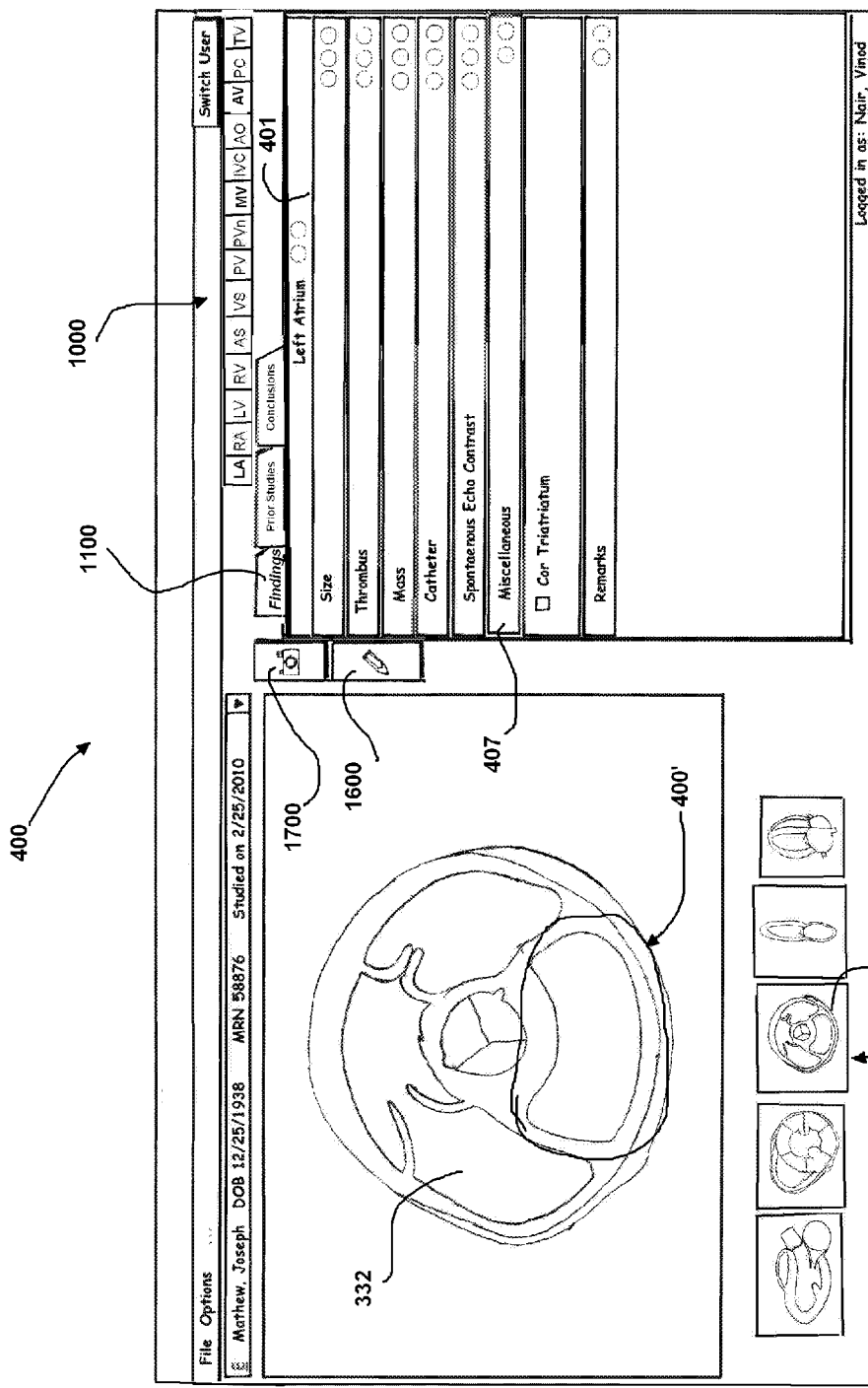
FIG. 11 is a screen shot showing the findings input screen for the left atrium primary reporting structure where the smaller image of the subcostal view has been selected thereby showing an enlarged image/view of this smaller image/view and also showing the various input areas for properties or attributes of this primary reporting structure.

FIG. 11 is a screen shot showing the findings input screen 400 for the left atrium primary reporting structure where the smaller image of the short axis at the level of the aortic valve 330 has been selected thereby displaying an enlarged image/view 332 of this smaller image/view 330, and also showing the various input areas for properties or attributes of this primary reporting structure (items 401 through 408). The particular primary reporting structure (left atrium 400) for which the input screen is being displayed is highlighted in the enlarged image/view 332 (here circle 400' tells the user 90 that the left atrium input screen 400 is being displayed on the display 100). Various means of highlighting the primary reporting structure in the enlarged anatomical image/view can be used, such as a different color, bolding, shading, enlargement, along with any combination of the highlighting methods. In FIG. 10, no highlighting of the enlarged anatomical image view is shown because the particular primary reporting structure (left atrium 400) for which the input page is displayed is not found on the enlarged anatomical image/view.

Figure 12:
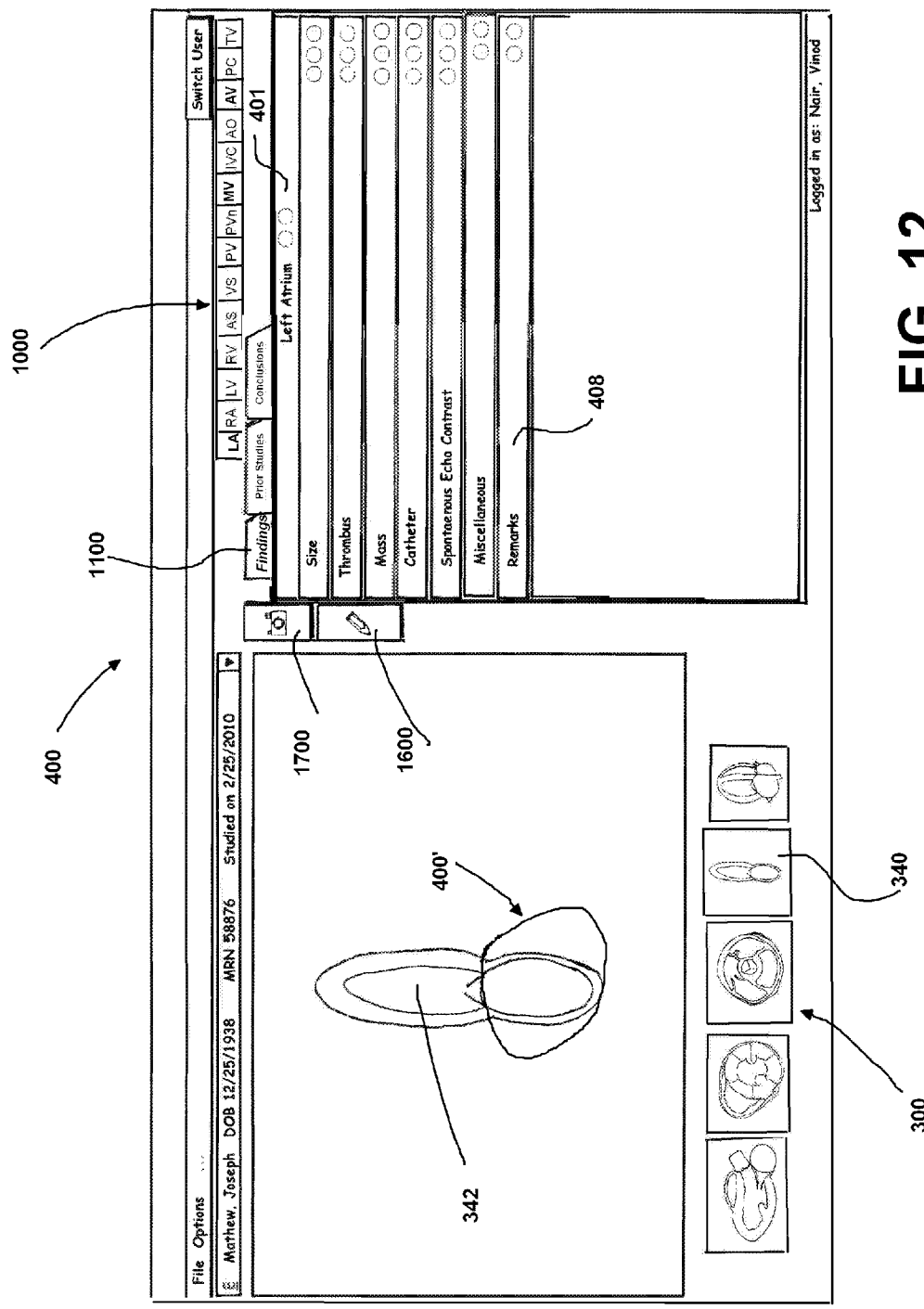
FIG. 12 is a screen shot showing the findings input screen for the left atrium primary reporting structure where the smaller image of the two chamber view has been selected thereby displaying an enlarged image/view of this smaller image/view, and also showing the various input areas for properties or attributes of this primary reporting structure.

FIG. 12 is a screen shot showing the findings input screen for the left atrium primary reporting structure where the smaller image of the two chamber view 340 has been selected thereby displaying an enlarged image/view 342 of this smaller image/view 340, and also showing the various input areas for properties or attributes of this primary reporting structure (items 401 through 408). The particular primary reporting structure (left atrium 400) for which the input screen is being displayed is highlighted in the enlarged image/view 342 (here circle 400' tells the user 90 that the left atrium input screen 400 is being displayed on the display 100).

Figure 13:
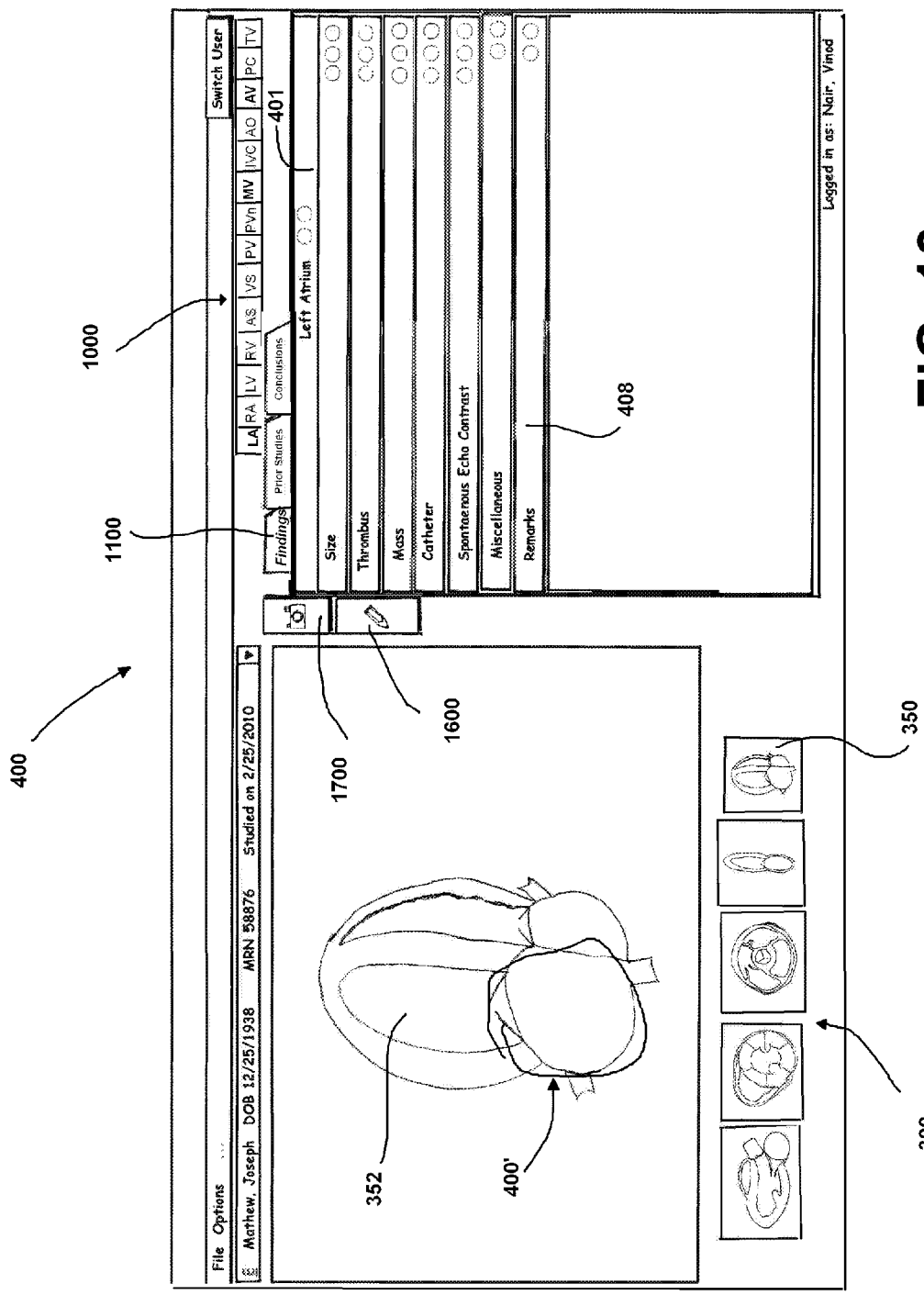
FIG. 13 is a screen shot showing the findings input screen for the left atrium primary reporting structure where the smaller image of the short axis basil has been selected thereby showing an enlarged image/view of this smaller image/view and also showing the various input areas for properties or attributes of this primary reporting structure.

FIG. 13 is a screen shot showing the findings input screen for the left atrium primary reporting structure where the smaller image of the subcostal view 350 has been selected thereby displaying an enlarged image/view 352 of this smaller image/view 340, and also showing the various input areas for properties or attributes of this primary reporting structure (items 401 through 408). The particular primary reporting structure (left atrium 400) for which the input screen is being displayed is highlighted in the enlarged image/view 352 (here circle 400' tells the user 90 that the left atrium input screen 400 is being displayed on the display 100).

Figure 14:
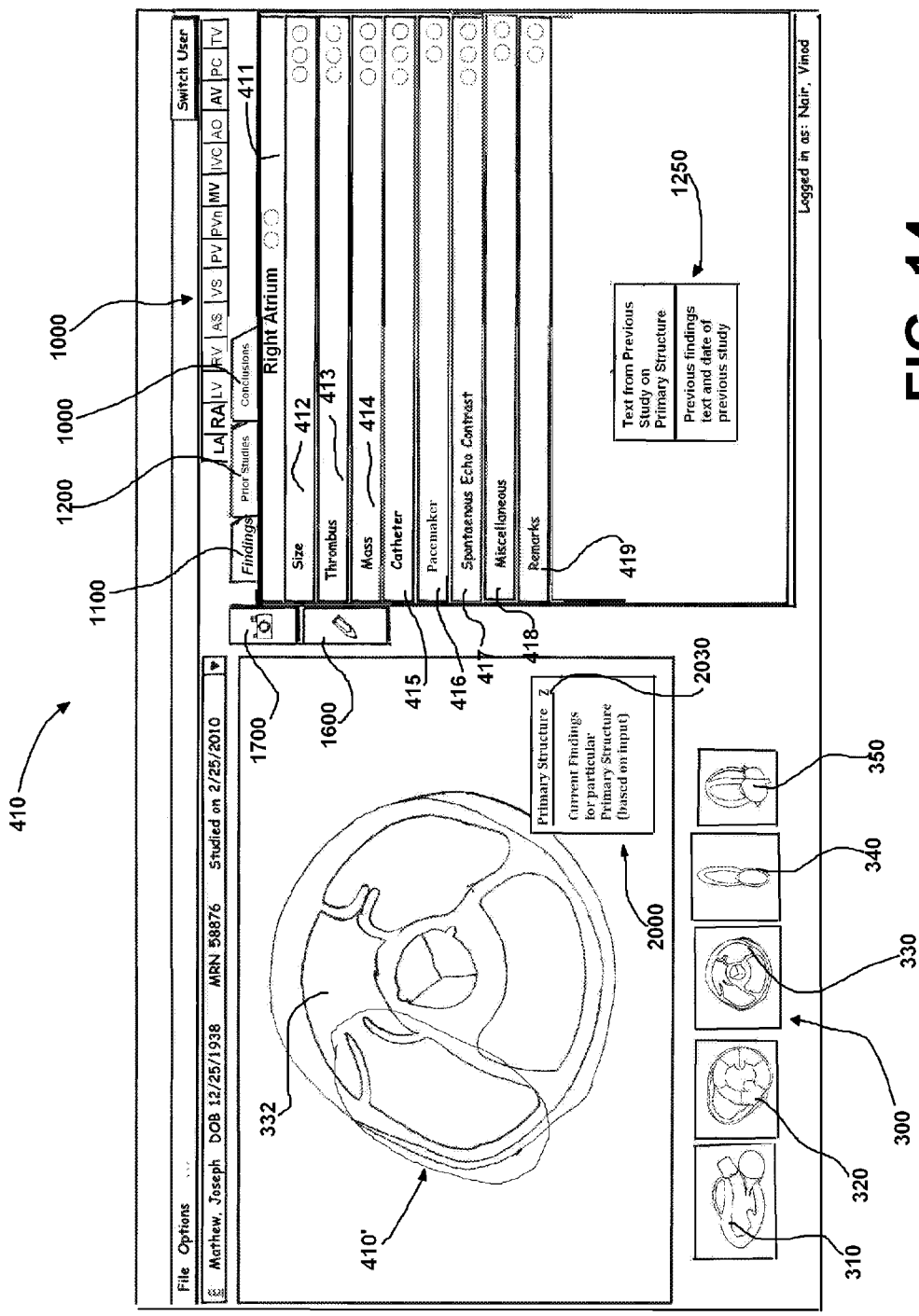
FIG. 14 is a screen shot showing the findings input screen for the right atrium primary reporting structure where the smaller image of the short axis apical has been selected thereby showing an enlarged image/view of this smaller image/view and also showing the various input areas for properties or attributes of this primary reporting structure.

In one embodiment, the data displayed includes a collection of prior studies relating to the patient. FIG. 14 is a screen shot showing the findings input screen for the right atrium 410 primary reporting structure where the smaller image of the short axis at the level of the aortic valve 330 has been selected thereby showing an enlarged image/view 332 of this smaller image/view and also showing the various input areas for properties or attributes of this primary reporting structure (items 411 through 419). Also shown on this input screen is a pop up version 1250 of the findings text from a previous intra modal study (which report had been previously entered into the method and apparatus 10), for this particular primary reporting structure (in this case the right atrium whose right atrium 410 input screen is displayed). This previous findings version 1250 will pop up a pre-set period of time and then disappear. If the user 90 desires to see any of the prior studies he merely selects the prior studies tab 1200 and will be directed to a page where all prior studies are available (see FIG. 9 for the Left Atrium) for the particular primary reporting structure whose report input screen is currently being displayed (in this case the right atrium 410 primary reporting structure input screen). Also shown in this input screen is a pop up version of the current text on the right atrium as being the primary reporting structure whose input screen is currently being displayed.

Figure 15:
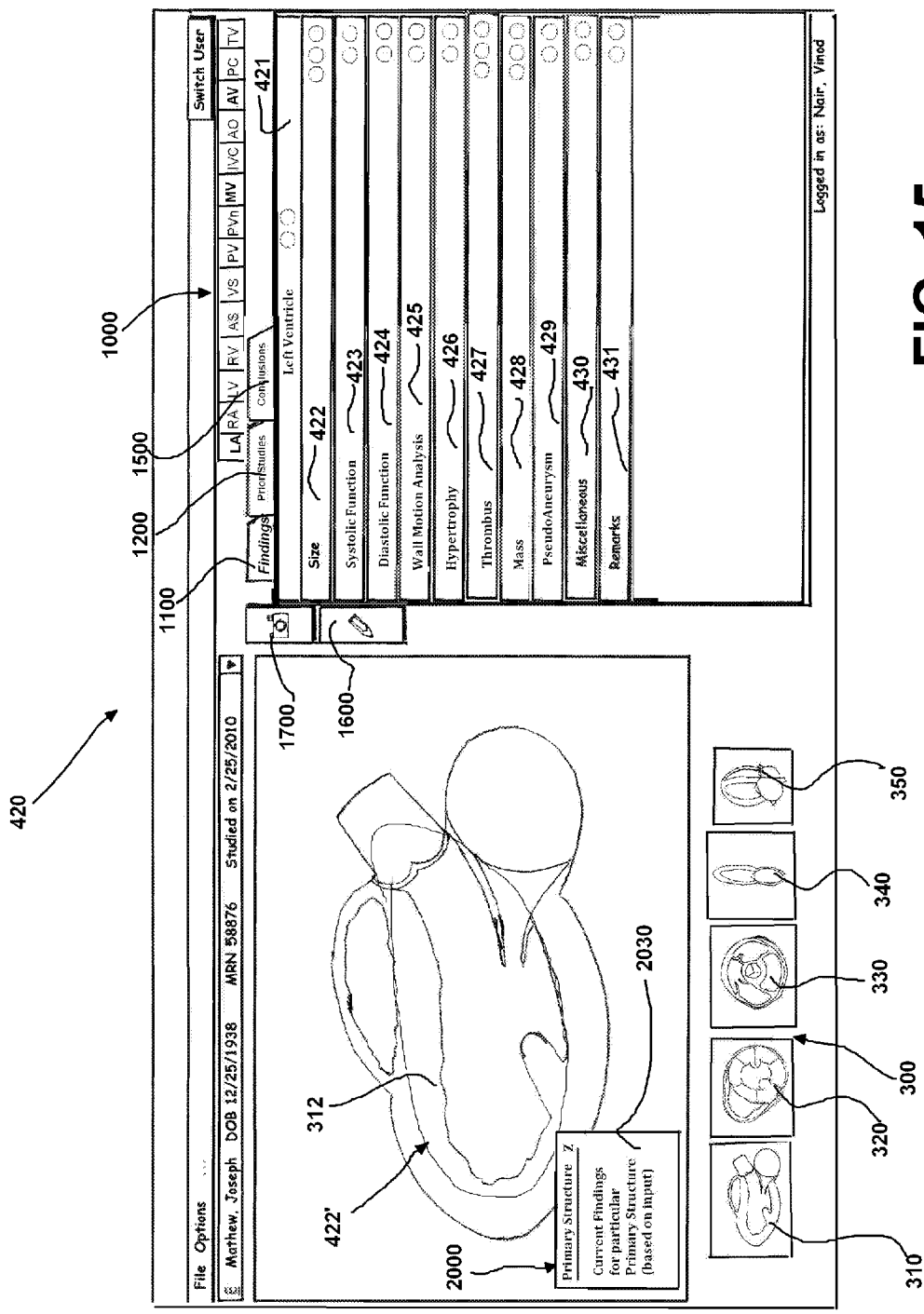
FIG. 15 is a screen shot showing the findings input screen for the left ventricle primary reporting structure where the smaller image of the Parasternal long axis view has been selected thereby showing an enlarged image/view of this smaller image/view (with the left ventricle highlighted) and also showing the various input areas for properties or attributes of this primary reporting structure with no property or attribute actually being selected (and also showing the current text string for the findings on this primary reporting structure).

FIG. 15 is a screen shot showing the findings input screen 420 for the left ventricle primary reporting structure where the smaller image 310 of the Parasternal long axis view has been selected thereby showing an enlarged image/view 312 of this smaller image/view (with the left ventricle highlighted as 422') and also showing the various input areas for properties or attributes of this primary reporting structure with no property or attribute actually being selected (items 421 through 431). Also shown is pop up display 2000 is the current text string 2030 for the findings on this primary reporting structure—left ventricle).

FIGS. 16-21 illustrate screen shots in inputting information for the method and apparatus 10 to calculate a wall motion analysis. In one embodiment anatomical images/views of the heart related to septal motion can be provided on the display 100 which are selectable (such as by smaller anatomical images/views or through pull down menu choices), and such anatomical images/views are themselves broken down into a plurality of selectable segmental portions. The anatomical images/views for wall motion analysis can include long and short axis, along with two and four chamber views. In one embodiment WMSI can be calculated by the software based on input made in selecting one, more, or all of the smaller segmental portions, with each smaller segmental portion providing the option to select from a set of gradations of wall motion. For example, segmental portions for the individual sections of the heart can be selected graphically by clicking on the particular segmental section of the heart can and then selecting an indicator from the set of 1, 2, 3, and 4 (such as toggling through such indicators). The WMSI based on conventionally available formula can be is automatically calculated by the software based on such input, and included in the findings section of the generated report.

Figure 16:
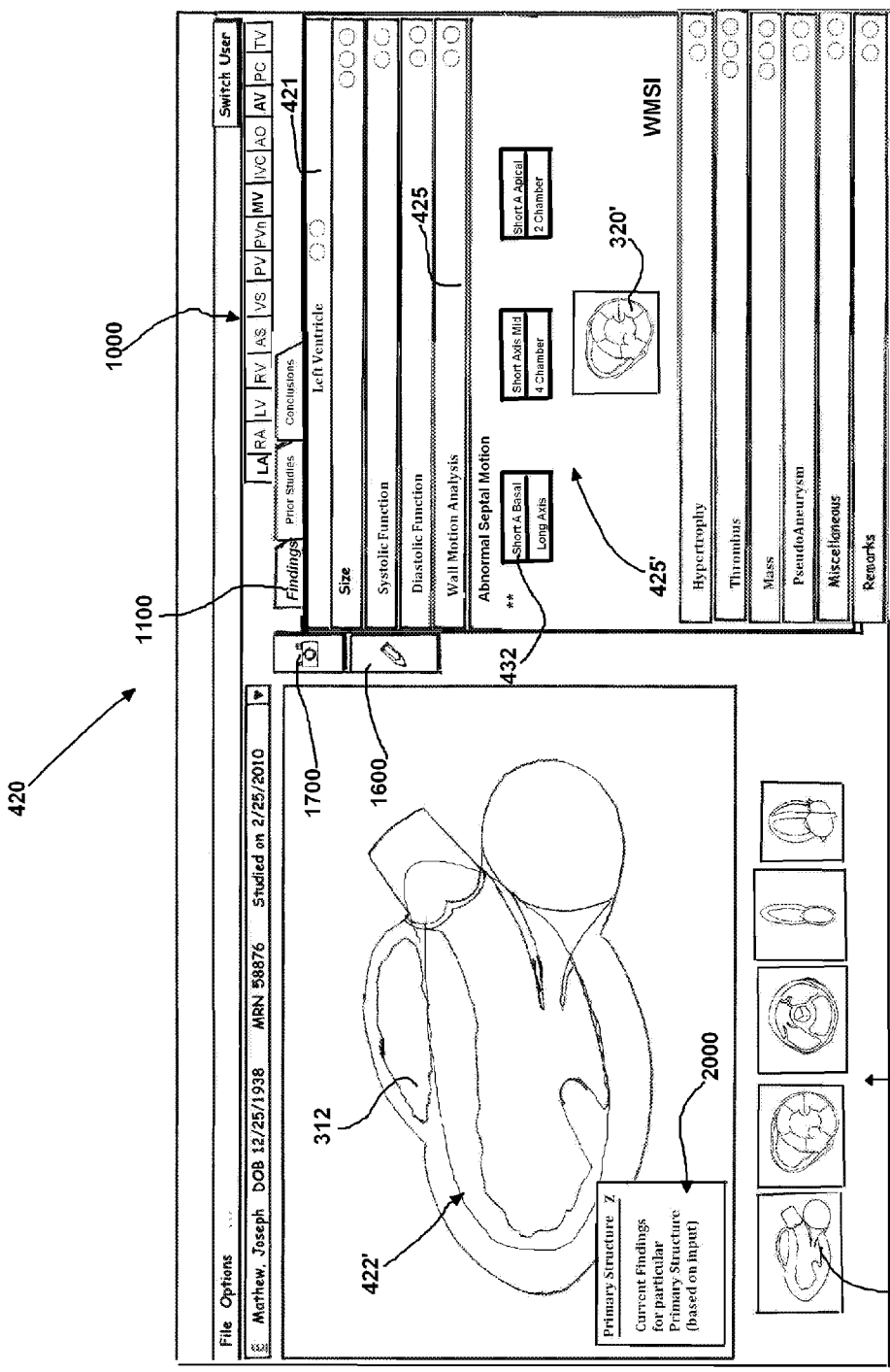
FIG. 16 is a screen shot showing the Wall Motion Analysis property or attribute selected along with the Short A Basal selected/highlighted and a small image/view of the short axis left ventricle displayed with this small image/view being broken into a plurality of reporting segments for entering input for a wall motion calculation.

FIG. 16 is a screen shot showing the Wall Motion Analysis 425 property or attribute selected along with the Short A Basal 432 selected/highlighted and a small image/view 320' of the short axis left ventricle displayed with this small image/ view being broken into a plurality of reporting segments 320" for entering input for a wall motion calculation.

Figure 17:
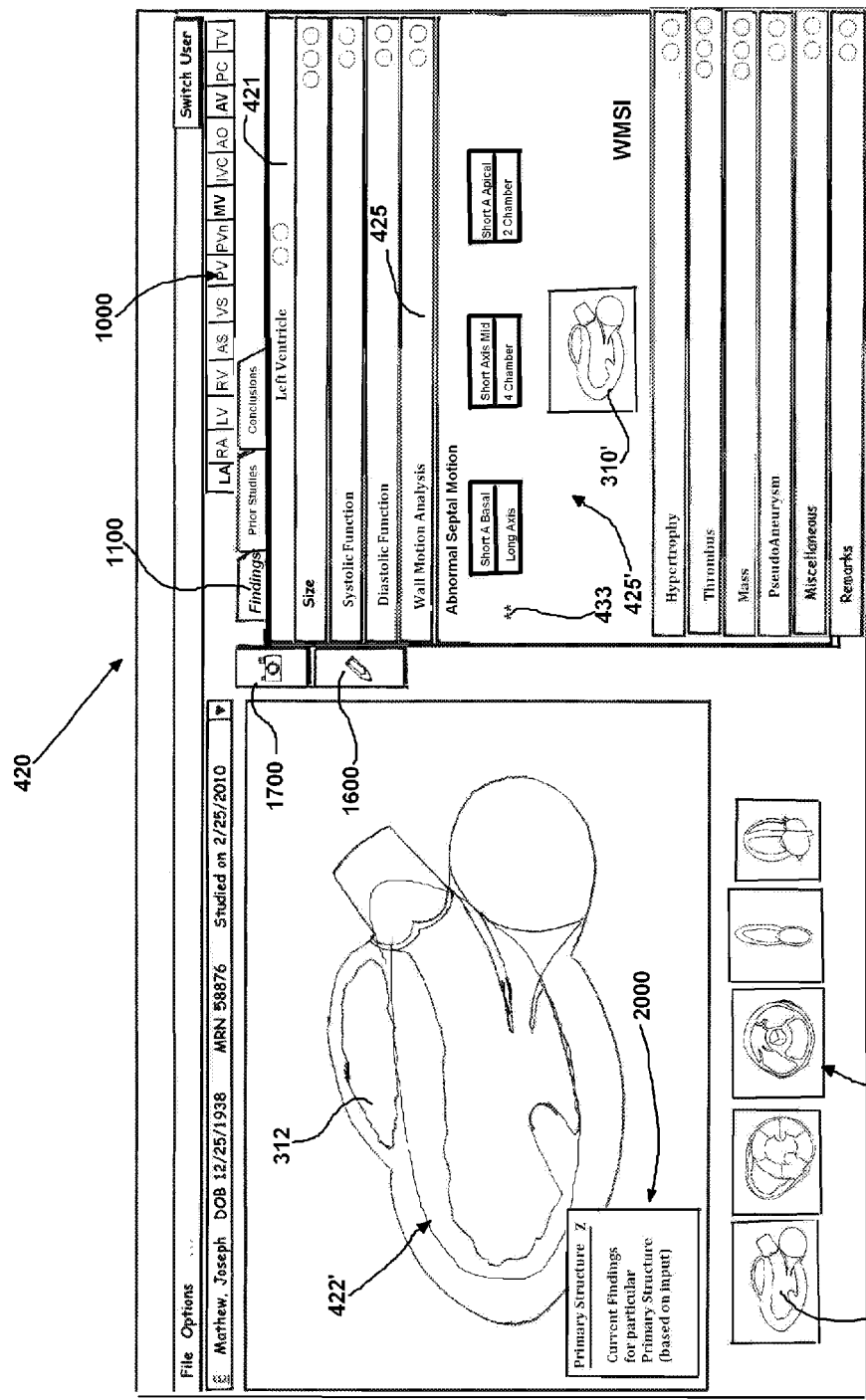
FIG. 17 is a screen shot showing the Wall Motion Analysis property or attribute selected along with the Long Axis selected/highlighted and a small image/view of the Parasternal long axis image/view displayed with this small image/view being broken into a plurality of reporting segments for entering input for a wall motion calculation.

FIG. 17 is a screen shot showing the Wall Motion Analysis 425 property or attribute selected along with the Long Axis 433 selected/highlighted and a small image/view of the Parasternal long axis image/view 310' displayed with this small image/view being broken into a plurality of reporting segments 310" for entering input for a wall motion calculation.

Figure 18:
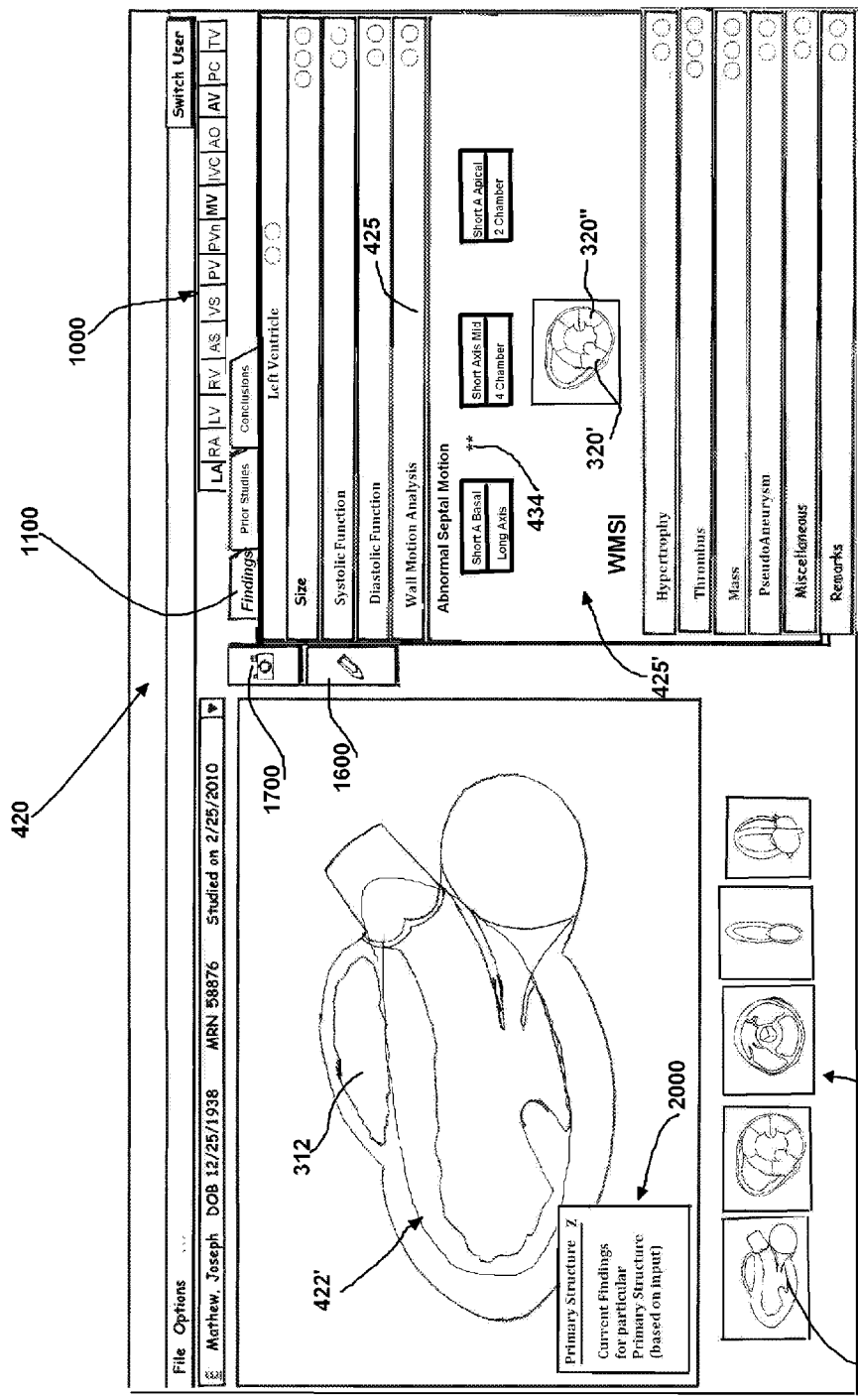
FIG. 18 is a screen shot showing the Wall Motion Analysis property or attribute selected along with the Short Axis Mid selected/highlighted and a small image/view of the short axis left ventricle image/view displayed with this small image/view being broken into a plurality of reporting segments for entering input for a wall motion calculation.

FIG. 18 is a screen shot showing the Wall Motion Analysis 425 property or attribute selected along with the Short Axis Mid 434 selected/highlighted and a small image/view of the short axis left ventricle image/view 320' displayed with this small image/view being broken into a plurality of reporting segments 320" for entering input for a wall motion calculation.

Figure 19:
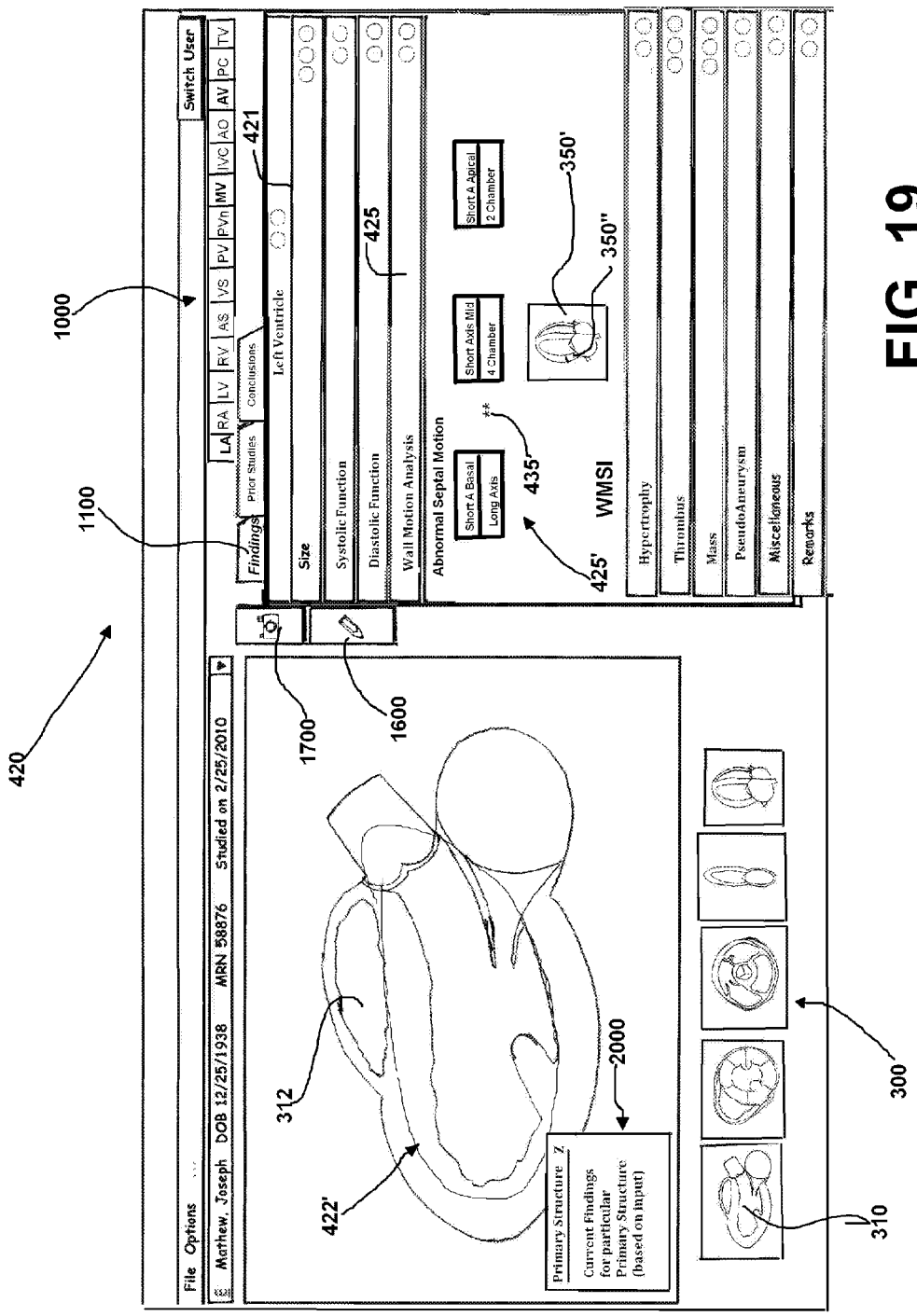
FIG. 19 is a screen shot showing the Wall Motion Analysis property or attribute selected along with the 4 Chamber view selected/highlighted and a small image/view of the subcostal image/view displayed with this small image/view being broken into a plurality of reporting segments for entering input for a wall motion calculation.

FIG. 19 is a screen shot showing the Wall Motion Analysis 425 property or attribute selected along with the 4 Chamber view 435 selected/highlighted and a small image/view 350' of the subcostal image/view displayed with this small image/view being broken into a plurality of reporting segments 350" for entering input for a wall motion calculation.

Figure 20:
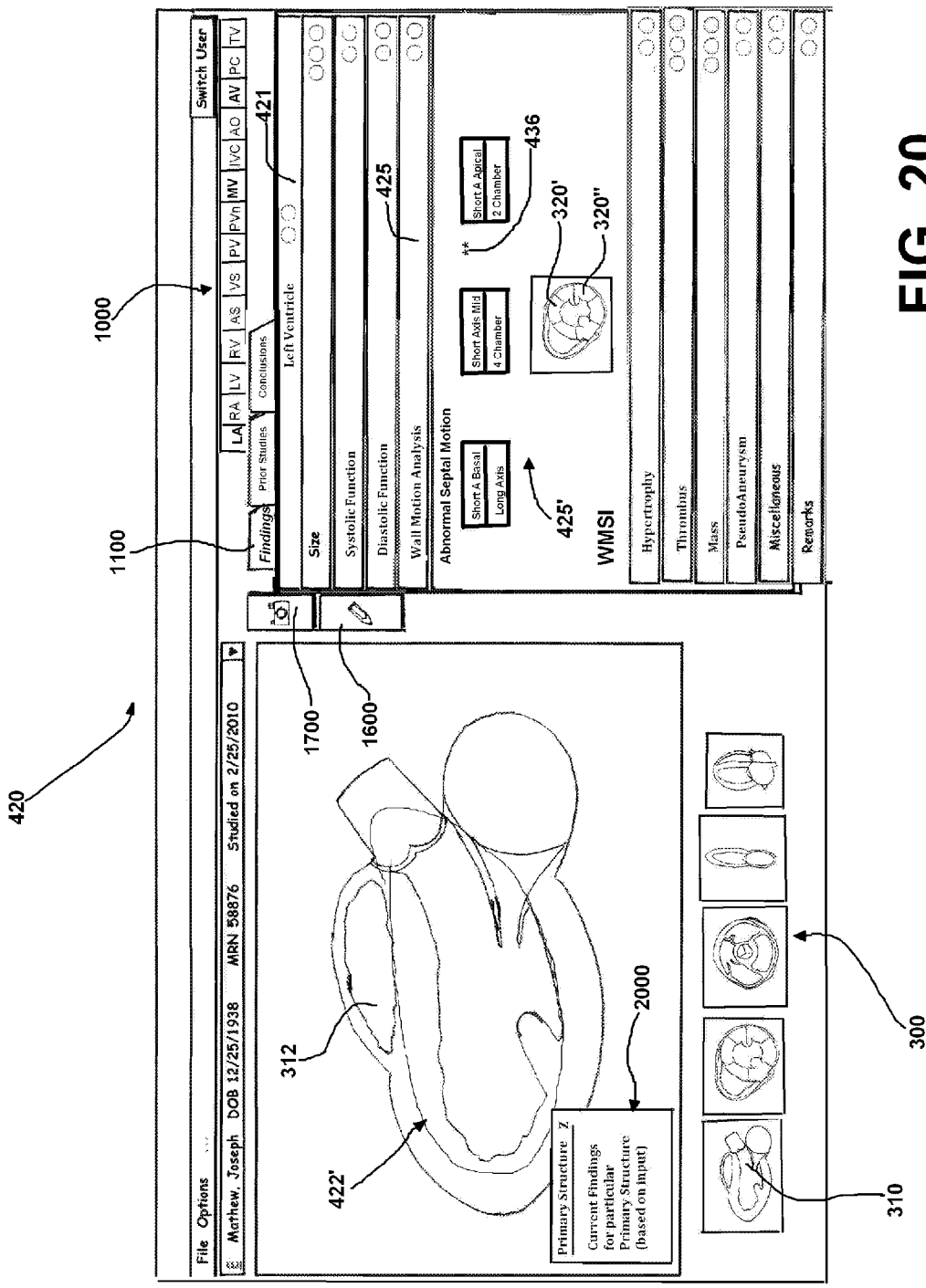
FIG. 20 is a screen shot showing the Wall Motion Analysis property or attribute selected along with the Short A Apical view selected/highlighted and a small image/view of the short axis left ventricle image/view displayed with this small image/view being broken into a plurality of reporting segments for entering input for a wall motion calculation.

FIG. 20 is a screen shot showing the Wall Motion Analysis 425 property or attribute selected along with the Short A Apical view 436 selected/highlighted and a small image/view 320' of the short axis left ventricle image/view displayed with this small image/view being broken into a plurality of reporting segments 320" for entering input for a wall motion calculation.

Figure 21:
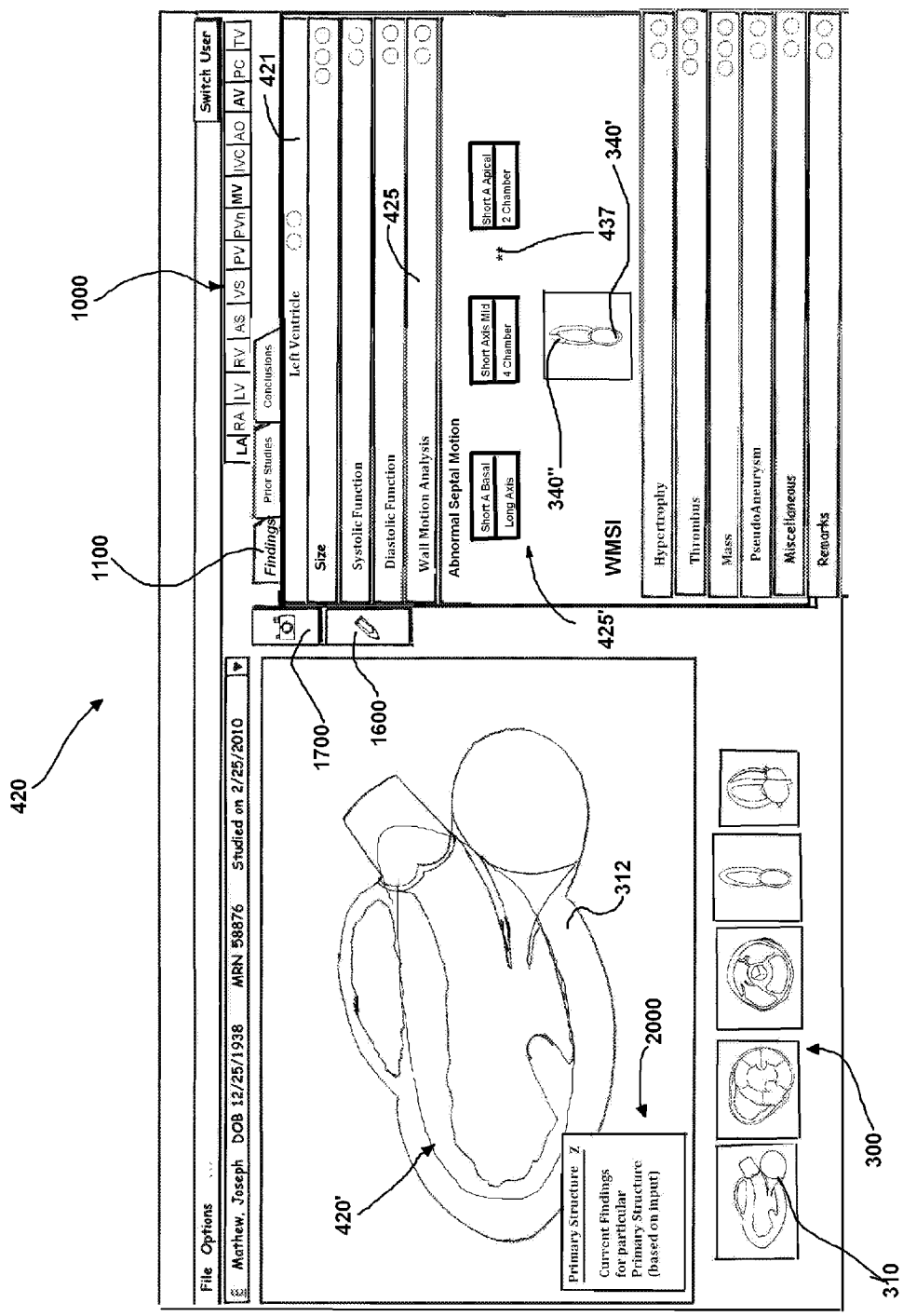
FIG. 21 is a screen shot showing the Wall Motion Analysis property or attribute selected along with the 2 Chamber view selected/highlighted and a small image/view of the two chamber image/view displayed with this small image/view being broken into a plurality of reporting segments for entering input for a wall motion calculation.

FIG. 21 is a screen shot showing the Wall Motion Analysis 425 property or attribute selected along with the 2 Chamber view 437 selected/highlighted and a small image/view 340' of the two chamber image/view displayed with this small image/view being broken into a plurality of reporting segments 340" for entering input for a wall motion calculation.

Figure 22:
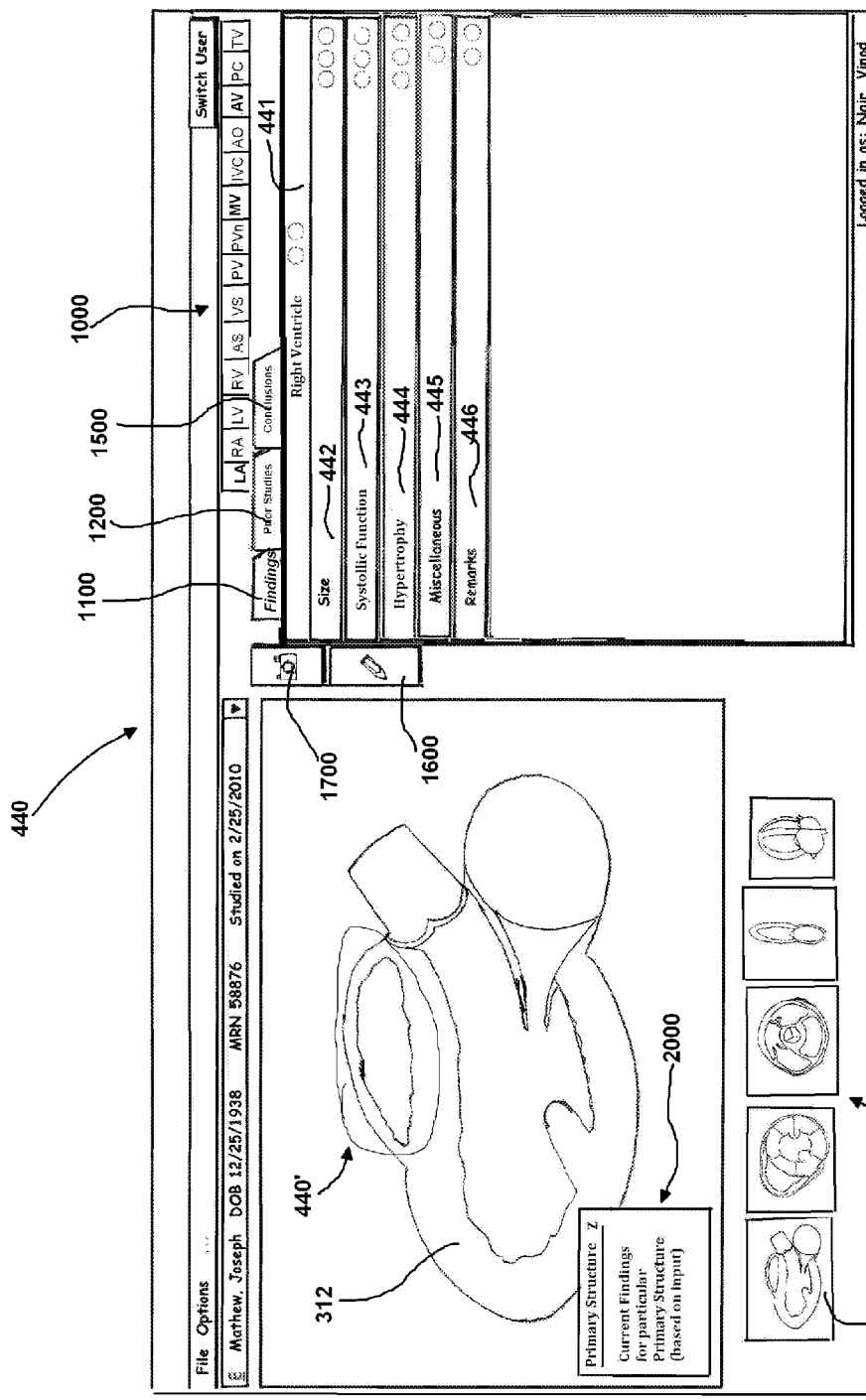
FIG. 22 is a screen shot showing the findings input screen for the right ventricle primary reporting structure where the smaller image of the Parasternal long axis view has been selected thereby showing an enlarged image/view of this smaller image/view (with the right ventricle highlighted) and also showing the various input areas for properties or attributes of this primary reporting structure with no property or attribute actually being selected (and also showing the current text string for the findings on this primary reporting structure).

FIG. 22 is a screen shot showing the findings input screen 440 for the right ventricle primary reporting structure where the smaller image 310 of the Parasternal long axis view has been selected thereby showing an enlarged image/view 312 of this smaller image/view (with the right ventricle highlighted as 440'), and also showing the various input areas for properties or attributes of this primary reporting structure with no property or attribute actually being selected (items 441 through 446). Also shown is pop up display 2000 is the current text string 2030 for the findings on this primary reporting structure—right ventricle).

Figure 23:
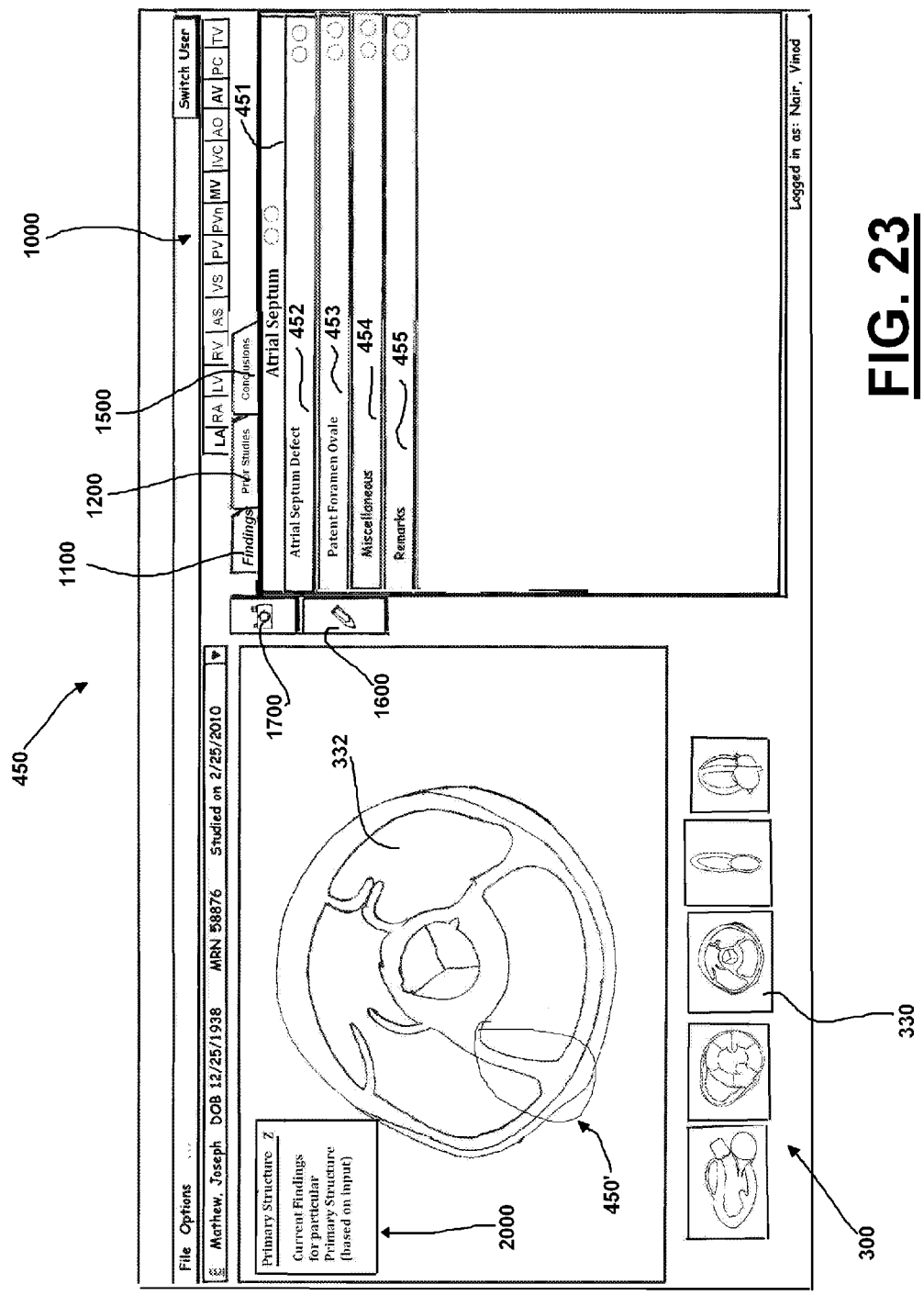
FIG. 23 is a screen shot showing the findings input screen for the atrial septum primary reporting structure where the smaller image of the short axis aorta valve view has been selected thereby showing an enlarged image/view of this smaller image/view (with the atrial septum highlighted) and also showing the various input areas for properties or attributes of this primary reporting structure with no property or attribute actually being selected (and also showing the current text string for the findings on this primary reporting structure).

FIG. 23 is a screen shot showing the findings input screen 450 for the atrial septum primary reporting structure where the smaller image 330 of the short axis aorta valve view has been selected thereby showing an enlarged image/view 332 of this smaller image/view (with the atrial septum highlighted as 450'), and also showing the various input areas for properties or attributes of this primary reporting structure with no property or attribute actually being selected (items 451 through 455). Also shown is pop up display 2000 is the current text string 2030 for the findings on this primary reporting structure—atrial septum).

Figure 24:
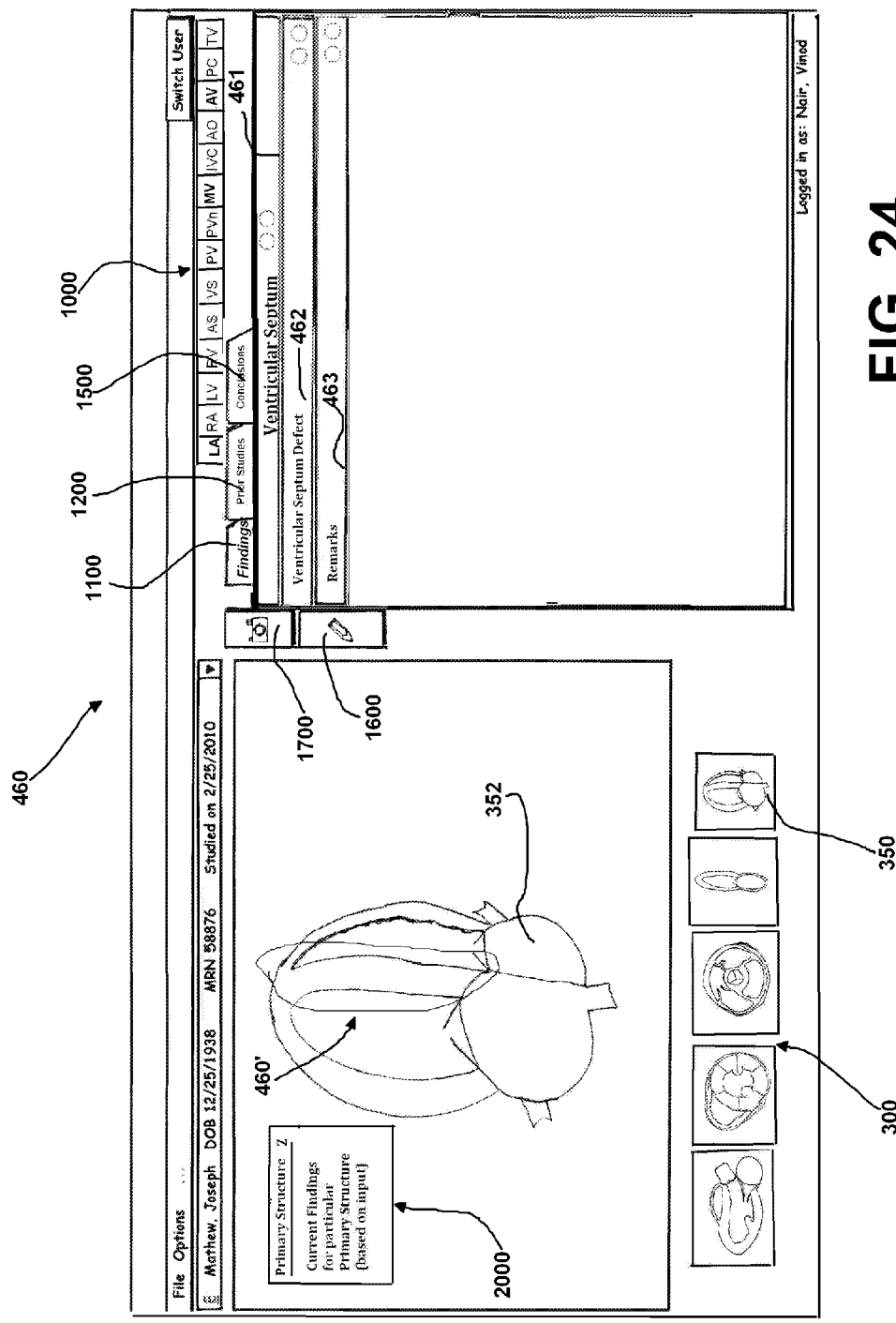
FIG. 24 is a screen shot showing the findings input screen for the ventricular septum primary reporting structure where the smaller image of the subcostal view has been selected thereby showing an enlarged image/view of this smaller image/view (with the ventricular septum highlighted) and also showing the various input areas for properties or attributes of this primary reporting structure with no property or attribute actually being selected (and also showing the current text string for the findings on this primary reporting structure).

FIG. 24 is a screen shot showing the findings input screen 460 for the ventricular septum primary reporting structure where the smaller image 350 of the subcostal view has been selected thereby showing an enlarged image/view 352 of this smaller image/view (with the ventricular septum highlighted as 460'), and also showing the various input areas for properties or attributes of this primary reporting structure with no property or attribute actually being selected (items 461 through 463). Also shown is pop up display 2000 is the current text string 2030 for the findings on this primary reporting structure—ventricular septum).

Figure 25:
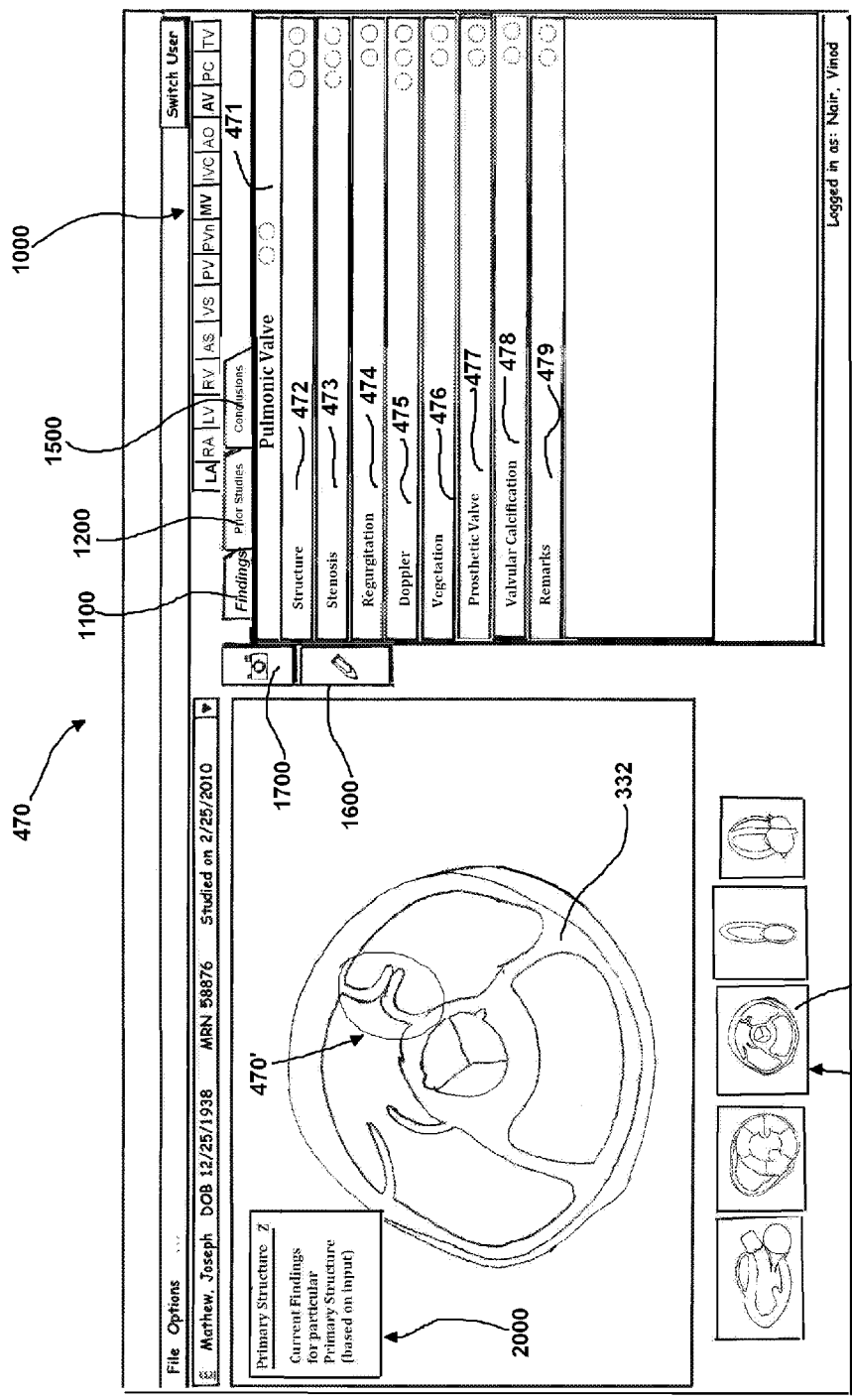
FIG. 25 is a screen shot showing the findings input screen for the pulmonic valve primary reporting structure where the smaller image of the short axis aorta valve view has been selected thereby showing an enlarged image/view of this smaller image/view (with the pulmonic valve highlighted) and also showing the various input areas for properties or attributes of this primary reporting structure with no property or attribute actually being selected (and also showing the current text string for the findings on this primary reporting structure).

FIG. 25 is a screen shot showing the findings input screen 470 for the pulmonic valve primary reporting structure where the smaller image 330 of the short axis aorta valve view has been selected thereby showing an enlarged image/view 332 of this smaller image/view (with the pulmonic valve highlighted as 470'), and also showing the various input areas for properties or attributes of this primary reporting structure with no property or attribute actually being selected (items 471 through 479). Also shown is pop up display 2000 is the current text string 2030 for the findings on this primary reporting structure—pulmonic valve).

Figure 26:
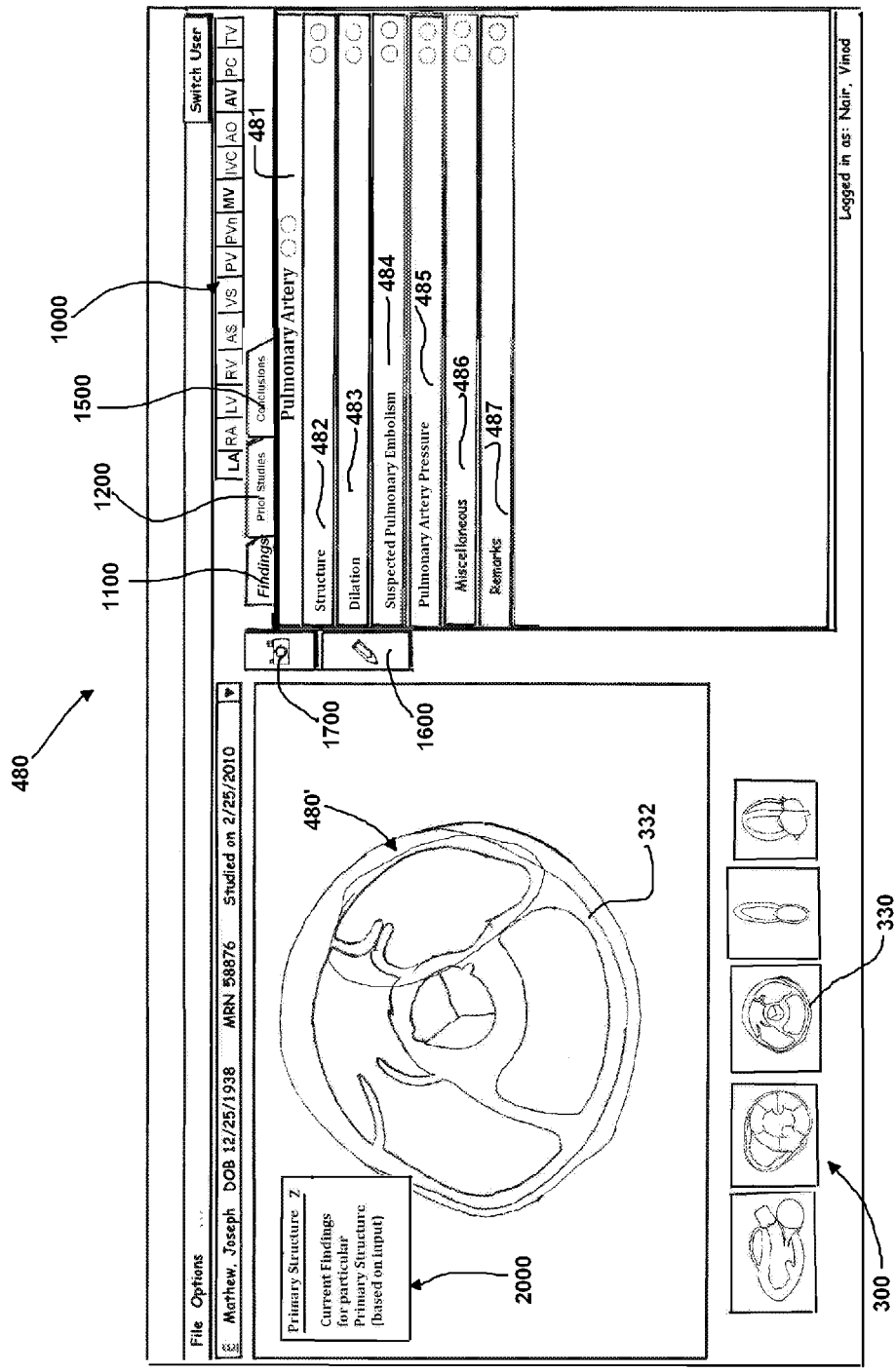
FIG. 26 is a screen shot showing the findings input screen for the pulmonary artery primary reporting structure where the smaller image of the short axis aorta valve view has been selected thereby showing an enlarged image/view of this smaller image/view (with the pulmonary artery highlighted) and also showing the various input areas for properties or attributes of this primary reporting structure with no property or attribute actually being selected (and also showing the current text string for the findings in this primary reporting structure).

FIG. 26 is a screen shot showing the findings input screen 480 for the pulmonary artery primary reporting structure where the smaller image 330 of the short axis aorta valve view has been selected thereby showing an enlarged image/view 332 of this smaller image/view (with the pulmonary artery highlighted as 480'), and also showing the various input areas for properties or attributes of this primary reporting structure with no property or attribute actually being selected (items 481 through 487). Also shown is pop up display 2000 is the current text string 2030 for the findings on this primary reporting structure—pulmonary artery).

Figure 27:
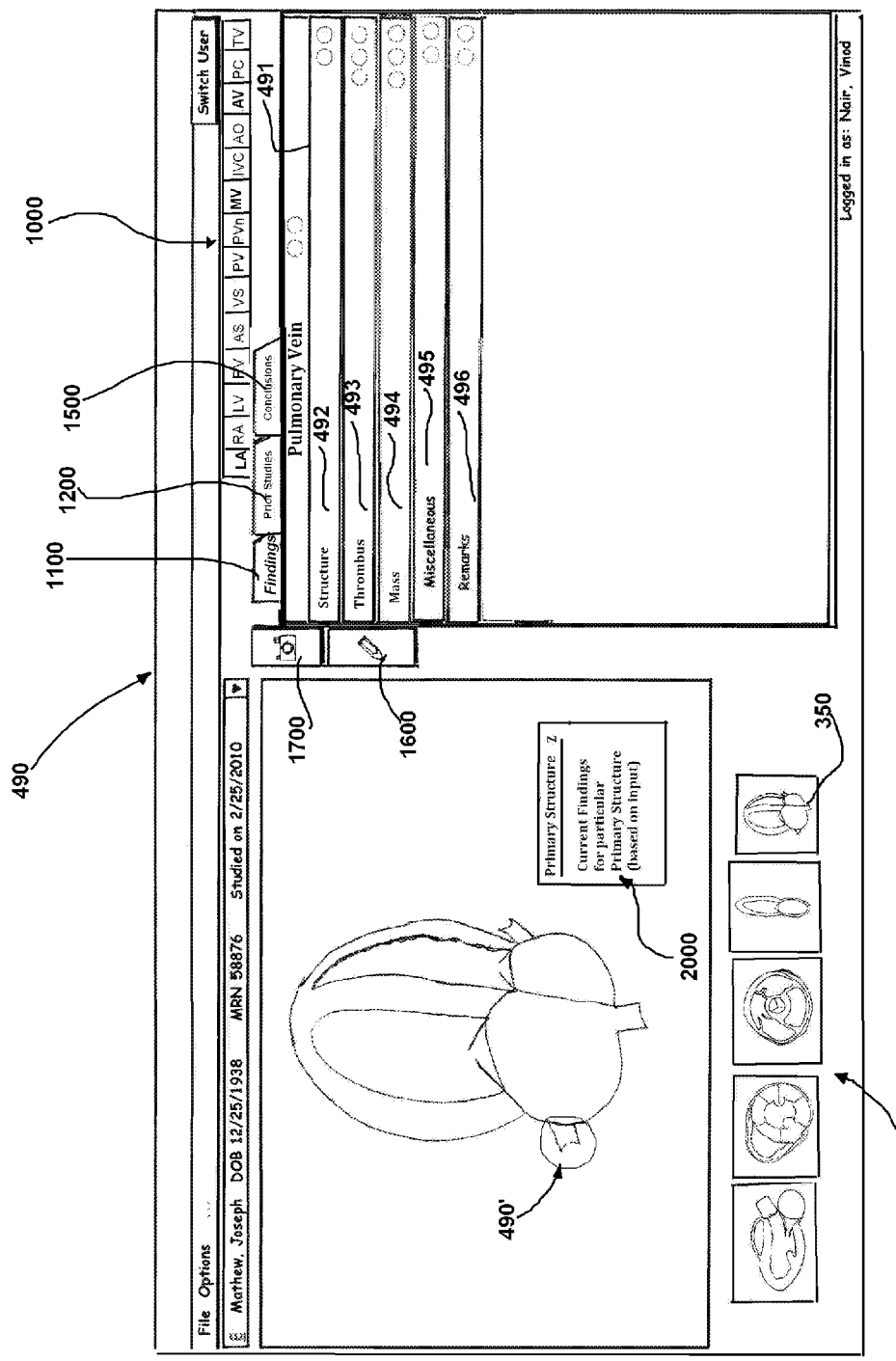
FIG. 27 is a screen shot showing the findings input screen for the pulmonary vein primary reporting structure where the smaller image of the subcostal view has been selected thereby showing an enlarged image/view of this smaller image/view (with the pulmonary vein highlighted) and also showing the various input areas for properties or attributes of this primary reporting structure with no property or attribute actually being selected (and also showing the current text string for the findings on this primary reporting structure).

FIG. 27 is a screen shot showing the findings input screen 490 for the pulmonary vein primary reporting structure where the smaller image 350 of the subcostal view has been selected thereby showing an enlarged image/view 352 of this smaller image/view (with the pulmonary vein highlighted as 490'), and also showing the various input areas for properties or attributes of this primary reporting structure with no property or attribute actually being selected (items 491 through 496). Also shown is pop up display 2000 is the current text string 2030 for the findings on this primary reporting structure—pulmonary vein).

Figure 28:
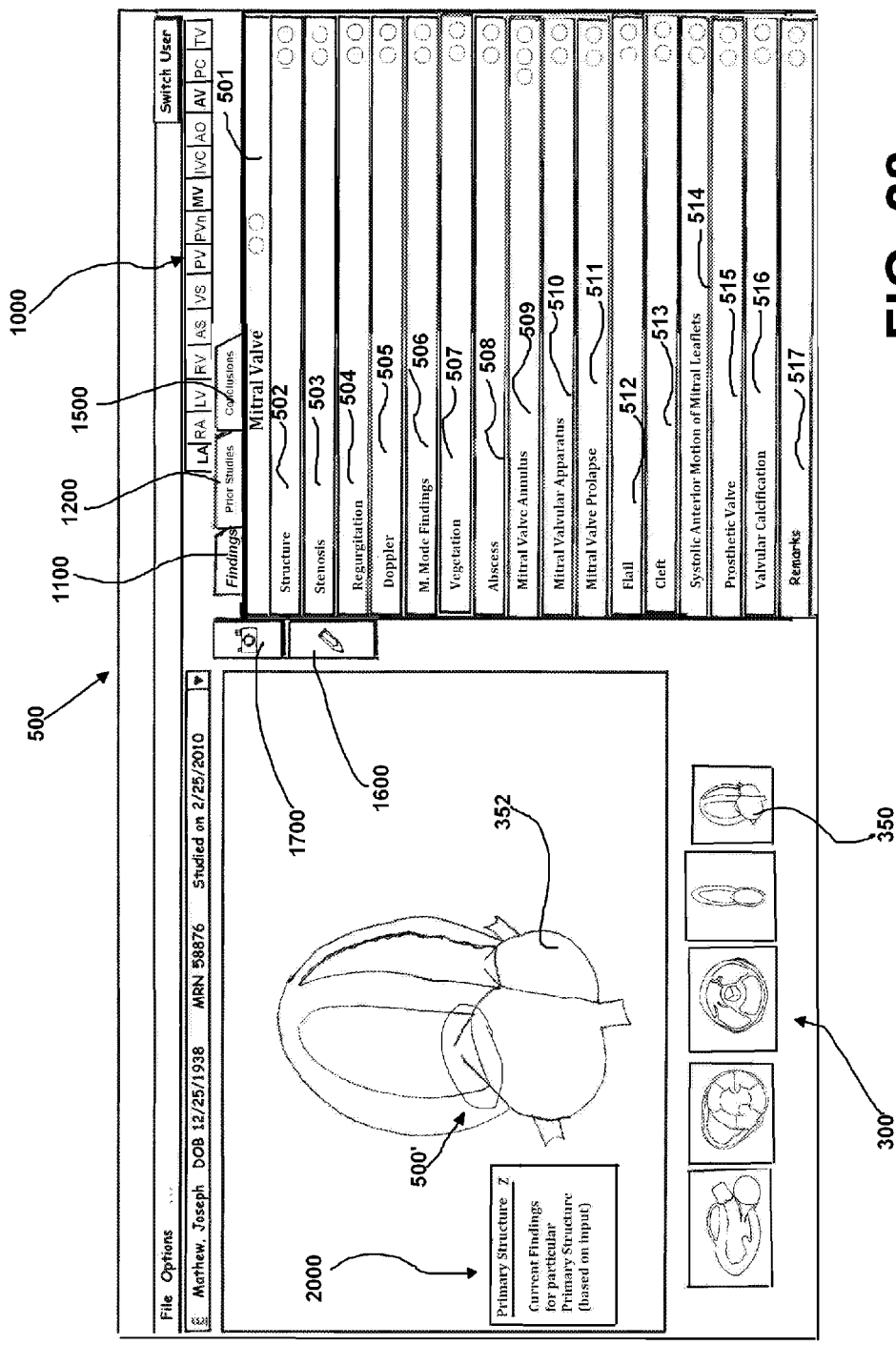
FIG. 28 is a screen shot showing the findings input screen for the mitral valve primary reporting structure where the smaller image of the subcostal view has been selected thereby showing an enlarged image/view of this smaller image/view (with the mitral valve highlighted) and also showing the various input areas for properties or attributes of this primary reporting structure with no property or attribute actually being selected (and also showing the current text string for the findings on this primary reporting structure).

FIG. 28 is a screen shot showing the findings input screen 500 for the mitral valve primary reporting structure where the smaller image 350 of the subcostal view has been selected thereby showing an enlarged image/view 352 of this smaller image/view (with the mitral valve highlighted as 500'), and also showing the various input areas for properties or attributes of this primary reporting structure with no property or attribute actually being selected (items 501 through 517). Also shown is pop up display 2000 is the current text string 2030 for the findings on this primary reporting structure—mitral valve).

Figure 29:
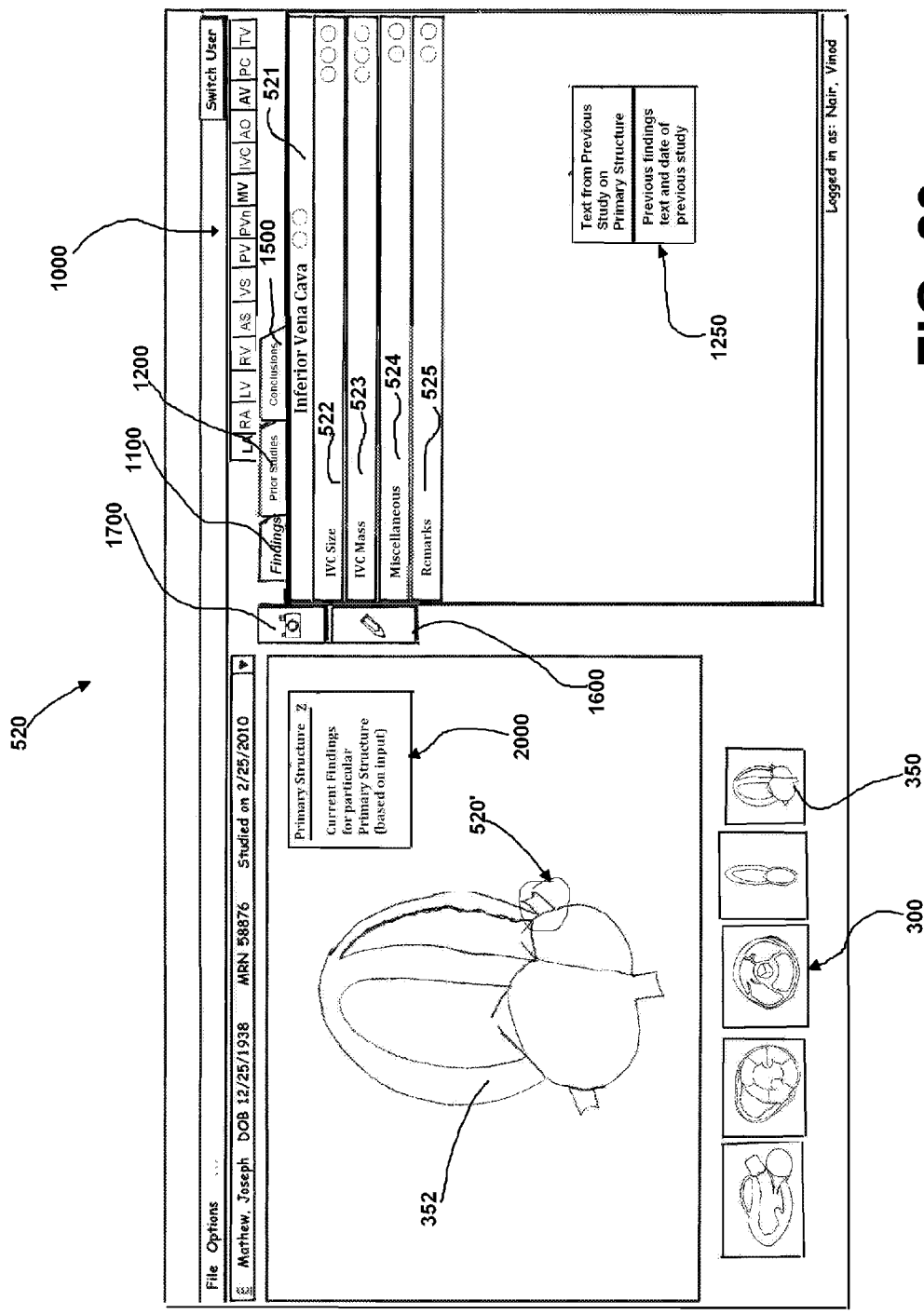
FIG. 29 is a screen shot showing the findings input screen for the inferior vena cava primary reporting structure where the smaller image of the subcostal view has been selected thereby showing an enlarged image/view of this smaller image/view (with the inferior vena cava highlighted) and also showing the various input areas for properties or attributes of this primary reporting structure with no property or attribute actually being selected (and also showing the current text string for the findings on this primary reporting structure).

FIG. 29 is a screen shot showing the findings input screen 520 for the inferior vena cava primary reporting structure where the smaller image of the subcostal view 350 has been selected thereby showing an enlarged image/view 352 of this smaller image/view (with the inferior vena cava highlighted as 520'), and also showing the various input areas for properties or attributes of this primary reporting structure with no property or attribute actually being selected (items 521 through 525). Also shown is pop up display 2000 is the current text string 2030 for the findings on this primary reporting structure—inferior vena cava).

Figure 30:
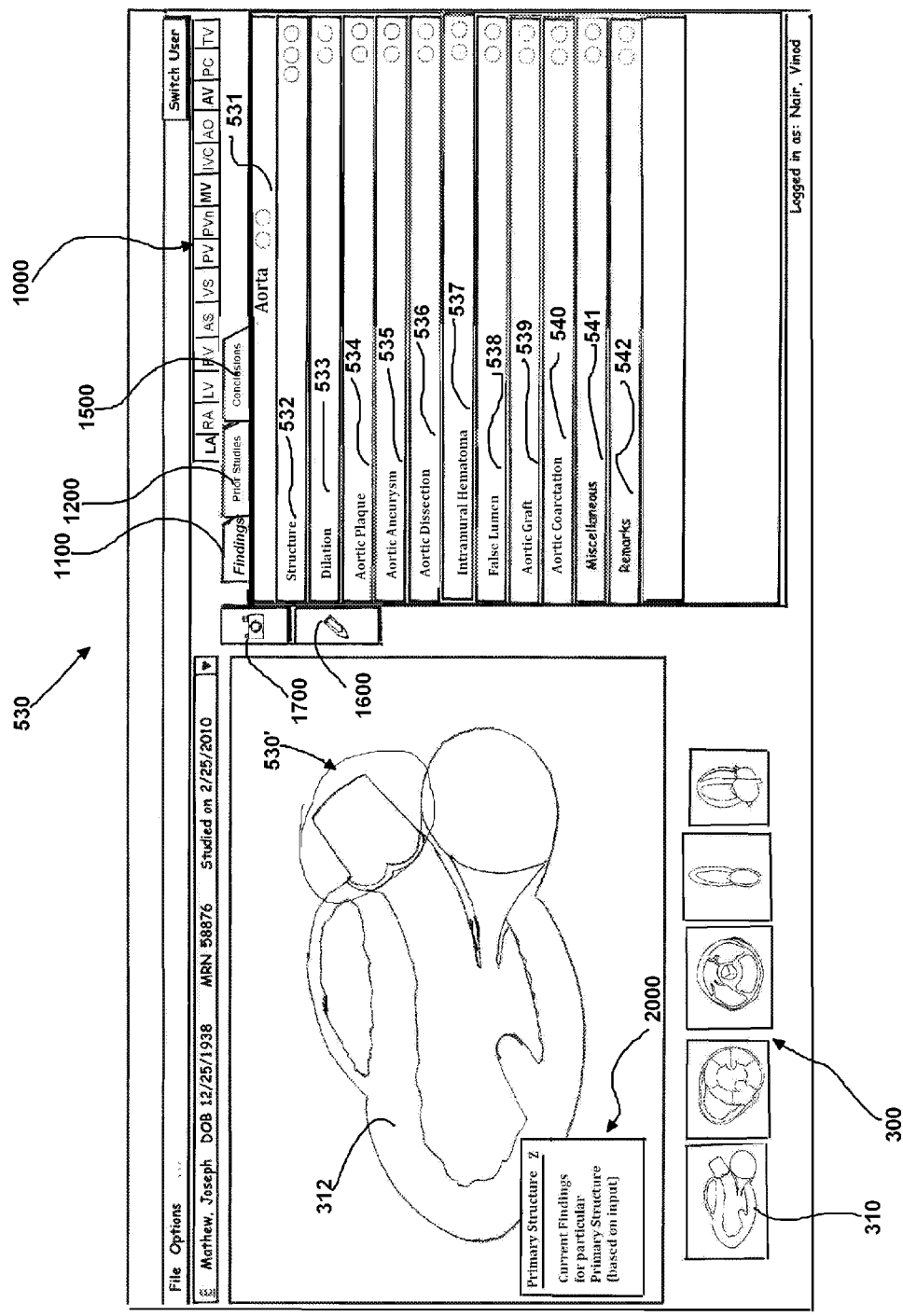
FIG. 30 is a screen shot showing the findings input screen for the aorta primary reporting structure where the smaller image of the Parasternal long axis view has been selected thereby showing an enlarged image/view of this smaller image/view (with the aorta highlighted) and also showing the various input areas for properties or attributes of this primary reporting structure with no property or attribute actually being selected (and also showing the current text string for the findings on this primary reporting structure).

FIG. 30 is a screen shot showing the findings input screen 530 for the aorta primary reporting structure where the smaller image 310 of the Parasternal long axis view has been selected thereby showing an enlarged image/view 312 of this smaller image/view (with the aorta highlighted as 530'), and also showing the various input areas for properties or attributes of this primary reporting structure with no property or attribute actually being selected (items 531 through 542).

Also shown is pop up display 2000 is the current text string 2030 for the findings on this primary reporting structure—aorta).

Figure 31A:
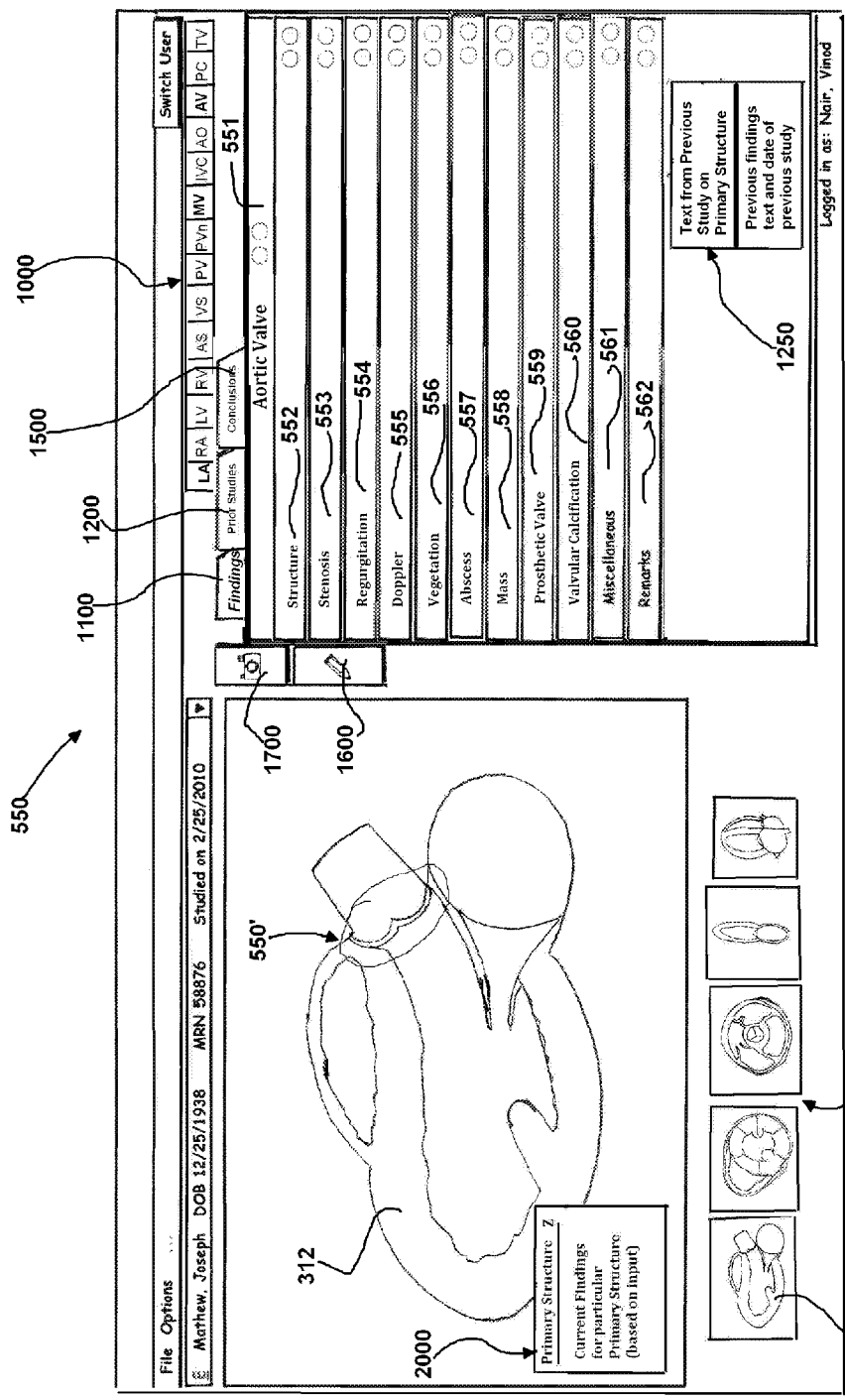
FIGS. 31A and 31B are screen shots showing the findings input screen for the aortic valve primary reporting structure where the smaller image of the Parasternal long axis view has been selected thereby showing an enlarged image/view of this smaller image/view (with the aortic valve highlighted) and also showing the various input areas for properties or attributes of this primary reporting structure with no property or attribute actually being selected (and also showing the current text string for the findings on this primary reporting structure).
Figure 31B:
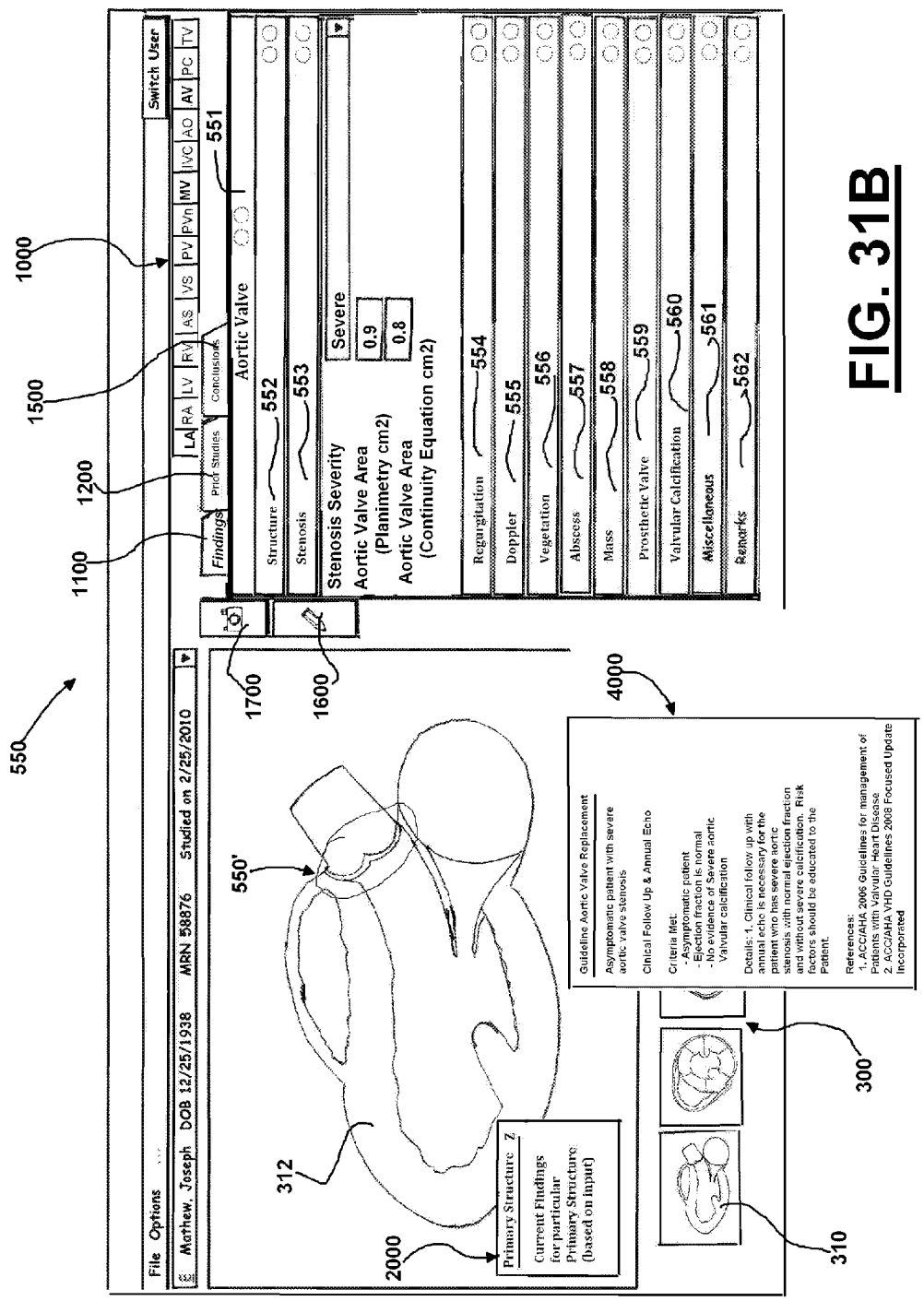

FIGS. 31A and 31B are screen shots showing the findings input screen 550 for the aortic valve primary reporting structure where the smaller image 310 of the Parasternal long axis view has been selected thereby showing an enlarged image/view 312 of this smaller image/view (with the aortic valve highlighted as 550'), and also showing the various input areas for properties or attributes of this primary reporting structure with no property or attribute actually being selected (items 551 through 562). Also shown is pop up display 2000 is the current text string 2030 for the findings on this primary reporting structure—aortic valve).

Figure 32:
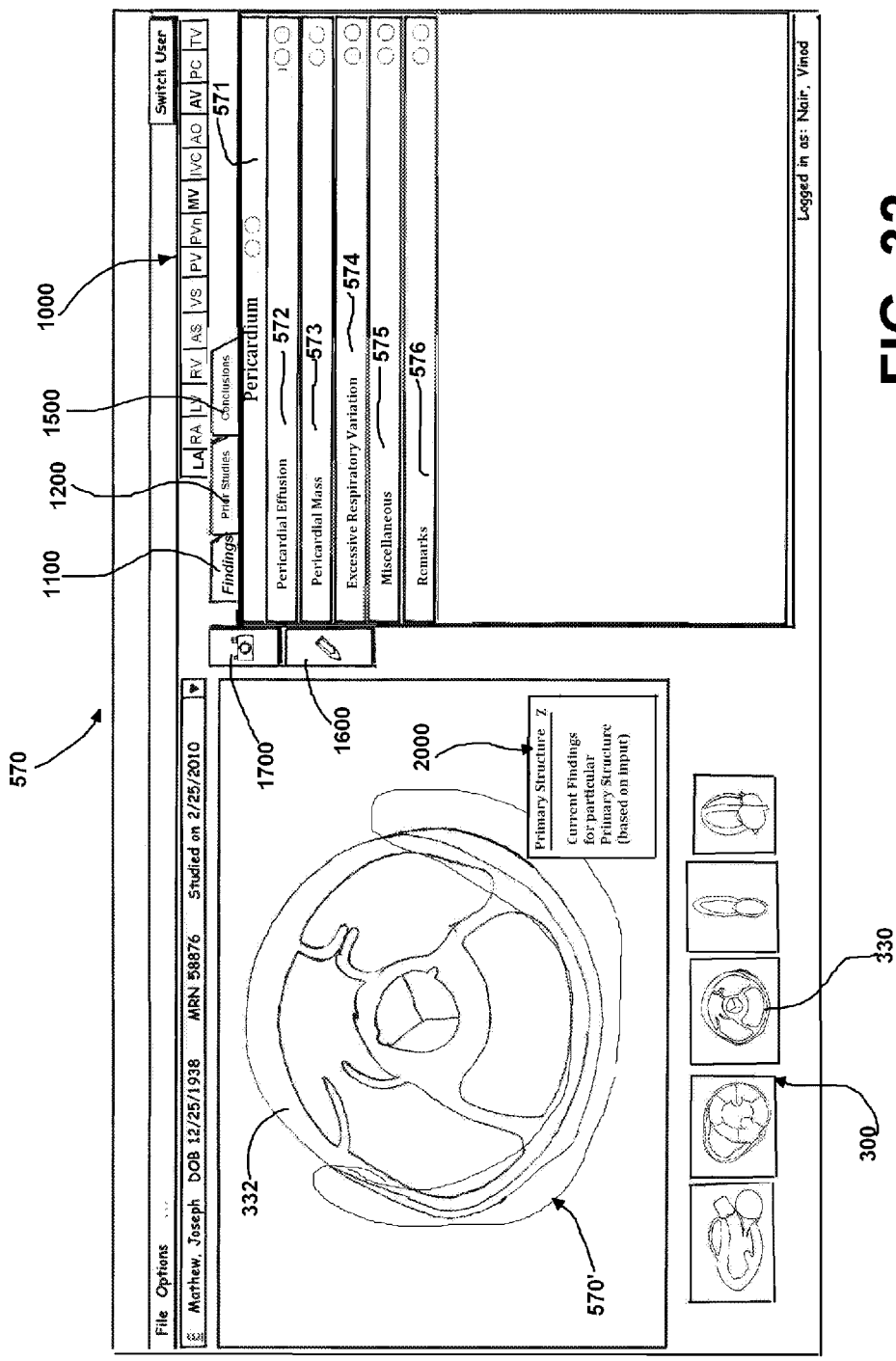
FIG. 32 is a screen shot showing the findings input screen for the pericardium primary reporting structure where the smaller image of the short axis aorta valve view has been selected thereby showing an enlarged image/view of this smaller image/view (with the pericardium highlighted) and also showing the various input areas for properties or attributes of this primary reporting structure with no property or attribute actually being selected (and also showing the current text string for the findings on this primary reporting structure).

FIG. 32 is a screen shot showing the findings input screen 570 for the pericardium primary reporting structure where the smaller image 330 of the short axis aorta valve view has been selected thereby showing an enlarged image/view 332 of this smaller image/view (with the pericardium highlighted as 570'), and also showing the various input areas for properties or attributes of this primary reporting structure with no property or attribute actually being selected (items 571 through 576). Also shown is pop up display 2000 is the current text string 2030 for the findings on this primary reporting structure—pericardium).

Figure 33:
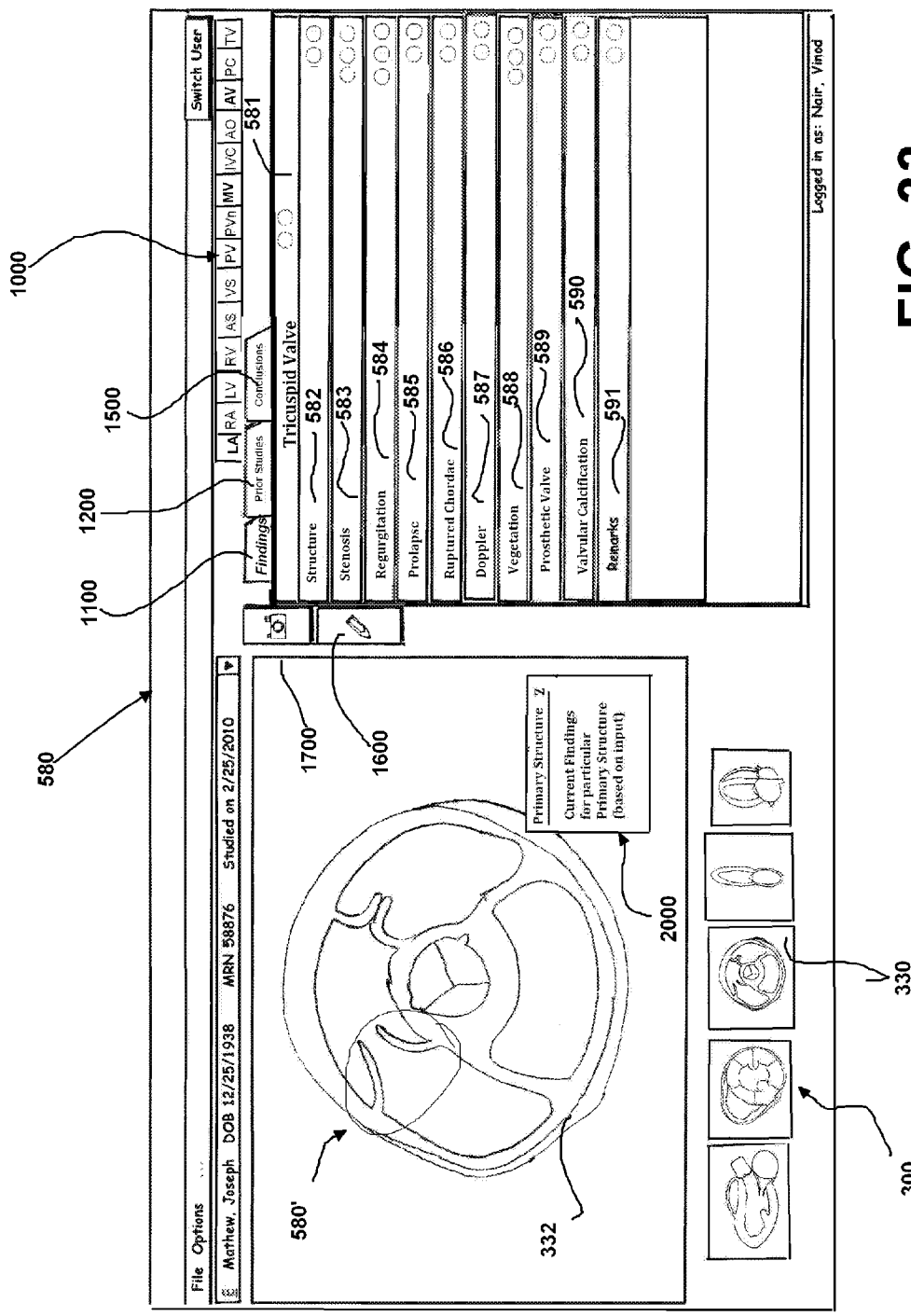
FIG. 33 is a screen shot showing the findings input screen for the tricuspid valve primary reporting structure where the smaller image of the short axis aorta valve view has been selected thereby showing an enlarged image/view of this smaller image/view (with the tricuspid valve highlighted) and also showing the various input areas for properties or attributes of this primary reporting structure with no property or attribute actually being selected (and also showing the current text string for the findings on this primary reporting structure).

FIG. 33 is a screen shot showing the findings input screen 580 for the tricuspid valve primary reporting structure where the smaller image 330 of the short axis aorta valve view has been selected thereby showing an enlarged image/view 332 of this smaller image/view (with the tricuspid valve highlighted as 580'), and also showing the various input areas for properties or attributes of this primary reporting structure with no property or attribute actually being selected (items 581 through 591). Also shown is pop up display 2000 is the current text string 2030 for the findings on this primary reporting structure—tricuspid valve).

Figure 34:
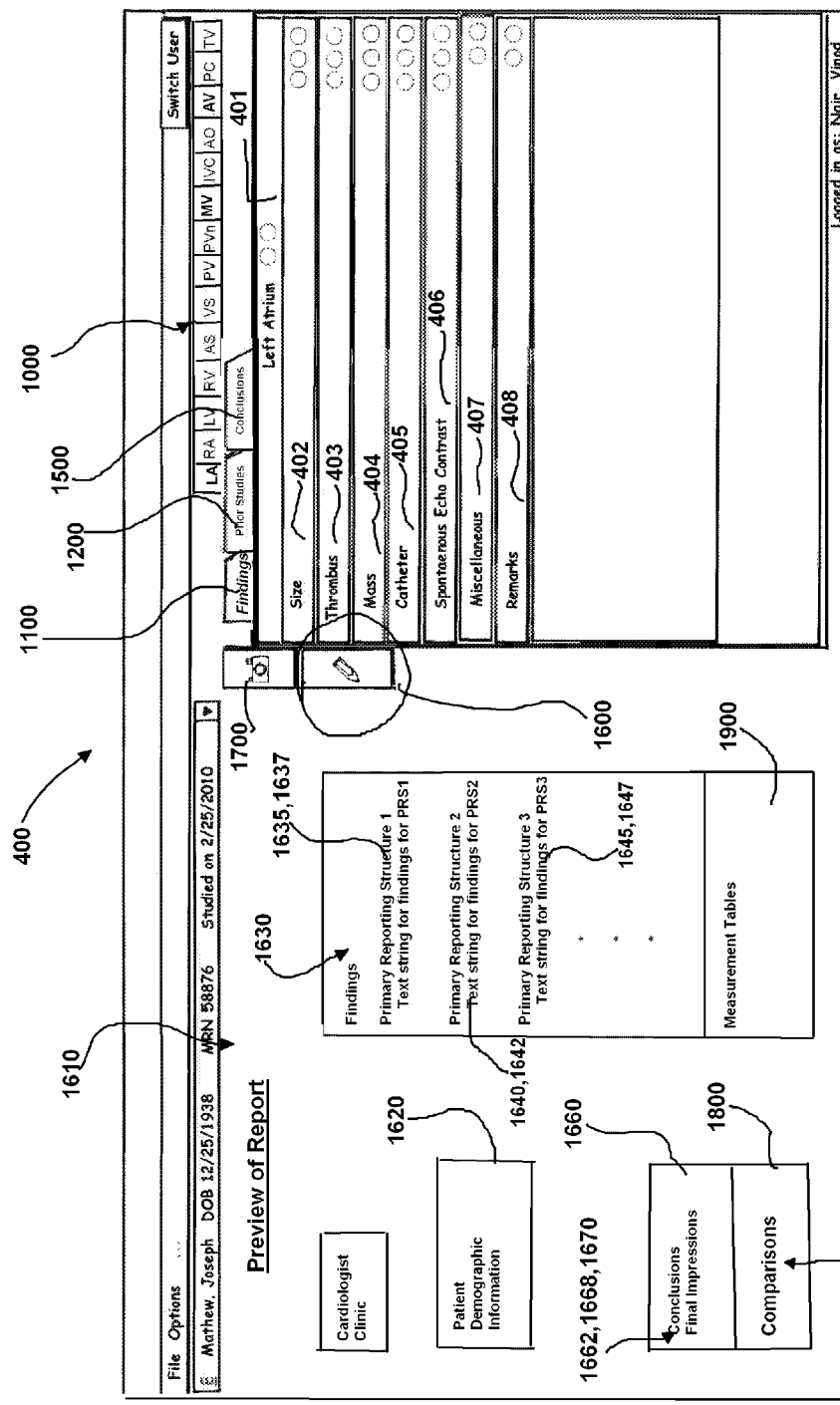
FIG. 34 is a screen shot showing a "Preview of Report" input screen where findings are selected for the primary reporting structure of the Left Atrium. The report can have five sections: (a) Cardiologist/clinic; (b) Patient Demographic; c) Conclusions/final impressions along with Comparisons; (d) Findings on the Primary Reporting Structures; and (e) Measurement Tables.

FIG. 34 is a screen shot showing a "Preview of Report" input screen 400 for the primary reporting structure of the Left Atrium. The user 90 can be provided the option to view a preview version 1610 of the report as it currently exists based on input to the method and apparatus 10. In one embodiment the user can select a report view icon 1600 which then displays the current version of the report 1610. In one embodiment the preview version 1610 of the report is shown in place of the enlarged anatomical image or view currently being displayed on the display (e.g., 312). In one embodiment a user can switch between a current version of the report being generated and the enlarged anatomical image or view (by clicking on the graphical image icon 1700). In one embodiment a user can select a image view icon 1700 to again display the enlarged anatomical image or view (e.g., 312). In FIG. 34 the report preview button 1600 has been selected causing the display (on the left side of the display 100) a preview 1610 of the interim report 3010. In this screen the Findings tab 1100 has also been selected showing on the right hand side of display 100 the attributes or properties of the currently selecting primary reporting structure (in this case the left atrium input screen 400). The interim report 1610 can have five sections: (a) Cardiologist/clinic; (b) Demographic 1620; (c) Conclusions/final impressions along 1660; (d) Comparisons 1800; (e) Findings on the Primary Reporting Structures 1630; and (f) Measurement Tables 1900. Preview 1610 can be obtained at any time by selecting the report preview button 1600 (while in any one of the input screens—400, 410, 420, 440, 450, 460, 470, 480, 500, 520, 530, 550, 570, and/or 580). The report text shown in the interim report 1610 includes all of the primary reporting structures for which input has been received by the method and apparatus 10.

Figure 35:
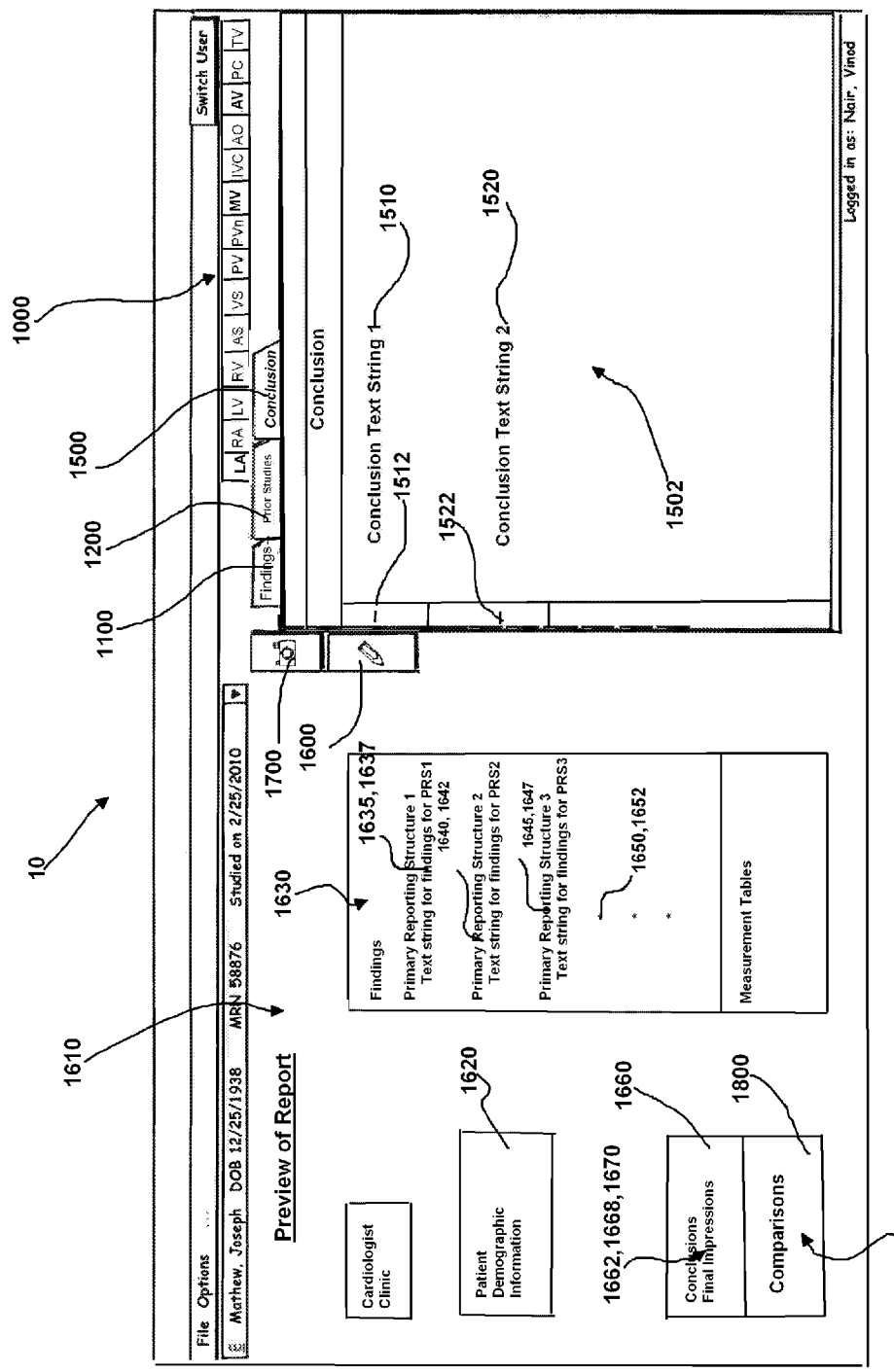
FIG. 35 is a screen shot showing a "Preview of Report" input screen where Conclusions is selected and showing conclusion text strings 1 and 2. The report can have five sections: (a) Cardiologist/clinic; (b) Patient Demographic; c) Conclusions/final impressions along with Comparisons; (d) Findings on the Primary Reporting Structures; and (e) Measurement Tables.

FIG. 35 is a screen shot showing a "Preview of Report" input screen where Conclusions tab 1500 has been selected and showing conclusion text strings 1 and 2. In this screen the preview report tab 1600 has also been selected showing a preview of the interim report on the left hand side of display 100, which interim report can have five sections: (a) Cardiologist/clinic; (b) Demographic 1620; (c) Conclusions/final impressions along 1660; (d) Comparisons 1800; (e) Findings on the Primary Reporting Structures 1630; and (f) Measurement Tables 1900. Conclusions which are incorporated into section 1660 of the report (and finally into the final report 3010) can be obtained by selectively importing any one of the findings or impressions on a primary reporting structure which appear in a pop up findings window 2000 on one of the input screens—to import the findings from a particular primary reporting structure the user 90 simply selects the conclusion importation icon 2030 which appears in the current findings pop up box 2000 for any one of the primary reporting structure input screens. Clicking on the icon 2030 imports the findings (as the findings currently exist at the time of importation) for the particular primary reporting structure. In one embodiment any imported current findings on a particular primary reporting structure which findings are subsequently changed or modified, the imported version of such findings in the conclusion section will likewise be changed. In one embodiment no change is made after importation even where the specifically imported findings are changed.

In one embodiment, when selecting the conclusions tab 1500, the user has a free ability to change and/or modify any imported conclusion text string. For example, in FIG. 35 on the conclusions input display 1502 is shown imported text string 1 (1510) along with imported conclusion text string 2 (1520). If desired the user can reorder string 1510 and 1520. To include string 1 in the conclusions section 1660 of the report the user can select include button 1512. Similarly, to include string 2 in the conclusions section 1660 of the report the user can select include button 1522. The user 90 has the option to modify the text of any conclusion text string (such as by right clicking on the string and selecting edit). The user can also delete one or more of the conclusion text strings.

In one embodiment a user 90 is provided an option for the method and apparatus 10 to make a comparison between one or more of the findings or results of a first cardiology test or procedure with one or more the findings or results of a second cardiology test or procedure. FIGS. 34 and 35 also illustrate a comparison feature of method and apparatus 10. In one embodiment the method and apparatus 10 can automatically compare one or more items (attributes or properties of one or more of the primary reporting structures) of the currently reported test results to one or more prior tests results. In one embodiment a user 90 is given an option of which particular test components are to be compared and what factors will trigger a comparison (e.g., test data varies by greater than X percent). In one embodiment a comparison is made if the variance between one or more of the findings or results of a first cardiology test or procedure with one or more of the results or findings of a second cardiology test or procedure falls within a predefined limit. For example, if the variance exceeds a specified percentage. In one embodiment the user is provided with the option of specifying the range or percentage.

In one embodiment the following example reporting language can be used for the comparison: (1) Compared to the previous study dated Oct. 12, 1999, the left ventricle and left atrium is dilated; (2) Compared to the previous study dated Oct. 12, 1999, the severity of Aortic Regurgitation appears to be unchanged|Worsened|Improved; and (3) Compared to the previous study dated Oct. 12, 1999, the left ventricular Ejection Fraction is unchanged|Detoriated|Improved. FIGS. 34 and 35 both show comparison sections 1800 in the preview report 1510 which include report comparison text strings 1810, 1820, and 1830 (examples of comparison text strings are included in this paragraph).

In one embodiment the comparison will appear in the pop up comparison screen having the comparison strings for the particular primary reporting structure being inputted at the time. In one embodiment the user 90 is provided with the option of deleting one or more automatically generated comparisons from the final version of the report. In one embodiment the method and apparatus 10 automatically creates and inserts the comparison text strings and inserts them into the comparison 1800 section based on the comparison text string rules set up for method and apparatus 10.

In one embodiment the comparison is made in the findings for a primary reporting structure. In one embodiment the comparison is made for an attribute or property of a primary reporting structure.

In one embodiment a user is provided with the option to remove the automatic comparison from the generated report on the cardiology examination.

In one embodiment comparisons to one or more attributes or properties of a primary reporting structure can be added to the combined findings text string. In one embodiment such comparison is done only for the last report or test data included in method and apparatus 10. In one embodiment a user can choose from a set of possible comparisons and/or sets of report or test data. In one embodiment a user can select one or more cut off variances for one or more attributes or properties of primary reporting structures before a comparison is automatically included in the combined findings text string. In one embodiment different variances for different properties or attributes can be selected. On one embodiment intra modal comparisons can be selected for one or more attributes or properties or one or more primary reporting structures. On one embodiment inter modal comparisons can be selected for one or more attributes or properties or one or more primary reporting structures. On one embodiment inter and intra modal comparisons can be selected for one or more attributes or properties or one or more primary reporting structures. In one embodiment a database report attributes can be provided and populated with findings and/or data from previous reports.

Overall Method

Figure 36:
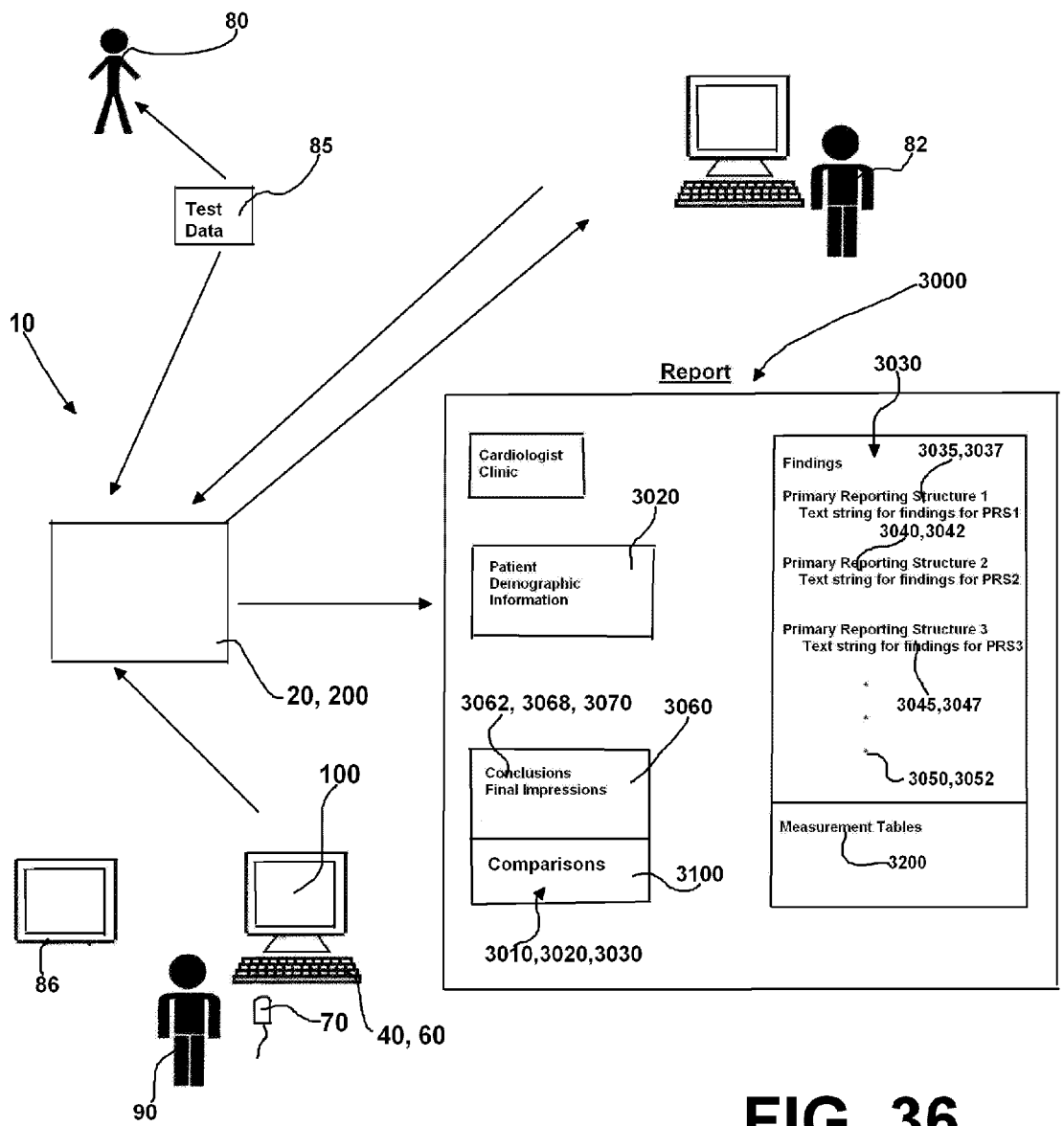
FIG. 36 is an overall schematic diagram of one embodiment of the method and apparatus.

FIG. 36 is a schematic diagram of one embodiment of the overall method and apparatus 10.

One embodiment provides a method of clinical evaluation of a cardiology patient. The method includes the providing of a computer having a database. A user interface is provided which is connected to the computer and which includes a display screen. As part of the method, one or more images are displayed on the display screen which are anatomical representations, each of a different portion of a human heart.

The display can include patient data that is displayed on the display screen. In one embodiment the patient data relates specifically to the anatomical representation of the portion of the human heart that is being viewed on the display screen.

In one embodiment, multiple images can be displayed as optional parts of the human heart. In one embodiment one or more of those optional portions can be selectively enlarged for more easy inspection by a physician or other operator.

In one embodiment, the method includes entering data that relates specifically to the displayed image.

In one embodiment the method can include an interpreting cardiologist reviewing the data as part of a medical evaluation of a patient.

In one embodiment the method and apparatus 10 can comprise a report generation system 10. Report generation system 10 can comprise a computing device 20, graphic input interface 100, and a relational database 200.

In a preferred embodiment, computing device 20 can comprise a display 30, keyboard 40, and memory 50. In an alternative embodiment display 30 can include a touch input 60. In an alternate embodiment, computing device 20 can include pointing device 70, which can be used an alternative input device within report generation system 10. Pointing device 70 can comprise a mouse, trackball, light pen, bar-code scanner, digitizing pad, or other pointing device.

In one embodiment the method includes the steps of:
(1) obtaining a plurality of test data 85 on a patient 80
(2) inputting test data into a database 200
(3) accessing plurality of custom text findings related to primary reporting structures
(4) providing
   (A) User interface(s) 40, 60, 70
     and
   (B) Display(s) 100
     and
   (C) Database(s) 200
     (i) report findings on primary reporting structures
     (ii) based on input method and apparatus generating custom report text for each such finding.
     (iii) based on input method and apparatus determining applicable guidelines (ACC/AHA Appropriateness Guidelines—American Cardiology)
     (iv) based on input method and apparatus making calculations
(5) preparing a report comprising
   (A) findings on primary reporting structures
   (B) including trend data on properties or attributes of primary reporting structure View Based Navigation In one embodiment findings for report generation will be through a graphical navigation interface 100 pictorially representing multiple sections of a body organ such as the heart. In one embodiment input will be pictorially and graphically selected (without keyboard use and having to switch between dialog boxes, tabs or windows). In one embodiment a report on the entire study can be generated from a single screen 100.

One embodiment enables a report on a cardiology study to be generated from a single graphical input screen 100. In one embodiment is provided a graphical input display 100 having images of various anatomical images or views of the human heart for data entry (images/views 300).

In one embodiment an echocardiogram, by convention can be interpreted in standard five views; these views are available for the cardiologist to review (view 1-View 5). In the method and apparatus these standard views are provided in the plurality of smaller anatomical images/views 300. The selected view (from plurality 300) is enlarged and is available for detailed reporting by the cardiologist selecting from such enlarged view the primary reporting structure on which he currently desires to report and then be navigated to the input screen for such primary reporting structure. Graphical selection from enlarged views avoids the cardiologist being required to search through multiple selections and screens to locate region of interest before reporting on such primary reporting structure.

In one embodiment a report 3010 can be generated by the user using an input screen to graphically select reporting segments (e.g., primary reporting structures), and then selecting on the display reporting indices (e.g., reporting properties or attributes of the primary reporting structures).

In one embodiment, multiple anatomical images/views are displayed on the display screen 100 with the option of displaying in an enlarged format one of the multiple small anatomical images/views simultaneously (each small anatomical image/view being an anatomical representation/view depicting different portions and/or views of a human heart). In one embodiment, multiple anatomical images/views 300 are displayed on the display screen 100, and the ability to select from one of this set 300 to display a larger version of the selected anatomical image/view. In one embodiment a subset of a plurality of anatomical images/views 300 are displayed on a display screen 100 and the ability is provided of scrolling, and revealing additional selectable anatomical images/views from the plurality of images/views 300. In one embodiment, a user 90 can change from one anatomical image/view already displayed to another anatomical image/view to be displayed without typing on a keyboard (for example, merely selecting a smaller anatomical image/view from a plurality 300 of anatomical images/views).

In one embodiment, when generating a report for a particular test multiple anatomical images/views for reporting can be displayed on a display 100. In one embodiment, for reporting on an echocardiogram test, a plurality of the following views 300 are provided: Parasternal long axis view 310; Short axis of left ventricle view 320; short axis view at the level of aortic valve 330; apical two chamber view 340; four chamber view 350; subcostal view; short axis basil 320'; and short axis apical 320'.

In one embodiment, the user 90 can select a smaller anatomical image/view on display screen 100 and have a larger version of this displayed on the display screen (e.g., in FIG. 1 selecting small image 310 displaying larger image 312) while the input area for reporting on the primary reporting structure remains the same (the left atrium reporting page 400 remains the same). In one embodiment, after selecting the different anatomical image/view to be displayed as an enlarged image, the user has the option to select any primary reporting structure on such enlarged view and be shown a findings input screen for such new primary reporting structure (see FIGS. 10-14).

In one embodiment the user can access a findings input screen for any of the primary reporting structures from a set of icons for such primary reporting structures—called the tabular navigation bar 1000.

Users can navigate between different findings input screens for different primary reporting structures in two manners: (1) selecting the primary reporting structure from its area in the displayed enlarged anatomical image or view and/or (2) selecting the primary reporting structure from the listing of icons of primary reporting structures—tabular navigation bar 1000.

In one embodiment a preferred graphical anatomical image or view can be selected by the method and apparatus 10 based on a selected primary reporting structure (such as by selecting a particular primary reporting structure from the tabular navigation bar 1000 having a listing of primary reporting structures 1000).

In one embodiment, a physician or operator can selectively enlarge one image or another image and by switching (e.g. clicking with computer mouse 70 or touch screen) from one small image to another (clicking on one of the plurality of smaller images 300 as shown in FIGS. 10-14). In one embodiment, from the enlarged image or view the user can select a primary reporting structure in which to submit report input and be directed to a reporting input screen for such primary reporting structure. One example of this would be, while in the Pulmonic valve input screen 470 (shown in FIG. 25), to select the tricuspid valve structure (highlighted as 580') from the enlarged view 332, which will navigate the user to the input screen 580 for the tricuspid valve primary reporting structure (FIG. 33). Using the graphical interface in this manner the input screen for any of the primary reporting structures can be entered by selecting such primary reporting structure from the enlarged image/view on such input screen (or if the primary reporting structure is not shown in the enlarged image/view selecting a new enlarged image/view from the plurality of images/view 300 actually showing the primary reporting structure desired, and then selecting such primary reporting structure from the new enlarged image view).

In one embodiment the primary reporting structure for which a report input screen is displayed can be highlighted (for example, 400' in FIG. 1) in the enlarged anatomical image/view displayed on the input screen. In one embodiment the user has the option to switch reporting input screens for primary reporting structures by selecting a particular primary reporting structure on the displayed enlarged anatomical representation/view. For example, in FIG. 1, the user can select on enlarged image 312 the Left Ventricle section and navigate to input screen 420 for the left Ventricle (FIG. 15) wherein the left ventricle will be highlighted (422') in the enlarged image/view 312.

As another example of graphically navigating between input screens for different primary reporting structures, FIG. 1 shows a highlighted left atrium 400' in the enlarged anatomical image/view displayed for the left atrium input screen 400. The user has the option to switch reporting input screens (for input on primary reporting structures) by selecting a particular primary reporting structure on the displayed enlarged anatomical image/view. For example, the user can select from the enlarged image 312 the Left Ventricle (shown as highlighted section 422' in FIG. 15) and navigate to input screen 420 for the left Ventricle (FIG. 15) wherein the left ventricle will be highlighted (422') in the enlarged image/view 312.

Certain of the enlarged anatomical images/views may not include every one of the primary reporting structures (for example, FIG. 10 shows enlarged image 322 with no highlighted portion when in the left atrium input screen 400 because the left atrium is not visible with the short axis left ventricle view 320). For graphical navigation between input screens for different primary reporting structures, if in a particular reporting input screen (e.g., left ventricle input screen 420) with the short axis left ventricle view 320 enlarged, if the left atrium input screen 420 is desired to be entered, a user 90 may have to select a second enlarged anatomical image/view to display enlarged (which second image/view does include the desired primary reporting structure such as the parasternal 310), and then select the primary reporting structure on the second enlarged view (which selected primary reporting structure in such second enlarged view displays the findings input reporting screen for the desired primary reporting structure). The user can always select non-graphically the desired primary reporting structure from the tabular navigation bar 1000 which contains selection tabs for each of the primary reporting structures and is accessible from each of the input pages for each of the primary reporting structures. For the left ventricle, the "LA" tab would be selected to return to the Left Atrium input page 400.

In one embodiment, is provided the ability to select from a set of smaller anatomical images/views (e.g., as shown in FIG. 1 images 300 including 310, 320, 330, 340, and 350)

displayed on the display 100 to display a larger anatomical image/view (e.g., image 312 on FIG. 1) on the display screen 100, wherein selection can be achieved by clicking with computer mouse 70, or selecting on a touch screen 100'. In one embodiment, the ability to display another selected larger anatomical image/view from that currently being displayed on the display screen 100 is provided by selecting a different smaller anatomical image/view from the set of smaller multiple anatomical images or views (e.g., FIGS. 10 through 14).

In one embodiment the following primary reporting structures can be provided for reporting on an echocardiagram test: Left Atrium 400; Right Atrium 410; Left Ventricle 420; Right Ventricle 440; Atrial Septum 450; Ventricular Septum 460; Pulmonic Valve 470; Pulmonary Artery 480; Pulmonary Veins 490; Mitral Valve 500; Inferior Vena Cava 520; Aorta 530; Aortic Valve 550; Pericardium 570; and Tricuspid Valve 580.

In one embodiment the user has the option to graphically navigate from the graphical interface graphically showing anatomical images or views to iconic reporting tabs for the primary reporting structures of the heart. In one embodiment the primary reporting structures can be correlated to one or more quick access icons. In one embodiment the quick access icons can be in tab form. In one embodiment, is provided a set of selectable tabs correlated to the set of primary reporting structures wherein selection of a tab for one of the primary reporting structures displays one of the larger anatomical images/views. In one embodiment each of the tabs or buttons have indicia indicating which anatomical image or view will be displayed.

In one embodiment, a plurality of the anatomical images/views is divided into sets of graphically selectable primary reporting structures (each structure corresponding anatomically to the anatomical portion of the anatomical image or view in which the primary reporting structure is found).

In one embodiment the selected primary reporting structure of the displayed anatomical image/view is highlighted and/or contrasted compared to the remainder of the displayed anatomical image/view. In one embodiment selecting (or clicking on) the highlighted primary reporting structure will toggle through the set of possible anatomical images/views displaying the primary reporting structure (but in different anatomical views) with the selected primary reporting structure being highlighted and/or contrasted compared to the remaining anatomical image/view on the display for the newly displayed anatomical image/display.

In one embodiment the primary reporting structures can be a plurality of the following: (1) Basal anterior; (2) Basal anteroseptal; (3) Basal inferoseptal; (4) Basal inferior; (5) Basal inferolateral; (6) Basal anterolateral; (7) Mid anterior; (8) Mid anteroseptal; (9) Mid inferoseptal; (10) Mid inferior; (11) Mid inferolateral; (12) Mid anterolateral; (13) Apical anterior; (14) Apical septal; (15) Apical inferior; (16) Apical lateral; and/or (17) Apex.

Report Generation Based on Inputted Selections and Pre-Programmed Rules

In the particular report input screens for the individual primary reporting structures, selection of particular input options for the provided attributes or properties for the primary reporting structure will automatically create a combined findings text string (For example, text string 2020 in FIG. 1) which will be included in a final report 3010, such as in the findings 3030 section, for the particular primary reporting structure. One or more text clauses can be included in the combined findings text string on the particular primary reporting structure depending on the particular input (either by input to the method and apparatus 10 from testing data and/or selections/input made by the user with the display) for the primary reporting structure and/or particular reporting attributes or properties for the primary reporting structure will automatically create a text string to be included in a report section on the primary reporting structure. This is because one or more of the selections are correlated with a database of text string conclusions for such selections.

Table 1—Echocardiogram and Caratid Custom Text includes, for the Echocardiogram and Caratid Reporting Functions of the method and apparatus 10 list of menu choices and text string findings correlated with the menu choices. The left hand column includes menu choices of first, second, third, and additional tiers of menu options with such tiers of options being separated by a forward slash. Custom text correlated with the particular choices are provided on the right hand column.

Table 3 includes the menu tree for each of the listed reporting modalities along with the first, second, and additional tiers of choices provided. Numerical measurement input options are provided in the sub-tables included in each section of this table. Business rules and calculations performed by method and apparatus for each of the reporting modalities are also included under the specific reporting modality.

The input display can automatically display the current version of the combined findings text strings for the particular primary reporting structure depending on the particular input (either by input to the method and apparatus 10 from testing data and/or selections/input made by the user with the display) for the primary reporting structure and/or particular reporting attributes or properties for the primary reporting structure (such as through pop up findings window 2000, or by clicking on report preview tab 1600. Displaying the current version of the findings allows the user to conveniently see in real time the current version of the findings for the particular primary reporting structure based on the current input.

Tab Based Navigation

Overall Report View

In one embodiment the display 100 can include a quick view option for previewing the current version of the overall report based on the input as currently existing. This can be quick preview tab 1600.

One feature is a graphical highlighting indication feature allowing users 90 to see quickly which of the primary reporting structures are being currently reported on.

Highlighted Progress Bar

Progress Bar Showing Primary Reporting Structures Reported On And/Or Completed

In one embodiment the display can include a graphical indication on the display showing what primary reporting structures have been reported on for a particular report. In one embodiment the graphical display can be the same iconic tabs (tabular navigation bar 1000) which can be used to navigate to the various input pages for the primary reporting structures for a report.

One feature is a graphical highlighting indication feature allowing users 90 to see quickly which of the primary reporting structures are being currently reported on.

In one embodiment the method and apparatus has a tabular navigation bar 1000 listing a plurality of the primary reporting structures, and a highlighting feature allowing users to quickly identify which of the primary reporting structures have received input for reporting (such as by input in their respective reporting pages), and conversely, which have not yet received input. In one embodiment a user 90 is provided with a graphical indication that a particular primary reporting structure has been (or has not been reported on). This graphical indication provides the user with a quick way of determining what primary reporting structures have, and what primary reporting structures have not received report input, or have been and have not been reported upon For example, in FIG. 1 tabular navigation bar 1000 has LA, MV, and AV highlighted (by being bolded compared to the remaining items in the listing) indicating that the left atrium, mitral valve, and aortic valve primary reporting structures each have inputted data for these in their respective input pages (LA—400; MV—500; and AV—550).

Individual Input Screens for Primary Reporting Structures

In one embodiment each of the primary reporting structures are further broken down into a plurality of reporting attributes or properties. In one embodiment each of the primary reporting structures are correlated with a set of reporting selections.

In one embodiment a report is possible report is broken down into a first plurality of reporting segments. In one embodiment one or more of these reporting segments are broken down into a plurality of reporting indices. In one embodiment one or more of these reporting indices are correlated with predefined reporting text.

In one embodiment a branching function is provided to the graphical user interface in which selection of a first tier of options will cause branching to a second tier of options, and selection of one or more of the second tier cause character strings to be inserted in the cardiology report. In one embodiment three or more tiers of options can be used.

In one embodiment, the displayed larger anatomical image/view can be coordinated with a plurality of reporting segments for such selected anatomical image/view.

In one embodiment selection of a selectable portion (for a primary reporting structure) of anatomical image/view displays a findings input screen for entering findings on one or more reporting attributes or properties correlated with the selected primary reporting structure.

In one embodiment a plurality of reporting attributes or structures relating specifically to the primary reporting structure are displayed along with the larger anatomical image/view including the primary reporting structure.

In one embodiment one or more reporting attributes or properties for a primary reporting structure each have a plurality of selectable reporting options for such attribute or property. In one embodiment a plurality of reportable conditions are correlated with one or more of the reporting attributes or properties. In one embodiment a plurality of reportable conditions are correlated with a custom text reporting string for such reportable conditions, attribute or properties, and primary reporting structure.

In one embodiment the input screen includes a plurality of tiered menu selections for properties or attributes of a primary reporting structure. For example, a particular selection can include first, second and third tiers of menus. For example, a second tier of reporting selections or indices for a particular property or attribute can be indexed to a particular findings data string and when selected will be incorporated into the cardiology report. In one embodiment one or more of the first or second tier of reporting indices include data which has been obtained from testing data. For example, size 402 provides access to dimension which includes a dimensional size of 3.7 cm which has been imported to the method and apparatus 10 from prior testing of the patient.

In one embodiment the method and apparatus 10 includes a pop-up findings segment 2000 on the current primary reporting segment. The pop up can display the current text 2020 of finding segment for the current primary reporting structure for the input page on the primary reporting structure. This allows the user 90 to see in real time how his selections made on the input screen 100 impacts the findings for such primary reporting structure.

In this example (FIGS. 1 and 2), dimension includes a graphical box 402' which if selected shows a graph 402" (FIG. 2)*comparing* this size from one or more previous studies. The popping up of this graph with a prior study can allow the user 90 to easily make a historical selection regarding this reporting tier such as "decreased" where the size has decreased from another study.

As another example, selection of first tier thrombus 403 provides access to the following second tier of reporting indices: size, location, shape, texture, mobility, height, and width. Selection of second tier size provides access to third tier reporting indices "small", "moderate", and/or "large". Selection of one of these third tier of reporting indices will actually insert associated report text to be inserted into the report along with such report text being included in summary box 2000. In certain circumstances first tier selections actually insert report text in the report and summary box 2000.

In one embodiment the graphical interface includes a pop up display of the findings segment on the primary reporting structure whose input screen is currently shown on input display 100 which pop up includes a snap shot of the current report text for the particularly selected geographic/component of the heart being reported on. The data summary 2000 can include an area 2010 describing the geographic/component area along with a second area 2020 for the snap shot of report text. The data summary box 2000 can also include an include symbol 2030 which can include/import text in the second area 2020 in the conclusions section of the generated report.

In one embodiment report text is generated by making selections on a graphical input screen. In one embodiment a set of suggested cardiology report data string conclusions is indexed to selections made on the graphical input screen. In one embodiment a plurality of the suggested conclusions for the cardiology report based on input by cardiologist automatically show up. In one embodiment a user is provided the option to customize one or more of the suggested conclusions. This can be changed from interpreting physician to interpreting physician. For example a conclusion of "severely dilated" can be changed to "severely enlarged."

In one embodiment a plurality of users each have their own custom database of conclusions when each user customized the default set of suggested conclusions. In one embodiment every person who logs in has a customer database of the sentences used (assuming they changed at least one suggested sentence).

In one embodiment the custom text and reportable conditions can be shown in the Table 1 which includes a database of Reportable Conditions and Custom Reporting Text Correlated With Such Reportable Conditions. In one embodiment a user is provided with the option of changing one or more of the custom texts.

In one embodiment the current version of the reporting text for the primary reporting structure is displayed on the input screen when reporting on the particular primary reporting structure.

The display having an enlarged anatomical image/view of the heart (in FIG. 1 a graphical Parasternal long axis view 312 is shown with the currently selected primary reporting structure (left ventricle 400), and such currently selected primary reporting structure is highlighted (schematically shown by 400') on the enlarged anatomical image/view 312 to provide the user 90 with an image/graphical indication of which of the plurality of primary reporting structures such findings input screen will be inputted.

The display 100 also includes a set 300 of smaller anatomical images/views of the heart (in this case five (5) views including the Parasternal long axis 310, short axis of left ventricle 320, short axis at the level of the aortic valve 330, two chamber view 340, and subcostal view 350).

The display 100 also has a textual listing 1000 of the plurality of primary reporting structures such findings input screen will be inputted.

A user can navigate between reporting input screens for each of the plurality of primary reporting structures. With echocardiograms the plurality of primary reporting structure input screens can include: Left Atrium 400; Right Atrium 410; Left Ventricle 420; Right Ventricle 440; Atrial Septum 450; Ventricular Septum 460; Pulmonic Valve 470; Pulmonary Artery 480; Pulmonary Veins 490; Mitral Valve 500; Inferior Vena Cava 520; Aorta 530; Aortic Valve 550; Pericardium 570; and Tricuspid Valve 580.

In FIG. 1 the display 100 input screen for left atrium 400 includes a plurality of tabs 1000 (having acronyms of the Primary Reporting Structures) which the user can select to navigate to a reporting input screen for a particular Primary Reporting Structure. Also in this figure is the current version 2000 of the text string for the findings on this primary reporting structure. The user has the option to navigate between each of the primary reporting structure to enter input screens such primary reporting attributes.

The user can navigate between input screens for each of the primary reporting structures in two manners: (1) selecting a specific primary reporting structure from the selection of primary reporting structure tabs, and (2) selecting a particular primary structure from the enlarged image or view shown in the current input screen for the currently selected primary reporting structure.

One feature is a graphical indication of which primary reporting properties have been reported on and which have not for the current report. In one embodiment a user is provided with a graphical indication that a particular primary reporting structure has been (or has not been reported on). This graphical indication provides the user with a quick way of determining what primary reporting structures have, and what primary reporting structures have not received report input, or have been and have not been reported upon.

Each findings input screen for a primary reporting structure can include a plurality of selectable reporting attributes or properties for such primary reporting structure. The particular listings of selectable reporting attributes or properties on the primary reporting structure input screens have been selected for ease of use by users in making reports on the particular tests for which findings are to be made by cardiologists.

With an echocardiogram the following table lists one possible set of primary reporting structures and first level of reporting attributes or properties.

Below is a listing of Echocardiograph Primary Reporting Structures and First Level of Reporting Attributes or Properties (the Primary Reporting Structures are underlined and the Attributes or Properties are placed in paragraphs and separated by semicolons):

Table—Echocardiograph Primary Reporting Structures and First Level of Reporting Attributes or Properties Left Atrium 400
 Size 402; Thrombus 403; Mass 404; Catheter 405; Spontaneous Echo Contrast 406; Miscellaneous 407; and Remarks 408
Right Atrium 410
 Size 412; Thrombus 413; Mass 414; Catheter 415; Spontaneous Echo Contrast 416; Miscellaneous 417; and Remarks 418
Left Ventricle 420
 Size 422; Systolic Function 423; Diastolic Function 424; Wall Motion Analysis 425; Hypertrophy 426; Thrombus 427; Mass 428; PseudoAneurysm 429; Miscellaneous 430; and Remarks 431
Right Ventricle 440
 Size 442; Systolic Function 443; Hypertrophy 444; Miscellaneous 445; and Remarks 446
Atrial Septum 450
 Atrial Septum Defect 452; Patent Foramen Ovale 453; Miscellaneous 454; and Remarks 456
Ventricular Septum 460
 Ventricular Septum Defect 462; and Remarks 463
Pulmonic Valve 470
 Structure 472; Stenosis 473; Regurgitation 474; Doppler 475; Vegetation 476; Prosthetic Valve 477; Valvular Calcification 478; and Remarks 479
Pulmonary Artery 480
 Structure 482; Dilation 483; Suspected Pulmonary Embolism 484; Pulmonary Artery Pressure 485; Miscellaneous 486; and Remarks 487
Pulmonary Veins 490
 Structure 492; Thrombus 493; Mass 494; Miscellaneous 495; and Remarks 496
Mitral Valve 500
 Structure 502; Stenosis 503; Regurgitation 504; Doppler 505; M Mode Findings 506; Vegetation 507; Abscess 508; Mitral Valve Annulus 509; Mitral Valvular Apparatus 510; Mitral Valve Prolapse 511; Flail 512; Cleft 513; Systolic Anterior Motion of Mitral Leaflets 514; Prosthetic Valve 515; Valvular Calcification 516; and Remarks 517
Inferior Vena Cava 520
 IVC Size 522; IVC Mass 523; Miscellaneous 524; and Remarks 525
Aorta 530
 Structure 532; Dilation 533; Aortic Plaque 534; Aortic Aneurysm 535; Aortic Dissection 536; Intramural Hematoma 537; False Lumen 538; Aortic Graft 539; Aortic Coarctation 540; Miscellaneous 541; and Remarks 542
Aortic Valve 550
 Structure 552; Stenosis 553; Regurgitation 554; Doppler 555; Vegetation 556; Abscess 557; Mass 558; Prosthetic Valve 559; Valvular Calcification 560; Miscellaneous 561; and Remarks 562
Pericardium 570
 Pericardial Effusion 572; Pericardial Mass 573; Excessive Respiratory Variation 574; Miscellaneous 575; Remarks 576
Tricuspid Valve 580
 Structure 582; Stenosis 583; Regurgitation 584; Prolapse 585; Ruptured Chordae 586; Doppler 587; Vegetation 588; Prosthetic Valve 589; Valvular Calcification 590; and Remarks 591.

Each findings input screen for a primary reporting structure can include an overall normal findings quick selection for the primary reporting structure. The following overall normal selections are available on the input screen for their respective primary reporting structure: Left Atrium 401; Right Atrium 411; Left Ventricle 421; Right Ventricle 441; Atrial Septum 451; Ventricular Septum 461; Pulmonic Valve 471; Pulmonary Artery 481; Pulmonary Veins 491; Mitral Valve 501; Inferior Vena Cava 521; Aorta 531; Aortic Valve 551; Pericardium 571; and Tricuspid Valve 581. Selecting such overall normal findings allows the user to avoid having to individually input findings for the plurality of attributes or properties for such primary reporting structure.

The user 90 is provided the option to select "not overall normal for primary reporting structure" and enter individual reporting selections for the provided reporting attributes or properties on such primary reporting structure. The user is also provided the option of selecting "overall normal for primary reporting structure" after entering particular reporting attributes or properties on such primary reporting structure and have the findings on such primary reporting structure revert to an "all normal for primary reporting structure" findings custom text report findings string.

A plurality of the reporting attributes or properties for the particular primary reporting structure can each include an overall normal findings quick selection for reporting findings on the particular attribute or property. Selecting such quick normal findings allows the user to avoid having to individually input findings for the particular attribute or property. For example, in FIG. 1 for the Left Atrium 400 input screen the following overall normal selections are available: size 402; Thrombus 403'; Mass 404; Catheter 405'; and Spontaneous Echo Contrast 406.

In FIG. 1 the reporting attribute or property "size" 402 has been selected revealing a menu of further reporting selections on the selected attribute or property: Chamber Size, Dimension, Volume, and Volume Index. Also in this figure the left ventricle has been highlighted on the enlarged image/view 312 to indicate that such primary property is being reported on in the current input screen (schematic circle 400' around the left ventricle indicates that the reporting screen for the left ventricle is being shown).

Because the report findings are made on a test/examination which includes testing instruments providing numeral values, various of the findings for properties or attributes of the primary reporting structures can be imported into the method and apparatus 10 from either the testing equipment and/or technicians (schematically indicated in FIG. 36 by the arrow from test data 85). Accordingly, various of the properties or attributes may be pre-inputted when a user 90 is inputting findings in the display 100. In FIG. 1, for example, the chamber size dimension of 3.7 cm has been imported into the method and apparatus 10 from the testing equipment (or from a technician inputting the data from testing output).

Certain of the findings may be based on calculations from output of testing results. Such calculations may be based on conventional formulas, equations, or algorithms. For example, in FIG. 1, the Volume Index (ml/m2) can be calculated automatically based on input to the method and apparatus 10 and using formulas, equations, or algorithms.

In one embodiment a database 200 of a plurality of custom text report findings are provided which are correlated to particular inputs for reporting attributes or properties for particular primary reporting structures, or correlated with particular inputs for primary reporting structures. Table 1 includes a database of reporting choices correlated with custom text findings to be incorporated into a report. Table 1 provides one embodiment where custom text findings strings are correlated to particular reporting attributes or properties for particular primary reporting structures, or text findings correlated to particular selections on primary reporting structures.

In one embodiment a user is provided the option to customize one or more of the suggested conclusions. In one embodiment the conclusions can be changed from interpreting physician to interpreting physician. For example a conclusion of "severely dilated" can be changed to "severely enlarged." In one embodiment a plurality of users each have their own custom database of conclusions when each user customized the default set of suggested conclusions. In one embodiment every person who logs in has a customer database of the sentences used (assuming they changed at least one suggested sentence).

In one embodiment an electronic patient record is generated from the discreet data elements.

Automatic Suggestion of Findings Based on Inputted Test Data being Compared to Specified Default Values In one embodiment the method and apparatus 10 will compare one or more inputted values from test data and/or findings to a set of default values and provide the user with a suggested findings (or text string findings) for one or more primary reporting structures and/or one or more attributes or properties of a primary reporting structure.

In one embodiment the method and apparatus 10 analyzes inputted test data to a set of predefined criteria, and suggests or chooses a custom text reporting string for a reportable condition, attribute or property, and primary reporting structure. In one embodiment the set of predefined criteria are set by a user. In one embodiment a set of default predefined criteria are provided.

In one embodiment the method and apparatus 10 includes a set of default reference values for one or more cardiology tests for one or more primary reporting structures and/or one or more attributes or properties of a primary reporting structure. In one embodiment the following cardiology tests, primary reporting structures, and/or attributes or properties of primary reporting structures have default reference values which can be compared. In one embodiment the user is provided the option to change one or more of these. In one embodiment any subset of the following list can be provided and compared. In one embodiment women and men are provided with separate default or reference values for one of more of the cardiology tests, primary reporting structures, and/or attributes or properties of primary reporting structures Table of Reference Values/Ranges for Primary Reporting Structures, Attributes or Physical Properties of Primary Reporting Structures Echocardiogram Left Atrial Diameter; Left Atrial Volume; Right Atrial Diameter; Left Ventricle Diastolic Dimension; Left Ventricle Diastolic Volume; Left Ventricle Diastolic Volume; Left Ventricle Mass; Left Ventricle Septal Thickness; Posterior wall thickness; Basal RV diameter; Mid RV diameter; RVOT diameter; PA diameter; Ejection Fraction

| Men (values) and separate list of values for Women | | |
|---|---|---|
| Reference Range | From | To |
| Mildly Abnormal | — | — |
| Moderately Abnormal | — | — |
| Severely Abnormal | — | |

Nuclear

LV Ejection Fraction; LV End Diastolic Volume; LV End Systolic Volume; RV Ejection Fraction; Rest LV Ejection Fraction; Rest LV End Diastolic Volume; Rest LV End Systolic Volume

| Men (values) and separate list of values for Women | | |
|---|---|---|
| Reference Range | From | To |
| Normal | — | — |
| Mildly Reduced | — | — |
| Moderately Reduced | — | — |
| Severely Reduced | ≤ | — |
| Hyperkinetic | ≥= | — |

Stress Echocardiogram
 Ejection Fraction

| Men (values) and separate list of values for Women | | |
|---|---|---|
| Reference Range | From | To |
| Normal | — | — |
| Borderline | — | — |
| Mildly Decreased | — | — |
| Moderately Decreased | — | — |
| Severely Decreased | ≤ | — |
| Hyperdynamic | ≥= | — |

Auto Compare Historical Changes

In one embodiment, the method includes generating a graph which illustrates a pattern relating to some of the patient data that is a part of the database of the computer.

In one embodiment previous study parameters (across different test modalities) can be retrieved while a study is being interpreted. For example, a history of the particular structure being reported will thus be available for an interpreting cardiologist. For example, if the left atrium (one of the cardiac chambers) of a heart patient is being evaluated by echocardiogram, previous reports made on the left atrium can be retrieved not only from the echocardiogram study but also from other reported test modalities (including for example CT angiogram), such prior reports being retrieved for review by input selection of the user.

In one embodiment a current study can be compared with previous studies, that comparison data being part of a new report. In one embodiment is allowed the display of pre-defined data elements such as demographics and trend plotting. In one embodiment is enabled related fields in the same and different study modalities to be displayed such as for example ejection fraction from echocardiogram to be compared with ejection fraction from nuclear perfusion scan. Such related fields and different modalities could be easily compared.

In one embodiment a user can select various conditions in which an automatic comparison will be made. Automatic text comparison between historical studies. Automatic presentation of "significant" differences. In one embodiment the user can program the trigger points for automatic comparison.

Historical Data Comparisons

In the generated report there can be a plurality of hyperlinks where discreet data can be compared to earlier studies (either intra modality and/or intra modality) for trends. This can help the referring physician evaluate the report and determine a treatment course for the patient. Additionally, when generating the report the cardiologist for any numerical value which is inputted where there is an earlier study containing a measurement for the same item, the cardiologist can pull up a graph which graphically plots the trend.

Pop Up Graphs

In one embodiment the method and apparatus 10 can plot graphs for one or more of the following discreet data fields showing trends: (1) LA Dimension; (2) RA Dimension; (3) LV End diastolic dimension; (4) LV End systolic dimension; (5) LV End diastolic septal thickness; (6) LV End diastolic postero basal free wall thickness; (7) LV Mass; (8) LV Mass index; (9) LV Ejection Fraction; (10) LV Peak Velocity; (11) LV Peak gradient; (12) LV Mean velocity; (13) LV Mean gradient; (14) LV Cardiac output; (15) LV Cardiac index; (16) LV Diastolic dimension; (17) Pulmonary Artery Systolic Pressure; (18) MV Area by planimetry; (19) MV Area by PHT; (20) MV Deceleration Time; (21) MV E velocity; (22) MV A velocity; (23) Mitral annular E' velocity; (24) MV E/E'; (25) Aorta Ascending aorta diameter; (26) AV Aortic cusp separation; (27) AV Aortic valve area (planimetry); (28) AV Aortic valve area (Continuity Equation); (29) AV Trans aortic peak velocity; and/or (30) AV Trans aortic mean velocity. In various embodiments any combination of the above referenced can be graphed on the display.

In one embodiment the user has the option when a graph pops up graphs, to select the graph to display additional information regarding past test variable.

In one embodiment the method and apparatus 10 can automatically pull up the portion of a prior study (if a prior study is available) when the user clicks on the segment of the graphical depiction of the heart—the portion of the prior study pertinent to this section will show up on screen for the cardiologist to review (it will disappear after a set period of time—e.g., one minute). This prior portion of the earlier report can be obtained by clicking on the prior study tab of the method and apparatus 10.

Trending Comparisons with Prior Attributes or Properties

In one embodiment the method and apparatus 10 provides the user with information on prior report findings and/or test data for the same individual. For example, for individual reporting attributes or properties for a primary reporting structure a pop up graph can be accessed. FIG. 2 shows a pop up graph on the display comparing prior data for the chamber size attribute or property for the left atrium primary reporting structure. To access the pop up comparison graph the pop up graph icon can be selected. In one embodiment pop up graph icons are highlighted when comparison data is available.

In one embodiment a trend comparison can be made between the current reporting data/findings and one or more of the prior data contained in the database of discreet reporting attributes.

In one embodiment a graphical comparison on a particular reporting attribute of a primary reporting structure is displayed on the display for the input screen when inputting findings for a particular primary reporting structure.

Intra and Intermodality Comparisons Automatically Included in Generated Report

In one embodiment the method and apparatus 10 can automatically make a comparison between one or more of the results or findings of a first cardiology test or procedure with one or more of the results or findings of a second cardiology test or procedure and include such comparison in the report (or text or report, or insert a comparison text string in the report) and include such comparison in a comparison text string and include the text string in the report.

Automatic Comparison in Generated Report of Historical Testing

In one embodiment, the data displayed includes a collection of prior studies relating to the patient.

In one embodiment the method and apparatus 10 can automatically compare one or more items of the currently reported test results to one or more prior tests results. In one embodiment a user is given an option of which particular test components are to be compared and what factors will trigger a comparison (e.g., test data varies by greater than X percent).

In one embodiment the following example reporting language can be used for the comparison: (1) Compared to the previous study dated Oct. 12, 1999, the left ventricle and left atrium is dilated; (2) Compared to the previous study dated Oct. 12, 1999, the severity of Aortic Regurgitation appears to be unchanged|Worsened|Improved; and (3) Compared to the previous study dated Oct. 12, 1999, the left ventricular Ejection Fraction is unchanged|Detoriated|Improved.

In one embodiment the comparison will appear in the pop up screen having the findings for the particular primary reporting structure being inputted at the time. In one embodiment the user is provided with the option of deleting one or more automatically generated comparisons from the final version of the report.

In one embodiment a user is provided an option for the method and apparatus 10 to make a comparison between one or more of the findings or results of a first cardiology test or procedure with one or more the findings or results of a second cardiology test or procedure.

In one embodiment a comparison is made if the variance between one or more of the findings or results of a first cardiology test or procedure with one or more of the results or findings of a second cardiology test or procedure falls within a predefined limit. For example, if the variance exceeds a specified percentage. In one embodiment the user is provided with the option of specifying the range or percentage.

In one embodiment the comparison is made in the findings for a primary reporting structure. In one embodiment the comparison is made for an attribute or property of a primary reporting structure.

In one embodiment a user is provided with the option to remove the automatic comparison from the generated report on the cardiology examination.

In one embodiment comparisons to one or more attributes or properties of a primary reporting structure can be added to the combined findings text string. In one embodiment such comparison is done only for the last report or test. In one embodiment a user can choose from a set of possible comparisons. In one embodiment a user can select one or more cut off variances for one or more attributes or properties of primary reporting structures before a comparison is automatically included in the combined findings text string. In one embodiment different variances for different properties or attributes can be selected. On one embodiment intra modal comparisons can be selected for one or more attributes or properties or one or more primary reporting structures. On one embodiment inter modal comparisons can be selected for one or more attributes or properties or one or more primary reporting structures. On one embodiment inter and intra modal comparisons can be selected for one or more attributes or properties or one or more primary reporting structures. In one embodiment a database report attributes can be provided and populated with findings and/or data from previous reports.

In one embodiment the reporting attributes can include one or more of the attributes provided in the Table Of Comparisons For Discrete Reporting Attributes. In one embodiment the following choices can be provided to a user (note that the "X" can be a different number for any of the possible selections). In one embodiment a user is provided with the option(s) for the method and apparatus 10 to automatically make one or more of the following comparisons and include such comparison in the generated report.

| TABLE OF COMPARISONS FOR DISCRETE REPORTING ATTRIBUTES | |
|---|---|
| Echocardiogram Comparisons | |
| Compare with Previous Echocardiogram | |
| __ Chamber Size (LA, RA, LV, RV) | |
| __ Ejection Fraction | Report variance greater than X% |
| __ Left Ventricular Mass | |
| __ Left Ventricular Mass Index | |
| __ Wall Motion | |
| __ Pericardial Effusion Size | |
| __ Stenosis Severity (MV, AV, TV, PV) | |
| __ Regurgitation Severity (MV, AV, TV, PV) | |
| __ Area by Planimetry (MV, AV) | Report variance greater than X% |
| __ Area by Pressure Half Time (MV, AV) | Report variance greater than X% |
| __ Area by Planimetry - Continuity Equation (AV) | Report variance greater than X% |
| __ Aorta - Aortic Root Diameter | Report variance greater than X% |
| Compare with Previous Nuclear (Rest) | |
| __ Ejection Fraction | Report variance greater than X% |
| __ Wall Motion | |
| Compare with Previous Stress Echocardiogram (Rest) | |
| __ Ejection Fraction | Report variance greater than X% |
| __ Wall Motion | |
| Stress Echocardiogram Comparison | |
| Compare with Previous Stress Echo (Stress) vs. Stress Echo (Stress) | |
| __ Ejection Fraction | Report variance greater than X% |
| __ Wall Motion | |
| Compare with Previous Nuclear (Rest) vs. Stress Echo (Rest) | |
| __ Ejection Fraction | Report variance greater than X% |
| __ Wall Motion | |
| Compare with Previous Nuclear (Stress) vs. Stress Echo (Stress) | |
| __ Ejection Fraction | Report variance greater than X% |
| __ Wall Motion | |
| Compare with Previous Echocardiogram vs. Stress Echo (Rest) | |
| __ Ejection Fraction | Report variance greater than X% |
| __ Wall Motion | |
| Nuclear Comparison | |
| Compare with Previous Nuclear (Stress) vs. Nuclear (Rest) | |
| __ Ejection Fraction | Report variance greater than X% |
| __ LV End Diastolic Volume | Report variance greater than X% |
| __ LV End Systolic Volume | Report variance greater than X% |
| __ TCD/TID Value | Report variance greater than X% |
| __ Wall Motion | |

-continued

TABLE OF COMPARISONS FOR
DISCRETE REPORTING ATTRIBUTES

Compare with Previous Echocardiogram
vs. Nuclear (Rest)

___ Ejection Fraction                     Report variance
                                          greater than X%
___ Wall Motion
Compare with Previous Stress Echocardiogram
(Rest) vs. Nuclear (Rest)

___ Ejection Fraction                     Report variance
                                          greater than X%
___ Wall Motion
Compare with Previous Stress Echocardiogram
(Stress) vs. Nuclear (Stress)

___ Ejection Fraction                     Report variance
                                          greater than X%
___ Wall Motion Carotid
  Compare with Previous Caratoid
    Stenosis—segment by segment (for example, "Compared with previous study on Dec. 20, 1999, right internal caratid artery Senosis remains unchanged/changed/is not seen in this study/improved).
Exercise Treadmill Test
  ST Depression (for example, "Both Normal: this study when compared with the previous study dated Jan. 1, 2009, there is no interval change."; "Previous normal, current abnormal: this study when compared with the previous study dated Jan. 1, 2009, new ST segment depression is noted in leads V4, V5 and V6."; "Previous Abnormal, current abnormal: this study when compared with the previous study dated Jan. 1, 2009, persistent ST segment depression is noted in leads V4, V5 and V6.; "Previous Abnormal, current normal: this study when compared with the previous study dated Jan. 1, 2009, ST segment depression is noted in leads V4, V5 and V6 is not evident. This is suggestive of resolved ischemia."

In one embodiment this comparison can be intra modality. Example: Compare Echocardiogram with a previous echocardiogram for: (1) Chamber Size (LA,RA,LV,RV); (2) Ejection Fraction; (3) Left Ventricular Mass; (4) Left Ventricular Mass Index; (5) Wall Motion; (6) Pericardial Effusion Size; (7) Stenosis Severity (MV,AV,TV,PV); (8) Regurgitation Severity (MV,AV,TV,PV); (9) Area By Planimetry (with deviation)(MV,AV); (10) Area By Pressure Half Time (with deviation)(MV); (11) Area By Planimetry—Continuity Equation (with deviation)(AV); and/or (12) Aorta—Aortic Root Diameter (with deviation). As another example, compare based on predetermined events: (1) Chamber Size—Valvular Stenosis (Mitral, Aortic, Pulmonary and Tricuspid)—Report even if no change; (2) Valvular Regurgitation (Mitral, Aortic, Pulmonary and Tricuspid); and/or (3) Ejection Fraction: An Ejection Fraction difference of 5% or More should be considered to be significant (In the settings page this value should be able to be changed); and/or (4) Wall Motion Abnormality.

In one embodiment this comparison can be inter modality. In one embodiment this comparison can be both inter and intra modality. Example: Compare Echocardiography findings to Nuclear Stress Testing for: (1) EF—Compare EF in Echo with EF in Nuclear; (2) EF—Compare EF in Echo with EF in Cath; (2) Wall Motion Abnormalities—Segment/Segment Echo and Nuclear; (3) Echocardiogram with Nuclear (Rest) for (a) Ejection Fraction and (b) Wall Motion. Compare Echocardiogram with Stress Echocardiogram (Rest) for (a) Ejection Fraction and (2) Wall Motion.

Pop Up Text Box of Findings with Prior Intra Modality Studies

In one embodiment findings from one or more various prior studies can be displayed on the display for comparison by the user when preparing the current report.

In one embodiment data from intra modal studies (e.g., same type of studies on the same individual such as an echocardiogram to echocardiogram) can be displayed on the display.

In one embodiment if a prior report is in the method and apparatus 10, when reporting on a primary reporting structure, the method and apparatus 10 will display on the input screen the particular combined findings string for the primary reporting structure from the prior report.

In one embodiment a portion of the text of a prior report is displayed on the display for the input screen when inputting findings for a particular primary reporting structure.

In one embodiment a portion of the text of a prior report is automatically displayed on the display for a predetermined period of time on the input screen when inputting findings for a particular primary reporting structure. In one embodiment this particular combined findings string for the primary reporting structure automatically pops up on the display (see FIG. 4) for a predefined period of time (in one embodiment the user can select the predefined period of time, in another embodiment the findings text string remains on during the entire time the input display screen for the particular primary reporting structure is displayed on the display.

In one embodiment the findings of a prior report on the same primary reporting structure is displayed on the display screen when inputting the findings for the current report on the selected primary reporting structure.

In one embodiment, where prior studies have been performed, the method and apparatus 10 provides the option is to display the prior report's findings related to the chosen primary reporting structure. In one embodiment the option is provided to display the whole prior report. In one embodiment where multiple prior reports have been performed, the option is provided to select and display any one of the selected prior report's findings related to the chosen primary reporting structure. In one embodiment multiple prior report findings related to the chose primary reporting structure can be simultaneously displayed. In one embodiment entire multiple prior reports can be accessed from the findings input screen for the chosen primary reporting structure.

In one embodiment the user is provided with the option to view reports on prior studies. In one embodiment this option is selectable on the display screen be selecting a prior studies icon or tab.

In one embodiment a database report attributes can be provided and populated with findings and/or data from previous reports. In one embodiment the reporting attributes can include one or more of the attributes provided in the Table 2 Of Discrete Reporting Attributes or Properties.

In one embodiment a portion of the text of a prior report is automatically displayed on the display for a predetermined period of time on the input screen when inputting findings for a particular primary reporting structure.

In one embodiment a portion of the text of a prior report is displayed on the display for the input screen when inputting findings for a particular primary reporting structure.

In one embodiment the findings of a prior report on the same primary reporting structure is displayed on the display screen when inputting the findings for the current report on the selected primary reporting structure.

In one embodiment, where prior studies have been performed, the method and apparatus 10 provides the option to display the prior report's findings related to the chosen primary reporting structure. In one embodiment the option is provided to display the whole prior report. In one embodiment where multiple prior reports have been performed, the option is provided to select and display any one of the selected prior report's findings related to the chosen primary reporting structure. In one embodiment multiple prior report findings related to the chosen primary reporting structure can be simultaneously displayed. In one embodiment entire multiple prior reports can be accessed from the findings input screen for the chosen primary reporting structure.

Conclusions

A report can include a plurality of findings on particular primary reporting structures. A report can also include the cardiologists conclusions or final impressions. With the method and apparatus 10 the user can automatically include particular text strings from the reported findings on the particular primary reporting structure.

The input display allows the user to select one or more findings for a particular primary reporting structure to be included into the conclusions section of the report. A quick incorporation feature is provided where the user viewing the currently displayed current version of the combined findings text string into the conclusions section. In one embodiment only the text included in the current display is incorporated into the conclusions section even if the ultimate text of the conclusions section is changed based on input after selecting the option to incorporate the findings text string into the conclusions section. In one embodiment the final version of the text incorporated into the conclusions section changes automatically with changes based on input after selecting the option to incorporate the findings text string into the conclusions section. In one embodiment only correlated findings text strings from already selected attributes or properties are included in the conclusion even where additional findings text strings from additionally selected attributes or properties are added to the combined findings text string.

In one embodiment the user is provided option to add additional conclusions to the one or more findings text strings previously imported into the conclusions section. In one embodiment the user is provided the option to add text to one of more of the imported findings text strings. In one embodiment the added text is added to the end of the imported findings text string (in another embodiment the added text is added at the beginning). In one embodiment the user cannot change the actual imported findings text strings other than to add remarks to the beginning or end of the imported findings text strings. In one embodiment the individual imported findings text strings are listing in the conclusion section in order of timing of importation. In one embodiment the user is provided the option to re-order the order of one or more of the imported findings text strings from one or more of the primary reporting structures.

Option to extract current version of findings for a primary reporting structure into the conclusions/final impressions section of the generated report.

Option to edit/delete any extracted findings.

Option to switch order.

Option to add customized findings.

In an input screen for reporting findings on a primary reporting structure.

In one embodiment is provided the ability to view in the electronic version of the final report pop up graphing comparisons of historical testing parameters when viewing the report, such as by clicking on hypertext in the report.

FIGS. 2, 9, and 34-35 are screen shots illustrating the insertion of primary reporting structure findings into the Conclusions/Impressions of the Report by checking off the boxes. In FIG. 2 icon 2030 can be selected to import the findings into a text string for the conclusions (as text string 1210). In FIG. 9 icon 1212 can be selected to include text string 1210 in the conclusions section of the final report (schematically shown as text string 1662 of section 1660 in the preview screen of FIG. 34). In the final report shown in FIG. 36 such would be conclusion text string 3062 and findings text string 3035.

Automatic Review of Applicable Cardiology Guidelines and Automatic Determination of Applicability In one embodiment the method and apparatus 10 can analyze the input data in the various discreet fields and compare this data with a database of practice guidelines for cardiologists to determine whether one or more guidelines are pertinent to a patient. For example, there may be an applicable guideline for aortic stenosis in a patient with symptoms. In this vein the method and apparatus 10 automatically reviews a universe of guidelines which can be included in the method and apparatus 10.

In one embodiment the universe of guidelines included in the method and apparatus 10 for review can be periodically updated based on publication of new and/or modified guidelines. Such an automatic review eliminates human error where the cardiologist and/or requesting physician must try to manually remember the guidelines and their applicable to a particular patient.

In one embodiment the method and apparatus 10 undergoes a review process for determining a set of possible applicable guidelines, and where the method and apparatus 10 determines that a patient fits a particular guideline, the method and apparatus 10 can display recommendations from the guideline (such as on the input screen along with including the guideline and/or recommendation). In one embodiment in the generated report a hyperlink to the applicable guideline can be provided where selecting the hyperlink provides access to a description of the guideline. In the report itself clicking on the hypertext will show a portion of the guideline which is appropriate to the factors which caused the guideline to be connected to the report. In one embodiment access to the full guideline can be provided to the individual reviewing the report (who can be the referring physician, cardiologist, or another individual reviewing the report).

Because some of the guidelines require both clinical information (e.g., evaluations) along with data from the cardiology tests being reported on, the method and apparatus 10 in determining applicability of a particular guideline may request additional information some guidelines may require additional input by the requesting physician and/or reporting cardiologist to determine applicability of the guideline and appropriate recommendation from the guideline. In this instance the method and apparatus 10 will perform a first review from the input to the report, which review will temporarily flag one or more potential guidelines (meaning the data input to the cardiology report meets the initial requirements of one or more particular guidelines for applicability). For each of these temporarily flagged guidelines, the method and apparatus 10 can require a set of additional information/input (e.g., is the patient experience chest pains or is he symptomatic). Based on the additional input, applicability of the particular guidelines are determined. For one or more of the guidelines which are determined to be applicable after input of requested clinical information, the method and apparatus 10 can generate recommendations based on the guidelines which can be included in the report.

In one embodiment where clinical information is also part of the entire medical record, the method and apparatus 10 can use such electronically available clinical information to determine applicability of one or more particular guidelines without the need to request/require additional information. In this case the method and apparatus 10 can generate recommendations based on the guidelines determined to be applicable which can be included in the report.

In one embodiment some of guidelines in the method and apparatus 10 can flag possible data inconsistency, or a failure to report on one or more items that a guideline recommends should be reported. The method and apparatus 10 can review the input data and compare such data to the universe of guidelines. The review can be based on certain input items/information/data triggering the guidelines.

In one embodiment the method and apparatus 10, based on the inputted data, determines potential and/or actual applicability of one or more of the following Practice Guidelines and/or Quality Standards listed in the Table of Practice Guidelines and Standards. In one embodiment a subset of the list is reviewed for applicability by the method and apparatus 10. In one embodiment the set is a comprehensive collection of all ACC evidence-based clinical documents in the field of cardiovascular medicine. These documents provide recommendations for the practice of cardiology as well as strategies for cardiovascular quality improvement.

In various embodiments the method and apparatus 10 can include predefined text in the generated report and provide in the report a link to the applicable practice guideline, or a hyperlink in an electronic version of the report to access a copy of the guideline electronically such as through the internet.

FIG. 31B shows one example of the method and apparatus 10 determining that a particular guideline is applicable. In FIG. 31B, the aortic valve input screen 550 has been selected to input findings. In this screen, the Aortic valve is shown 0.9 by Planimetry method and 0.8 square centimeters in the continuity equation method (either entered manually by the technician, physician, or automatically calculated by method and apparatus). In the findings pop up screen 2000 the following text will be generated for the aortic valve primary reporting structure based on the input—"Noted evidence of aortic stenosis. Severe aortic stenosis noted . . . [GUIDELINE ICON INSERTED HERE AS HYPERLINK]".

In this case method and apparatus 10, based on the input and comparison to guidelines entered in its database, identified applicable guidelines for this patent and generated text showing that severe aortic stenosis is present along with a "Guideline" icon is included within the generated text. A user clicking on this icon will show a pop up summary version 4000 of the applicable guideline—which pop up version is also shown in FIG. 31B.

In various embodiments one or more of the following guidelines are programmed into method and apparatus 10, so that it compares the inputted data and identifies applicable guidelines based on the inputted data, along with generating text and an icon that an applicable guideline has been identified.

Table of Practice Guidelines and Standards
Arrhythmias
(1) ECG: Recommendations for the Standardization and Interpretation of the Electrocardiogram; (2) ST-Elevation and Non-ST-Elevation Myocardial Infarction: Performance Measures for Adults With; (3) Sleep Apnea and Cardiovascular Disease; (4) Atrial Fibrillation, Key Data Elements and Definitions for Measuring the Clinical Management and Outcomes of Patients With; (5) Device-Based Therapy of Cardiac Rhythm Abnormalities Guidelines for; (6) Atrial Fibrillation: Performance Measures for Management of Patients With Nonvalvular Atrial Fibrillation or Atrial Flutter; (7) Ventricular Arrhythmias and the Prevention of Sudden Cardiac Death: Guidelines for Management of Patients With; (8) Evaluation of Syncope; (9) Signal-Averaged Electrocardiography; (10) Tilt Table Testing for Assessing Syncope; (11) Invasive Electrophysiology Studies, Catheter Ablation, and Cardioversion: (12) Update of the Clinical Competence Statement On; (13) Atrial Fibrillation: 2006 Guidelines for Management of Patients With; (14) Hypertrophic Cardiomyopathy.

Cardiovascular Surgery
(1) Device-Based Therapy of Cardiac Rhythm Abnormalities: Guidelines for; (2) Perioperative Cardiovascular Evaluation for Noncardiac Surgery: 2007 Guidelines; (3) Cardiac Rehabilitation for Referral to and Delivery of Cardiac Rehabilitation/Secondary Prevention Services: Performance Measures on; (4) Coronary Artery Bypass Graft Surgery (CABG): Guideline Update for.

Congenital Heart Disease
(1) Adults With Congenital Heart Disease: Guidelines for the Management of (2) Care of the Patient with Adult Congenital Heart Disease: Bethesda Conference 32; (3) Congenital Heart Disease After Pediatrics: An Expanding Patient Population: BC 22; (4) Atherosclerosis Imaging Techniques: BC 34; (5) Hypertrophic Cardiomyopathy;

General Cardiology
(1) Appropriateness Criteria for Coronary Revascularization; (2) Intensive Glycemic Control and the Prevention of Cardiovascular Events: Implications of the ACCORD, ADVANCE, and VA Diabetes Trials; (3) Women in Cardiology 2008: Decade of Change; (4) Multimodality Noninvasive Cardiovascular Imaging; (5) Structured Reporting in Cardiovascular Imaging; (6) Key Data Elements and Definitions for Cardiac Imaging; (7) Clinical Data Standards; (8) Classification of Care Metrics; (9) Reperfusion Therapy: Statement on Performance Measurement and ST-Elevation and Non-ST-Elevation Myocardial Infarction: Performance Measures for Adults; (10) Adults With Congenital Heart Disease: Guidelines for the Management of; (11) Standards for Measures Used for Public Reporting of Efficiency in Health Care; (12) Reducing the Gastrointesinal Risks of Antiplatelet Therapy and NSAID Use; (13) Valvular Heart Disease: 2008 Focused Update Incorporated Into the ACC/AHA 2006 Guidelines for the Management of Patients With; (14) Noninvasive Risk Stratification Techniques for Identifying Patients at Risk for Sudden Cardiac Death; (15) Sleep Apnea and Cardiovascular Disease; (16) Atrial Fibrillation, Key Data Elements and Definitions for Measuring the Clinical Management and Outcomes of Patients With; (17) Public Reporting: Principles for Public Reporting of Physician Data; (18) Lipoprotein Management in Patients With Cardiometabolic Risk; (19) Stress Echocardiography: Appropriateness Criteria for; (20) COCATS 3: Recommendations for Training in Adult Cardiovascular Medicine Core Cardiology Training (Revision of the 2002 COCATS Training Statement); (21) ST-Elevation Myocardial Infarction: Guidelines for the Management of Patients with; (22) Chronic Stable Angina: 2002 Guideline Update for Management of Patients with; (23) Endomyocardial Biopsy in the Management of Cardiovascular Disease: The Role of; (24) Universal Definition of Myocardial Infarction; (25) Perioperative Cardiovascular Evaluation for Noncardiac Surgery: 2007 Guidelines; (26) Vascular Imaging With Computed Tomography and Magnetic Resonance; (27) Unstable Angina/Non-ST-Segment Elevation Myocardial Infarction:

Guidelines for; (28) Cardiac Interventional Procedures; (29) Echocardiography, Appropriateness Criteria for Transthoracic and Transesophageal; (30) Emerging Infectious Diseases and Biological Terrorism Threats Conference Report on: The Clinical and Public Health Implications for the Prevention and Control of Cardiovascular Diseases; (31) Cardiovascular Disease Prevention in Women: Evidence-Based Guidelines for: 2007 Update; (32) Clinical Data Standards: Methodology for the Development of; (33) Pay For Performance: American College of Cardiology 2006 Principles to Guide Physician Pay-for-Performance Programs; (34) Cardiac Computed Tomography and Cardiac Magnetic Resonance Imaging: Appropriateness Criteria for; (35) Evaluation of Syncope; (36) Diagnosis and Management of Chronic Heart Failure in the Adult; (37) Single-Photon Emission Computed Tomography (SPECT MPI): Appropriateness Criteria for; (38) Training in Pediatric Cardiology: Recommendations for; (39) Chronic Stable Coronary Artery Disease; (40) Integrating Complementary Medicine Into Cardiovascular Medicine; (41) Beta Blocker Use for MI Within 24 Hours of Hospital Arrival: Commitment to Respond to; Exercise Testing: 2002 Guideline Update for; (42) Cardiology's Workforce Crisis: A Pragmatic Approach: BC35; (43) Implications of Recent Clinical Trials for the National Cholesterol Education; (44) Program Adult Treatment Panel III Guidelines; (45) Professionalism and Ethics; (46) Hypertension, ACC/AHA/Physician Consortium for Performance Improvement; (47) Emergency Cardiac Care: BC 31; (48) Myocardial Infarction Redefined; (49) Ethics in Cardiovascular Medicine: Bethesda Conference 29; (50) Practice Guidelines and Quality of Care: BC 28; (51) Access to Cardiovascular Care: BC 23; (52) Future Personnel Needs for Cardiovascular Health Care: BC 25; (53) Eligibility Recommendations for Competitive Athletes With Cardiovascular Abnormalities: BC 36 (Revision of BC 16 & 26); (54) Acute Coronary Syndromes (ACS); (55) Preventing Heart Attack and Death in Patients with Atherosclerotic Cardiovascular Disease Guidelines for; (56) Alpha Blockers for Hypertension; Safety of Statins; (57) Statins: Frequently Asked Questions; (58) Challenges and Opportunities in Quantifying the Quality of Care for Acute Myocardial Infarction; (59) Guide to Warfarin Therapy; (60) Radiation Safety in the Practice of Cardiology; (61) Access to Cardiovascular Care; (62) Industry Relations; (63) Echocardiography in Emergency Medicine; (64) Ethical Coding and Billing Practices for Cardiovascular Medicine Specialists; (65) Future of Academic Cardiology: Bethesda. Conference 30; (66) Therapeutic Substitution;

Heart Failure/Transplant (1) Endomyocardial Biopsy in the Management of Cardiovascular Disease: The Role of; (2) Ventricular Arrhythmias and the Prevention of Sudden Cardiac Death: Guidelines for Management of Patients With; (3) Chronic Heart Failure: ACC/AHA Clinical Performance Measures for Adults With; (4) Chronic Heart Failure: ACC/AHA Key Data Elements and Definitions for Measuring the Clinical Management and Outcomes of Patients With; (5) Beta Blocker Use for MI Within 24 Hours of Hospital Arrival: Commitment to Respond to COMMIT/CCS-2 Trial Results; (6) Mechanical Cardiac Support 2000: Current Applications and Future Trial Design; (7) Cardiac Transplantation: BC 24; (8) Atherosclerosis Imaging Techniques: BC 34; (9) Hypertrophic Cardiomyopathy;

Interventional Cardiology (1) Reperfusion Therapy: Statement on Performance Measurement and; (2) Atrial Fibrillation, Key Data Elements and Definitions for Measuring the Clinical Management and Outcomes of Patients With; (3) Percutaneous Coronary Intervention (PCI): 2005 Guideline Update for; (4) Unstable Angina/Non-ST-Segment Elevation Myocardial Infarction: Guidelines for the Management of Patients With; (5) Cardiac Interventional Procedures; (6) Thienopyridines: Science Advisory: Prevention of Premature Discontinuation of Dual Antiplatelet Therapy in Patients With Coronary Artery Stents; (7) Standards for Acquisition, Measurement, and Reporting of Intravascular Ultrasound Studies (IVUS); (8) Cardiac Catheterization Laboratory Standards; (9) Data Definitions, Cardiac Catheterization Module v3.0; (10) Vascular Medicine and Catheter-Based Peripheral Vascular Interventions; (11) Fluoroscopically Guided Invasive Cardiovascular Procedures, Physician Knowledge to;

Non-Invasive Cardiology (1) Appropriateness Criteria for Coronary Revascularization; (2) Multimodality Noninvasive Cardiovascular Imaging; (3) Structured Reporting in Cardiovascular Imaging; (4) Key Data Elements and Definitions for Cardiac Imaging; (5) Adults With Congenital Heart Disease: Guidelines for the Management of; (6) Noninvasive Risk Stratification Techniques for Identifying Patients at Risk for Sudden Cardiac Death; (7) Stress Echocardiography: Appropriateness Criteria for; (8) Atrial Fibrillation: Performance Measures for Management of Patients With Nonvalvular Atrial Fibrillation or Atrial Flutter; (9) Endomyocardial Biopsy in the Management of Cardiovascular Disease: The Role of; (10) Cardiac Rehabilitation for Referral to and Delivery of Cardiac Rehabilitation/Secondary Prevention Services: Performance Measures on; (11) Vascular Imaging With Computed Tomography and Magnetic Resonance; (12) Cardiac Interventional Procedures; (13) Echocardiography, Appropriateness Criteria for Transthoracic and Transesophageal; (14) Emerging Infectious Diseases and Biological Terrorism Threats Conference Report on: The Clinical and Public Health Implications for the Prevention and Control of Cardiovascular Diseases; (15) Electrophysiological Studies and Procedures: Key Data Elements and Definitions for; (16) Cardiac Computed Tomography and Cardiac Magnetic Resonance Imaging: Appropriateness Criteria for; (17) Single-Photon Emission Computed Tomography (SPECT MPI): Appropriateness Criteria for; (18) Cardiac Imaging With Computed Tomography and Magnetic Resonance; (19) Electrocardiography and Ambulatory Electrocardiography; (20) Exercise Testing: 2002 Guideline Update for; (21) Signal-Averaged Electrocardiography; (22) Ambulatory Blood Pressure Monitoring; (23) Stress Testing; (24) Echocardiography in Emergency Medicine; (25) Coronary Artery Calcium Scoring By Computed Tomography in Global Cardiovascular Risk Assessment and in Evaluation of Patients With Chest Pain; (26) Standards for Acquisition, Measurement, and Reporting of Intravascular Ultrasound Studies (IVUS); (27) Echocardiography;

Prevention/Vascular (1) Appropriateness Criteria for Coronary Revascularization; (2) Intensive Glycemic Control and the Prevention of Cardiovascular Events: Implications of the ACCORD, ADVANCE, and VA Diabetes Trials; (3) Valvular Heart Disease: 2008 Focused Update Incorporated Into the ACC/AHA 2006 Guidelines for the Management of Patients With; (4) Stress Echocardiography: Appropriateness Criteria for; (5) Atrial Fibrillation: Performance Measures for Management of Patients With; (6) Nonvalvular Atrial Fibrillation or Atrial Flutter; (7) Cardiac Rehabilitation for Referral to and Delivery of Cardiac Rehabilitation/Secondary Prevention Services: Performance Measures on; (8) Vascular Imaging With Computed Tomography and Magnetic Resonance; (9) Unstable Angina/Non-ST-Segment Elevation Myocardial Infarction: Guidelines for the Management of Patients With; (10) Echocardiography, Appropriateness Criteria for Transthoracic and Transesophageal; (11) Emerging Infectious Diseases and Biological Terrorism Threats: Conference Report on: The Clinical and Public Health Implications for the Prevention and Control of Cardiovascular Diseases; (12) Secondary Prevention for Patients With Coronary and Other Atherosclerotic Vascular Disease: 2006 Update AHA/ACC Guidelines for; (13) Evaluation of Syncope; (14) Peripheral Arterial Disease (Lower Extremity, Renal, Mesenteric, and Abdominal Aortic): Guidelines for the Management of Patients With; (15) Chronic Stable Coronary Artery Disease; (16) Vascular Medicine and Catheter-Based Peripheral Vascular Interventions; (17) Preventing Heart Attack and Death in Patients with Atherosclerotic Cardiovascular Disease: Guidelines for; (18) Atherosclerosis Imaging Techniques: BC 34; (19) Preventive Cardiology: How Can We Do Better? BC 33; (20) Assessment of Cardiovascular Risk by Use of Multiple-Risk Factor Assessment Equations; (21) Coronary Artery Calcium Scoring By Computed Tomography in Global Cardiovascular Risk Assessment and in Evaluation of Patients With Chest Pain; (22) Preventive Cardiology and Atherosclerotic Disease; (23) Smoking as a Health Hazard; (24) Matching the Intensity of Risk Factor Management with the Hazard for Coronary Disease Events: BC 27;

Each of the above referenced printed publications are incorporated herein by reference.

Additionally, the user has the option to graphically navigate from the graphical interface graphically showing component parts of the heart to reporting tabs for the component parts of the heart.

In one embodiment the method and apparatus 10 uses a web based request and/or reporting based system. In one embodiment testing data is stored in a remote server. In one embodiment the generated reports are stored in a remote server.

Automatic Calculation of Certain Properties or Attributes
Wall Motion Index Calculation In one embodiment anatomical images/views of the heart related to septal motion can be provided on the display which are selectable (such as by smaller anatomical images/views or through pull down menu choices), and such anatomical images/views are themselves broken down into a plurality of selectable segmental portions. The anatomical images/views for wall motion analysis can include long and short axis, along with two and four chamber views. In one embodiment WMSI can be calculated by the software based on input made in selecting one, more, or all of the smaller segmental portions, with each smaller segmental portion providing the option to select from a set of gradations of wall motion. For example, segmental portions for the individual sections of the heart can be selected graphically by clicking on the particular segmental section of the heart can and then selecting an indicator from the set of 1, 2, 3, and 4 (such as toggling through such indicators). The WMSI based on conventionally available formula can be is automatically calculated by the software based on such input, and included in the findings section of the generated report.

In one embodiment the method and apparatus 10 uses one or more of the following formulas or business rules in reporting, and automatically calculates one or more of the following properties or attributes for one or more of the following primary reporting structures for reporting on one or more cardiology tests or procedures.

Left Atrium
  LA Volume:
    Prolate Ellipse Method:

$$LA\ \text{Volume} = D1 \times D2 \times D3 \times 0.523$$

BiPlane Area Length Method:

$$LA\ \text{Volume} = \frac{(LA\ \text{Area1} \times LA\ \text{Area2} \times 0.85)}{LA\ \text{Length}}$$

LV Calculations
  LV Ejection Fraction $$EF = ((LVEDV - LVESV)/LVEDV) \times 100$$

LV Fractional Shortening (FS)

$$FS = (LVEDD - LVESD/LVEDD) \times 100$$

Left Ventricular Mass($g/m^2$):

$$LV\text{Mass}(g) = (1.04[(LVEDST + LVEDD + LVEDPWT)3 - LVED]-14)$$

$$LVMassIndex(g/m^2) =$$
$$\frac{(1.04[(LVEDST + LVEDD + LVEDPWT)3 - LVEDD] - 14\ g)}{\text{Body surface area. (Devereux's formula)}}$$

Left Ventricular Wall Motion Score Index

WMSI=Sum of wall motion scores/number of Visualized segments

Left Ventricular End Diastolic Pressure $$LVEDP = DBP - (AR\ EDV)^2 \times 4$$

M-Mode Measurements
Doppler $$\text{Pressure Gradient} = 4 \times (v_2)^2$$

$$LA\ \text{Systolic pressure} = SBP - 4 \times MRV^2$$

$$LVEDP = DBP - (AR\ EDV)^2 \times 4$$

Continuity Equation:

$$A_2 = A \times TVI_1/TVI_2$$

Pressure Half Time (PHT)

$$PHT = 0.29 \times DT$$

Mitral Valve Area (MVA)

$$MVA = 220/PHT$$

Mitral Regurgitant Volume (MRV):

MRV=Mitral inflow volume(Forward stroke volume (FSV))−Systemic Stroke volume

MRV=(Mitral annulus Area×Mitral $TVI$)−($LVOT$ Area×$LVOT\ TVI$)

Mitral Regurgitant Fraction (MRF)

$$MRF = MRV/FSV \times 100$$

Method of Ordering/Scheduling a Test
One embodiment includes one or more of the following steps:
  (1) Enforcing Appropriateness in test ordering
  (2) Automatic Scheduling and study notification
  (3) Appointment Request Receipt In one embodiment the method and apparatus 10 can include a test procedure appointment scheduling option which can provide: (1) a suggested date for test and (2) listing of available tests. In one embodiment the listing of available tests to be scheduled includes sublistings for indicators which would allow such tests (such as according to the ACC/AHA Appropriateness Guidelines—American Cardiology). In one embodiment the referring physician can request multiple tests in same request (such as by clicking on an "add" button).

In one embodiment, the data displayed includes referring physician order. In one embodiment, the data displayed includes scheduling information. In one embodiment, the data displayed includes study parameters.

In one embodiment there can be optional notices to referring physician: (a) when study scheduled with patient; and/or (b) when study actually reported. In one embodiment the notices can be through email or other notification modality. In one embodiment the notice will not disclose patient name (to be HIPPA compliant) and can be "generic without name X studies scheduled and/or Y studies reported" inviting the user to log into the system to get more information.

In one embodiment each referring physician will have a unique username and password which will be linked to a set of patient data.

In one embodiment when a referring physician sends in request to schedule a study he is provided with an option to print out a receipt from the cardiology office website that gives the patient the date of the scheduled test and a confirmation number for the appointment. The appointment can be used to track the appointment beyond the patient's name. The receipt can also give the phone number and/or address of the location for the scheduled tests. A individualized text message can be provided in the receipt for the cardiology office regarding information that can be conveyed to the patient (e.g., we will contact you within one working day or you should call us). However, an actual appointment will not actually be scheduled until the patient is contacted directly by the clinic.

In one embodiment when scheduling an appointment the referring physician has the option to select date, time, technician, and cardiologist reading and reporting the test results. In one embodiment the method and apparatus 10 queries regarding whether "additional tests should be scheduled for the same day for a single patient."

In one embodiment the method and apparatus 10 uses a web based request and/or reporting based system. In one embodiment testing data is stored in a remote server. In one embodiment the generated reports are stored in a remote server.

Enforcing Appropriateness in Test Ordering

In one embodiment is provided a method and apparatus to enforce appropriateness guidelines for scheduling a cardiology procedure.

In this embodiment a physician 82 can request a cardiology test be performed. In response to this request method and apparatus 10 can provide physician 82 with a plurality of appropriate reasons for scheduling/prescribing the specific cardiology test, and require that one or more of the provided reasons be selected before allowing the scheduling of the test. In one embodiment the provided reasons are ACC/AHA appropriate guidelines.

Figures 37, 38:
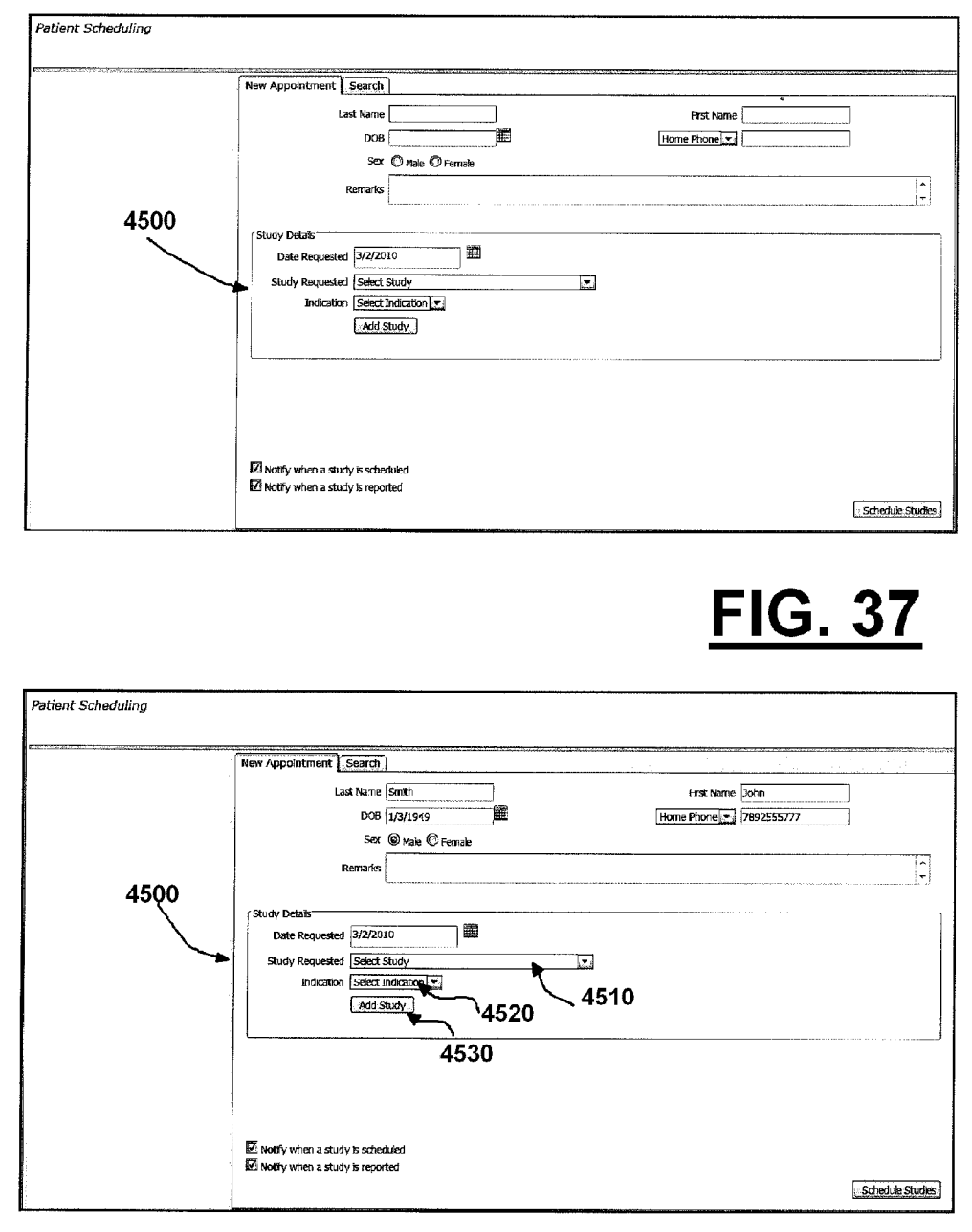

FIGS. 37-40 show one embodiment in which method and apparatus 10 can enforce appropriateness guidelines in scheduling a study. FIG. 37 shows a screen shot of a study request input section 4500 wherein a physician 82 can request a new study be performed by a cardiology clinic. It is envisioned that new studies will usually be ordered by the referring physician 82. A study can be requested after entering the patient's 80 demographic information. FIG. 38 shows the screen shot of FIG. 37 wherein the patient's 80 demographic information is inputted.

Figure 39:
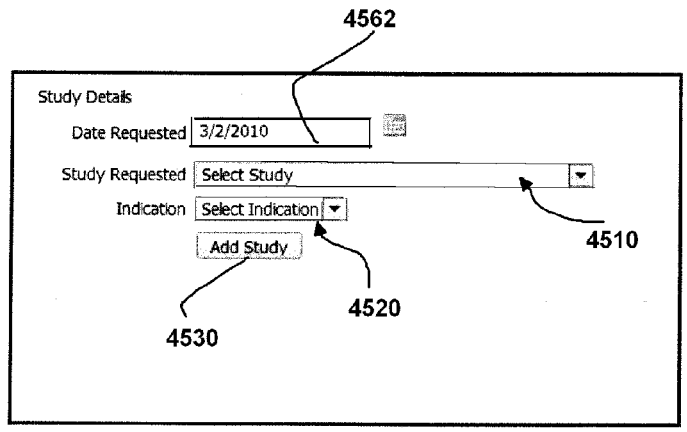

FIG. 38 shows selection tab of study from set of studies 4510, selection of indicator from set of acceptable indicators for study to be scheduled 4520, and Add Study button 4530. FIG. 39 shows an enlarged section of the screen shot of FIG. 37 wherein the Study Details 4500 section has been enlarged before selecting a particular study to schedule using the "Study Requested" tab 4510 selection. chosen study to be scheduled 4512

Figure 40:
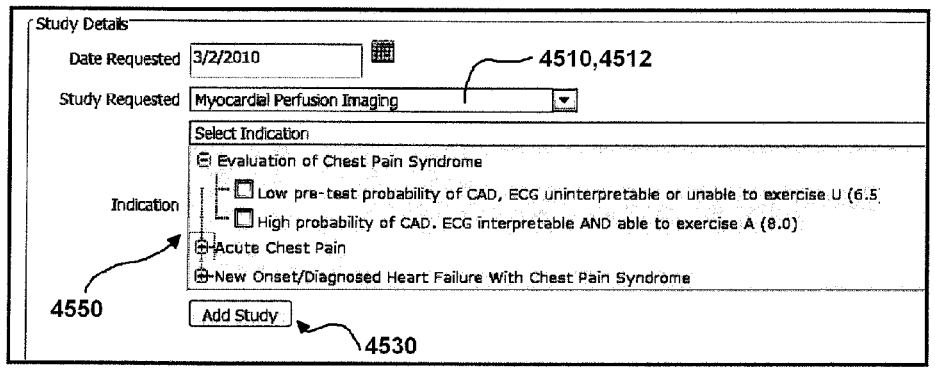
Figure 46:
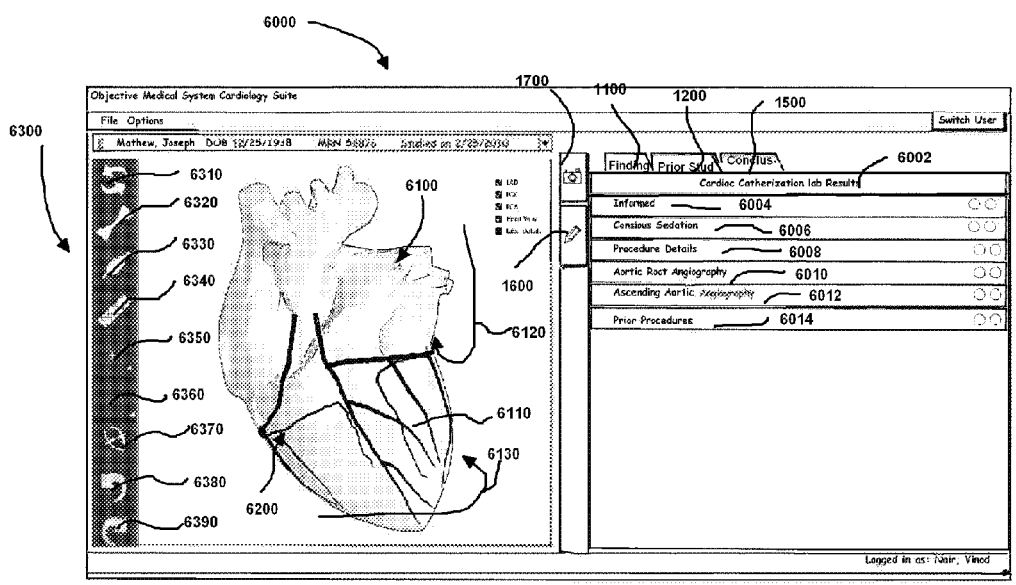
FIGS. 46-50 illustrate one embodiment for the angiogram reporting modality.

FIG. 40 shows the screen shot of FIG. 39 wherein a particular study (Myocardial Perfusion Imaging) 4512 from the set of possible studies contained in the "Study Requested" tab 4510 (such as the set of studies for which method and apparatus can be used to generate reports on. In this screen shot a new study is selected (Myocardial perfusion imaging), and the method and apparatus 10 now displays the appropriate indication based on ACC/AHA appropriateness guidelines (http://www.asnc.org/imageuploads/AUCCardiacRadionuclideImaging2009).

As indicated in FIG. 40 the physician 82 requesting the study will be required to select one or more of the conditions from a set of appropriate conditions (listed in 4550) in method and apparatus 10 for patient 80 which selected condition is considered appropriate for performing a particular study before a particular study can be scheduled. In one embodiment the set of appropriate conditions for a plurality of cardiology studies are contained in a database which method and apparatus 10 can access. In one embodiment the set of appropriate conditions are compiled from published ACC/AHA appropriateness guidelines for a particular study. In one embodiment sets of appropriate conditions are compiled for each of a plurality of cardiology studies and contained in a database which method and apparatus 10 can access.

The Table of Appropriateness Criteria include criteria which can populate the database accessible to method and apparatus 10.

TABLE OF APPROPRIATENESS CRITERIA
Appropriateness Criteria by Modality

1. Symptoms potentially due to suspected cardiac etiology, including but not limited to dyspnea, shortness of breath, lightheadedness, syncope, TIA, cerebrovascular events
2. Prior testing that is concerning for heart disease (i.e., chest X-ray, baseline scout images for stress echocardiogram, ECG, elevation of serum BNP)
3. Patients who have sustained or nonsustained SVT or VT
4. Initial evaluation of LV function following acute MI
5. Re-evaluation of LV function following MI during recovery phase when results will guide therapy
6. Evaluation of known or suspected pulmonary hypertension
7. Evaluation of hypotension or hemodynamic instability of uncertain or suspected cardiac etiology
8. Evaluation of acute chest pain with suspected myocardial ischemia in patients with nondiagnostic laboratory markers and ECG
9. Evaluation of suspected complication of myocardial ischemia/infarction
10. Evaluation of respiratory failure with suspected cardiac etiology
11. Evaluation of patient with known or suspected acute pulmonary embolism to guide therapy (i.e., thrombectomy and thrombolytics)
12. Initial evaluation of murmur in patients for whom there is a reasonable suspicion of valvular or structural heart disease
13. Initial evaluation of patient with suspected mitral valve prolapse
14. Initial evaluation of known or suspected native valvular stenosis
15. Routine (yearly) evaluation of an asymptomatic patient with severe native valvular stenosis
16. Re-evaluation of a patient with native valvular stenosis who has had a change in clinical status
17. Initial evaluation of known or suspected native valvular regurgitation
18. Routine (yearly) re-evaluation of an asymptomatic patient with severe native valvular regurgitation with no change in clinical status
19. Re-evaluation of native valvular regurgitation in patients with a change in clinical status Prosthetic Valve -continued TABLE OF APPROPRIATENESS CRITERIA
Appropriateness Criteria by Modality 20. Initial evaluation of prosthetic valve for establishment of baseline after placement
21. Re-evaluation of patients with prosthetic valve with suspected dysfunction or thrombosis or a change in clinical status A (9) Infective Endocarditis (Native or Prosthetic Valves)
22. Initial evaluation of suspected infective endocarditis (native and/or prosthetic valve) with positive blood cultures or a new murmur
23. Evaluation of native and/or prosthetic valves in patients with transient fever but without evidence of bacteremia or new murmur
24. Re-evaluation of infective endocarditis in patients with any of the following: virulent organism, severe hemodynamic lesion, aortic involvement, persistent bacteremia, a change in clinical status, or symptomatic deterioration
25. Evaluation for cardiovascular source of embolic event (PFO/ASD, thrombus, neoplasm)
26. Evaluation of cardiac mass (suspected tumor or thrombus)
27. Evaluation of pericardial conditions including but not limited to pericardial mass, effusion, constrictive pericarditis, effusive-constrictive conditions, patients post-cardiac surgery, or suspected pericardial tamponade
28. Known or suspected Marfan disease for evaluation of proximal aortic root and/or mitral valve
29. Initial evaluation of suspected hypertensive heart disease
30. Routine evaluation of patients with systemic hypertension without suspected hypertensive heart disease
31. Heart Failure
32. Initial evaluation of known or suspected heart failure (systolic or diastolic)
33. Re-evaluation of known heart failure (systolic or diastolic) to guide therapy in a patient with a change in clinical status
34. Pacing Device Evaluation
35. Evaluation for dyssynchrony in a patient being considered for CRT
36. Patient with known implanted pacing device with symptoms possibly due to suboptimal pacing device settings to re-evaluate for dyssynchrony and/or revision of pacing device settings
37. Initial evaluation of known or suspected hypertrophic cardiomyopathy
38. Re-evaluation of known hypertrophic cardiomyopathy in a patient with a change in clinical status to guide or evaluate therapy
39. Evaluation of suspected restrictive, infiltrative, or genetic cardiomyopathy
40. Screening study for structure and function in first-degree relatives of patients with inherited cardiomyopathy
41. Baseline and serial re-evaluations in patients undergoing therapy with cardiotoxic agents
42. Evaluation of suspected acute aortic pathology including dissection/transsection
43. Guidance during percutaneous noncoronary cardiac interventions including but not limited to septal ablation in patients with hypertrophic cardiomyopathy, mitral valvuloplasty, PFO/ASD closure, radio frequency ablation
44. To determine mechanism of regurgitation and determine suitability of valve repair
45. To diagnose/manage endocarditis with a moderate or high pre-test probability (e.g., bacteremia, especially staph bacteremia or fungemia)
46. Persistent fever in patient with intracardiac device
47. Use of TEE as the Initial Test*-Common Uses-Atrial Fibrillation/Flutter
48. Evaluation of patient with atrial fibrillation/flutter to facilitate clinical decision-making with regards to anticoagulation and/or cardioversion and/or radiofrequency ablation
49. Evaluation for cardiovascular source of embolic Appropriateness Guidelines For Nuclear Perfusion Test Detection of Coronary Artery Disease:
a. Symptomatic patient with chest pain
   i. Intermediate CAD probability, ECG interpretable and able to exercise
   ii. Intermediate CAD probability, ECG uninterpretable OR unable to exercise
   iii. High pre-test probability of CAD, ECG interpretable and able to exercise
   iv. High pretest probability of CAD, ECG uninterpretable OR unable to exercise.
b. Acute chest pain: Intermediate pre-test probability without ST elevation and negative initial cardiac enzymes.
c. New-onset heart failure with chest pain
d. New onset heart failure without chest pain
e. Asymptomatic New-Onset Atrial fibrillation
f. Asymptomatic Ventricular Tachycardia
g. Risk assessment (asymptomatic): Moderate to high risk (Framingham)
h. Risk Assessment (Asymptomatic): High risk population
i. Risk Assessment: Prior normal SPECT Repeat SPECT after 2 years
j. Risk Assessment: Known CAD on catheterization OR prior SPECT MPI study in patients who have not had revascularization procedure. Greater than or equal to 2 years to evaluate worsening disease
k. Risk Assessment: Worsening Symptoms—prior abnormal coronary angiogram or SPECT
l. Risk Assessment With Prior Test Results: UA/NSTEMI, STEMI, or Chest Pain Syndrome-Coronary Angiogram
m. Risk Assessment With Prior Test Results—Intermediate Duke Treadmill Score, intermediate CI-ID
n. Risk Assessment: Preoperative Evaluation for Non-Cardiac Surgery-Intermediate-Risk Surgery—Intermediate pre-operative risk and poor exercise tolerance.
o. Risk Assessment: Preoperative Evaluation for Non-Cardiac Surgery—High-Risk Surgery—Minor pre-operative risk and poor exercise tolerance.
p. Risk Assessment: Following Acute Coronary Syndrome—STEMI-Hemodynamically Stable
q. Risk Assessment: Following Acute Coronary Syndrome-UA/NSTEMI-No Recurrent Ischemia OR No Signs of HF
r. Risk Assessment: Preoperative Evaluation for Non-Cardiac Surgery—High-Risk Surgery
s. Risk Assessment: Post-Revascularization (PCI or CABG)-
t. Symptomatic
u. Risk Assessment With Prior Test Results: Asymptomatic-Prior Coronary Calcium Agatston Score (>400).

Once the appropriate conditions for scheduling the requested study, the "Add Study" tab 4530 can be selected and the study will be set in line.for scheduling.

Automatic Scheduling and Study Notification

In one embodiment method and apparatus 10 provides a referring physician 82, after a cardiology procedure has been scheduled, with an appointment request receipt 4600. The appointment request receipt 4600 includes the name of patient, the test procedure 4560, and requested date of procedure 4562.

FIGS. 39-45 illustrate one embodiment of this method.

In one embodiment, where multiple cardiology procedures are requested for a patient, method and apparatus 10 examines each procedure, facilities required for such procedure, and time required, and determines if there is a conflict in scheduling the procedures on the same day and/or at the same cardiology facility before allowing a requested date to be listed for a requested study.

In one embodiment method and apparatus 10, for a particular referring physician, provides a database of scheduled procedures by such physician.

In one embodiment, after a report is entered on a procedure for a patient, method and apparatus 10 notifies electronically referring physician such as by email or text message. In one embodiment referring physician has access to completed report by logging into method and apparatus 10 and viewing the report (See FIGS. 41 through 44).

Figures 41, 42, 43, 44:
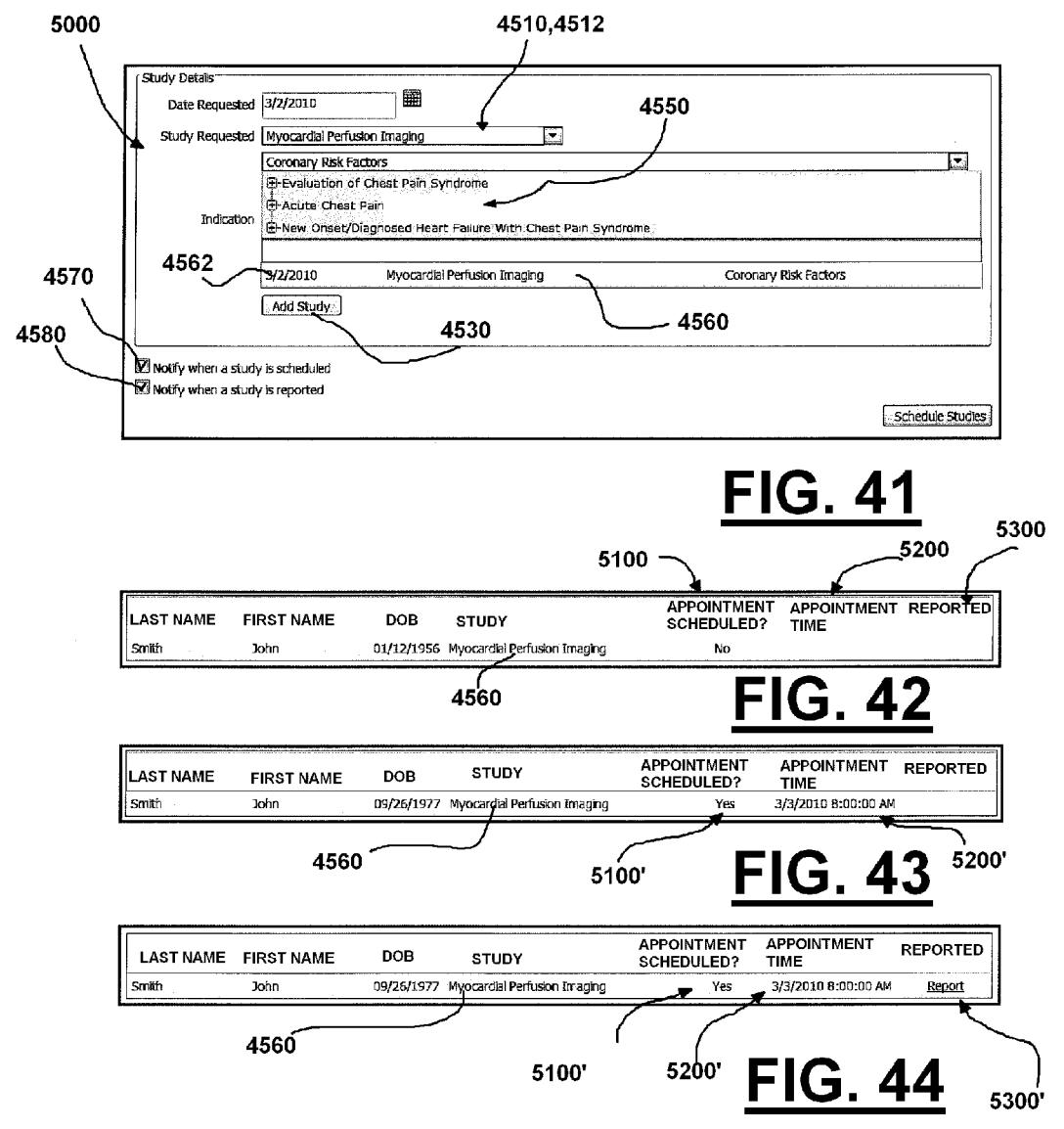

In FIG. 41 is shown a New Study requisition screen 5000 with the "Study Details" 4500 section enlarged. Method and apparatus 10 provides an option for the referring physician 82 to be notified (box 4570) when the study is scheduled by the cardiology facility performing the study and/or when the study has been reported on (box 4580).

In FIG. 42 method and apparatus 10 indicates to the referring physician 82 that the listed study 4560 has been requested (by the referring physician), but that no appointment for the study has been scheduled at this time 5100.

In FIG. 43 method and apparatus 10 indicates to the referring physician 82 that the listed study has been requested (by the referring physician), and that an appointment for the study has been scheduled at this time (with the appointment date and time listed 5200').

In FIG. 44 method and apparatus 10 indicates to the referring physician 82 that the listed study has been requested (by the referring physician), an appointment for the study has been scheduled at this time (with the appointment date and time listed 5200'), and that a report has been made on the study which can be viewed by the referring physician by clicking on the "Report" icon in the screen shot 5300'.

FIG. 45 shows a patient receipt 4600 with the study requested to be scheduled 4560 and requested study date 4562. This receipt can be given to the patient by referring physician to remind patient that a study has requested to be scheduled for him.

In one embodiment method and apparatus 10 can perform one or more of the following functions:

Reports
    Ability to view report by the referring physician over web
    Patients per diagnosis over a time span
    Patients per insurance type over a time span
    Report of referring physicians statistics (number of patients referred by each referring physician over a time period)
    Report of Insurance providers over a time span
    Report of interpreting physicians statistics In one embodiment one or more of the following searches and default views are provided in the method and apparatus 10.

Searches
    Last Name
    First Name
    Full Name (Last name, First name)
    Date
    Medical Record Number
    Insurance name
    Date range Default Views
    Sorted by Date of Study
    Sorted by Interpreting Physicians
    Sorted by Referring Physicians Data Mining Capabilities
    One embodiment includes data mining capabilities including predefined data elements, demographics and trend plotting of multiple components reported in any created under method and apparatus 10. In one embodiment data mining can occur under any of numerical discrete items for the attached listing of discrete data elements. In one embodiment data mining can occur under any of the numerical discrete data elements.

Miscellaneous
    Security access to stored data preferably is provided by the medical report generation method and apparatus 10. Security access may be provided by distinguishing between each user's data and reports through the use of a user name.

In one embodiment, the method includes providing a second computer with a second display screen and making the report available to the second computer on the second computer display screen.

In one embodiment, the computer and display screen are touch screen operated.

In one embodiment is provided a method and apparatus 10 for report generation in which the contents of a relational database are used to generate a cardiology report. The database can include a plurality of option-text variables for use in preparing a cardiology report, a plurality of variable records for storing pre-defined character strings to replace the option-text variables.

In one embodiment report generation can be by touch input screen such as by commercially available touch input screens. For example, the Apple IPHONE® touch input screen.

In one embodiment the method and apparatus 10 includes a reporting function to the technicians which are performing tests to show technicians what tests are scheduled for them for particular days and times. From this list the technician clicks on the particular scheduled test and a reporting screen comes up where various information about patient has already been filled out (name, ssn, etc.). For an Echo test the technician puts in height and weight and method and apparatus 10 automatically calculate body mass index (BMI) and body surface area (BSA). These calculations are based on formulas.

In one embodiment the method and apparatus 10 will provide a display for technician input having input locations for the values which are to be obtained for the specific test. In the prior art the values were handwritten or typed in on paper reports. In one embodiment the input values can be selected from tables of possible input values without any typing by the technician—such as by the technician pointing and clicking a mouse on the selected input value. Point and click from tree type menu system. However, technician has the option to key in input values.

Additionally, for the input screen where there is a possible input that is a calculation from two or more other inputs the method and apparatus 10 can automatically calculate such value from the inputs. In one embodiment inputs for calculated values cannot be inputted by the technician—the method and apparatus 10 calculates these values instead from the relevant inputs.

General Method

In one embodiment, the data displayed includes referring physician order. In one embodiment, the data displayed includes scheduling information. In one embodiment, the data displayed includes study parameters. In one embodiment, the data displayed includes a collection of prior studies relating to the patient.

In one embodiment, a physician reading the reported data on the display can add an interpretation of the data by selecting one of multiple displayed options. As an example, one of the options can include for example "normal" or "abnormal".

In one embodiment, an operator or physician can input new data that relates to the image displayed on the display screen.

In one embodiment, the computer automatically generates a report that contains at least in part any new patient data that was input by a physician or operator.

In one embodiment, the method includes providing a second computer with a second display screen and making the report available to the second computer on the second computer display screen.

In one embodiment, the display data can be modified by a physician who is operating the computer.

In one embodiment, test data from one or more of the following tests is displayed on the display screen: echocardiogram, halter monitor, perfusion test, stress echocardiogram, stress test, adenosine myocardial perfusion.

In one embodiment, the method includes generating a graph which illustrates a pattern relating to some of the patient data that is a part of the database of the computer.

In one embodiment, the computer and display screen are touch screen operated.

In one embodiment is provided a document generation system for enhancing or replacing the dictation and transcription process. More particularly, a computer-based documentation system is provided which processes document templates in conjunction with pre-defined character strings to generate cardiology reports.

In one embodiment is provided a method and apparatus 10 for report generation in which the contents of a relational database are used to generate a cardiology report. The database can include a plurality of option-text variables for use in preparing a cardiology report, a plurality of variable records for storing pre-defined character strings to replace the option-text variables.

In one embodiment a branching function is provided to the graphical user interface in which selection of a first tier of options will cause branching to a second tier of options, and selection of one or more of the second tier cause character strings to be inserted in the cardiology report. In one embodiment three or more tiers of options can be used.

One embodiment will include a method and apparatus 10 which is an integrated solution for cardiac procedures encompassing one or more of the following: reporting, storing, data mining, retrieving and online-analysis.

In one embodiment data entry for report generation will be through a graphical interface pictorially representing multiple sections of a body organ such as the heart. In one embodiment data input will be pictorially and graphically selected (without keyboard use and having to switch between dialog boxes, tabs or windows). In one embodiment a report on the entire study can be generated from a single screen.

In one embodiment report generation (e.g., report detail component selection) can be by voice activated commands.

In one embodiment report generation can be by touch input screen such as by commercially available touch input screens. For example, the Apple IPHONE® touch input screen.

In one embodiment the method and apparatus 10 will enable capture of predefined data elements in Echocardiography.

In one embodiment related fields in the same and different study modalities (example: ejection fraction from echocardiogram to be compared with ejection fraction from nuclear perfusion scan) can be automatically compared.

In one embodiment a plurality of guidelines for Echocardiogram and/or Nuclear Cardiology are automatically incorporated into the report. In one embodiment hypertext is provided in the report which will direct one to such guidelines. In one embodiment such guidelines are periodically updated in newer versions of the method and apparatus In one embodiment a report is possible report is broken down into a first plurality of reporting segments. In one embodiment one or more of these reporting segments are broken down into a plurality of reporting indices. In one embodiment one or more of these reporting indices are correlated with predefined reporting text.

In one embodiment selecting a particular reporting segment provides access to a plurality of reporting indices or choices. In one embodiment a plurality of reporting indices or choices are correlated with predefined reporting text.

In one embodiment a report can be generated by the user using an input screen to graphically select reporting segments, and then graphically selecting reporting indices.

In one embodiment various measurement data can be inputted and migrated to the method and apparatus 10 via another's measurements.

In one embodiment the method will include the following steps:
  (1) Studies will be initiated by the referring physician
    (a) Option regarding time/date of the study
    (b) Indication for the study
    (c) Insurance information
    (d) If a recent study has been ordered notify the referring physician and verify that the study is needed
    (e) Look at the appropriateness guideline and prompt the physician if not appropriate and to change the diagnosis
  (2) Scheduling component will schedule the study and print a ticket for patient
    (a) Date and time of the study
    (b) Preparations for the study
    (c) Provide a phone number/web address if there is a question
  (3) The system will notify the patient the previous day regarding the study by a phone call
    (a) To-do: Dialing phone number
    (b) To-do: Text to speech
  (4) If patients no shows for the study, a letter will be generated notifying the patient of the absence and urging the patient to reschedule the study. A second letter will be generated for the referring physician notifying the no show.
    (a) Security of emailing the referring physician—HIPAA Rules (OMS Website)
  (5) Study is performed on specified date.
    (a) Technician authenticates—group security policies
    (b) Retrieve previous studies; for review of the technician
    (c) If a value that is different from the last study is being entered, cue the technician
    (d) Based on the values entered, generate conclusion automatically (using Business Rules)
  (6) Study is forwarded to the interpreting physician
    (a) Authenticates
    (b) Retrieves previous studies, normal values for each fields
    (c) Data entry.
    (d) Highlights specific areas that are important for the study based on the diagnosis
    (e) If there is a discrepancy between the values entered by this study and last study prompts the physician.
    (f) Plots graphs of the values
    (g) Highlights abnormal values
    (h) Does calculations as needed based on the values entered.
    (i) Auto-generates conclusions
  (7) Interpreting physician reads the study and completes reporting.
  (8) Study is forwarded to the referring physician.

Coronary Angiogram Modality

In one embodiment method and apparatus 10 can be used to report on an coronary angiogram test. FIGS. 46 through 50 shown this embodiment. In this embodiment a plurality of findings text strings are correlated with actions performed on a three dimensional image of the heart 6100 which is displayed on input screen 600 and articulable by the user submitting the input.

The reporting is performed in a coronary angiogram modality having a three dimensional rotatable and articulable image 6100 of heart (which is see thru) by dragging and dropping various elements representing objects used in a procedure (or a current condition of the heart) on a three dimensional image of the heart.

Objects that can be dragged and dropped into the heart can include include: balloon catheters, intra-coronary stents, bypass graft collateral vessels, and branches of the vessel.

Additionally, the coronary anatomy (the characteristics of the coronary artery) can be changed by direct interaction with the three dimensional image.

A report can dynamically generated based on the selections actions performed in input screen 6100.

Figure 47:
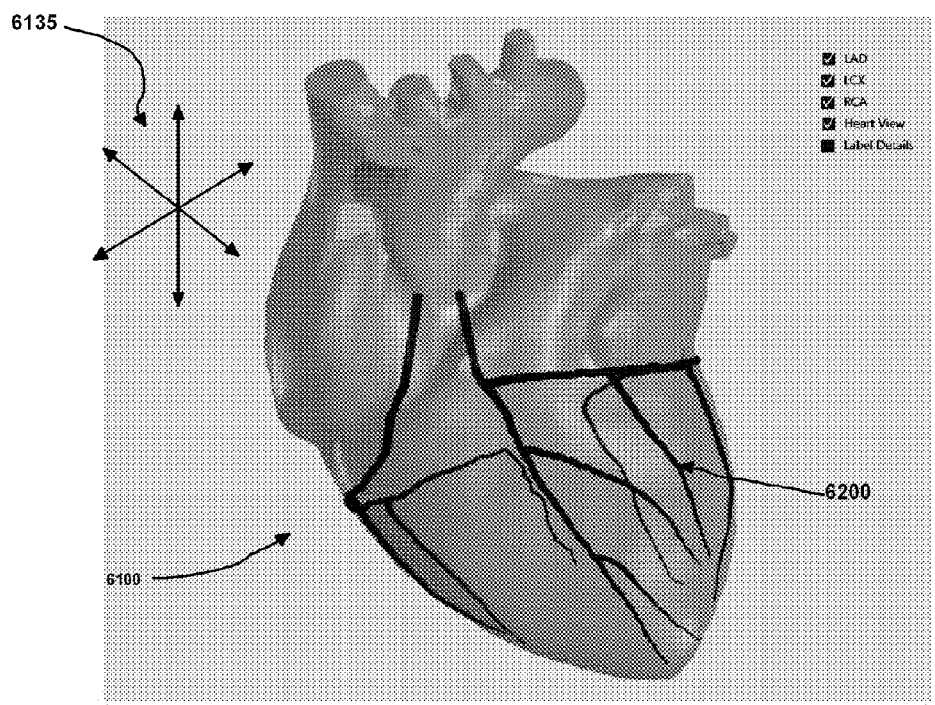

FIG. 47 shows an enlarged view of three dimensional image 6100 of the heart with the baseline coronary arteries 6200. This image 6100 can be graphically manipulated to provide different views to the user 90.

For example, image 6100 can be rotated by left clicking on mouse 70 and dragging (schematically indicated by arrows 6120 and 6130). Image 6100 can be magnified by right clicking and dragging on image 6100. This image 6100 can be rotated by left clicking on the mouse 70 and dragging. The image can be magnified and shrunk by right clicking and dragging on the image (schematically indicated by enlargement and shrinking arrows 6135).

On the left side tool bar 6300 (vertical) represents the objects that can be used to perform manipulation of the baseline coronary artery 3200 structure. From top to bottom the icons include refresh 6310; add stenosis (coronary obstruction) 6320; add balloon catheter 6330; add intracoronary stent 6340; Add button for bypass graft and branches 6350; subtract button for bypass graft and branches 6360; and add piercing 6370.

Figure 48:
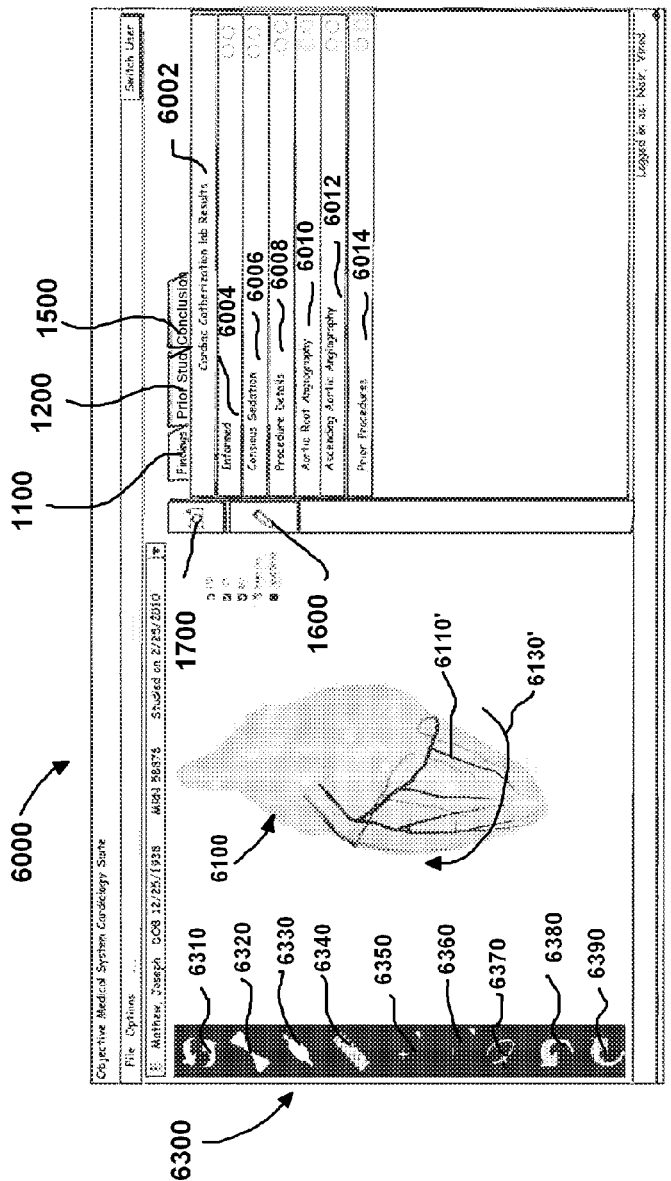

FIG. 48 shows input screen 6000 with a view of three dimensional image 6100 of the heart is rotated by left clicking and dragging the mouse so that Left Circumflex artery can be well visualized (such rotation is schematically indicated by arrow 6130').

Figure 49:
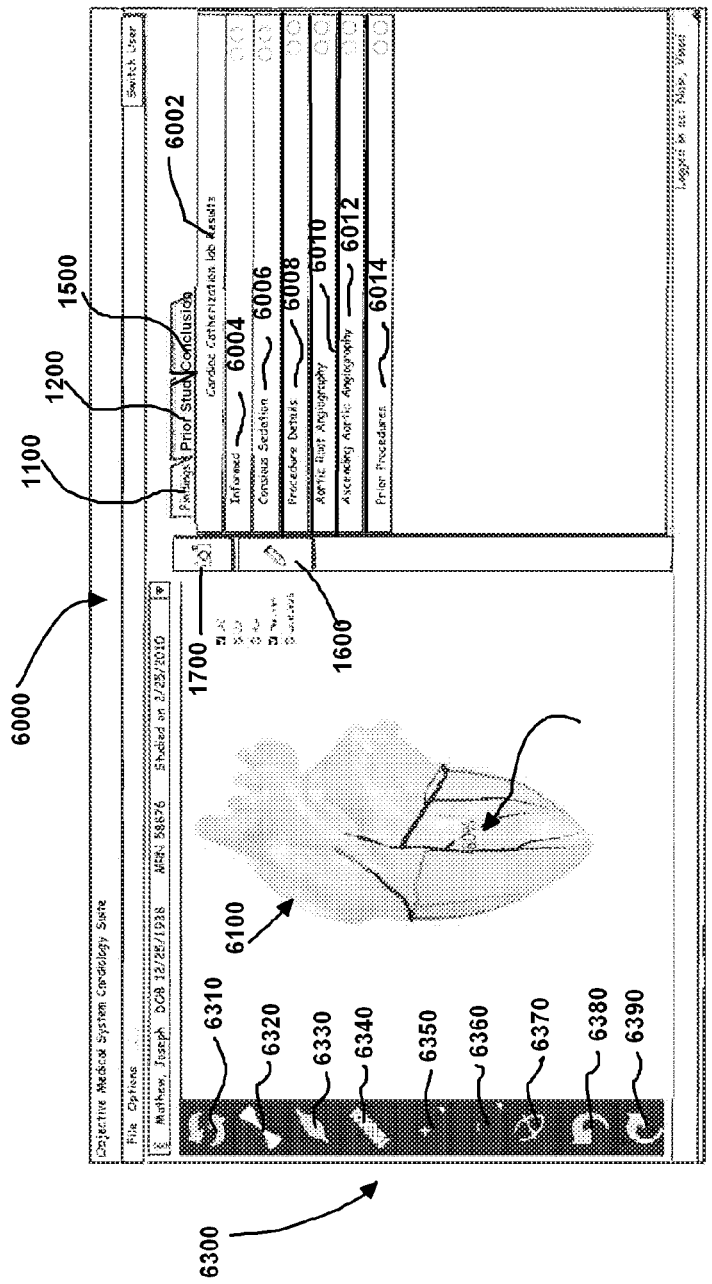

FIG. 49 shows input screen 6000 with image 6100 having a "stenosis object" dragged and dropped (e.g., by clicking on button 6320 and dragging) on to Mid Left Anterior Descending Artery (location identified by the arrow). The stenosis value is set to 80%. Dragging and dropping would would automatically generate the following findings text in the angiogram report.

"Left Anterior Descending Artery

The left anterior descending artery arises from the left aortic cusp.

It gives rise to 2 diagonal branches and 2 septals. Mid LAD is noted to have 80% stenosis."

Figure 50:
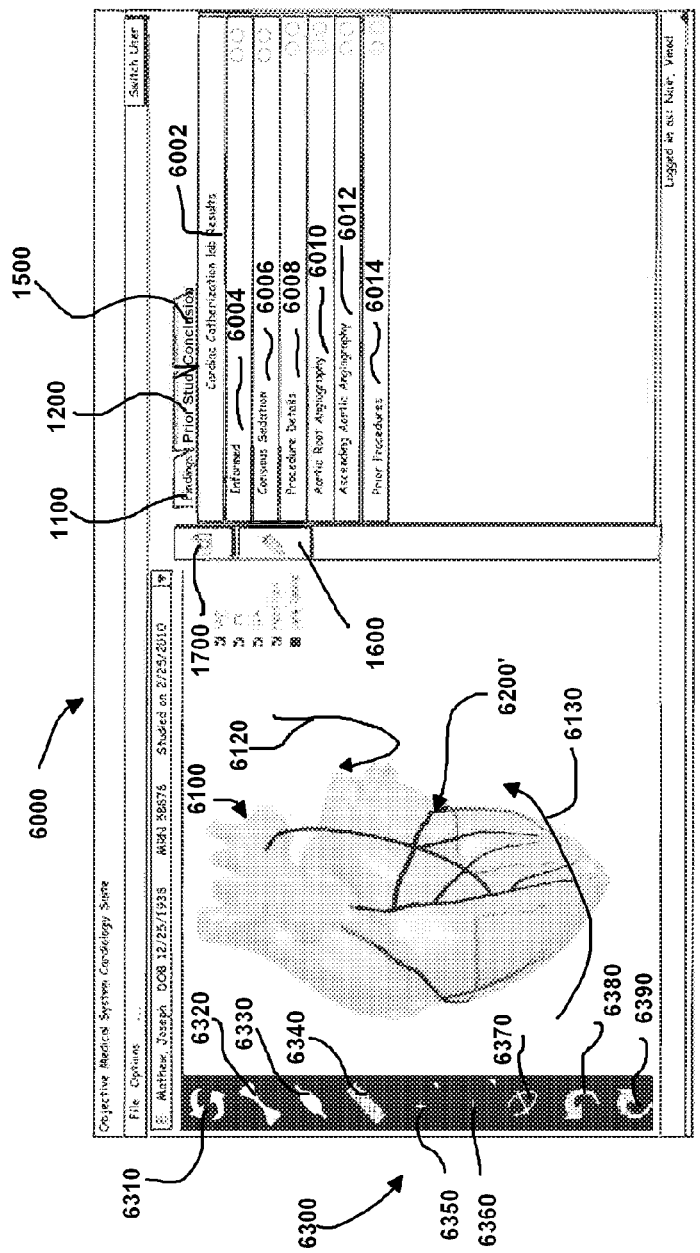

FIG. 50 shows input screen 6000 with a bypass graft was added after selecting (+) button 6350 and choosing add bypass graft (in a drop down menu provide by the method and apparatus). After this action the start point and end point of the graft was added, and this results in the bypass graft to be drawn using three dimensional co-ordinates (i.e., added to the base initial branch set up or baseline arteries 6200). This action will generate a modified set of arteries 6200' on image 6100 along with generating a findings text string in the report specifying the change.

"Bypass Grafts:

1 bypass graft visualized.

Saphenous venous bypass graft to the Mid LAD. The graft is widely patent.'

Using the input screen 6000 and modifications to image 6100 are articulated by the user in input screen, a coronary angiogram can be reported by dragging and dropping objects on the three dimensional images. Tabs 1100, 1200, 15,00, 1600, and 1700 work as in other embodiments. In addition to this, the module incorporates intra, intermodality comparison, trending and guideline based clinical support.

In this embodiment there is one primary reporting structure—Cardiac Catherization lab Results of the heart. Reporting attributes or properties for this primary reporting structure can include Informed Consent 6004; Conscious Sedation 6006; Procedure Details 6008; Aortic Root Angiography 6010; Ascending Aortic Angiography 6012; and Prior Procedures 6014.

In one embodiment, the following reporting selections are available for input report screen 6000 with attributes or properties for the primary reporting structure.

Findings 1100
    Informed Consent 6004
        Obtained
            Obtained from
                Patient
                Family
        Not obtained
            Emergency Nature of Procedure
            Patient Unable to Give Consent
            Legal Guardian Not Available
    Conscious Sedation 6006
        IV Sedation
            Angio Elements
                Element Type
                    Sedation Drug
                    Local Anesthetic
                    Catheter
                    Sheath
                Element Name
        Dose
            ml
            mg
        Adverse Event
            Comment
    Procedure Details 6008
        Access Site
            Right Radial
            Right Brachial
            Right Common Femoral Artery
            Left Radial
            Left Brachial
            Left Common Femoral ARtery
        Sheath Size
        Local Anesthetic
            Angio Elements
                Element Type
                    Sedation Drug
                    Local Anesthetic
                    Catheter
                    Sheath
                Element Name
        Left Coronary Angiography
            Angio Elements
                Element Type
                    Sedation Drug
                    Local Anesthetic
                    Catheter
                    Sheath
                Element Name
        French Size
        Right Coronary Angiography
            Angio Elements
                Element Type
                    Sedation Drug
                    Local Anesthetic
                    Catheter
                    Sheath
                Element Name
        Left Heart Catheterization
        Right Heart Catheterization
        Left Ventriculogram
        Closure Device
            Device Name
                Angio Seal -continued Bypass Graft
Saphenous Venous
  Angio Elements
    Element Type
      Sedation Drug
      Local Anesthetic
      Catheter
      Sheath
    Element Name
LIMA Cannulation
  Angio Elements
    Element Type
      Sedation Drug
      Local Anesthetic
      Catheter
      Sheath
    Element Name
RIMA Cannulation
  Angio Elements
    Element Type
      Sedation Drug
      Local Anesthetic
      Catheter
      Sheath
    Element Name
Left Heart Catheterization
  LV Gram Catheter
  Aortic Valve
  Left Ventriculography
  LV Systolic Pressure_mmHG
  LV Diastolic Pressure_mmHG
  Aortic Systolic Pressure_mmHG
  Aortic Diastolic Pressure_mmHG
  Trans-Aortic Pressure_mmHG
Right Heart Catheterization
  Femoral Vein
    Left Common Femoral Vein
    Right Common Femoral Vein
  Advance
    With Difficulty
    Without Difficulty
  Catheter
  Angio Elements
    Element Type
      Sedation Drug
      Local Anesthetic
      Catheter
      Sheath
    Element Name
  Catheter Size
  Oxygen Saturation Measured
  Cardiac o/p, i/p Measured
    Right Atrial_%
    Right Ventricular_%
    Pulmonary Arterial_%
    Left Ventricular_%
    Central Aortic_%
    Cardiac o/p, i/p Measured
      Method
        Thermodilution Technique
        Flicks Method
      Cardiac Output_Lit/Min
      Cardiac Index_Lit/Min/Meters2
  Right Atrial Mean Pressure_mmHG
  PA Systolic Pressure_mmHG
  PA Diastolic Pressure_mmHG
  PA Mean Pressure_mmHG
  Pulmonary Capillary Mean Pressure_mmHG
Aortic Root Angiography 6010
  Aortic Root Size
    Normal
    Dilated
  Aortic Regurgitation
    Mild
    Moderate
    Severe
    Aneurysmal
Ascending Aortic Angiography 6012
  Ascending Aortic Size
    Normal -continued Mildly Dilated
    Moderately Dilated
    Severely Dilated
    Aneurysmal
Prior Procedures 6014
  CABG
    Area for description
  Valve Surgery
    Area for description The following is a list of reference numerals:

LIST FOR REFERENCE NUMERALS

| (Reference No.) | (Description) |
|---|---|
| 10 | report generation system |
| 20 | computing device |
| 30 | display |
| 40 | keyboard |
| 50 | memory |
| 60 | touch input |
| 70 | pointing device |
| 80 | patient |
| 82 | referring physician |
| 85 | test data |
| 86 | display of cardiology test results |
| 90 | user |
| 100 | graphic input interface |
| 200 | relational database |
| 300 | plurality of anatomical images or views |
| 310 | parasternal long axis view |
| 312 | enlarged image |
| 320 | short axis of left ventricle view |
| 330 | short axis view at the level of the aortic valve |
| 340 | apical two chamber view |
| 350 | four chamber view. |
| 360 | subcostal view |
| 370 | short axis basil |
| 380 | short axis apical |
| 400 | Left Atrium |
| 401 | overall normal |
| 402 | Size |
| 403 | Thrombus |
| 404 | Mass |
| 405 | Catheter |
| 406 | Spontaneous Echo Contrast |
| 407 | Miscellaneous |
| 408 | Remarks |
| 410 | Right Atrium |
| 411 | overall normal |
| 412 | Size |
| 413 | Thrombus |
| 415 | Mass |
| 416 | Catheter |
| 417 | Spontaneous Echo Contrast |
| 418 | Miscellaneous |
| 419 | Remarks |
| 420 | Left Ventricle |
| 421 | overall normal |
| 422 | Size |
| 423 | Systolic Function |
| 424 | Diastolic Function |
| 425 | Wall Motion Analysis |
| 426 | Hypertrophy |
| 427 | Thrombus |
| 428 | Mass |
| 429 | PseudoAneurysm |
| 430 | Miscellaneous |
| 431 | Remarks |
| 432 | Short A Basal |
| 433 | Long Axis |
| 434 | Short Axis Mid |
| 435 | Chamber |
| 436 | Short A Apical |
| 437 | Chamber |

-continued

LIST FOR REFERENCE NUMERALS

| (Reference No.) | (Description) |
|---|---|
| 440 | Right Ventricle |
| 441 | overall normal |
| 442 | Size |
| 443 | Systolic Function |
| 444 | Hypertrophy |
| 445 | Miscellaneous |
| 446 | Remarks |
| 450 | Atrial Septum |
| 451 | overall normal |
| 452 | Atrial Septum Defect |
| 453 | Patent Foramen Ovale |
| 454 | Miscellaneous |
| 455 | Remarks |
| 460 | Ventricular Septum |
| 461 | overall normal |
| 462 | Ventricular Septum Defect |
| 463 | Remarks |
| 470 | Pulmonic Valve |
| 471 | overall normal |
| 472 | Structure |
| 473 | Stenosis |
| 474 | Regurgitation |
| 475 | Doppler |
| 476 | Vegetation |
| 477 | Prosthetic Valve |
| 478 | Valvular Calcification |
| 479 | Remarks |
| 480 | Pulmonary Artery |
| 481 | overall normal |
| 482 | Structure |
| 483 | Dilation |
| 484 | Suspected Pulmonary Embolism |
| 485 | Pulmonary Artery Pressure |
| 486 | Miscellaneous |
| 487 | Remarks |
| 490 | Pulmonary Veins |
| 491 | overall normal |
| 492 | Structure |
| 493 | Thrombus |
| 494 | Mass |
| 495 | Miscellaneous |
| 496 | Remarks |
| 500 | Mitral Valve |
| 501 | overall normal |
| 502 | Structure |
| 503 | Stenosis |
| 504 | Regurgitation |
| 505 | Doppler |
| 506 | M Mode Findings |
| 507 | Vegetation |
| 508 | Abscess |
| 509 | Mitral Valve Annulus |
| 510 | Mitral Valvular Apparatus |
| 511 | Mitral Valve Prolapse |
| 512 | Flail |
| 513 | Cleft |
| 514 | Systolic Anterior Motion of Mitral Leaflets |
| 515 | Prosthetic Valve |
| 516 | Valvular Calcification |
| 517 | Remarks |
| 520 | Inferior Vena Cava |
| 521 | overall normal |
| 522 | IVC Size |
| 523 | IVC Mass |
| 524 | Miscellaneous |
| 525 | Remarks |
| 530 | Aorta |
| 531 | overall normal |
| 532 | Structure |
| 533 | Dilation |
| 534 | Aortic Plaque |
| 535 | Aortic Aneurysm |
| 536 | Aortic Dissection |
| 537 | Intramural Hematoma |
| 538 | False Lumen |
| 539 | Aortic Graft |

-continued

LIST FOR REFERENCE NUMERALS

| (Reference No.) | (Description) |
|---|---|
| 540 | Aortic Coarctation |
| 541 | Miscellaneous |
| 542 | Remarks |
| 550 | Aortic Valve |
| 551 | overall normal |
| 552 | Structure |
| 553 | Stenosis |
| 554 | Regurgitation |
| 555 | Doppler |
| 556 | Vegetation |
| 557 | Abscess |
| 558 | Mass |
| 559 | Prosthetic Valve |
| 560 | Valvular Calcification |
| 561 | Miscellaneous |
| 562 | Remarks |
| 570 | Pericardium |
| 571 | overall normal |
| 572 | Pericardial Effusion |
| 573 | Pericardial Mass |
| 574 | Excessive Respiratory Variation |
| 575 | Miscellaneous |
| 576 | Remarks |
| 580 | Tricuspid Valve |
| 581 | overall normal |
| 582 | Structure |
| 583 | Stenosis |
| 584 | Regurgitation |
| 585 | Prolapse |
| 586 | Ruptured Chordae |
| 587 | Doppler |
| 588 | Vegetation |
| 589 | Prosthetic Valve |
| 590 | Valvular Calcification |
| 591 | Remarks |
| 1000 | tabular navigation bar |
| 1100 | findings tab |
| 1200 | prior studies tab |
| 1202 | conclusion input display |
| 1210 | text string 1 |
| 1212 | select area for text string 1 |
| 1220 | text string 2 |
| 1222 | select area for text string 2 |
| 1250 | pop up graphic showing text from previous study for subject primary reporting structure for same modality |
| 1500 | conclusions tab |
| 1502 | conclusions input display |
| 1510 | text string 1 |
| 1512 | select area for text string 1 |
| 1520 | text string 2 |
| 1522 | select area for text string 2 |
| 1600 | report view tab |
| 1610 | preview screen for report |
| 1620 | Demographic information |
| 1630 | Findings |
| 1635 | Findings String for PRS1 |
| 1637 | Text String for PRS1 |
| 1640 | Findings String for PRS2 |
| 1642 | Text String for PRS2 |
| 1645 | Findings String for PRS3 |
| 1647 | Text String for PRS3 |
| 1650 | Findings String for PRS4 |
| 1652 | Text String for PRS4 |
| 1660 | Conclusions Section |
| 1662 | First Imported Conclusion |
| 1668 | Second Imported Conclusion |
| 1670 | Free Drafted Conclusion |
| 1700 | anatomical image/view |
| 1800 | Comparison String Section |
| 1810 | Comparison String 1 |
| 1820 | Comparison String 2 |
| 1830 | Comparison String 3 |
| 1900 | Measurement Section of Report |
| 2000 | pop up findings box |
| 2010 | first area |
| 2020 | second area |

LIST FOR REFERENCE NUMERALS

| (Reference No.) | (Description) |
|---|---|
| 2030 | symbol |
| 3000 | preview screen for report |
| 3010 | final report |
| 3020 | Demographic information |
| 3030 | Findings |
| 3035 | Findings String for PRS1 |
| 3037 | Text String for PRS1 |
| 3040 | Findings String for PRS2 |
| 3042 | Text String for PRS2 |
| 3045 | Findings String for PRS3 |
| 3047 | Text String for PRS3 |
| 3050 | Findings String for PRS4 |
| 3052 | Text String for PRS4 |
| 3100 | Comparison |
| 3110 | Comparison String 1 |
| 3120 | Comparison String 2 |
| 3130 | Comparison String 3 |
| 4000 | Pop up summary version of identified applicable guideline |
| 4500 | study details section of screen for appointment scheduling |
| 4510 | selection of study from set of studies |
| 4512 | chosen study to be scheduled |
| 4520 | selection of indicator from set of acceptable indicators for study to be scheduled |
| 4530 | Add Study button |
| 4550 | set of acceptable indicators for study requested to be scheduled |
| 4560 | name of study requested to be scheduled |
| 4562 | requested date for scheduling study |
| 4570 | request to be notified when study is actually scheduled |
| 4580 | request to be notified when a report on study is completed |
| 4600 | patient receipt for a study that has been requested to be scheduled |
| 5000 | study scheduling inputting screen |
| 5100 | Indication of whether Appointment for study has actually been scheduled |
| 5200 | appointment time |
| 5300 | indicator that report on study has been made and is available |
| 6000 | input screen |
| 6002 | Cardiac Catherization lab Results |
| 6004 | Informed Consent |
| 6006 | Conscious Sedation |
| 6008 | Procedure Details |
| 6010 | Aortic Root Angiography |
| 6012 | Ascending Aortic Angiography |
| 6014 | Prior Procedures |
| 6100 | three dimensional rotatable and articulable image of heart which is see thru |
| 6110 | see thru portion |
| 6120 | rotation arrow |
| 6130 | rotation arrow |
| 6135 | enlargement and shrinking arrows |
| 6200 | initial branch set up (baseline coronary arteries) |
| 6300 | plurality of modification options |
| 6310 | refresh |
| 6320 | add stenosis (coronary obstruction) |
| 6330 | add balloon catheter |
| 6340 | add intracoronary stent |
| 6350 | add button for bypass graft and branches |
| 6360 | subtract button for bypass graft and branches |
| 6370 | add piercing |

Table of Abbreviations
The following is a list of abbreviations which are used in this application.

| Abbreviation | Description |
|---|---|
| A | Late diastolic filling due to atrial contractions |
| A' | Late diastolic velocity of the mitral annulus |
| Ao | Aorta |
| CHF | Congestive heart failure |
| CI | Cardiac Index |
| CO | Cardiac output |
| D | Diastolic forward flow velocity |
| DT | Deceleration time |
| E | Peak velocity of early diastolic filling of mitral inflow |
| E' | Peak early diastolic velocity of the mitral valve |
| Ea | Mitral annulus early diastolic velocity (same as E) |
| E/A | ratio of E and A velocities |
| ECG | Electrocardiogram |
| IVC | Inferior vena cava |
| IVRT | Isovolumetric contraction time |
| IVCT | Isovolumetric contraction time |
| IAS: | Inter-atrial septum |
| IVS: | Inter-ventricular septum |
| LA: | Left atrium |
| LV: | Left ventricle |
| LVOT: | Left ventricular outflow tract |
| MV | Mitral valve |
| PFO | Patent Foramenovale |
| PHT | Pressure half-time |
| PISA | Proximal isovelocity surface area |
| PW | Posterior wall |
| S | Systolic forward flow velocity |
| S' | Systolic velocity of the mitral annulus |
| SV | Stroke volume |
| SVC | Superior vena cava |
| TEE | Transesophagial echocardiography |
| TTE | Transthoracic echocardiography |
| TVI | Time velocity integral |
| 2D | Two-dimensional |
| VS | Ventricular septum |
| LVEDP: | Left Ventricular End Diastolic Pressure |
| LVH: | Left Ventricular Hypertrophy |
| RA: | Right atrium |
| RV: | Right ventricle |
| PHT: | Pressure Half time |
| SAM: | Systolic Anterior Motion of the Mitral Valve |
| ERO: | Effective Regurgitation Area |
| TGA: | Transposition of the great arteries |

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

| Attribute or Property Selection | Custom Text String to be added to Report Findings |
|---|---|
| Echocardiogram Custom Text | |
| Primary Reporting Structure - Left Atrium | |
| Overall Normal - LeftAtriumIsNormal | Left atrium appears to be normal in size and dimension |
| ChamberSize/NotAssessed | Left atrium size could not be assessed |
| ChamberSize/Normal | Left atrium is normal in size |
| ChamberSize/MildlyIncreased | Left atrium is mildly increased in size |
| ChamberSize/ModeratelyIncreased | Left atrium is moderately increased in size |
| ChamberSize/SeverelyIncreased | Left atrium is severely increased in size |
| ChamberSize/Decreased | Left atrium is decreased in size |
| LeftAtriumDimension | [INPUTTED VALUE] |
| Thrombus/Present | Noted an echo density in the left atrium suggestive of thrombus |
| Thrombus/NotPresent | No evidence of intracavity thrombus noted |
| ThrombusP/ThrombusSize/Small | Thrombus is small in size |
| ThrombusP/ThrombusSize/Moderate | Thrombus is moderate in size |
| ThrombusP/ThrombusSize/Large | Thrombus is large in size |
| ThrombusP/ThrombusLocation/Superior | It is located in the superior aspect of left atrium cavity |
| ThrombusP/ThrombusLocation/Inferior | It is located in the inferior aspect of left atrium cavity |
| ThrombusP/ThrombusLocation/Lateral | It is located in the lateral aspect of left atrium cavity |
| ThrombusP/ThrombusLocation/AtrialSeptum | It is located in the proximity of the atrial septum |
| ThrombusP/ThrombusLocation/FossaOvails | It is located in the proximity of the fossa ovalis |
| ThrombusP/ThrombusLocation/Appendage | It is located in the left atrial appendage |
| ThrombusP/ThrombusShape/Flat | The echodensity is flat in shape |
| ThrombusP/ThrombusShape/Protruding | The echodensity protruding in shape |
| ThrombusP/ThrombusShape/Pedunculated | The echodensity pedunculated |
| ThrombusP/ThrombusShape/Papillary | The echodensity papillary in shape |
| ThrombusP/ThrombusShape/Spherical | The echodensity spherical in shape |
| ThrombusP/ThrombusShape/Regular | The echodensity regular in shape |
| ThrombusP/ThrombusShape/Irregular | The echodensity irregular in shape |
| ThrombusP/ThrombusShape/Multilobular | The echodensity multilobular in shape |
| ThrombusP/ThrombusShape/Infilterating | The echodensity infilterating |
| ThrombusP/ThrombusShape/Frondlike | The echodensity appears to be is frondlike in shape |
| ThrombusP/ThrombusTexture/Calcified | It is of calcified texture |
| ThrombusP/ThrombusTexture/Echogenic | It is of echogenic texture |
| ThrombusP/ThrombusTexture/Hypoechoic | It is of hypoechoic texture |
| ThrombusP/Thrombus/ThrombusTexture/Layered | It is of layered texture |
| ThrombusP/ThrombusTexture/Solid | It is of solid texture |
| ThrombusP/ThrombusMobility/Fixed | The echodensity is fixed |
| ThrombusP/ThrombusMobility/Mobile | The echodensity is mobile |
| Mass/Present | Noted an echo density in the left atrium suggestive of mass |
| Mass/NotPresent | No evidence of intracavity mass noted |
| MassP/MassSize/Small | It is small in size |
| MassP/MassSize/Moderate | It is moderate in size |
| MassP/MassSize/Large | It is large in size |
| MassP/MassLocation/Superior | It is located superior aspect of the left atrial cavity |
| MassP/MassLocation/Inferior | It is located inferior aspect of the left atrial cavity |
| MassP/MassLocation/Lateral | It is located lateral aspect of the left atrial cavity |
| MassP/MassLocation/AtrialSeptum | It is located in the proximity of the atrial septum |
| MassP/MassLocation/FossaOvails | It is located in the proximity of the fossa ovalis |
| MassP/MassLocation/Appendage | It is located in the left atrial appendage |
| MassP/MassShape/Flat | It is flat in shape |
| MassP/MassShape/Protruding | It is protruding in shape |
| MassP/MassShape/Pedunculated | It is pedunculated |
| MassP/MassShape/Papillary | It is papillary in shape |
| MassP/MassShape/Spherical | It is spherical in shape |
| MassP/MassShape/Regular | It is regular in shape |
| MassP/MassShape/Irregular | It is irregular in shape |
| MassP/MassShape/Multilobular | It is multilobular |
| MassP/MassShape/Infilterating | It is infilterating |
| MassP/MassShape/Frondlike | It appears to be frondlike in shape |
| MassP/MassSite/AtrialSeptum | The echodensity is attached to the atrial septum |
| MassP/MassSite/FossaOvails | The echodensity attached to the fossa ovalis |
| MassP/MassSite/Body | The echodensity to the body of left atrium |
| MassP/MassSite/MitralValve | The echodensity to the mitral valve |
| MassP/MassMobility/Fixed | It is fixed |
| MassP/MassMobility/Mobile | It is mobile |
| MassP/MassType/Myxoma | The appearance of the echodensity is suggestive of myxoma |
| MassP/MassType/Papilloma | The appearance of the echodensity is suggestive of papilloma |

| Attribute or Property Selection | Custom Text String to be added to Report Findings |
| --- | --- |
| MassP/MassType/Fibroelastoma | The appearance of the echodensity suggestive of fibroelastoma |
| CatheterP/CatheterLocation/Cavity | It is noted to be in the left atrial cavity |
| CatheterP/CatheterLocation/Appendage | It is noted to be in the left atrial appendage |
| Catheter/Present | Noted a linear echo density in the left atrium, which is suggestive of a catheter |
| Catheter/NotPresent | No evidence of catheter noted, suggestive of spontaneous echo-contrast |
| SpontaneousEcho/Present | An echogenic swirling pattern noted |
| SpontaneousEcho/NotPresent | No evidence of spontaneous echo contrast noted |
| SpontaneousEchoP/SpontaneousLocation/Cavity | Spontaneous echo contrast is noted in the left atrial cavity |
| SpontaneousEchoP/SpontaneousLocation/Appendage | Spontaneous echo contrast is noted in the left atrial appendage |
| SpontaneousEchoP/SpontaneousCavityAndAppendage | Spontaneous echo contrast is noted in the left atrial cavity and appendage |
| SpontaneousEchoP/SpontaneousSeverity/Mild | The echo-contrast is mild in severity |
| SpontaneousEchoP/SpontaneousSeverity/MildToModerate | The echo-contrast is mild to moderate in severity |
| SpontaneousEchoP/SpontaneousSeverity/Moderate | The echo-contrast is moderate in severity |
| SpontaneousEchoP/SpontaneousSeverity/ModerateToSevere | Moderately severe echo-contrast is noted |
| SpontaneousEchoP/SpontaneousSeverity/Severe | Severe echo-contrast is noted |
| Miscellaneous/Cortriatriatum | Left atrial appearance of cor-triatriatum |
| Primary Reporting Structure - Right Atrium | |
| Overall Normal - RightAtriumisNormal | Right atrium is Normal |
| ChamberSize/NotAssessed | Right atrial size could not be assessed |
| ChamberSize/Normal | Right atrium is normal in size |
| ChamberSize/MildlyIncreased | Right atrium is mildly increased in size |
| ChamberSize/ModeratelyIncreased | Right atrium is moderately increased in size |
| ChamberSize/SeverelyIncreased | Right atrium is severely increased in size |
| ChamberSize/Decreased | Right atrium is decreased in size |
| Chamber Size/RightAtriumDimension | [INPUTTED VALUE] |
| Thrombus/Present | Noted an echo density in the right atrium suggestive of thrombus |
| Thrombus/NotPresent | No evidence of Intracavity thrombus noted |
| ThrombusP/ThrombusSize/Small | The echodensity is small in size |
| ThrombusP/ThrombusSize/Moderate | The echodensity is moderate in size |
| ThrombusP/ThrombusSize/Large | The echodensity is large in size |
| ThrombusP/ThrombusLocation/Extenting | It is noted to extend from Inferior vena cava |
| ThrombusP/ThrombusLocation/Cavity | It is noted in the right atrial cavity |
| ThrombusP/ThrombusLocation/Appendage | It is noted in the right atrial appendage |
| ThrombusP/ThrombusShape/Flat | The echodensity is flat in shape |
| ThrombusP/ThrombusShape/Protruding | The echodensity is protruding in shape |
| ThrombusP/ThrombusShape/Pedunculated | The echodensity is pedunculated |
| ThrombusP/ThrombusShape/Papillary | The echodensity is papillary in shape |
| ThrombusP/ThrombusShape/Spherical | The echodensity is spherical in shape |
| ThrombusP/ThrombusP/ThrombusShape/Regular | The echodensity is regular in shape |
| ThrombusP/ThrombusShape/Irregular | The echodensity is irregular in shape |
| ThrombusP/ThrombusShape/Multilobular | The echodensity is multilobular |
| ThrombusP/ThrombusShape/Infilterating | The echodensity is infilterating |
| ThrombusP/ThrombusShape/Frondlike | The echodensity appears to be is frondlike |
| ThrombusP/ThrombusTexture/Calcified | It is of calcified texture |
| ThrombusP/ThrombusTexture/Echogenic | It appears to be echogenic |
| ThrombusP/ThrombusTexture/Hypoechoic | It appears to be hypoechoic |
| ThrombusP/ThrombusTexture/Layered | It appears to be layered |
| ThrombusP/ThrombusTexture/Solid | It appears to be solid |
| ThrombusP/ThrombusMobility/Fixed | The echo-density is fixed |
| ThrombusP/ThrombusMobility/Mobile | The echo-density is mobile |
| Mass/Present | Noted an echo density in the right atrium suggestive of mass |
| Mass/NotPresent | No evidence of intracavity mass noted |
| MassP/MassSize/Small | The echodensity is small in size |
| MassP/MassSize/Moderate | The echodensity is moderate in size |
| MassP/MassSize/Large | The echodensity is large in size |
| MassP/MassLocation/Extenting | It extends from Inferior vena cava |
| MassP/MassLocation/Cavity | It is located in the right atrial cavity |
| MassP/MassLocation/Appendage | It is located in the right atrial appendage |
| MassP/MassShape/Flat | It is flat in shape |
| MassP/MassShape/Protruding | It appears to be protruding |
| MassP/MassShape/Pedunculated | It appears to be pedunculated |
| MassP/MassShape/Papillary | It appears to be papillary |
| MassP/MassShape/Spherical | It appears to be spherical |
| MassP/MassShape/Regular | It appears to be regular in shape |
| MassP/MassShape/Irregular | It appears to be irregular in shape |
| MassP/MassShape/Multilobular | It appears to be multilobular |
| MassP/MassShape/Infilterating | It appears to be infilterating |
| MassP/MassShape/Frondlike | It appears to be frondlike |
| MassP/MassMobility/Fixed | The echodensity is fixed |

-continued

| Attribute or Property Selection | Custom Text String to be added to Report Findings |
|---|---|
| MassP/MassMobility/Mobile | The echodensity is mobile |
| MassP/MassType/Myxoma | The appearance is suggestive of myxoma |
| MassP/MassType/Papilloma | The appearance is suggestive of papilloma |
| MassP/MassType/Fibroelastoma | The appearance is suggestive of fibroelastoma |
| CatheterP/CatheterLocation/Cavity | It is noted to be in the right atrial cavity |
| CatheterP/CatheterLocation/Appendage | It is noted to be in the right atrial appendage |
| Catheter/Present | Noted a linear echo density in the right atrium, which is suggestive of a catheter |
| Catheter/NotPresent | No evidence of catheter noted |
| Pacemaker/PacemakerLocation/Cavity | Noted a linear echo density in the right atrial cavity, which is suggestive of pacemaker lead |
| Pacemaker/PacemakerLocation/Appendage | Noted a linear echo density in the right atrial appendage, which is suggestive of pacemaker lead |
| SpontaneousEcho/Present | An echogenic swirling pattern noted, suggestive of spontaneous echo-contrast |
| SpontaneousEcho/NotPresent | No evidence of spontaneous echo contrast noted |
| SpontaneousEchoP/SpontaneousLocation/Cavity | It is noted in the right atrial cavity |
| SpontaneousEchoP/SpontaneousLocation/Appendage | It is noted in the right atrial appendage |
| SpontaneousEchoP/SpontaneousCavityAndAppendage | It is noted in the right atrial cavity and appendage |
| SpontaneousEchoP/SpontaneousSeverity/Mild | It is mild in severity |
| SpontaneousEchoP/SpontaneousSeverity/MildToModerate | It is mild to moderate in severity |
| SpontaneousEchoP/SpontaneousSeverity/Moderate | It is moderate in severity |
| SpontaneousEchoP/SpontaneousSeverity/ModerateToSevere | It is moderate to severe in severity |
| SpontaneousEchoP/SpontaneousSeverity/Severe | It is severe in severity |
| Miscellaneous/DilatedCoronarySinus | Noted dilated coronary sinus, this is consistent with elevated right atrial pressure or a persistent left superior vena cava |
| Miscellaneous/DilatedHepaticVeins | Noted dilated hepatic with is increased to right atrial pressure |
| Miscella neous/DilatedIVC | Noted dilated inferior vena cava with poor inspiratory collapse, this is consistent with elevated right atrial pressure |
| Miscellaneous/InterAtrialSeptum | Noted bowing of the inter atrial septum to the left, this is consistant with increased right atrial pressure |
| Miscellaneous/PressureElevated | Noted elevated right atrial pressure |
| Miscellaneous/ProminantEustachian | Noted prominant eustachian valve |
| Miscellaneous/ProminantChiari | Noted prominant chiari network |
| Miscellaneous/HyoplasticRightAtrium | Noted hyoplastic right atrium |
| Miscellaneous/CardiacTransplantAppearance | Noted cardiac transplant appearance |
| Primary Reporting Structure - Left Ventricle ||
| Overall Normal - LeftVentricleIsNormal | Left ventricle appears to be normal in size and dimension |
| ChamberSize/NotAssessed | Left ventricle size could not be assessed |
| ChamberSize/Normal | Left ventricular size is normal |
| ChamberSize/MildlyIncreased | Left ventricle is mildly increased in size |
| ChamberSize/ModeratlyIncreased | Left ventricle is moderately increased in size |
| ChamberSize/SeverelyIncreased | Left ventricle is severely increased in size |
| ChamberSize/Decreased | Left ventricle is decreased in size |
| ChamberSize/LVEndDiastolicDimension | [INPUTTED VALUE] |
| ChamberSize/LVEndSystolicDimension | [INPUTTED VALUE] |
| ChamberSize/LVEndDiastolicSeptalThickness | [INPUTTED VALUE] |
| ChamberSize/LVEndDiastolicPosteroBasalFreeWallThickness | [INPUTTED VALUE] |
| ChamberSize/LeftVentricular/Mass | [INPUTTED VALUE] |
| ChamberSize/LeftVentricular/MassIndex | [CALCULATED VALUE] |
| Systolic Function/Global/Borderline | Borderline left ventricular systolic dysfunction is noted |
| Systolic Function/Global/Hyperdynamic | Hyperdynamic left ventricular systolic function is noted |
| Systolic Function/Global/MildlyDecreased | Left ventricular systolic function is mildly decreased |
| Systolic Function/Global/ModeratelyDecreased | Left ventricular systolic function is moderately decreased |
| Systolic Function/Global/Normal | Left ventricular systolic function is normal |
| Systolic Function/Global/SeverelyDecreased | Left ventricular systolic function is severely decreased |
| SystolicFunction/Present | |
| SystolicFunction/NotPresent | |
| LVFractionalShortening | |
| LVEjectionFraction | |
| WallMotionAbnormallty/Present | |
| WallMotionAbnormality/NotPresent | |

-continued

| Attribute or Property Selection | Custom Text String to be added to Report Findings |
|---|---|
| LVWallMotionScoreIndex | Calculated Wall Motion Score Index (WMSI) is |
| LVAbnorma l/SeptalMotion/ExcessiveRespiratoryChange | Noted evidence of excessive respiratory change of the septum |
| LVAbnormal/SeptalMotion/FlattenedInDiastole | Left ventricular septum flattens in diastoly |
| LVAbnormal/SeptalMotion/FlattenedInSystole | Left ventricular septum flattens in systoly |
| LVAbnormal/SeptalMotion/FlattenedInSystoleAndDiastole | Left ventricular septum flattens in both systoly and diastoly |
| LVAbnormal/SeptalMotion/Paradoxical/PreExcitation | The ventricular septum exhibits paradoxical motion, suggestive of pre excitation |
| LVAbnormal/SeptalMotion/Paradoxical/RVPacemaker | The ventricular septum exhibits paradoxical motion, suggestive of left ventricular pacemaker |
| LVAbnormal/SeptalMotion/Paradoxical/RVVolumeOrPressureOverload | The ventricular septum exhibits paradoxical motion, suggestive of left ventricular pressure and or volume overload |
| LVAbnormal/SeptalMotion/SeptalBounce | Noted evidence of septal bounce |
| LVAbnormal/SeptalMotion/Paradoxical/LeftBundleBranchBlock | The ventricular septum exhibits paradoxical motion, suggestive of left bundle branch block |
| LVAbnormal/SeptalMotion/Paradoxical/PostOperativeStatus | The ventricular septum exhibits paradoxical motion, suggestive of post operative status |
| LVHypertrophy/Present | Noted left ventricular hypertrophy |
| LVHypertrophy/NotPresent | No evidence of left ventricular hypertrophy |
| LVAsymmetric/AnteriorHypertrophy | Asymmetric anterior left ventricular hypertrophy is noted |
| LVAsymmetric/ApicalHypertrophy | Asymmetric apical left ventricular hypertrophy is noted |
| LVAsymmetric/BasalHypertrophy | Asymmetric basal left ventricular hypertrophy is noted |
| LVAsymmetric/LateralHypertophy | Asymmetric lateral left ventricular hypertrophy is noted |
| LVAsymmetric/PosteriorHypertrophy | Asymmetric posterior left ventricular hypertrophy is noted |
| LVAsymmetric/SeptalHypertrophy | Asymmetric septal left ventricular hypertrophy is noted |
| LVEccentricHypertrophy | Eccentric left ventricular hypertrophy is noted |
| LVConcentricHypertrophy | Concentric left ventricular hypertrophy is noted |
| Hypertrophy/SeverityMild | Hypertrophy is mild in severity |
| HypertrophySeverity/MildToModerate | Hypertrophy is mild to moderate in severity |
| HypertrophySeverity/Moderate | Hypertrophy is moderate in severity |
| HypertrophySeverity/ModerateToSevere | Moderate to severe hypertrophy is noted |
| HypertrophySeverity/Severe | Severe hypertrophy is noted |
| LVThrombus/Present | Noted an echo density in the left ventricle suggestive of thrombus |
| LVThrombus/NotPresent | No evidence of Intracavity thrombus noted |
| LVThrombusSize/Small | The echo-density is small in size |
| LVThrombusSize/Moderate | The echo-density is moderate in size |
| LVThrombusSize/Large | The echo-density is severe in size |
| LVThrombusLocation/Apical | It is located at the apex of left ventricle |
| LVThrombusLocation/Basal | It is located at the base of left ventricle |
| LVThrombusLocation/Lateral | It is noted along the left ventricle lateral wall |
| LVThrombusLocation/Septal | It is noted along the left ventricular septum |
| LVThrombusShape/Flat | The echo-density is flat |
| LVThrombusShape/Protruding | The echo-density is protruding |
| LVThrombusShape/Pedunculated | The echo-density is pedunculated |
| LVThrombusShape/Papillary | The echo-density is papillary |
| LVThrombusShape/Spherical | The echo-density is spherical |
| LVThrombusShape/Regular | The echo-density is regular in shape |

| Attribute or Property Selection | Custom Text String to be added to Report Findings |
|---|---|
| LVThrombusShape/Irregular | The echo-density is irregular in shape |
| LVThrombusShape/Multilobular | The echo-density is multilobular |
| LVThrombusShape/Infilterating | The echo-density appears to be infilterating |
| LVThrombusShape/Frondlike | The echo-density appears to be frondlike |
| LVThrombusTexture/Calcified | The echo-density is of calcified |
| LVThrombusTexture/Echogenic | It is echogenic |
| LVThrombusTexture/Hypoechoic | It is hypoechoic |
| LVThrombusTexture/Layered | The echo-density appears to be layered |
| LVThrombusTexture/Solid | The echo-density appears to be solid |
| LVThrombusMobility/Fixed | The echo-density is fixed |
| LVThrombusMobility/Mobile | The echo-density is mobile |
| LVMass/Present | Noted an echo density in the left ventricle suggestive of mass |
| LVMass/NotPresent | No evidence of intracavity mass noted |
| LVMass/LVMassSize/Small | The echo-density is small in size |
| LVMassSize/Moderate | The echo-density is moderate in size |
| LVMass/LVMassSize/Large | The echo-density is large in size |
| LVMass/LVMassLocation/Apical | It is located at the apex of left ventricle |
| LVMass/LVMassLocation/Basal | It is located at the base of left ventricle |
| LVMass/LVMassLocation/Lateral | It is noted along the left ventricle lateral wall |
| LVMass/LVMassLocation/Septal | It is noted along the left ventricular septum |
| LVMass/LVMassShape/Flat | The echo-density appears to be flat |
| LVMass/LVMassShape/Protruding | The echo-density appears to be protruding |
| LVMass/LVMassShape/Pedunculated | The echo-density appears to be pedunculated |
| LVMass/LVMassShape/Papillary | The echo-density appears to be papillary |
| LVMass/LVMassShape/Spherical | The echo-density appears to be is spherical |
| LVMass/LVMassShape/Regular | The echo-density appears to be regular in shape |
| LVMass/LVMassShape/Irregular | The echo-density appears to be irregular in shape |
| LVMass/LVMassShape/Multilobular | The echo-density appears to be multilobular |
| LVMass/LVMassShape/Infilterating | The echo-density appears to be infilterating |
| LVMass/LVMassShape/Frondlike | The echo-density appears to be frondlike |
| LVMass/LVMassMobility/Fixed | The echo-density is fixed |
| LVMass/LVMassMobility/Mobile | The echo-density is mobile |
| LVMass/LVMassTexture/Calcified | It appears to be calcified |
| LVMass/LVMassTexture/Echogenic | It appears to be echogenic |
| LVMass/LVMassTexture/Hypoechoic | It appears to be hypoechoic |
| LVMass/LVMassTexture/Layered | The echo-density is layered |
| LVMass/LVMassTexture/Solid | The echo-density is solid |
| LVPseudoAneurysm/Present | Noted left ventricular pseudo aneurysm |
| LVPseudoAneurysm/NotPresent | No evidence of left ventricular pseudo aneurysm |
| LVPseudoAneurysm/LVPseudoAneurysmType/Apical | Pseudoaneurysm of the left ventricular apical segment is noted |
| LVPseudoAneurysm/LVPseudoAneurysmType/Anterior | Pseudoaneurysm of the anterior left ventricular wall is noted |
| LVPseudoAneurysm/LVPseudoAneurysmType/Basal | Pseudoaneurysm of the left ventricular basal segment is noted |
| LVPseudoAneurysm/LVPseudoAneurysmType/Inferior | Pseudoaneurysm of the inferior left ventricular wall is noted |
| LVPseudoAneurysm/LVPseudoAneurysmType/Lateral | Pseudoaneurysm of the left ventricular lateral segment is noted |
| LVPseudoAneurysm/LVPseudoAneurysmType/Posterior | Pseudoaneurysm of the posterior left ventricular wall is noted |
| LVPseudoAneurysm/LVPseudoAneurysmType/Septal | Pseudoaneurysm of the left ventricular septum is noted |

| Attribute or Property Selection | Custom Text String to be added to Report Findings |
|---|---|
| Primary Reporting Structure - Right Ventricle | |
| Overall Normal - IsNormal | Right ventricle appears to be normal in size and dimension |
| ChamberSize/NotAssessed | Right ventricle size could not be assessed |
| ChamberSize/Normal | Right ventricle is normal in size |
| ChamberSize/MildlyIncreased | Right ventricle is mildly increased in size |
| ChamberSize/ModeratelyIncreased | Right ventricle is moderately increased in size |
| ChamberSize/SeverelyIncreased | Right ventricle is severely increased in size |
| ChamberSize/Decreased | Right ventricle is decreased in size |
| SystolicFunction/Present | |
| SystolicFunction/NotPresent | |
| SystolicFunctionP/RightVentricleGlobal/Borderline | Borderline right ventricular systolic function is noted |
| SystolicFunctionP/RightVentricleGlobal/Hyperdynamic | Hyperdynamic right ventricular systolic function is noted |
| SystolicFunctionP/RightVentricleGlobal/MildlyDecreased | Mildly decreased right ventricular systolic function is noted |
| SystolicFunctionP/RightVentricleGlobal/ModeratelyDecreased | Moderately decreased right ventricular systolic function is noted |
| SystolicFunctionP/RightVentricleGlobal/Normal | Right ventricular systolic function is normal |
| SystolicFunctionP/RightVentricleGlobal/SeverelyDecreased | Severely decreased right ventricular systolic function is noted |
| SystolicFunctionP/SeptumSegmentalAbnormality/Excessive RespiratoryChange | Noted evidence of excessive respiratory change of the septum |
| SystolicFunctionP/SeptumSegmentalAbnormality/FlattenedInDiastole | Right ventricular septum flattens in diastoly |
| SystolicFunctionP/SeptumSegmentalAbnormality/FlattenedInSystole | Right ventricular septum flattens in systoly |
| SystolicFunctionP/SeptumSegmentalAbnormality/FlattenedInSystoleAndDiastole | Right ventricular septum flattens in both systoly and diastoly |
| SystolicFunctionP/SeptumSegmentalAbnormality/ParadoxicalPreExcitation | The ventricular septum exhibits paradoxical motion, suggestive of pre excitation |
| SystoticFunctionP/SeptumSegmentalAbnormality/ParadoxicalRVPacemaker | The ventricular septum exhibits paradoxical motion, suggestive of right ventricular pacemaker |
| SystolicFunctionP/SeptumSegmentalAbnormality/ ParadoxicalRVVolumeOrPressureOverload | The ventricular septum exhibits paradoxical motion, suggestive of right ventricular pressure and or volume overload |
| SystolicFunctionP/SeptumSegmentalAbnormality/SeptalBounce | Noted evidence of septal bounce, suggestive of left bundle branch block |
| SystolicFunctionP/SeptumSegmentalAbnormality/ ParadoxicalLeftBundleBranchBlock | The ventricular septum exhibits paradoxical motion, suggestive of post operative status |
| SystolicFunctionP/SeptumSegmentalAbnormality/ ParadoxicalPostOperativeStatus | The ventricular septum exhibits paradoxical motion |
| SystolicFunctionP/FreewallSegmentalAbnormality/Akinesis | Right ventricular freewall is akinetic |
| SystolicFunctionP/FreewallSegmentalAbnormality/Aneurysmal | Right ventricular freewall is aneurysmal |
| SystolicFunctionP/FreewallSegmentalAbnormality/Dyskinesis | Dyskinesis of the right ventricular free wall is noted |
| SystolicFunctionP/FreewallSegmentalAbnormality/MildHypokinesis | Right ventricular freewall is mildly hypokinetic |
| SystolicFunctionP/FreewallSegmentalAbnormality/ModerateHypoldnesis | Right ventricular freewall is moderately hypokinetic |
| SystolicFunctionP/FreewallSegmentalAbnormality/SevereHypokinesis | Right ventricular freewall is severely hypokinetic |
| SystolicFunctionP/LaterwallSegmentalAbnormality/Akinesis | Akinesis of the right ventricular lateral wall is noted |
| SystolicFunctionP/LaterwallSegmentalAbnormality/Aneurysmal | Right ventricular lateral wall is aneurysmal |
| SystolicFunctionP/LaterwallSegmentalAbnormality/Dyskinesis | Dyskinesis of the right ventricular lateral wall is noted |
| SystolicFunctionP/LaterwallSegmentalAbnormality/MildHypokinesis | Mild hypokinesis of the right ventricular lateral wall is noted |
| SystolicFunctionP/LaterwallSegmentalAbnormality/ModerateHypokinesis | Moderate hypokinesis of the right ventricular lateral wall is noted |
| SystolicFunctionP/LaterwallSegmentalAbnormality/SevereHypokinesis | Severe hypokinesis of the right ventricular lateral wall is noted |
| HypertrophySeverity/Mild | Mild RV hypertrophy noted |

| Attribute or Property Selection | Custom Text String to be added to Report Findings |
|---|---|
| HypertrophySeverityMildToModerate | Mild to moderate RV hypertrophy noted |
| HypertrophySeverity/Moderate | Moderate RV hypertrophy noted |
| HypertrophySeverity/ModerateToSevere | Moderate to severe RV hypertrophy noted |
| HypertrophySeverity/Severe | Severe RV hypertrophy noted |
| Miscellaneous/RVCorPulmonale | Noted evidence of cor-pulmonale |
| MIscellaneous/RVDysplasia | Noted evidence of RV dysplasia |
| Miscellaneous/RVInfarction | RV Dilatataion with evidence of hypokinesis of the RV freewall is noted and this is suggestive of RV infarction |
| Primary Reporting Structure - Mitral Valve ||
| Overall Normal - IsNormal | Mitral valve is normal |
| Prolapse/Present | Noted prolapse of the mitral valve |
| Prolapse/NotPresent | No evidence of prolapse in mitral valve noted |
| Prolapse/Leaflets/Anterior | Prolapse of the anterior leaflet is noted |
| Prolapse/Leaflets/Posterior | Prolapse of the posterior leaflet is noted |
| Prolapse/Leaflets/AnteriorAndPosterior | Both anterior and posterior leaflet is noted |
| Prolapse/Severity/Mild | Mild prolapse of the mitral valve is noted |
| Prolapse/Severity/MildToModerate | Mild to moderate prolapse of the mitral valve is noted |
| Prolapse/Severity/ModerateToSevere | Moderate to severe prolapse of the mitral valve is noted |
| Prolapse/Severity/Moderate | Moderate prolapse of the mitral valve is noted |
| Prolapse/Severity/Severe | Severe prolapse of the mitral valve is noted |
| Prolapse/Phase/Holosystolic | The prolapse is holosystolic |
| Prolapse/Phase/LateSystolic | The prolapse is latesystolic |
| Prolapsed/Anterior/MedialSegment | The anterior medial segment is involved in the prolapse |
| Prolapsed/Anterior/MiddleSegment | The anterior middle segment is involved in the prolapse |
| Prolapsed/Anterior/LateralSegment | The anterior lateral segment is involved in the prolapse |
| Prolapsed/Posterior/MedialScallop | The posterior medial scallop segment is involved in the prolapse |
| Prolapsed/Posterior/MiddleScallop | The posterior middle scallop segment is involved in the prolapse |
| Prolapsed/Posterior/LateralScallop | The posterior lateral scallop segment is involved in the prolapse |
| Flail/Present | Flail present |
| Flail/NotPresent | Flail not present |
| Flail/Leaflets/Anterior | The anterior leaflet is flailing |
| Flail/Leaflets/Posterior | The posterior leaflet is flailing |
| Flail/Leaflets/AnteriorAndPosterior | Both anterior and posterior leaflet is flailing |
| Flail/Severity/Mild | Mild flailing of the mitral leaflet noted |
| Flall/Severity/MildToModerate | Mild to moderate flailing of the mitral leaflet noted |
| Flail/Severity/Moderate | Moderate flailing of the mitral leaflet noted |
| Flail/Severity/ModerateToSevere | Moderate to severe flailing of the mitral leaflet noted |
| Flail/Severity/Severe | Severe flailing of the mitral leaflet noted |
| Flail/Anterior/MedialSegment | The anterior medial segment is involved in the flail |
| Flail/Anterior/MiddleSegment | The anterior middle segment is involved in the flail |
| Flail/Anterior/LateralSegment | The anterior lateral segment is involved in the flail |
| Flail/Posterior/MedialScallop | The posterior medial scallop segment is involved in the flail |
| Flail/Posterior/MiddleScallop | The posterior middle scallop segment is involved in the flail |
| Flail/Posterior/Lateral Scallop | The posterior lateral scallop segment is involved in the flail |
| Ruptured/Present | Ruptured chordae present |
| Ruptured/NotPresent | Ruptured chordae not present |
| Ruptured/Leaflets/Anterior | Noted ruptured of the anterior chordae |
| Ruptured/Leaflets/Posterior | Noted ruptured of the posterior chordae |
| Ruptured/Leaflets/Ante riorAndPosterior | Noted ruptured of the anterior and posterior chordae |
| Chordal/Shortening | Noted evidence of chordal shortening |
| Chordal/Fusion | Noted evidence of chordal fusion |
| Leaflet/Elongation/Present | Leaflet elongation present |
| Leaflet/Elongatlon/NotPresent | Leaflet elongation not present |
| Elongated/Leaflets/Posterior | Posterior leaflet is elongated |
| Elongated/Leaflets/Anterior | Anterior leaflet is elongated |
| Elongated/Leaflets/AnteriorAndPosterior | Both anterior and posterior leaflet is elongated |
| Elongated/Severity/Mild | Anterior leaflet is mildly elongated |
| Elongated/Severity/MildToModerate | Anterior leaflet is mild to moderately elongated |

| Attribute or Property Selection | Custom Text String to be added to Report Findings |
| --- | --- |
| Elongated/Severity/Moderate | Anterior leaflet is moderately elongated |
| Elongated/SeverityModerateToSevere | Anterior leaflet is moderate to severely elongated |
| Elongated/Severity/Severe | Anterior leaflet is severely elongated |
| Anterior/Leaflet/Thickening/Present | Anterior leaflet thickening present |
| Anterior/Leaflet/Thickening/NotPresent | Anterior leaflet thickening not present |
| Anterior/Leaflet/Mobility/Normal | Anterior mitral leaflet has normal mobility |
| Anterior/Leaflet/Mobility/MildlyDecreased | Anterior mitral leaflet has mildly decreased mobility |
| Anterior/Leaflet/Mobility/ModeratelyDecreased | Anterior mitral leaflet has moderately decreased mobility |
| Anterior/Leaflet/Mobility/Immobile | Anterior mitral leaflet is immobile |
| Anterior/Leaflet/Thickening/Severity/Mild | Anterior leaflet is mildly thickened |
| Anterior/Leaflet/Thickening/Severity/MildToModerate | Anterior leaflet is mild to moderately thickened |
| Anterior/Leaflet/Thickening/Severity/Moderate | Anterior leaflet is moderately thickened |
| Anterior/Leaflet/Thickening/Severity/ModerateToSevere | Anterior leaflet is moderate to Severely thickened |
| Anterior/Leaflet/Thickening/Severity/Severe | Anterior leaflet is severely thickened |
| Posterior/Leaflet/Thickening/Present | Posterior leaflet thickening present |
| Posterior/Leaflet/Thickening/NotPresent | Posterior leaflet thickening not present |
| Posterior/Leaflet/Mobility/Normal | Posterior mitral leaflet has normal mobility |
| Posterior/Leaflet/Mobility/MildlyDecreased | Posterior mitral leaflet has mildly decreased mobility |
| Posterior/Leaflet/Mobility/ModeratelyDecreased | Posterior mitral leaflet has moderately decreased mobility |
| Posterior/Leaflet/Mobility/Immobile | Posterior mitral leaflet is immobile |
| Posterior/Leaflet/Thickening/Severity/Mild | Posterior leaflet is mildly thickened |
| Posterior/Leaflet/Thickening/Severity/MildToModerate | Posterior leaflet is mild to moderately thickened |
| Posterior/Leaflet/Thickening/Severity/Moderate | Posterior leaflet is moderately thickened |
| Posterior/Leaflet/Thickening/Severity/ModerateToSevere | Posterior leaflet is moderate to severely thickened |
| Posterior/Leaflet/Thickening/Severity/Severe | Posterior leaflet is severely thickened |
| AnnularCalcification/Present | Annular calcification present |
| AnnularCalcification/NotPresent | Annular calcification not present |
| AnnularCalcification/Severity/Mild | Noted mild mitral annular calcification |
| AnnularCalcification/Severity/MildToModerate | Noted mild to moderate mitral annular calcification |
| AnnularCalcification/Severity/Moderate | Noted moderate mitral annular calcification |
| AnnularCalcification/Severity/ModerateToSevere | Noted moderate to severe mitral annular calcification |
| AnnularCalcification/Severity/Severe | Noted severe mitral annular calcification |
| SubvalvularCalcification/Present | Subvalvular calcification present |
| SubvalvularCalcification/NotPresent | Subvalvular calcification not present |
| SubvalvularCalcification/Severity/Mild | Noted mild calcification of the mitral subvalvular apparatus |
| SubvalvularCalcification/Severity/MildToModerate | Noted mild to moderate calcification of the mitral subvalvular apparatus |
| SubvalvularCalcification/Severity/Moderate | Noted moderate calcification of the mitral subvalvular apparatus |
| SubvalvularCalciflcation/Severity/ModerateToSevere | Noted moderate to severe calcification of the mitral subvalvular apparatus |
| SubvalvularCalcification/Severity/Severe | Noted severe calcification of the mitral subvalvular apparatus |
| SubvalvularThickening/Present | Subvalvular thickening present |
| SubvalvularThickening/NotPresent | Subvalvular thickening not present |
| SubvalvularThickening/Severity/Mild | Noted mild thickening of the mitral subvalvular apparatus |
| SubvalvularThickening/Severity/MildtoModerate | Noted mild to moderate thickening of the mitral subvalvular apparatus |
| SubvalvularThickening/Severity/Moderate | Noted moderate thickening of the mitral subvalvular apparatus |
| SubvalvularThickening/Severity/ModerateToSevere | Noted moderate to severe thickening of the mitral subvalvular apparatus |
| SubvalvularThickening/Severity/Severe | Noted severe thickening of the mitral subvalvular apparatus |
| AnnularDilatation/Present | Annular calcification present |
| AnnularDilatation/NotPresent | Annular calcification not present |
| AnnularDilatation/Severity/Mild | Mild dilatation of the mitral annulus is noted |
| AnnularDilatation/Severity/MildToModerate | Mild to moderate dilatation of the mitral annulus is noted |
| AnnularDilatation/Severity/Moderate | Moderate dilatation of the mitral annulus is noted |
| AnnularDilatation/Severity/ModerateToSevere | Moderate to severe dilatation of the mitral annulus is noted |
| AnnularDilatation/Severity/Severe | Severe dilatation of the mitral annulus is noted |
| Vegetation/Present | Noted an echo density in the mitral valve suggestive of vegetation |
| Vegetation/NotPresent | No evidence of vegetation noted |
| Vegetation/Location/Posterior | Noted vegetation to the posterior mitral leaflet |
| Vegetation/Location/Anterior | Noted vegetation to the anterior mitral leaflet |
| Vegetation/Location/AnteriorAndPosterior | Noted vegetation to the anterior and posterior mitral leaflet |

| Attribute or Property Selection | Custom Text String to be added to Report Findings |
|---|---|
| Vegetation/Mobility/Mobile | It is mobile |
| Vegetation/Mobility/Fixed | It is fixed |
| Vegetation/Mobility/PedunculatedAndMobile | It is mobile and pedunculated |
| Vegetation/Size/Small | It is small in size |
| Vegetation/Size/Moderate | It is moderate in size |
| Vegetation/Size/Large | It is large in size |
| Vegetation/ISNormal | It is normal |
| Abscess/Location/AnteriorLeaflet | It is located adjacent to an anterior leaflet |
| Abscess/LocatIon/PosteriorLeaflet | It is located adjacent to an posterior leaflet |
| Abscess/Location/AnteriorLeafletAndAnnulus | It is located adjacent to an anterior leaflet and annulus |
| Abscess/Location/PosteriorLeafletAndAnnulus | It is located adjacent to an posterior leaflet and annulus |
| Abscess/Location/IntravalvularFibrosa | It is located adjacent to an intravalvular fibrosa |
| Abscess/Size/Small | Noted as small abscess at the level of mitral valve |
| Abscess/Size/Moderate | Noted as moderate abscess at the level of mitral valve |
| Abscess/Size/Large | Noted as large abscess at the level of mitral valve |
| Cleft/Present | Cleft present |
| Cleft/NotPresent | Cleft not present |
| Cleft/Leaflets/Posterior | It involves the posterior leaflets |
| Cleft/Leaflets/Anterior | It involves the anterior leaflets |
| Cleft/Leaflets/AnteriorAndPosterior | It involves the anterior and posterior leaflets |
| Cleft/Severity/Mild | Mild cleft mitral leaflet is noted |
| CleftSeverity/MildToModerate | Mild to moderate cleft mitral leaflet is noted |
| Cleft/Severity/Moderate | Moderate cleft mitral leaflet is noted |
| Cleft/Severity/ModerateToSevere | Moderate to severe cleft mitral leaflet is noted |
| Cleft/Severity/Severe | Severe cleft mitral leaflet is noted |
| Sam/Present | Systolic anterior motion present |
| Sam/NotPresent | Systolic anterior motion not present |
| Sam/Components/AnteriorLeaflet | It involves the anterior leaflets |
| Sam/Components/PosteriorLeaflet | It involves the posterior leaflets |
| Sam/Components/Chordae | It involves the chordae leaflets |
| Sam/Severity/Mild | Mild systolic anterior motion of the mitral leaflet noted |
| Sam/Severity/MildToModerate | Mild to moderate systolic anterior motion of the mitral leaflet noted |
| Sam/Severity/Moderate | Moderate systolic anterior motion of the mitral leaflet noted |
| Sam/Severity/ModerateToSevere | Moderate to severe systolic anterior motion of the mitral leaflet noted |
| Sam/Severity/Severe | Severe systolic anterior motion of the mitral leaflet noted |
| DilatedAnnulus/Present | Dilated mitral valve annulus is noted |
| DilatedAnnulus/NotPresent | No evidence of dilated mitral valve annulus is noted |
| DiastolicFluttering/Present | Diastolic fluttering present |
| DiastolicFluttering/NotPresent | Diastolic fluttering not present |
| DiastolicFluttering/Leaflets/Posterior | Noted diastolic fluttering of the posterior leaflets |
| DiastolicFluttering/Leaflets/Anterior | Noted diastolic fluttering of the anterior leaflets |
| DiastolicFluttering/Leaflets/AnteriorAndPosterior | Noted diastolic fluttering of the anterior and posterior leaflets |
| ProstheticValve/Present | Prosthetic valve present |
| ProstheticValve/NotPresent | Prosthetic valve not present |
| ProstheticValve/MaterialType/Bioprosthetic | Bioprosthetic valve is noted at the mitral location |
| ProstheticValve/MaterialType/Metallic | Metallic valve is noted at the mitral location |
| ProstheticValve/FunctionsNormally | Noted prosthetic valve functions normally |
| MetallicProstheticValve/Type/Tilting Disk | Metallic prosthetic valve is tilting disk type |
| MetallicProstheticValve/Type/Bileaflet | Metallic prosthetic valve is bileaflet type |
| MetallicProstheticValve/Type/BallAndCage | Metallic prosthetic valve is ball and cage type |
| BioProstheticValve/Type/Porcine | Bioprosthetic valve is porcine valve |
| BioProstheticValve/Type/Homograft | Bioprosthetic valve is homograft type |
| BioProstheticValve/Type/Pericardial | Bioprosthetic valve is pericardial valve |
| BioProstheticValve/Type/NativePulmonic | Bioprosthetic valve is native pulmonic valve |
| MetallicValveManufacturer/StarrEdwa rds | It appears to be starr edwards valve |
| MetallicValveManufacturer/BjorkShiley | It appears to be bjorkshiley valve |
| MetallicValveManufacturer/MedronicHall | It appears to be medronic hall valve |
| MetallicValveManufacturer/Omniscience | It appears to be omniscience valve |
| MetallicValveManufacturer/StJude | It appears to be stjude valve |
| MetallicValveManufacturer/Carbomedics | It appears to be carbomedics valve |
| MetallicValveManufacturer/EdwardsDuromedics | It appears to be edwards duromedics valve |
| ProstheticValveDysfunction//Type/Rocking | Noted rocking of the prosthetic valve |
| ProstheticValveDysfunctionType/Vegetation | Noted vegetation of the prosthetic valve |
| ProstheticValveDysfunctionType/Thrombus | Noted thrombus of the prosthetic valve |
| ProstheticValveDysfunctionType/Mass | Noted mass of the prosthetic valve |
| ProstheticValveDysfunctionType/Dehiscence | Noted dehiscence of the prosthetic valve |
| ProstheticValveDysfunctionType/Stenosis | Noted stenosis of the prosthetic valve |

| Attribute or Property Selection | Custom Text String to be added to Report Findings |
|---|---|
| ProstheticValveDysfunctionType/PhysiologicRegurgitation | Noted physiologic regurgitation of the prosthetic valve |
| ProstheticValveDysfunctionType/ProstheticRegurgitation | Noted prosthetic regurgitation of the prosthetic valve |
| ProstheticValveDysfunctionType/PeriProstheticRegurgitation | Noted peri prosthetic regurgitation of the prosthetic valve |
| ProstheticValveDysfunctionType/Abscess | Noted abscess of the prosthetic valve |
| ProstheticValveDysfunctionType/Pannus | Noted pannus of the prosthetic valve |
| ProstheticValveDysfunctionType/Fistula | Noted fistula of the prosthetic valve |
| ProstheticValveDysfunctionType/Fracture | Noted fracture of the prosthetic valve |
| ProstheticValveDysfunctionType/Perforation | Noted perforation of the prosthetic valve |
| Stenosis/Present | Noted evidence of mitral stenosis |
| Stenosis/NotPresent | No evidence of mitral stenosis noted |
| Stenosis/Severity/Mild | Mild stenosis noted |
| Stenosis/Severity/MildTo Moderate | Mild to moderate stenosis noted |
| Stenosis/Severity/Moderate | Moderate stenosis noted |
| Stenosis/Severity/ModerateTo Severe | Moderate to severe stenosis noted |
| Stenosis/Severity/Severe | Severe stenosis noted |
| MeanTransMitral/Velocity | Mean transmitral velocity |
| MeanTransMitral/Gradient | Mean transmitral gradient |
| Regurgitation/Present | Noted evidence of mitral regurgitation |
| Regurgitation/NotPresent | No evidence of mitral regurgitation noted |
| Regurgitation/Severity/Mild | Mild mitral regurgitation is noted |
| Regurgitation/Severity/MildToModerate | Mild to moderate mitral regurgitation is noted |
| Regurgitation/Severity/Moderate | Moderate mitral regurgitation is noted |
| Regurgitation/Severity/ModerateToSevere | Moderate to severe mitral regurgitation is noted |
| Regurgitation/Severity/Severe | Severe mitral regurgitation is noted |
| Regurgitation/JetDirection1/Anterior | Regurgitant jet is directed towards the anterior aspect of left atrium |
| Regurgitation/JetDirection1/Posterior | Regurgitant jet is directed towards the posterior aspect of left atrium |
| Regurgitation/JetDirection/Central | Regurgitant jet is central |
| Regurgitation/JetDirection/ImpingingOnWall | Regurgitant jet impinges on wall of left atrium |
| Regurgitation/JetDirection/ImpingingOnPulmonaryVeins | Regurgitant jet impinges on pulmonary veins |
| DiastolicRegurgitation | Diastolic mitral regurgitation is noted |
| MrVolumePulse/DopplerMethod | Doppler method mr volume pulse |
| MrVolumeColor/DopplerMethod | Doppler method mr volume color |
| MrFractionPulse/DopplerMethod | Doppler method mr fraction pulse |
| MrFractionColor/DopplerMethod | Doppler method mr fraction color |
| ErOAreaPulse/DopplerMethod | Doppler method Er oarea pulse |
| ErOAreaColor/DopplerMethod | Doppler method Er oarea color |
| IsProsthetic | Miscellaneous Isprosthetic |
| IsRheumatic | Noted to have rheumatic changes |
| IsMyxomatous | Noted myxomatous degeneration of the mitral leaflets |
| IncreasedEPointSeptalSeperation | Noted increased E-point septal seperation |
| PreSystolicClosure | Noted pre systolic closure of the mitral valve |
| Bnotch | Noted BNotch on the mitral valve |
| Ring | Noted evidence of mitral ring |
| Commissurotomy | Noted evidence of prior mitral valve commissurotomy |
| MrJetLAarearatio | Miscellaneous Mr Jet LA Area Ratio |
| PulmonaryVenousFlowPattern/Normal | Pulmonary venous flow is normal |
| PulmonaryVenousFlowPattern/BluntedSystolicFlow | Pulmonary venous flow show systolic flow blunting |
| PulmonaryVenousFlowPattern/SystolicFlowReversal | Pulmonary venous flow show systolic flow reversal |
| ValvularCalcification/Mild | Mild mitral valvular calcification is noted |
| ValvularCalcification/Moderate | Moderate mitral valvular calcification is noted |
| ValvularCalcification/ModeratelySevere | Moderately severe mitral valvular calcification is noted |
| ValvularCalcification/Severe | Severe mitral valvular calcification is noted |
| Primary Reporting Structure - Aortic valve | |
| Overall Normal - IsNormal | Aortic valve is normal |
| AbnormalLeaflets/DiffuseThickeningWithNormalExcursion | Diffuse thickened aortic leaflet with normal excursion noted |
| AbnormalLeaflets/Diffusethickeningwithreducedexcursion | Diffuse thickened aortic leaflet with reduced excursion noted |
| AbnormalLeaflets/Doming | Doming of aortic leaflet noted |
| AbnormalLeaflets/FocalThickening | Focal thickening of the aortic leaflet is noted |
| ProstheticValveMaterialType/Bioprosthetic | Bio prosthetic valve is noted at the level of aortic valve |
| ProstheticValveMaterialType/Metallic | Metallic valve is noted at the level of aortic valve |
| ProstheticValveFunctions/Normally | Prosthetic valve functions normally |
| MetallicProstheticType/BallAndCage | Metallic prosthetic valve is ball and cage type |
| MetallicProstheticType/Bileaflet | Metallic prosthetic valve is bileaflet type |
| MetallicProstheticType/TiltingDisk | Metallic prosthetic valve is tilting disk type |

| Attribute or Property Selection | Custom Text String to be added to Report Findings |
|---|---|
| BioProstheticType/Homograft | Bio prosthetic valve is homograft type |
| BioProstheticType/NativePulmonic | Bio prosthetic valve is native pulmonic valve |
| BioProstheticType/Pericardial | Bio prosthetic valve is pericardial valve |
| BioProstheticType/Porcine | Bio prosthetic valve is porcine valve |
| MetallicValveManufacturer/BjorkShiley | It appears to be bjork shiley valve |
| MetallicValveManufacturer/Carbomedics | It appears to be carbomedics valve |
| MetallicValveManufacturer/EdwardsDuromedics | It appears to be edwards duromedics valve |
| MetallicValveManufacturer/MedronicHall | It appears to be medronic hall valve |
| MetallicValveManufacturer/Omniscience | It appears to be omniscience valve |
| MetallicValveManufacturer/StarrEdwards | It appears to be starr edwards valve |
| MetallicValveManufacturer/StJude | It appears to be st jude valve |
| DysfunctionType/Abscess | Noted abscess of the prosthetic valve |
| DysfunctionType/Dehiscence | Noted dehiscence of the prosthetic valve |
| DysfunctionType/Fistula | Noted fistula of the prosthetic valve |
| DysfunctionType/Fracture | Noted fracture of the prosthetic valve |
| DysfunctionType/Mass | Noted mass of the prosthetic valve |
| DysfunctionType/Pannus | Noted pannus of the prosthetic valve |
| DysfunctionType/Perforation | Noted perforation of the prosthetic valve |
| DysfunctionType/PeriProstheticRegurgitation | Noted peri prosthetic regurgitation of the prosthetic valve |
| DysfunctionType/PhysiologicRegurgitation | Noted physiologic regurgitation of the prosthetic valve |
| DysfunctionType/ProstheticRegurgitation | Noted prosthetic regurgitation of the prosthetic valve |
| DysfunctionType/Rocking | Noted rocking of the prosthetic valve |
| DysfunctionType/Stenosis | Noted stenosis of the prosthetic valve |
| DysfunctionType/Thrombus | Noted thrombus of the prosthetic valve |
| DysfunctionType/Vegetation | Noted vegetation of the prosthetic valve |
| Vegetation/Present | Noted an echo density in the aortic valve suggestive of vegetation |
| Vegetation/NotPresent | No evidence of vegetation noted |
| VegetationLocation/LeftCoronaryCusp | The echodensity appears to be attached to the left coronary cusp |
| VegetationLocation/NonCoronaryAndLeftCoronaryCusp | The echodensity appears to be attached to the non coronary and left coronary cusp |
| VegetationLocation/NonCoronaryCusp | The echodensity appears to be attached to the non coronary cusp |
| VegetationLocation/RightCoronaryAndLeftCoronaryCusp | The echodensity appears to be attached to the right coronary and left coronary cusp |
| Vegetationlocation/RightCoronaryAndNonCoronaryCusp | The echodensity appears to be attached to the right coronary and non coronary cusp |
| VegetationLocation/RightCoronaryCusp | The echodensity appears to be attached to the right coronary cusp |
| VegetationLocation/RightLeftAndNonCoronaryCusp | The echodensity appears to be attached to the right left and non coronary cusp |
| VegetationMobility/Mobile | The echodensity is mobile |
| VegetationMobility/Fixed | The echodensity is fixed |
| VegetationMobility/PedunculatedAndMobile | The echodensity is mobile and pedunculated |
| VegetationSize/Small | A small echodensity is noted on the aortic valve, suggestive of vegetation |
| VegetationSize/Moderate | A moderate sized echodensity is noted on the aortic valve, suggestive of vegetation |
| VegetationSize/Large | A large echodensity is noted on the aortic valve, suggestive of vegetation |
| AbscessLocation/Annulus | The abscess is located at the level of the aortic annulus |
| AbscessLocation/LeftCoronaryCusp | The abscess is located at the level of left coronary cusp of aortic valve |
| AbscessLocation/NonCoronaryCusp | The abscess is located at the level of non coronary cusp of aortic valve |
| AbscessLocation/RightCoronaryCusp | The abscess is located at the level of right coronary cusp of aortic valve |
| AbscessSize/Small | A small echo-lucent area suggestive of an abscess is noted at the level of the aortic valve |
| AbscessSize/Moderate | A moderate sized echo-lucent area suggestive of an abscess is noted at the level of the aortic valve |
| AbscessSizeLarge | A large echo-lucent area suggestive of an abscess is noted at the level of the aortic valve |
| Mass/Present | Noted an echo density in the aortic valve, suggestive of a mass |
| Mass/NotPresent | No evidence of intracavity mass noted |
| MassLocation/LeftCoronaryCusp | The mass is noted on the left coronary cusp |
| MassLocation/RightCoronaryCusp | The mass is noted on the right coronary cusp |
| MassLocation/NonCoronaryCusp | The mass is noted on the non coronary cusp |
| MassSize/Small | A small echo-density is noted at the level of the aortic valve, the appearance is suggestive of a mass |
| MassSize/Moderate | A moderate echo-density is noted at the level of the aortic valve, the appearance is suggestive of a mass |

-continued

| Attribute or Property Selection | Custom Text String to be added to Report Findings |
|---|---|
| MassSize/Large | A large echo-density is noted at the level of the aortic valve, the appearance is suggestive of a mass |
| Stenosis/Present | Noted evidence of aortic stenosis |
| Stenosis/NotPresent | No evidence of aortic stenosis noted |
| StenosisSeverity/Mild | Mild aortic stenosis noted |
| StenosisSeverity/MildToModerate | Mild to moderate aortic stenosis noted |
| StenosisSeverity/Moderate | Moderate aortic stenosis noted |
| StenosisSeverity/ModerateToSevere | Moderate to severe aortic stenosis noted |
| StenosisSeverity/Severe | Severe aortic stenosis noted |
| Regurgitation/Present | Noted evidence of aortic regurgitation |
| Regurgitation/NotPresent | No evidence of aortic regurgitation noted |
| AvSeverity/Mild | Mild aortic regurgitation is noted |
| AvSeverityMildToModerate | Mild to moderate aortic regurgitation is noted |
| AvSeverity/Moderate | Moderate aortic regurgitation is noted |
| AvSeverity/ModerateToSevere | Moderate to severe aortic regurgitation is noted |
| AvSeverity/Severe | Severe aortic regurgitation is noted |
| Pht | Pressure half time |
| AvDiastolicFlowReversal/AbdominalAorta | Noted holodiastolic flow reversal in the abdominal aorta |
| AvDiastolicFlowReversal/Both | Noted holodiastolic flow reversal in the both abdominal and descending aorta |
| AvDiastolicFlowReversal/DescendingAorta | Noted holodiastolic flow reversal in the descending aorta |
| Perforation/Annulus | Noted perforation of annulus |
| Perforation/LeftCoronaryCusp | Noted perforation of the left coronary cusp of aortic valve |
| Perforation/NonCoronaryCusp | Noted perforation of the non coronary cusp of aortic valve |
| Perforation/RightCoronaryCusp | Noted perforation of the right coronary cusp of aortic valve |
| NumberOfLeaflets/Bicuspid | Aortic valve is bicuspid |
| NumberOfLeaflets/Quadricuspid | Noted quadricuspid aortic leaflets |
| NumberOfLeaflets/Tricuspid | Aortic valve is tricuspid |
| NumberOfLeaflets/Unicuspid | Aortic valve is unicuspid |
| ValvularCalcification/Mild | Mild aortic valvular calcification is noted |
| ValvularCalcification/Moderate | Moderate aortic valvular calcification is noted |
| ValvularCalcification/Severe | Severe aortic valvular calcification is noted |
| Primary Reporting Structure - Pulmonic valve | |
| Overall Normal - IsNormal | Pulmonary vein is normal |
| Thrombus/Present | Noted an evidence of echo density in the pulmonary vein suggestive of thrombus |
| Thrombus/NotPresent | No evidence of intracavity thrombus noted |
| ThrombusLocation/FourPulmonaryVeins | It is noted in the four pulmonary veins |
| ThrombusLocation/LeftLower | It is noted in the left lower pulmonary vein |
| ThrombusLocation/LeftUpper | It is noted in the left upper pulmonary vein |
| ThrombusLocation/LeftUpperAndLeftLower | It is noted in the left upper and in the left lower pulmonary vein |
| ThrombusLocation/LeftUpperAndRightLower | It is noted in the left upper and in the right lower pulmonary vein |
| ThrombusLocation/RightLower | It is noted in the right lower pulmonary vein |
| ThrombusLocationRightUpper | It is noted in the right upper pulmonary vein |
| ThrombusLocation/RightUpperAndLeftLower | It is noted in the right upper and in the left lower pulmonary vein |
| ThrombusLocation/RightUpperAndRightLower | It is noted in the right upper and in the right lower pulmonary vein |
| ThrombusLocationThree PulmonaryVeins | It is noted in the three pulmonary veins |
| Mass/Present | Noted an evidence of echo density in the pulmonary vein suggestive of mass |
| Mass/NotPresent | No evidence of intracavity mass noted |
| MassLocation/FourPulmonaryVeins | It is noted in the four pulmonary veins |
| MassLocation/LeftLower | It is noted in the left lower pulmonary vein |
| MassLocation/LeftUpper | It is noted in the left upper pulmonary vein |
| MassLocation/LeftUpperAndLeftLower | It is noted in the left upper and in the left lower pulmonary vein |
| MassLocation/LeftUpperAndRightLower | It is noted in the left upper and in the right lower pulmonary vein |
| MassLocation/RightLower | It is noted in the right lower pulmonary vein |
| MassLocation/RightUpper | It is noted in the right upper pulmonary vein |
| MassLocation/RightUpperAndLeftLower | It is noted in the right upper and in the left lower pulmonary vein |
| MassLocation/RightUpperAndRightLower | It is noted in the right upper and in the right lower pulmonary vein |
| MassLocation/ThreePulmonaryVeins | It is noted in the three pulmonary veins |
| PulmonaryVein/LeftPartialAnomalousReturn | Noted pulmonary vein left partial anomalous return |
| PulmonaryVein/RightPartialAnomalousReturn | Noted pulmonary vein right partial anomalous return |
| PulmonaryVenousHypoplasia | Noted pulmonary venous hypoplasia |
| PulmonaryVenousFlowPattern/Normal | Pulmonary venous flow is normal |

-continued

| Attribute or Property Selection | Custom Text String to be added to Report Findings |
|---|---|
| PulmonaryVenousFlowPattern/SystolicBlunting | Pulmonary venous flow show systolic blunting |
| PulmonaryVenousFlowPattern/SystolicFlowReversal | Pulmonary venous flow show systolic flow reversal |

Primary Reporting Structure - Tricuspid Valve

| | |
|---|---|
| Overall Normal - IsNormal | Tricuspid valve is normal |
| Prolapse/Present | Noted prolapse of the tricuspid valve |
| Prolapse/NotPresent | No evidence of prolapse in tricuspid valve noted |
| ProlapseLeaflets/Anterior | Prolapse of anterior leaflet is noted |
| ProlapseLeaflets/Posterior | Prolapse of posterior leaflet is noted |
| ProlapseLeaflets/Septal | Prolapse of septal leaflet is noted |
| ProlapseSeverity/Mild | It is mild in grade |
| ProlapseSeverity/MildToModerate | It is mild to moderate in grade |
| ProlapseSeverity/ModerateToSevere | It is moderate to severe in grade |
| ProlapseSeverity/Moderate | It is moderate in grade |
| ProlapseSeverity/Severe | It is severe in grade |
| ProlapsePhase/Holosystolic | The prolapse is holosystolic in timing |
| ProlapsePhase/LateSystolic | The prolapse is late systolic in timing |
| RupturedChordae/Present | |
| RupturedChordae/NotPresent | |
| RupturedChordaeFlailLeaflets/Anterior | Noted ruptured chordae to the anterior tricuspid leaflet |
| RupturedChordaeFlailLeaflets/Septal | Noted ruptured chordae to the septal tricuspid leaflet |
| RupturedChordaeFlailLeaflets/Posterior | Noted ruptured chordae to the posterior tricuspid leaflet |
| Vegetation/Present | Noted an echo density in the tricuspid valve suggestive of vegetation |
| Vegetation/NotPresent | No evidence of vegetation noted |
| VegetationSize/Small | It is small in size |
| VegetationSize/Mode rate | It is moderate in size |
| VegetationSize/Large | It is large in size |
| VegetationMobility/Mobile | It is mobile |
| VegetationMobllity/PedunculatedAndMobile | It is mobile and pedunculated |
| VegetationMobility/Fixed | It is fixed |
| VegetationLocation/Anterior | Noted vegetation to the anterior tricuspid leaflet |
| VegetationLocation/Posterior | Noted vegetation to the posterior tricuspid leaflet |
| VegetationLocation/Septal | Noted vegetation to the septal tricuspid leaflet |
| DilatedAnnulus/Present | Noted dilated tricuspid annulus |
| DilatedAnnulus/NotPresent | No evidence of dilated tricuspid annulus noted |
| DilatedSize/Mild | Tricuspid annulus is mildly dilated |
| DilatedSize/Moderate | Tricuspid annulus is moderately dilated |
| DilatedSize/Severe | Tricuspid annulus is severely dilated |
| Stenosis/Present | Noted an evidence of tricuspid stenosis |
| Stenosis/NotPresent | No evidence of tricuspid stenosis noted |
| StenosisSeverity/Mild | It is mild in grade |
| StenosisSeverity/MildToModerate | It is mild to moderate in grade |
| StenosisSeverity/ModerateToSevere | It is moderate to severe in grade |
| StenosisSeverity/Severe | It is severe in grade |
| StenosisSeverity/Moderate | It is moderate in grade |
| Regurgitation/Present | Noted evidence of regurgitation |
| Regurgitation/NotPresent | No evidence of regurgitation noted |
| Regurgitation/Severity/Mild | Tricuspid regurgitation is mild in grade |
| Regurgitation/Severity/MildToModerate | Tricuspid regurgitation is mild to moderate in grade |
| Regurgitation/Severity/Moderate | Tricuspid regurgitation is moderate in grade |
| Regurgitation/Severity/ModerateToSevere | Tricuspid regurgitation is moderate to severe in grade |
| Regurgitation/Severity/Severe | Tricuspid regurgitation is severe in grade |
| RegurgitationJetDirection/Central | The regurgitant jet is directed towards central to the dome |
| RegurgitationJetDirection/Eccentric | The regurgitant jet is directed towards eccentric to the dome |
| RegurgitationJetDirection/ExtendingToDome | The regurgitant jet is directed towards extending to the dome |
| RegurgitationJetDirection/ImpingingOnTheWall | The regurgitant jet is directed towards impinging on the wall to the dome |
| RegurgitationJetDirection/RAFreeWall | The regurgitant jet is directed towards right atrial free wall |
| RegurgitationJetDirection/Septum | The regurgitant jet is directed towards septum |
| Doppler/Present | |
| Doppler/NotPresent | |
| HepaticVenousFlowPattern/Normal | Hepatic flow pattern is normal |
| HepaticVenousFlowPattern/Blunted | Hepatic flow pattern is blunted |
| HepaticVenousFlowPattern/Reversed | Hepatic flow pattern is reversed |
| Atresia | Noted evidence of atresia |
| EbsteinsAnomaly | Noted evidence of ebsteins anomaly |
| IsRheumatic | Noted evidence of rheumatic |

| Attribute or Property Selection | Custom Text String to be added to Report Findings |
| --- | --- |
| ProstheticValve/MaterialType/Bioprosthetic | Bioprosthetic valve is noted at the level of tricuspid valve |
| ProstheticValve/MaterialType/Metallic | Metallic valve is noted at the level of tricuspid valve |
| ProstheticValve/FunctionsNormally | Prosthetic valve functions normally |
| MetallicProstheticValveType/TiltingDisk | Metallic prosthetic valve is tilting disk type |
| MetallicProstheticValveType/Bileaflet | Metallic prosthetic valve is bileaflet type |
| MetallicProstheticValveType/BallAndCage | Metallic prosthetic valve is ball and cage type |
| BioProstheticValveType/Porcine | Bio prosthetic valve is porcine valve |
| BioProstheticValveType/Homograft | Bio prosthetic valve is homograft type |
| BioProstheticValveType/Pericardial | Bio prosthetic valve is pericardial valve |
| BioProstheticValveType/NativePulmonic | Bio prosthetic valve is native pulmonic valve |
| MetallicValveManufacturer/StarrEdwards | It appears to be starr edwards valve |
| MetallicValveManufacturer/BjorkShiley | It appears to be bjork shiley valve |
| MetallicValveManufacturer/MedronicHall | It appears to be medronic hall valve |
| MetallicValveManufacturer/Omniscience | It appears to be omniscience valve |
| MetallicValveManufacturer/StJude | It appears to be st jude valve |
| MetallicValveManufacturer/Carbomedics | It appears to be carbomedics valve |
| MetallicValveManufacturer/EdwardsDuromedics | It appears to be edwards duromedics valve |
| ProstheticValveDysfunctionType/Rocking | Noted rocking of the prosthetic valve |
| ProstheticValveDysfunctionType/Vegetation | Noted vegetation of the prosthetic valve |
| ProstheticValveDysfunctionType/Thrombus | Noted thrombus of the prosthetic valve |
| ProstheticValveDysfunctionType/Mass | Noted mass of the prosthetic valve |
| ProstheticValveDysfunctionType/Dehiscence | Noted dehiscence of the prosthetic valve |
| ProstheticValveDysfunctionType/Stenosis | Noted stenosis of the prosthetic valve |
| ProstheticValveDysfunctionType/PhysiologicRegurgitation | Noted physiologic regurgitation of the prosthetic valve |
| ProstheticValveDysfunctionType/ProstheticRegurgitation | Noted prosthetic regurgitation of the prosthetic valve |
| ProstheticValveDysfunctionType/PeriProstheticRegurgitation | Noted peri prosthetic regurgitation of the prosthetic valve |
| ProstheticValveDysfunctionType/Abscess | Noted abscess of the prosthetic valve |
| ProstheticValveDysfunctionType/Pannus | Noted pannus of the prosthetic valve |
| ProstheticValveDysfunctionType/Fistula | Noted fistula of the prosthetic valve |
| ProstheticValveDysfunctionType/Fracture | Noted fracture of the prosthetic valve |
| ProstheticValveDysfunctionType/Perforation | Noted perforation of the prosthetic valve |
| ValvularCalcification/Mild | Mild tricuspid valvular calcification is noted |
| ValvularCalcification/Moderate | Moderate tricuspid valvular calcification is noted |
| ValvularCalcification/Severe | Severe tricuspid valvular calcification is noted |
| Primary Reporting Structure - Atrial Septum | |
| Overall Normal - IsNormal | Atrial septum appears to be normal |
| AtrialSeptalDefect/Present | Atrial septal defect is noted |
| AtrialSeptal Defect/NotPresent | No evidence of atrial septal defect |
| AtrialSeptalSize/Small | Atrial septal defect is small in size |
| AtrialSeptalSize/Moderate | Atrial septal defect is moderate in size |
| AtrialSeptalSize/Large | Atrial septal defect is large in size |
| AtrialSeptalLocation/Primum | The location of the ASD is consistent with primum type |
| AtrialSeptalLocation/Secondum | The location of the ASD is consistent with secundum type |
| AtrialSeptalLocation/SinusVenosus | The location of the ASD is consistent with sinus venosus type |
| AtrialSeptalShuntDirection/LeftToRight | Left to right shunt noted across the atrial septum |
| AtrialSeptalShuntDirection/RightToLeft | Right to left shunt noted across the atrial septum |
| AtrialSeptalShuntDirection/Bidirectional | bidirectional shunt noted across the atrial septum |
| PFOShuntDirection/LeftToRight | Left to right shunt is noted across the patent foramen ovale |
| PFOShuntDirection/RightToLeft | Right to left shunt is noted across the patent foramen ovale |
| PFOShuntDirection/Bidirectional | Bidirectional shunt is noted across the patent foramen ovale |
| BowingofAtrialSeptumtoleft | Bowing of the atrial septum to the left is noted, suggestive of increased right atrial pressure |
| Cortriatriatum | Noted evidence of cortriatriatum |
| HyoplasticRightAtrium | Noted evidence of hyoplastic right atrium |
| CardiacTransplantAppearance | Noted evidence of cardiac transplant |
| Primary Reporting Structure - Ventricular Septum | |
| Overall Normal - IsNormal | Ventricular septum is normal |
| Vsd/Present | Ventricular septal defect is noted |
| Vsd/NotPresent | No evidence of ventricular septal defect |
| VsdlocationIn/fundibular | It is located in infundibular |
| Vsdlocation/Inlet | It is noted at the septal inlet |
| Vsdlocation/Membraneous | It is located in membraneous septum |
| Vsdlocation/Muscular | It is noted at the muscular portion of the septum |
| VsdSize/Small | It is small in size |
| VsdSize/Moderate | It is moderate in size |
| VsdSize/Large | It is large in size |
| VsdShuntDirection/RightToLeft | Right to left shunt noted across the ventrucular septum |
| VsdShuntDirection/LeftToRight | Left to right shunt noted across the ventrucular septum |
| VsdShuntDirection/Bidirectional | Bidirectional shunt noted across the ventrucular septum |

-continued

| Attribute or Property Selection | Custom Text String to be added to Report Findings |
|---|---|
| Primary Reporting Structure - Aorta | |
| Overall Normal - IsNormal | Aorta is normal |
| StructurePresent | Aorta appears to be normal in size and dimension |
| AorticRoot | Dilatation of the aortic root |
| AorticRoot/AndAscendingAorta | Dilatation of the aortic root and ascending aorta |
| AorticRoot/AscendingAndDescendingAorta | Dilatation of the aortic root ascending and descending aorta |
| AorticRoot/AscendingAndTransverseAorta | Dilatation of the aortic root ascending and transverse aorta |
| AorticRoot/LimitedToSinusOfValsalva | Dilatation of the aortic root limited to sinus of valsalva |
| AorticRoot/SinusAndAscendingAorta | Dilatation of the aortic root sinus and ascending aorta |
| AorticRoot/SinusAscendingAndTransverseAorta | Dilatation of the aortic root sinus ascending and transverse aorta |
| AorticRoot/TransverseDescendingAndAscendingAorta | Dilatation of the aortic root transverse descending and ascending aorta |
| AscendingAndDescendingAorta | Dilatation of the ascending and descending aorta |
| AscendingAndTransverseAorta | Dilatation of the ascending and transverse aorta |
| AscendingAorta | Dilatation of the ascending aorta |
| AscendingAortaAndSinus | Dilatation of the ascending aorta and sinus |
| AscendingTransverseAndDescendingAorta | Dilatation of the ascending transverse and descending aorta |
| DescendingAorta | Dilatation of the descending aorta |
| AneurysmLocation/AscendingAndDescendingAorta | Aneurysmal dilatation of the ascending and descending aorta |
| AneurysmLocation/AscendingAndTransverseAorta | Aneurysmal dilatation of the ascending and transverse aorta |
| AneurysmLocation/AscendingAorta | Aneurysmal dilatation of the ascending aorta |
| AneurysmLocation/AscendingTransverseAndDescendingAorta | Aneurysmal dilatation of the ascending transverse and descending aorta |
| AneurysmLocation/DescendingAorta | Aneurysmal dilatation of the descending aorta |
| AneurysmLocation/TransverseAnddescendingAorta | Aneurysmal dilatation of the transverse and descending aorta |
| AneurysmLocation/TransverseAorta | Aneurysmal dilatation of the transverse aorta |
| PlaqueLocation/AscendingAndDescendingAorta | In the ascending and descending aorta |
| PlaqueLocation/AscendingAndTransverseAorta | In the ascending and transverse aorta |
| PlaqueLocation/AscendingAorta | In the ascending aorta |
| PlaqueLocation/AscendingTransverseAndDescendingAorta | In the ascending transverse and descending aorta |
| PlaqueLocation/DescendingAorta | In the descending aorta |
| PlaqueLocation/TransverseAnddescendingAorta | In the transverse and descending aorta |
| PlaqueLocation/TransverseAorta | In the transverse aorta |
| EcholucentCenter | It is noted to have echolucent center |
| Layered | It is noted to be layered |
| LayeredAndProtruding | It is noted to be layered and protruding |
| Multilobular | It is noted to be multilobular |
| Protruding | It is noted to be protruding |
| Small | Small aortic plaque is noted |
| Moderate | Moderate aortic plaque is noted |
| Large | Large aortic plaque is noted |
| AorticPlaque/Mobile | It is mobile |
| AorticGraftType/Homograft | Echocardiographic appearance suggestive of aortic homograft |
| AorticGraftType/Prosthetic | Echocardiographic appearance suggestive of aortic prosthetic |
| GraftLocation/AscendingAndTransverseAorta | The graft is noted in the ascending and transverse aorta |
| GraftLocation/AscendingAorta | The graft is noted in the ascending aorta |
| GraftLocation/AscendingTransverseAndDescendingaorta | The graft is noted in the ascending transverse and descending aorta |
| GraftLocation/DescendingAorta | The graft is noted in the descending aorta |
| GraftLocation/TransverseAortaAndDescendingAorta | The graft is noted in the transverse aorta and descending aorta |
| AorticArch/ToDescendingAorta | Noted evidence of aortic dissection originating in the aortic arch and extending to descending aorta |
| AorticRoot/ToArch | Noted evidence of aortic dissection originating in the aortic root and extending to arch |

| Attribute or Property Selection | Custom Text String to be added to Report Findings |
|---|---|
| AorticRoot/ToAscendingAorta | Noted evidence of aortic dissection originating in the aortic root and extending to ascending aorta |
| AorticRoot/ToDescendingAorta | Noted evidence of aortic dissection originating in the aortic root and extending to descending aorta |
| AscendingAorta/ToAorticArch | Noted evidence of aortic dissection originating in the ascending aorta and extending to aortic arch |
| AscendingAorta/ToDescendingAorta | Noted evidence of aortic dissection originating in the ascending aorta and extending to descending aorta |
| AorticLocation/DescendingAorta | Noted evidence of aortic dissection originating in the aortic location descending aorta |
| DissectionEntryPoint/AorticArch | The entry point is aortic arch |
| DissectionEntryPoint/AorticRoot | The entry point is aortic root |
| DissectionEntryPoint/AscendingAorta | The entry point is ascending aorta |
| DissectionEntryPoint/DescendingAorta | The entry point is descending aorta |
| DissectionExitPoint/AorticArch | The exit point is aortic arch |
| DissectionExitPoint/AorticRoot | The exit point is aortic root |
| DissectionExitPoint/AscendingAorta | The exit point is ascending aorta |
| DissectionExitPoint/DescendingAorta | The exit point is descending aorta |
| DissectionExitPoint/Multiple | The exit point is multiple |
| FalseLumen/HasThrombus | False lumen noted to have thrombus |
| FalseLumen/CompressesSVC | False lumen noted to have compresses superior vena cava |
| FalseLumen/Compressestruelumen | False lumen noted to have compresses true lumen |
| FalseLumen/Thrombusandcompressestruelumen | False lumen noted to have thrombus and compresses true lumen |
| IntramuralHematomaLocation/AorticArchToDescendingAorta | Noted evidence of intramural hematoma extending from aortic arch to descending aorta |
| IntramuralHematomaLocation/AorticRootToArch | Noted evidence of intramural hematoma extending from aortic root to arch |
| IntramuralHematomaLocation/AorticRootToAscendingAorta | Noted evidence of intramural hematoma extending from aortic root to ascending aorta |
| IntramuralHematomaLocation/AorticRootToDescendingAorta | Noted evidence of intramural hematoma extending from aortic root to descending aorta |
| IntramuralHematomaLocation/AscendingAortaToAorticArch | Noted evidence of intramural hematoma extending from ascending aorta to aortic arch |
| IntramuralHematomaLocation/AscendingAortaToDescendingAorta | Noted evidence of intramural hematoma extending from ascending aorta to descending aorta |
| IntramuralHematomaLocation/DescendingAorta | Noted evidence of intramural hematoma extending to descending aorta |
| Aorta/TGA | Noted evidence of transposition of the great arteries |
| Aorta/CorrectedTGA | Noted evidence of corrected transposition of the great arteries |
| Primary Reporting Structure - Inferior vena cava | |
| Overall Normal - IvcIsNormal | Inferior vena cava is normal |
| ChamberSize/NotAssessed | Inferior vena cava size could not be assessed |
| ChamberSize/Normal | Inferior vena cava is normal in size |
| ChamberSize/MildlyIncreased | Inferior vena cava is mildly increased in size |
| ChamberSize/ModeratelyIncreased | Inferior vena cava is moderately increased in size |
| ChamberSize/SeverelyIncreased | Inferior vena cava is severely increased in size |
| ChamberSize/Decreased | Inferior vena cava is decreased in size |
| IvcMass/Present | Noted an echo density in the inferior vena-cava, this is suggestive of thrombus |
| IvcMass/NotPresent | No evidence of intracavity mass noted |
| IvcMassSize/Small | It is small in size |
| IvcMassSize/Moderate | It is moderate in size |
| IvcMassSize/Large | It is large in size |
| IvcRespiratoryChange/GreaterThan50Percent | Inferior vena caval diameter changes greater than 50 percent during respiration |
| IvcRespiratoryChange/LesserThan50Percent | Inferior vena caval diameter changes less than 50 percent during respiration |
| IvcRespiratoryChange/Plethora | Noted inferior vena caval plethora |
| IvcRespiratoryChange/DilatedIVCAndPoorInspiratoryCollapse | Noted dilated inferior vena cava with poor inspiratory collapse |
| IvcFlowPattern/Normal | Inferior vena caval flow is normal |

| Attribute or Property Selection | Custom Text String to be added to Report Findings |
| --- | --- |
| IvcFlowPattern/SystolicFlowReversal | Systolic flow reversal of the inferior vena cava flow is seen |
| IvcFlowPattern/SystolicBlunting | Systolic blunting of the inferior vena cava flow is seen |
| IvcArtifact/PacerWire | There is an echo density in the inferior vena cava which is suggestive of pacemaker wire |
| IvcArtifact/VenousCatheter | There is an echo density in the inferior vena cava which is suggestive of catheter |
| IvcCongenitalAnomaly/AzygosContinuation/ToLeftSVC | Noted azygos continuation to left superior vena cava |
| IvcCongenitalAnomaly/AzygosContinuation/ToRightSVC | Noted azygos continuation to right superior vena cava |
| Primary Reporting Structure - Pericardium ||
| Overall Normal - PericardiamIsNormal | Pericardium is normal |
| PericardialEffusion/Present | Noted evidence of pericardial effusion |
| PericardialEffusion/NotPresent | No evidence of pericardial effusion noted |
| PericardialEffusionSize/Small | Pericardial effusion is small in size |
| PericardialEffusionSizeModerate | Pericardial effusion is moderate in size |
| PericardialEffusionSize/Large | Pericardial effusion is large in size |
| PericardialEffusionLocation/Anterior | Anterior pericardial effusion is noted |
| PericardialEffusionLocation/Posterior | Posterior pericardial effusion is noted |
| PericardialEffusionLocation/AnteriorAndPosterior | Circumferencial pericardial effusion is noted |
| PericardialEffusionContent/EffusiveConstrictive | The echo density within the pericardial sac is suggestive of effusive constrictive |
| PericardialEffusionContent/Fibrinous | The echo density within the pericardial sac is suggestive of fibrinous |
| PericardialEffusionContent/Fluid | The echo density within the pericardial sac is suggestive of fluid content |
| PericardialEffusionContent/FocalStrands | The echo density within the pericardial sac is suggestive of focal strands |
| PericardialTamponade | Noted echocardiac evidence of pericardial tamponade |
| Mass/Present | Noted an echo density attached to the pericardium suggestive of pericardial mass |
| Mass/NotPresent | No evidence of pericardial mass is noted |
| PleuralEffusion/Present | Noted evidence of pleural effusion |
| PleuralEffusion/NotPresent | No evidence of pleural effusion noted |
| PleuralEffusion/SizeSmall | It is small in size |
| PleuralEffusionSize/Moderate | It is moderate in size |
| PleuralEffusionSize/Large | It is large in size |
| PleuralEffusionLocation/Left | It is noted around left pericardium |
| PleuralEffusionLocation/Right | It is noted around right pericardium |
| PleuralEffusionLocation/RightAndLeft | It is noted around right and left pericardium |
| ExcessiveRespiratoryVariation/Present | Excessive respiratory variation noted |
| Excessive RespiratoryVariation/NotPresent | No evidence of excessive respiratory variation noted |
| ExcessiveRespiratoryVariationType/AorticDopplerFlowVelocities | Exaggerated respiratory variation of aortic doppler flow velocity |
| ExcessiveRespiratoryVariationType/HepaticDopplerFlowVelocities | Exaggerated respiratory variation of hepatic doppler flow velocity |
| Excessive RespiratoryVariationType/MitralDopplerFlowVelocities | Exaggerated respiratory variation of mitral doppler flow velocity |
| ExcessiveRespiratoryVariationType/MitralValveSlope | Exaggerated respiratory variation of mitral inflow slope is noted |
| ExcessiveRespiratoryVariationType/PulmonicDopplerFlowVelocities | Exaggerated respiratory variation of pulmonary doppler flow velocity |
| ExcessiveRespiratoryVariationType/TricuspidDopplerFlowVelocities | Exaggerated respiratory variation of tricuspid doppler flow velocity |
| Excessive RespiratoryVarlationType/Ventricles | Exaggerated respiratory variation of mitral and tricuspid inflow is noted |
| Ascites/Present | Noted evidence of ascites |
| Ascites/NotPresent | No evidence of ascites noted |
| AscitesSeverity/Mild | It is mild in severity |
| AscitesSeverity/MildToModerate | It is mild to moderate in severity |
| AscitesSeverityModerate | It is moderate in severity |
| AscitesSeverity/ModerateToSevere | It is moderate to severe in severity |
| AscitesSeverity/Severe | It is severe in severity |
| PericardialThickening | Noted evidence of pericardial thickening |
| PericardialConstriction | Noted evidence of constrictive pericarditis |
| PericardialEffusoConstrictive | Noted evidence of pericardial effuso constrictive |
| SeptalBounce | Noted evidence of septal bounce |
| FatPad | Noted evidence of pericardial fatpad |

-continued

| Attribute or Property Selection | Custom Text String to be added to Report Findings |
|---|---|
| Primary Reporting Structure - Pulmonary Artery | |
| Overall Normal - IsNormal | Pulmonary Artery appears to be normal |
| Dilatation/Present | Noted evidence of regurgitation in pulmonary artery |
| Dilatation/NotPresent | No evidence of regurgitation in pulmonary artery noted |
| DilatationSeverity/Mild | Pulmonary artery is noted to mildly dilated |
| DilatationSeverity/MildToModerate | Pulmonary artery is noted to mild to moderately dilated |
| DilatationSeverity/Moderate | Pulmonary artery is noted to moderately dilated |
| DilatationSeverity/ModerateToSevere | Pulmonary artery is noted to moderately to severely dilated |
| DilatationSeverity/Severe | Pulmonary artery is noted to severely dilated |
| SuspectPE/Present | Noted evidence of pulmonary embolism |
| SuspectPE/NotPresent | No evidence of pulmonary embolism noted |
| SuspectPELocation/LeftPulmonaryArtery | A mass noted in the left pulmonary artery which is suggestive of pulmonary embolism |
| SuspectPELocation/MainPulmonaryArtery | A mass noted in the main pulmonary artery which is suggestive of pulmonary embolism |
| SuspectPELocation/RightPulmonaryArtery | A mass noted in the right pulmonary artery which is suggestive of pulmonary embolism |
| PulmonaryArteryHypoplasia | Noted evidence of pulmonary artery hypoplasia |
| PulmonaryHypertension | Noted evidence of pulmonary hypertension |
| PatentDuctusArteriosus | Noted evidence of patent ductus arteriosus |
| PulmonaryBranchStenosis/LeftPulmonaryArtery | Noted evidence of left pulmonary artery stenosis |
| PulmonaryBranchStenosis/MainPulmonaryArtery | Noted evidence of main pulmonary artery stenosis |
| PulmonaryBranchStenosis/RightPulmonaryArtery | Noted evidence of right pulmonary artery stenosis |
| PulmonaryArterySystolicPressure | |
| Primary Reporting Structure - Pulmonary Vein | |
| Overall Normal - IsNormal | Pulmonary vein is normal |
| Thrombus/Present | Noted an evidence of echo density in the pulmonary vein suggestive of thrombus |
| Thrombus/NotPresent | No evidence of intracavity thrombus noted |
| ThrombusLocation/FourPulmonaryVeins | It is noted in the four pulmonary veins |
| ThrombusLocation/LeftLower | It is noted in the left lower pulmonary vein |
| ThrombusLocation/LeftUpper | It is noted in the left upper pulmonary vein |
| ThrombusLocation/LeftUpperAndLeftLower | It is noted in the left upper and in the left lower pulmonary vein |
| ThrombusLocationLeftUpperAndRightLower | It is noted in the left upper and in the right lower pulmonary vein |
| ThrombusLocation/RightLower | It is noted in the right lower pulmonary vein |
| ThrombusLocation/RightUpper | It is noted in the right upper pulmonary vein |
| ThrombusLocation/RightUpperAndLeftLower | It is noted in the right upper and in the left lower pulmonary vein |
| ThrombusLocation/RightUpperAndRightLower | It is noted in the right upper and in the right lower pulmonary vein |
| ThrombusLocation/ThreePulmonaryVeins | It is noted in the three pulmonary veins |
| Mass/Present | Noted an evidence of echo density in the pulmonary vein suggestive of mass |
| Mass/NotPresent | No evidence of intracavity mass noted |
| MassLocation/FourPulmonaryVeins | It is noted in the four pulmonary veins |
| MassLocation/LeftLower | It is noted in the left lower pulmonary vein |
| MassLocation/LeftUpper | It is noted in the left upper pulmonary vein |
| MassLocation/LeftUpperAndLeftLower | It is noted in the left upper and in the left lower pulmonary vein |
| MassLocation/LeftUpperAndRightLower | It is noted in the left upper and in the right lower pulmonary vein |
| MassLocation/RightLower | It is noted in the right lower pulmonary vein |
| MassLocation/RightUpper | It is noted in the right upper pulmonary vein |
| MassLocation/RightUpperAndLeftLower | It is noted in the right upper and in the left lower pulmonary vein |
| MassLocation/RightUpperAndRightLower | It is noted in the right upper and in the right lower pulmonary vein |
| MassLocation/ThreePulmonaryVeins | It is noted in the three pulmonary veins |
| PulmonaryVeinLeftPartialAnomalousReturn | Noted pulmonary vein left partial anomalous return |
| PulmonaryVeinRightPartialAnomalousReturn | Noted pulmonary vein right partial anomalous return |
| PulmonaryVenousHypoplasia | Noted pulmonary venous hypoplasia |
| PulmonaryVenousFlowPattern/Normal | Pulmonary venous flow is normal |
| PulmonaryVenousFlowPattern/SystolicBlunting | Pulmonary venous flow show systolic blunting |
| PulmonaryVenousFlowPattern/SystolicFlowReversal | Pulmonary venous flow show systolic flow reversal |
| Carotid Custom Text | |
| Primary Reporting Structure - Proximal right common carotid artery | |
| Overall Normal - IsNormal | Proximal right common carotid artery is normal |
| GsStenosisSeverity/Mild | Mild plaque is noted in proximal right common carotid artery |
| GsStenosisSeverity/MildToModerate | Mild to moderate plaque is noted in proximal right common carotid artery |
| GsStenosisSeverity/Moderate | Moderate plaque is noted in proximal right common carotid artery |

-continued

| Attribute or Property Selection | Custom Text String to be added to Report Findings |
|---|---|
| GsStenosisSeverity/ModerateToSevere | Moderate to severe plaque is noted in proximal right common carotid artery |
| GsStenosisSeverity/Severe | Severe plaque is noted in proximal right common carotid artery |
| GsDissection | Noted evidence of dissection in the proximal right common carotid artery |
| SpectralBroadening | Noted evidence of spectral broadening in the proximal right common carotid artery |
| ExtendsTo/ProximalCommonCarotidArtery | A metallic stent in the proximal right common carotid artery |
| ExtendsTo/MidCommonCarotidArtery | A metallic stent in the proximal right common carotid artery extending to mid right common carotid artery |
| ExtendsTo/DistalCommonCarotidArtery | A metallic stent in the proximal right common carotid artery extending to distal right common carotid artery |
| ExtendsTo/BifurcationCommonCarotidArtery | A metallic stent in the proximal right common carotid artery extending to bifurcation right common carotid artery |
| ExtendsTo/ProximalInternalCarotidArtery | A metallic stent in the proximal right common carotid artery extending to proximal right internal carotid artery |
| ExtendsTo/MidInternalCarotidArtery | A metallic stent in the proximal right common carotid artery extending to mid right internal carotid artery |
| ExtendsTo/DistalInternalCarotidArtety | A metallic stent in the proximal right common carotid artery extending to distal right internal carotid artery |
| ExtendsTo/ExternalCarotidArtery | A metallic stent in the proximal right common carotid artery extending to right external carotid artery |
| InstentRestenosisSeverity/Mild | Mild instent restenosis of the proximal right common carotid artery is noted |
| InstentRestenosisSeverity/MildToModerate | Mild to moderate instent restenosis of the proximal right common carotid artery is noted |
| InstentRestenosisSeverity/Moderate | Moderate instent restenosis of the proximal right common carotid artery is noted |
| InstentRestenosisSeverity/ModerateToSevere | Moderate to severe instent restenosis of the proximal right common carotid artery is noted |
| InstentRestenosisSeverity/Severe | Severe instent restenosis of the proximal right common carotid artery is noted |
| Primary Reporting Structure - Mid right common carotid artery ||
| Overall Normal - IsNormal | Mid right common carotid artery is normal |
| GsStenosisSeverity/Mild | Noted mild plaque in the mid right common carotid artery |
| GsStenosisSeverity/MildToModerate | Noted mild to moderate plaque in the mid right common carotid artery |
| GsStenosisSeverity/Moderate | Noted moderate plaque in the mid right common carotid artery |
| GsStenosisSeverity/ModerateToSevere | Noted moderate to severe plaque in the mid right common carotid artery |
| GsStenosisSeverity/Severe | Noted severe plaque in the mid right common carotid artery |
| GsDissection | Noted evidence of dissection in the mid right common carotid artery |
| SpectralBroadening | Noted evidence of spectral broadening in the mid right common carotid artery |
| ExtendsTo/ProximalCommonCarotidArtery | Noted evidence of metallic stent in the mid right common carotid artery extending to proximal right common carotid artery |
| ExtendsTo/MidCommonCarotidArtery | Noted evidence of metallic stent in the mid right common carotid artery |
| ExtendsTo/DistalCommonCarotidArtery | Noted evidence of metallic stent in the mid right common carotid artery extending to distal right common carotid artery |
| ExtendsTo/BifurcationCommonCarotidArtery | Noted evidence of metallic stent in the mid right common carotid artery extending to bifurcation right common carotid artery |
| ExtendsTo/ProximalInternalCarotidArtery | Noted evidence of metallic stent in the mid right common carotid artery extending to proximal right internal carotid artery |
| ExtendsTo/MidInternalCarotidArtery | Noted evidence of metallic stent in the mid right common carotid artery extending to mid right internal carotid artery |
| ExtendsTo/DistalInternalCarotidArtery | Noted evidence of metallic stent in the mid right common carotid artery extending to distal right internal carotid artery |
| ExtendsTo/ExternalCarotidArtery | Noted evidence of metallic stent in the mid right common carotid artery extending to right external carotid artery |
| InstentRestenosisSeverity/Mild | Noted mild instent restenosis of the mid right common carotid artery |
| InstentRestenosisSeverity/MildToModerate | Noted mild to moderate instent restenosis of the mid right common carotid artery |
| InstentRestenosisSeverity/Moderate | Noted moderate instent restenosis of the mid right common carotid artery |
| InstentRestenosisSeverity/ModerateToSevere | Noted moderate to severe instent restenosis of the mid right common carotid artery |
| InstentRestenosisSeverity/Severe | Noted severe instent restenosis of the mid right common carotid artery |
| Primary Reporting Structure - Distal right common carotid artery ||
| Overall Normal - IsNormal | Distal right common carotid artery is normal |
| GsStenosisSeverity/Mild | Noted mild plaque in the distal right common carotid artery |
| GsStenosisSeverity/MildToModerate | Noted mild to moderate plaque in the distal right common carotid artery |

-continued

| Attribute or Property Selection | Custom Text String to be added to Report Findings |
|---|---|
| GsStenosisSeverity/Moderate | Noted moderate plaque in the distal right common carotid artery |
| GsStenosisSeverity/ModerateToSevere | Noted moderate to severe plaque in the distal right common carotid artery |
| GsStenosisSeverity/Severe | Noted severe plaque in the distal right common carotid artery |
| GsDissection | Noted evidence of dissection in the distal right common carotid artery |
| SpectralBroadening | Noted evidence of spectral broadening in the distal right common carotid artery |
| ExtendsTo/ProximalCommonCarotidArtery | Noted evidence of metallic stent in the distal right common carotid artery extending to proximal right common carotid artery |
| ExtendsTo/MidCommonCarotidArtery | Noted evidence of metallic stent in the distal right common carotid artery extending to mid right common carotid artery |
| ExtendsTo/DistalCommonCarotidArtery | Noted evidence of metallic stent in the distal right common carotid artery |
| ExtendsTo/BifurcationCommonCarotidArtery | Noted evidence of metallic stent in the distal right common carotid artery extending to bifurcation right common carotid artery |
| ExtendsTo/ProximalInternalCarotidArtery | Noted evidence of metallic stent in the distal right common carotid artery extending to proximal right internal carotid artery |
| ExtendsTo/MidInternalCarotidArtery | Noted evidence of metallic stent in the distal right common carotid artery extending to mid right internal carotid artery |
| ExtendsTo/DistalInternalCarotidArtery | Noted evidence of metallic stent in the distal right common carotid artery extending to distal right internal carotid artery |
| ExtendsTo/ExternalCarotidArtery | Noted evidence of metallic stent in the distal right common carotid artery extending to right external carotid artery |
| InstentRestenosisSeverity/Mild | Noted mild instent restenosis of the distal right common carotid artery |
| InstentRestenosisSeverity/MildToModerate | Noted mild to moderate instent restenosis of the distal right common carotid artery |
| InstentRestenosisSeverity/Moderate | Noted moderate instent restenosis of the distal right common carotid artery |
| InstentRestenosisSeverity/ModerateToSevere | Noted moderate to severe instent restenosis of the distal right common carotid artery |
| InstentRestenosisSeverity/Severe | Noted severe instent restenosis of the distal right common carotid artery |
| Primary Reporting Structure - Bifurcation right common carotid artery | |
| Overall Normal - IsNormal | Bifurcation right common carotid artery is normal |
| GsStenosisSeverity/Mild | Noted mild plaque in the bifurcation right common carotid artery |
| GsStenosisSeverity/MildToModerate | Noted mild to moderate plaque in the bifurcation right common carotid artery |
| GsStenosisSeverity/Moderate | Noted moderate plaque in the bifurcation right common carotid artery |
| GsStenosisSeverity/ModerateToSevere | Noted moderate to severe plaque in the bifurcation right common carotid artery |
| GsStenosisSeverity/Severe | Noted severe plaque in the bifurcation right common carotid artery |
| GsDissection | Noted evidence of dissection in the bifurcation right common carotid artery |
| SpectralBroadening | Noted evidence of spectral broadening in the bifurcation right common carotid artery |
| ExtendsTo/ProximalCommonCarotidArtery | Noted evidence of metallic stent in the bifurcation right common carotid artery extending to proximal right common carotid artery |
| ExtendsTo/MidCommonCarotidArtery | Noted evidence of metallic stent in the bifurcation right common carotid artery extending to mid right common carotid artery |
| ExtendsTo/DistalCommonCarotidArtery | Noted evidence of metallic stent in the bifurcation right common carotid artery extending to distal right common carotid artery |
| ExtendsTo/BifurcationCommonCarotidArtery | Noted evidence of metallic stent in the bifurcation right common carotid artery |
| ExtendsTo/ProximalInternalCarotidArtery | Noted evidence of metallic stent in the bifurcation right common carotid artery extending to proximal right internal carotid artery |
| ExtendsTo/MidInternalCarotidArtery | Noted evidence of metallic stent in the bifurcation right common carotid artery extending to mid right internal carotid artery |
| ExtendsTo/DistalInternalCarotidArtery | Noted evidence of metallic stent in the bifurcation right common carotid artery extending to distal right internal carotid artery |
| ExtendsTo/ExternalCarotidArtery | Noted evidence of metallic stent in the bifurcation right common carotid artery extending to right external carotid artery |
| InstentRestenosisSeverity/Mild | Noted mild instent restenosis of the bifurcation right common carotid artery |
| InstentRestenosisSeverity/MildToModerate | Noted mild to moderate instent restenosis of the bifurcation right common carotid artery |
| InstentRestenosisSeverity/Moderate | Noted moderate instent restenosis of the bifurcation right common carotid artery |
| InstentRestenosisSeverity/ModerateToSevere | Noted moderate to severe instent restenosis of the bifurcation right common carotid artery |
| InstentRestenosisSeverity/Severe | Noted severe instent restenosis of the bifurcation right common carotid artery |

-continued

| Attribute or Property Selection | Custom Text String to be added to Report Findings |
|---|---|
| Primary Reporting Structure - Proximal left common carotid artery | |
| Overall Normal - IsNormal | Proximal left common carotid artery is normal |
| GsStenosisSeverity/Mild | Noted mild plaque in the left proximal common carotid artery |
| GsStenosisSeverity/MildToModerate | Noted mild to moderate plaque in the proximal left common carotid artery |
| GsStenosisSeverity/Moderate | Noted moderate plaque in the proximal left common carotid artery |
| GsStenosisSeverity/ModerateToSevere | Noted moderate to severe plaque in the proximal left common carotid artery |
| GsStenosisSeverity/Severe | Noted severe plaque in the proximal left common carotid artery |
| GsDissection | Noted evidence of dissection in the proximal left common carotid artery |
| SpectralBroadening | Noted evidence of spectral broadening in the proximal left common carotid artery |
| ExtendsTo/ProximalCommonCarotidArtery | Noted evidence of metallic stent in the proximal left common carotid artery |
| ExtendsTo/MidCommonCarotidArtery | Noted evidence of metallic stent in the proximal left common carotid artery extending to mid left common carotid artery |
| ExtendsTo/DistalCommonCarotidArtery | Noted evidence of metallic stent in the proximal left common carotid artery extending to distal left common carotid artery |
| ExtendsTo/BifurcationCommonCarotidArtery | Noted evidence of metallic stent in the proximal left common carotid artery extending to bifurcation left common carotid artery |
| ExtendsTo/ProximalInternalCarotidArtery | Noted evidence of metallic stent in the proximal left common carotid artery extending to proximal left internal carotid artery |
| ExtendsTo/MidInternalCarotidArtery | Noted evidence of metallic stent in the proximal left common carotid artery extending to mid left internal carotid artery |
| ExtendsTo/DistalInternalCarotidArtery | Noted evidence of metallic stent in the proximal left common carotid artery extending to distal left internal carotid artery |
| ExtendsTo/ExternalCarotidArtery | Noted evidence of metallic stent in the proximal left common carotid artery extending to left external carotid artery |
| InstentRestenosisSeverity/Mild | Noted mild instent restenosis of the proximal left common carotid artery |
| InstentRestenosisSeverity/MildToModerate | Noted mild to moderate instent restenosis of the proximal left common carotid artery |
| InstentRestenosisSeverity/Moderate | Noted moderate instent restenosis of the proximal left common carotid artery |
| InstentRestenosisSeverity/ModerateToSevere | Noted moderate to severe instent restenosis of the proximal left common carotid artery |
| InstentRestenosisSeverity/Severe | Noted severe instent restenosis of the proximal left common carotid artery |
| Primary Reporting Structure - Mid left common carotid artery | |
| Overall Normal - IsNormal | Mid left common carotid artery is normal |
| GsStenosisSeverity/Mild | Mild plaque is noted in mid left common carotid artery |
| GsStenosisSeverity/MildToModerate | Mild to moderate plaque is noted in mid left common carotid artery |
| GsStenosisSeverity/Moderate | Moderate plaque is noted in mid left common carotid artery |
| GsStenosisSeverity/ModerateToSevere | Moderate to severe plaque is noted in mid left common carotid artery |
| GsStenosisSeverity/Severe | Severe plaque is noted in mid left common carotid artery |
| GsDissection | Noted evidence of dissection in the mid left common carotid artery |
| SpectralBroadening | Noted evidence of spectral broadening in the mid left common carotid artery |
| ExtendsTo/ProximalCommonCarotidArtery | A metallic stent is noted in the mid left common carotid artery extending to proximal left common carotid artery |
| ExtendsTo/MidCommonCarotidArtery | A metallic stent is noted in the mid left common carotid artery |
| ExtendsTo/DistalCommonCarotid Artery | A metallic stent is noted in the mid left common carotid artery extending to distal left common carotid artery |
| ExtendsTo/BifurcationCommonCarotidArtery | A metallic stent is noted in the mid left common carotid artery extending to bifurcation left common carotid artery |
| ExtendsTo/ProximalInternalCarotidArtery | A metallic stent is noted in the mid left common carotid artery extending to proximal left internal carotid artery |
| ExtendsTo/MidInternalCarotidArtery | A metallic stent is noted in the mid left common carotid artery extending to mid left internal carotid artery |
| ExtendsTo/DistalInternalCarotidArtery | A metallic stent is noted in the mid left common carotid artery extending to distal left internal carotid artery |
| ExtendsTo/ExternalCarotidArtery | A metallic stent is noted in the mid left common carotid artery extending to left external carotid artery |
| InstentRestenosisSeverity/Mild | Noted mild instent restenosis |
| InstentRestenosisSeverity/MildToModerate | Noted mild to moderate instent restenosis |
| InstentRestenosisSeverity/Moderate | Noted moderate instent restenosis |
| InstentRestenosisSeverity/ModerateToSevere | Noted moderate to severe instent restenosis |
| InstentRestenosisSeverity/Severe | Noted severe instent restenosis |

| Attribute or Property Selection | Custom Text String to be added to Report Findings |
|---|---|
| Primary Reporting Structure - Distal left common carotid artery | |
| Overall Normal - IsNormal | Distal left common carotid artery is normal |
| GsStenosisSeverity/Mild | Noted mild plaque in the distal left common carotid artery |
| GsStenosisSeverity/MildToModerate | Noted mild to moderate plaque in the distal left common carotid artery |
| GsStenosisSeverity/Moderate | Noted moderate plaque in the distal left common carotid artery |
| GsStenosisSeverity/ModerateToSevere | Noted moderate to severe plaque in the distal left common carotid artery |
| GsStenosisSeverity/Severe | Noted severe plaque in the distal left common carotid artery |
| GsDissection | Noted evidence of dissection in the distal left common carotid artery |
| SpectralBroadening | Noted evidence of spectral broadening in the distal left common carotid artery |
| ExtendsTo/ProximalCommonCarotidArtery | Noted evidence of metallic stent in the distal left common carotid artery extending to proximal left common carotid artery |
| ExtendsTo/MidCommonCarotidArtery | Noted evidence of metallic stent in the distal left common carotid artery extending to mid left common carotid artery |
| ExtendsTo/DistalCommonCarotidArtery | Noted evidence of metallic stent in the distal left common carotid artery |
| ExtendsTo/BifurcationCommonCarotidArtery | Noted evidence of metallic stent in the distal left common carotid artery extending to bifurcation left common carotid artery |
| ExtendsTo/ProximalInternalCarotidArtery | Noted evidence of metallic stent in the distal left common carotid artery extending to proximal left internal carotid artery |
| ExtendsTo/MidInternalCarotidArtery | Noted evidence of metallic stent in the distal left common carotid artery extending to mid left internal carotid artery |
| ExtendsTo/DistalInternalCarotidArtery | Noted evidence of metallic stent in the distal left common carotid artery extending to distal left internal carotid artery |
| ExtendsTo/ExternalCarotidArtery | Noted evidence of metallic stent in the distal left common carotid artery extending to external left carotid artery |
| InstentRestenosisSeverity/Mild | Noted mild instent restenosis of the distal left common carotid artery |
| InstentRestenosisSeverity/MildToModerate | Noted mild to moderate instent restenosis of the distal left common carotid artery |
| InstentRestenosisSeverity/Moderate | Noted moderate instent restenosis of the distal left common carotid artery |
| InstentRestenosisSeverity/ModerateToSevere | Noted moderate to severe instent restenosis of the distal left common carotid artery |
| InstentRestenosisSeverity/Severe | Noted severe instent restenosis of the distal left common carotid artery |
| Primary Reporting Structure - Bifurcation left common carotid artery | |
| Overall Normal - IsNormal | Bifurcation left common carotid artery is normal |
| GsStenosisSeverity/Mild | Noted mild plaque in the bifurcation left common carotid artery |
| GsStenosisSeverity/MildToModerate | Noted mild to moderate plaque in the bifurcation left common carotid artery |
| GsStenosisSeverity/Moderate | Noted moderate plaque in the bifurcation left common carotid artery |
| GsStenosisSeverity/ModerateToSevere | Noted moderate to severe plaque in the bifurcation left common carotid artery |
| GsStenosisSeverity/Severe | Noted severe plaque in the bifurcation left common carotid artery |
| GsDissection | Noted evidence of dissection in the bifurcation left common carotid artery |
| SpectralBroadening | Noted evidence of spectral broadening in the bifurcation left common carotid artery |
| ExtendsTo/ProximalCommonCarotidArtery | Noted evidence of metallic stent in the bifurcation left common carotid artery extending to proximal left common carotid artery |
| ExtendsTo/MidCommonCarotidArtery | Noted evidence of metallic stent in the bifurcation left common carotid artery extending to mid left common carotid artery |
| ExtendsTo/DistalCommonCarotidArtery | Noted evidence of metallic stent in the bifurcation left common carotid artery extending to distal left common carotid artery |
| ExtendsTo/BifurcationCommonCarotidArtery | Noted evidence of metallic stent in the bifurcation left common carotid artery |
| ExtendsTo/ProximalInternalCarotidArtery | Noted evidence of metallic stent in the bifurcation left common carotid artery extending to proximal left internal carotid artery |
| ExtendsToMidInternalCarotidArtery | Noted evidence of metallic stent in the bifurcation left common carotid artery extending to mid left internal carotid artery |
| ExtendsTo/DistalInternalCarotidArtery | Noted evidence of metallic stent in the bifurcation left common carotid artery extending to distal left internal carotid artery |
| ExtendsTo/ExternalCarotidArtery | Noted evidence of metallic stent in the bifurcation left common carotid artery extending to left external carotid artery |
| InstentRestenosisSeverity/Mild | Noted mild instent restenosis of the bifurcation left common carotid artery |
| InstentRestenosisSeverity/MildToModerate | Noted mild to moderate instent restenosis of the bifurcation left common carotid artery |
| InstentRestenosisSeverity/Moderate | Noted moderate instent restenosis of the bifurcation left common carotid artery |

-continued

| Attribute or Property Selection | Custom Text String to be added to Report Findings |
|---|---|
| InstentRestenosisSeverity/ModerateToSevere | Noted moderate to severe instent restenosis of the bifurcation left common carotid artery |
| InstentRestenosisSeverity/Severe | Noted severe instent restenosis of the bifurcation left common carotid artery |
| Primary Reporting Structure - Proximal right internal carotid artery | |
| Overall Normal - IsNormal | Proximal right internal carotid artery is normal |
| GsStenosisSeverity/Mild | Mild plaque is noted in the proximal right internal carotid artery |
| GsStenosisSeverity/MildToModerate | Mild to moderate plaque is noted in the proximal right internal carotid artery |
| GsStenosisSeverity/Moderate | Moderate plaque is noted in the proximal right internal carotid artery |
| GsStenosisSeverity/ModerateToSevere | Moderate to severe plaque is noted in the proximal right internal carotid artery |
| GsStenosisSeverity/Severe | Severe plaque is noted in the proximal right internal carotid artery |
| GsDissection | Noted evidence of dissection in the proximal right internal carotid artery |
| SpectralBroadening | Noted evidence of spectral broadening in the proximal right internal carotid artery |
| ExtendsTo/ProximalCommonCarotidArtery | A metallic stent is noted in the proximal right internal carotid artery extending to proximal right common carotid artery |
| ExtendsTo/MidCommonCarotidArtery | A metallic stent is noted in the proximal right internal carotid artery extending to mid right common carotid artery |
| ExtendsTo/DistalCommonCarotidArtery | A metallic stent is noted in the proximal right internal carotid artery extending to distal right common carotid artery |
| ExtendsTo/BifurcationCommonCarotidArtery | A metallic stent is noted in the proximal right internal carotid artery extending to bifurcation right common carotid artery |
| ExtendsTo/ProximalInternalCarotidArtery | A metallic stent is noted in the proximal right internal carotid artery |
| ExtendsTo/MidInternalCarotidArtery | A metallic stent is noted in the proximal right internal carotid artery extending to mid right internal carotid artery |
| ExtendsTo/DistalInternalCarotidArtery | A metallic stent is noted in the proximal right internal carotid artery extending to distal right internal carotid artery |
| ExtendsTo/ExternalCarotidArtery | A metallic stent is noted in the proximal right internal carotid artery extending to right external carotid artery |
| InstentRestenosisSeverity/Mild | Noted mild instent restenosis of the proximal right internal carotid artery |
| InstentRestenosisSeverity/MildToModerate | Noted mild to moderate instent restenosis of the proximal right internal carotid artery |
| InstentRestenosisSeverity/Moderate | Noted moderate instent restenosis of the proximal right internal carotid artery |
| InstentRestenosisSeverity/ModerateToSevere | Noted moderate to severe instent restenosis of the proximal right internal carotid artery |
| InstentRestenosisSeverity/Severe | Noted severe instent restenosis of the proximal right internal carotid artery |
| Primary Reporting Structure - Mid right internal carotid artery | |
| Overall Normal - IsNormal | Mid right internal carotid artery is normal |
| GsStenosisSeverity/Mild | Mild plaque is noted in the mid right internal carotid artery |
| GsStenosisSeverity/MildToModerate | Mild to moderate plaque is noted in the mid right internal carotid artery |
| GsStenosisSeverity/Moderate | Moderate plaque is noted in the mid right internal carotid artery |
| GsStenosisSeverity/ModerateToSevere | Moderate to severe plaque is noted in the mid right internal carotid artery |
| GsStenosisSeverity/Severe | Severe plaque is noted in the mid right internal carotid artery |
| GsDissection | Noted evidence of dissection in the mid right internal carotid artery |
| SpectralBroadening | Noted evidence of spectral broadening in the mid right internal carotid artery |
| ExtendsTo/ProximalCommonCarotidArtery | A metallic stent is noted in the mid right internal carotid artery extending to proximal right common carotid artery |
| ExtendsTo/MidCommonCarotidArtery | A metallic stent is noted in the mid right internal carotid artery extending to mid right common carotid artery |
| ExtendsTo/DistalCommonCarotidArtery | A metallic stent is noted in the mid right internal carotid artery extending to distal right common carotid artery |
| ExtendsTo/BifurcationCommonCarotidArtery | A metallic stent is noted in the mid right internal carotid artery extending to bifurcation right common carotid artery |
| ExtendsTo/ProximalInternalCarotidArtery | A metallic stent is noted in the mid right internal carotid artery extending to proximal right internal carotid artery |
| ExtendsTo/Mid InternalCarotidArtery | A metallic stent is noted in the mid right internal carotid artery |
| ExtendsTo/DistalInternalCarotidArtery | A metallic stent is noted in the mid right internal carotid artery extending to distal right internal carotid artery |
| ExtendsTo/ExternalCarotidArtery | A metallic stent is noted in the mid right internal carotid artery extending to right external carotid artery |
| InstentRestenosisSeverity/Mild | Noted mild instent restenosis |
| InstentRestenosisSeverity/MildToModerate | Noted mild to moderate instent restenosis |
| InstentRestenosisSeverity/Moderate | Noted moderate instent restenosis |

-continued

| Attribute or Property Selection | Custom Text String to be added to Report Findings |
|---|---|
| InstentRestenosisSeverity/ModerateToSevere | Noted moderate to severe instent restenosis |
| InstentRestenosisSeverity/Severe | Noted severe instent restenosis |
| Primary Reporting Structure - Distal right internal carotid artery | |
| Overall Normal - IsNormal | Distal right internal carotid artery is normal |
| GsStenosisSeverity/Mild | Noted mild plaque in the distal right internal carotid artery |
| GsStenosisSeverity/MildToModerate | Noted mild to moderate plaque in the distal right internal carotid artery |
| GsStenosisSeverity/Moderate | Noted moderate plaque in the distal right internal carotid artery |
| GsStenosisSeverity/ModerateToSevere | Noted moderate to severe plaque in the distal right internal carotid artery |
| GsStenosisSeverity/Severe | Noted severe plaque in the distal right internal carotid artery |
| GsDissection | Noted evidence of dissection in the distal right internal carotid artery |
| SpectralBroadening | Noted evidence of spectral broadening in the distal right internal carotid artery |
| ExtendsTo/ProximalCommonCarotidArtery | Noted evidence of metallic stent in the distal right internal carotid artery extending to proximal right common carotid artery |
| ExtendsTo/MidCommonCarotidArtery | Noted evidence of metallic stent in the distal right internal carotid artery extending to mid right common carotid artery |
| ExtendsTo/DistalCommonCarotidArtery | Noted evidence of metallic stent in the distal right internal carotid artery extending to distal right common carotid artery |
| ExtendsTo/BifurcationCommonCarotidArtery | Noted evidence of metallic stent in the distal right internal carotid artery extending to bifurcation right common carotid artery |
| ExtendsTo/ProximalInternalCarotidArtery | Noted evidence of metallic stent in the distal right internal carotid artery extending to proximal right internal carotid artery |
| ExtendsTo/MidInternalCarotidArtery | Noted evidence of metallic stent in the distal right internal carotid artery extending to mid right internal carotid artery |
| ExtendsTo/DistalInternalCarotidArtery | Noted evidence of metallic stent in the distal right internal carotid artery |
| ExtendsTo/ExternalCarotidArtery | Noted evidence of metallic stent in the distal right internal carotid artery extending to right external carotid artery |
| InstentRestenosisSeverity/Mild | Noted mild instent restenosis of the distal right internal carotid artery |
| InstentRestenosisSeverity/MildToModerate | Noted mild to moderate instent restenosis of the distal right internal carotid artery |
| InstentRestenosisSeverity/Moderate | Noted moderate instent restenosis of the distal right internal carotid artery |
| InstentRestenosisSeverity/ModerateToSevere | Noted moderate to severe instent restenosis of the distal right internal carotid artery |
| InstentRestenosisSeverity/Severe | Noted severe instent restenosis of the distal right internal carotid artery |
| Primary Reporting Structure - Proximal left internal carotid artery | |
| Overall Normal - IsNormal | Proximal left internal carotid artery is normal |
| GsStenosisSeverity/Mild | Noted mild plaque in the proximal left internal carotid artery |
| GsStenosisSeverity/MildToModerate | Noted mild to moderate plaque in the proximal left internal carotid artery |
| GsStenosisSeverity/Moderate | Noted moderate plaque in the proximal left internal carotid artery |
| GsStenosisSeverity/ModerateToSevere | Noted moderate to severe plaque in the proximal left internal carotid artery |
| GsStenosisSeverity/Severe | Noted severe plaque in the proximal left internal carotid artery |
| GsDissection | Noted evidence of dissection in the proximal left internal carotid artery |
| SpectralBroadening | Noted evidence of spectral broadening in the proximal left internal carotid artery |
| ExtendsTo/ProximalCommonCarotidArtery | Noted evidence of metallic stent in the proximal left internal carotid artery extending to proximal left common carotid artery |
| ExtendsTo/MidCommonCarotidArtery | Noted evidence of metallic stent in the proximal left internal carotid artery extending to mid left common carotid artery |
| ExtendsTo/DistalCommonCarotidArtery | Noted evidence of metallic stent in the proximal left internal carotid artery extending to distal left common carotid artery |
| ExtendsTo/BifurcationCommonCarotidArtery | Noted evidence of metallic stent in the proximal left internal carotid artery extending to bifurcation left common carotid artery |
| ExtendsTo/ProximalInternalCarotidArtery | Noted evidence of metallic stent in the proximal left internal carotid artery |
| ExtendsTo/MidInternalCarotidArtery | Noted evidence of metallic stent in the proximal left internal carotid artery extending to mid left internal carotid artery |
| ExtendsTo/DistalInternalCarotidArtery | Noted evidence of metallic stent in the proximal left internal carotid artery extending to distal left internal carotid artery |
| ExtendsTo/ExternalCarotidArtery | Noted evidence of metallic stent in the proximal left internal carotid artery extending to left external carotid artery |
| InstentRestenosisSeverity/Mild | Noted mild instent restenosis of the proximal left internal carotid artery |
| InstentRestenosisSeverity/MildToModerate | Noted mild to moderate instent restenosis of the proximal left internal carotid artery |

| Attribute or Property Selection | Custom Text String to be added to Report Findings |
|---|---|
| InstentRestenosisSeverity/Moderate | Noted moderate instent restenosis of the proximal left internal carotid artery |
| InstentRestenosisSeverity/ModerateToSevere | Noted moderate to severe instent restenosis of the proximal left internal carotid artery |
| InstentRestenosisSeverity/Severe | Noted severe instent restenosis of the proximal left internal carotid artery |
| Primary Reporting Structure - Mid left internal carotid artery | |
| Overall Normal - IsNormal | Mid left internal carotid artery is normal |
| GsStenosisSeverity/Mild | Noted mild plaque in the mid left internal carotid artery |
| GsStenosisSeverity/MildToModerate | Noted mild to moderate plaque in the mid left internal carotid artery |
| GsStenosisSeverity/Moderate | Noted moderate plaque in the mid left internal carotid artery |
| GsStenosisSeverity/ModerateToSevere | Noted moderate to severe plaque in the mid left internal carotid artery |
| GsStenosisSeverity/Severe | Noted severe plaque in the mid left internal carotid artery |
| GsDissection | Noted evidence of dissection in the mid left internal carotid artery |
| SpectralBroadening | Noted evidence of spectral broadening in the mid left internal carotid artery |
| ExtendsTo/ProximalCommonCarotid Artery | Noted evidence of metallic stent in the mid left internal carotid artery extending to proximal left common carotid artery |
| ExtendsTo/MidCommonCarotidArtery | Noted evidence of metallic stent in the mid left internal carotid artery extending to mid left common carotid artery |
| ExtendsTo/DistalCommonCarotid Artery | Noted evidence of metallic stent in the mid left internal carotid artery extending to distal left common carotid artery |
| ExtendsTo/BifurcationCommonCarotidArtery | Noted evidence of metallic stent in the mid left internal carotid artery extending to bifurcation left common carotid artery |
| ExtendsTo/ProximalInternalCarotidArtery | Noted evidence of metallic stent in the mid left internal carotid artery extending to proximal left internal carotid artery |
| ExtendsTo/MidInternalCarotidArtery | Noted evidence of metallic stent in the mid left internal carotid artery |
| ExtendsTo/DistalInternalCarotidArtery | Noted evidence of metallic stent in the mid left internal carotid artery extending to distal left internal carotid artery |
| ExtendsTo/ExternalCarotidArtery | Noted evidence of metallic stent in the mid left internal carotid artery extending to left external carotid artery |
| InstentRestenosisSeverity/Mild | Noted mild instent restenosis of the mid left internal carotid artery |
| InstentRestenosisSeverity/MildToModerate | Noted mild to moderate instent restenosis of the mid left internal carotid artery |
| InstentRestenosisSeverity/Moderate | Noted moderate instent restenosis of the mid left internal carotid artery |
| InstentRestenosisSeverity/ModerateToSevere | Noted moderate to severe instent restenosis of the mid left internal carotid artery |
| InstentRestenosisSeverity/Severe | Noted severe instent restenosis of the mid left internal carotid artery |
| Primary Reporting Structure - Distal left internal carotid artery | |
| Overall Normal - IsNormal | Distal left internal carotid artery is normal |
| GsStenosisSeverity/Mild | Noted mild plaque in the distal left internal carotid artery |
| GsStenosisSeverity/MildToModerate | Noted mild to moderate plaque in the distal left internal carotid artery |
| GsStenosisSeverityModerate | Noted moderate plaque in the distal left internal carotid artery |
| GsStenosisSeverity/ModerateToSevere | Noted moderate to severe plaque in the distal left internal carotid artery |
| GsStenosisSeverity/Severe | Noted severe plaque in the distal left internal carotid artery |
| GsDissection | Noted evidence of dissection in the distal left internal carotid artery |
| SpectralBroadening | Noted evidence of spectral broadening in the distal left internal carotid artery |
| ExtendsTo/ProximalCommonCarotidArtery | Noted evidence of metallic stent in the distal left internal carotid artery extending to proximal left common carotid artery |
| ExtendsTo/MidCommonCarotidArtery | Noted evidence of metallic stent in the distal left internal carotid artery extending to mid left common carotid artery |
| ExtendsTo/DistalCommonCarotidArtery | Noted evidence of metallic stent in the distal left internal carotid artery extending to distal left common carotid artery |
| ExtendsTo/BifurcationCommonCarotidArtery | Noted evidence of metallic stent in the distal left internal carotid artery extending to bifurcation left common carotid artery |
| ExtendsTo/ProximalInternalCarotidArtery | Noted evidence of metallic stent in the distal left internal carotid artery extending to proximal left internal carotid artery |
| ExtendsTo/MidInternalCarotidArtery | Noted evidence of metallic stent in the distal left internal carotid artery extending to mid internal carotid artery |
| ExtendsTo/DistalInternalCarotidArtery | Noted evidence of metallic stent in the distal left internal carotid artery |
| ExtendsTo/ExternalCarotidArtery | Noted evidence of metallic stent in the distal left internal carotid artery extending to left external carotid artery |
| InstentRestenosisSeverity/Mild | Noted mild instent restenosis of the distal left internal carotid artery |

| Attribute or Property Selection | Custom Text String to be added to Report Findings |
|---|---|
| InstentRestenosisSeverity/MildToModerate | Noted mild to moderate instent restenosis of the distal left internal carotid artery |
| InstentRestenosisSeverity/Moderate | Noted moderate instent restenosis of the distal left internal carotid artery |
| InstentRestenosisSeverity/ModerateToSevere | Noted moderate to severe instent restenosis of the distal left internal carotid artery |
| InstentRestenosisSeverity/Severe | Noted severe instent restenosis of the distal left internal carotid artery |
| Primary Reporting Structure - Right external carotid artery | |
| Overall Normal - IsNormal | Right external carotid artery is normal |
| GsStenosisSeverity/Mild | Noted mild plaque in the right external carotid artery |
| GsStenosisSeverity/MildToModerate | Noted mild to moderate plaque in the right external carotid artery |
| GsStenosisSeverity/Moderate | Noted moderate plaque in the right external carotid artery |
| GsStenosisSeverity/ModerateToSevere | Noted moderate to severe plaque in the right external carotid artery |
| GsStenosisSeverity/Severe | Noted severe plaque in the right external carotid artery |
| GsDissection | Noted evidence of dissection in the right external carotid artery |
| SpectralBroadening | Noted evidence of spectral broadenirig in the right external carotid artery |
| ExtendsTo/ProximalCommonCarotidArtery | Noted evidence of metallic stent in the right external carotid artery extending to proximal right common carotid artery |
| ExtendsTo/MidCommonCarotidArtery | Noted evidence of metallic stent in the right external carotid artery extending to mid right common carotid artery |
| ExtendsTo/DistalCommonCarotidArtery | Noted evidence of metallic stent in the right external carotid artery extending to distal right common carotid artery |
| ExtendsTo/BifurcationCommonCarotidArtery | Noted evidence of metallic stent in the right external carotid artery extending to bifurcation right common carotid artery |
| ExtendsTo/ProximalInternalCarotidArtery | Noted evidence of metallic stent in the right external carotid artery extending to proximal right internal carotid artery |
| ExtendsTo/MidInternalCarotidArtery | Noted evidence of metallic stent in the right external carotid artery extending to mid right internal carotid artery |
| ExtendsTo/DistalInternalCarotidArtery | Noted evidence of metallic stent in the right external carotid artery extending to distal right internal carotid artery |
| ExtendsTo/ExternalCarotidArtery | Noted evidence of metallic stent in the right external carotid artery |
| InstentRestenosisSeverity/Mild | Noted mild instent restenosis of the right external carotid artery |
| InstentRestenosisSeverity/MildToModerate | Noted mild to moderate instent restenosis of the right external carotid artery |
| InstentRestenosisSeverity/Moderate | Noted moderate instent restenosis of the right external carotid artery |
| InstentRestenosisSeverity/ModerateToSevere | Noted moderate to severe instent restenosis of the right external carotid artery |
| InstentRestenosisSeverity/Severe | Noted severe instent restenosis of the right external carotid artery |
| Primary Reporting Structure - Left external carotid artery | |
| Overall Normal - IsNormal | Left external carotid artery is normal |
| GsStenosisSeverity/Mild | Noted mild plaque in the left external carotid artery |
| GsStenosisSeverity/MildToModerate | Noted mild to moderate plaque in the left external carotid artery |
| GsStenosisSeverity/Moderate | Noted moderate plaque in the left external carotid artery |
| GsStenosisSeverity/ModerateToSevere | Noted moderate to severe plaque in the left external carotid artery |
| GsStenosisSeverity/Severe | Noted severe plaque in the left external carotid artery |
| GsDissection | Noted evidence of dissection in the left external carotid artery |
| SpectralBroadening | Noted evidence of spectral broadening in the left external carotid artery |
| ExtendsTo/ProximalCommonCarotidArtery | Noted evidence of metallic stent in the left external carotid artery extending to proximal left common carotid artery |
| ExtendsTo/MidCommonCarotidArtery | Noted evidence of metallic stent in the left external carotid artery extending to mid left common carotid artery |
| ExtendsTo/DistalCommonCarotidArtery | Noted evidence of metallic stent in the left external carotid artery extending to distal left common carotid artery |
| ExtendsTo/BifurcationCommonCarotidArtery | Noted evidence of metallic stent in the left external carotid artery extending to bifurcation left common carotid artery |
| ExtendsTo/ProximalInternalCarotidArtery | Noted evidence of metallic stent in the left external carotid artery extending to proximal left internal carotid artery |
| ExtendsTo/MidInternalCarotidArtery | Noted evidence of metallic stent in the left external carotid artery extending to mid left internal carotid artery |
| ExtendsTo/DistalInternalCarotidArtery | Noted evidence of metallic stent in the left external carotid artery extending to distal left internal carotid artery |
| ExtendsTo/ExternalCarotidArtery | Noted evidence of metallic stent in the left external carotid artery |
| InstentRestenosisSeverity/Mild | Noted mild instent restenosis of the left external carotid artery |
| InstentRestenosisSeverity/MildToModerate | Noted mild to moderate instent restenosis of the left external carotid artery |
| InstentRestenosisSeverity/Moderate | Noted moderate instent restenosis of the left external carotid artery |

| Attribute or Property Selection | Custom Text String to be added to Report Findings |
|---|---|
| InstentRestenosisSeverity/ModerateToSevere | Noted moderate to severe instent restenosis of the left external carotid artery |
| InstentRestenosisSeverity/Severe | Noted severe instent restenosis of the left external carotid artery |
| Primary Reporting Structure - Right vertebral artery | |
| Overall Normal - IsNormal | Right vertebral artery is normal |
| SegmentOfStenosis/V1 | Noted evidence of stenosis of the V1 segment of the right vertebral artery |
| SegmentOfStenosis/V2 | Noted evidence of stenosis of the V2 segment of the right vertebral artery |
| SegmentOfStenosis/V3 | Noted evidence of stenosis of the V3 segment of the right vertebral artery |
| SegmentOfStenosis/V4 | Noted evidence of stenosis of the V4 segmentof the right vertebral artery |
| InnominateArteryStenosis | Right vertebral arterial flow is suggestive of innominate artery stenosis |
| AneurysmalSegment/V1 | Aneursym of the V1 segment of the right vertebral artery is noted |
| AneurysmalSegment/V2 | Aneursym of the V2 segment of the right vertebral artery is noted |
| AneurysmalSegment/V3 | Aneursym of the V3 segment of the right vertebral artery is noted |
| AneurysmalSegment/V4 | Aneursym of the V4 segment of the right vertebral artery is noted |
| FlowDirection/Antegrade | Right vertebral artery shows antegrade flow |
| FlowDirection/Retrograde | Right vertebral artery shows retrograde flow |
| FlowDirection/Bi-directional | Bi-directional flow direction in the right vertebral artery |
| SegmentOfDissection/V1 | Dissection of the V1 segment of the right vertebral artery is noted |
| SegmentOfDissection/V2 | Dissection of the V2 segment of the right vertebral artery is noted |
| SegmentOfDissection/V3 | Dissection of the V3 segment of the right vertebral artery is noted |
| SegmentOfDissection/V4 | Dissection of the V4 segment of the right vertebral artery is noted |
| EvidenceOfHypoplasia | Right vertebral artery appears to be hypoplasia |
| InstentRestenosisSeverity/Mild | Mild instent restenosis is noted |
| InstentRestenosisSeverity/MildToModerate | Mild to moderate instent restenosis is noted |
| InstentRestenosisSeverity/Moderate | Moderate instent restenosis is noted |
| InstentRestenosisSeverity/ModerateToSevere | Moderate to severe instent restenosis is noted |
| InstentRestenosisSeverity/Severe | Severe instent restenosis is noted |
| Primary Reporting Structure - Left vertebral artery | |
| Overall Normal - IsNormal | Left vertebral artery is normal |
| SegmentOfStenosis/V1 | Noted evidence of stenosis of the V1 segment of the left vertebral artery |
| SegmentOfStenosis/V2 | Noted evidence of stenosis of the V2 segment of the left vertebral artery |
| SegmentOfStenosis/V3 | Noted evidence of stenosis of the V3 segment of the left vertebral artery |
| SegmentOfStenosis/V4 | Noted evidence of stenosis of the V4 segment of the left vertebral artery |
| SubclavianStenosis | Left vertebral arterial flow is suggestive of subclavian artery stenosis |
| AneurysmalSegment/V1 | Aneursym of the V1 segment of the left vertebral artery is noted |
| AneurysmalSegment/V2 | Aneursym of the V2 segment of the left vertebral artery is noted |
| AneurysmalSegment/V3 | Aneursym of the V3 segment of the left vertebral artery is noted |
| AneurysmalSegment/V4 | Aneursym of the V4 segment of the left vertebral artery is noted |
| FlowDirection/Antegrade | Left vertebral artery shows antegrade flow |
| FlowDirection/Retrograde | Left vertebral artery shows retrograde flow |
| FlowDirection/Bi-directional | Bi-directional flow direction in the right vertebral artery |
| SegmentOfDissection/V1 | Dissection of the V1 segment of the left vertebral artery is noted |
| SegmentOfDissection/V2 | Dissection of the V2 segment of the left vertebral artery is noted |
| SegmentOfDissection/V3 | Dissection of the V3 segment of the left vertebral artery is noted |
| SegmentOfDissection/V4 | Dissection of the V4 segment of the left vertebral artery is noted |
| EvidenceOfHypoplasia | Noted hypoplasia in the left vertebral artery |
| InstentRestenosisSeverity/Mild | Noted mild instent restenosis |
| InstentRestenosisSeverity/MildToModerate | Noted mild to moderate instent restenosis |
| InstentRestenosisSeverity/Moderate | Noted moderate instent restenosis |
| InstentRestenosisSeverity/ModerateToSevere | Noted moderate to severe instent restenosis |
| InstentRestenosisSeverity/Severe | Noted severe instent restenosis |

Echocardiogram
Database Fields: Demographics

1. First Name
2. Last Name
3. DOB
4. Sex
5. Medical Record Number
6. Social Security Number
7. Race
8. IsActive
9. Physicians
10. Last Name
11. First Name
12. Degree
13. PhysicianType
14. Signature
15. Contact
16. Phone Office
17. Phone Home
18. Phone Mobile
19. Fax
20. Email
21. Address
22. City
23. ZipCode
24. State

Schedule 25.
26. First Name
27. Last Name
28. DOB
29. Schedule
30. NotifyScheduled
31. NotifyReported
32. SendTime
33. ViewedTime
34. IsActive
35. InsertedDate
36. IsNotified
37. NotifiedDate
38. NotifiedBy
39. Sex

Study

40. Study Date
41. erpretation Date
42. Study Start Time
43. Study End Time
44. Study Duration
45. Study Report Time
46. Technician
47. Type
48. Quality
49. erpretingPhysician
50. PerformedPhysician
51. Urgenterpretationneeded
52. Components
53. ReportGenerator
54. Location
55. Remarks
56. StudyDiagnosis
57. Study
58. StudyTypeDiagnosis
59. StudyType
60. Study Type

Diagnosis

61. Description
62. ICD
63. Notify
64. NotifyId
65. NotifyDate
66. Notifyby
67. NotifyWhom
68. Comments

Facility

69. FacilityID
70. FacilityName
71. FacilityAddress
72. FacilityPhone
73. FacilityFax
74. State
75. FacilityStartTime
76. FacilityEndTime
77. StudyDurationshort

Insurance

78. InsuranceID
79. InsuranceName
80. IsActive
81. Patient Insurance
82. Patient InsuranceID
83. InsuranceID
84. IsPrimary

Vitals

85. SBPshort
86. DBPshort
87. PRshort
88. ECGRhythm
89. Height
90. Weight
91. BSA
92. BMI
93. PRshort

Users

94. UserId
95. UserName
96. Password
97. FullName
98. UserRole
99. IsActive

Database Fields: Echocardiogram
Left Atrium

100. IsNormal
101. Size
102. Dimension
103. Volume (Normal Values) (Calculation)
104. VolumeIndex
105. Thrombus
106. ThrombusSize
107. ThrombusLocation
108. ThrombusShape
109. ThrombusTexture
110. ThrombusMobility
111. ThrombusHeight
112. ThrombusWidth
113. Mass
114. MassSize
115. MassShape
116. MassLocation
117. MassAttachment
118. MassMobility
119. MassHeight
120. MassWidth
121. MassType
122. Catheter
123. CatheterLocation
124. SpontaneousEchoContrast
125. SpontaneousEchoContrastLocation
126. SpontaneousEchoContrastSeverity
127. CorTriatriatum
128. NotVisualized

Right Atrium

129. IsNormal
130. RASize
131. RA Dimension
132. RAThrombus
133. RA Thrombus Size
134. RA Thrombus Location
135. RAThrombus Shape -continued

| | |
|---|---|
| 136. | RAThrombus Texture |
| 137. | RAThrombus Mobility |
| 138. | RAThrombus Height |
| 139. | RAThrombusWidth |
| 140. | RAMass |
| 141. | RAMass Size |
| 142. | RAMass Shape |
| 143. | RAMass Location |
| 144. | RAMass Mobility |
| 145. | RAMass Height |
| 146. | RAMass Width |
| 147. | RAMass Type |
| 148. | RACatheter |
| 149. | RAPacemaker |
| 150. | RACatheter Location |
| 151. | RAPacemaker Location |
| 152. | RASpontaneous Echo Contrast |
| 153. | RASpontaneous Echo Contrast Location |
| 154. | RASpontaneous Echo Contrast Severity |
| 155. | DilatedCoronarySinus |
| 156. | DilatedHepaticVeins |
| 157. | DilatedIVCWithPoorInspiratoryCollapse |
| 158. | erAtrialSeptumBowedLeft |
| 159. | RAPressureElevated |
| 160. | ProminantEustachianValve |
| 161. | ProminantChiariNetwork |
| 162. | HyoplasticRightAtrium |
| 163. | CardiacTransplantAppearance |
| 164. | NotVisualized |

Atrial Septum

| | |
|---|---|
| 165. | IsNormal |
| 166. | Bowing of Atrial Septum to Left |
| 167. | AtrialSeptalDefect (ASD) |
| 168. | Location |
| 169. | ASD Size |
| 170. | ASDShuntDirection |
| 171. | QpQsRatio |
| 172. | PatentForamenOvale (PFO) |
| 173. | PFOShuntDirection |
| 174. | NotVisualized |

Left Ventricle

| | |
|---|---|
| 175. | LVIsNormal |
| 176. | CavitySize |
| 177. | EndDiastolic Dimension (LVEDD) |
| 178. | EndSystolic Dimension (LVESD) |
| 179. | EndDiastolic posterobasal free wall thickness(LVEDPWT) |
| 180. | LVHSeverity |
| 181. | LeftVentricularMass (LVM) |
| 182. | LeftVentricularMassIndex (LVMI) |
| 183. | EndDiastolic SeptalThickness (LVEDST) |
| 184. | WallMotionAbnormality |
| 185. | WallMotionScoreIndex (WMSI) |
| 186. | EjectionFraction (EF) |
| 187. | GlobalFunction |
| 188. | FractionalShortening (FS) |
| 189. | LVHypertrophy |
| 190. | LVHypertrophyType |
| 191. | LVPseudoaneurysm |
| 192. | LVPseudoaneurysmType |
| 193. | AbnormalSeptalMotion |
| 194. | LV Thrombus |
| 195. | LV Thrombus Size |
| 196. | LV Thrombus Location |
| 197. | LV ThrombusShape |
| 198. | LV Thrombus Texture |
| 199. | LV ThrombusMobility |
| 200. | LV ThrombusHeight |
| 201. | LV ThrombusWidth |
| 202. | LVMassPresent |
| 203. | LV Mass Size |
| 204. | LV Mass Shape |
| 205. | LV Mass Location |
| 206. | LV Mass Mobility |
| 207. | LV Mass Height |
| 208. | LV Mass Width |
| 209. | LV Mass Texture |
| 210. | LVElevatedDiastolicFillingPressure |
| 211. | LVDiastolicFillingPressure |
| 212. | LV Outflow Tract Diameter (LVOTD) |
| 213. | LV Outflow Tract VTI (LVOTVTI) |
| 214. | LVOT Peak Velocity (LVOTPV) |
| 215. | LVOT Peak Gradient (LVOTPG) |
| 216. | LVOT Mean Velocity (LVOTMV) |
| 217. | LVOT Mean Gradient (LVOTMG) |
| 218. | Cardiac Output (LVCO) |
| 219. | Cardiac Index (LVCI) |
| 220. | SegmentBasalAS |
| 221. | SegmentBasalAnt |
| 222. | SegmentBasalAntLat |
| 223. | SegmentBasalPostLat |
| 224. | SegmentBasalInf |
| 225. | SegmentBasalIS |
| 226. | SegmentMidAS |
| 227. | SegmentMidAnt |
| 228. | SegmentMidAntLat |
| 229. | SegmentMidPostLat |
| 230. | SegmentMidInf |
| 231. | SegmentMidIS |
| 232. | SegmentApicalAS |
| 233. | SegmentApicalAnt |
| 234. | SegmentApicalAntLat |
| 235. | SegmentApicalPostLat |
| 236. | SegmentApicalInf |
| 237. | SegmentApicalIS |
| 238. | E/A |
| 239. | VP |
| 240. | Valsalva |
| 241. | NotVisualized |

Right Ventricle

| | |
|---|---|
| 242. | RV Diastolic Dimension |
| 243. | RVSystolicPressure |
| 244. | IsNormal |
| 245. | Cavity Size |
| 246. | Hypertrophy |
| 247. | Hypertrophy Severity |
| 248. | RV Global Function |
| 249. | RV Freewall Segmental Abnormality |
| 250. | RV Septum Segmental Abnormality |
| 251. | RV Lateralwall Segmental Abnormality |
| 252. | RV CorPulmonale |
| 253. | RV Dysplasia |
| 254. | RV Infarction |
| 255. | NotVisualized |

Aortic Valve

| | |
|---|---|
| 256. | IsNormal |
| 257. | Is Prosthetic |
| 258. | AVNumber Of Leaflets |
| 259. | AVAbnormal Leaflet |
| 260. | Abnormal LeafletsType |
| 261. | Aortic Prosthetic Valve |
| 262. | Aortic Prosthetic Valve Material Type |
| 263. | Aortic Prosthetic Valve Functions Normally |
| 264. | Aortic Metallic Prosthetic Valve Type |
| 265. | BioProsthetic Valve Type |
| 266. | Aortic Valve Manufacturer |
| 267. | Aortic Prosthetic Valve Dysfunction Type |
| 268. | Vegetation Present |
| 269. | Vegetation Location |
| 270. | AV Vegetation Mobility |
| 271. | Vegetation Size |
| 272. | Vegetation Height |
| 273. | Vegetation Width |
| 274. | Abscess |
| 275. | Abscess Location |
| 276. | Abscess Size |
| 277. | Abscess Height |
| 278. | Abscess Width |
| 279. | Perforation |
| 280. | Mass |
| 281. | Mass Location |
| 282. | Mass Size |
| 283. | Aortic Stenosis |

| # | |
|---|---|
| 284. | Aortic Stenosis Severity |
| 285. | Trans Aortic Peak Velocity |
| 286. | Trans Aortic Peak gradient |
| 287. | Trans Aortic Mean Velocity |
| 288. | Trans Aortic Mean Gradient |
| 289. | LVOT Diameter |
| 290. | Aortic Valve Area Planimetry |
| 291. | Aortic Regurgitation |
| 292. | AV Regurgitation Severity |
| 293. | AreaByPHT |
| 294. | Holodiastolic flow reversal |
| 295. | AorticCuspSeperation |
| 296. | AorticValveAreaContinuityEquation |
| 297. | AorticValveVTI |
| 298. | AorticRegurgitationDecelerationTime |
| 299. | Calcification |
| 300. | NotVisualized |

Mitral Valve

| # | |
|---|---|
| 301. | Is Prosthetic |
| 302. | Is Normal |
| 303. | Is Rheumatic |
| 304. | Is Myxomatous |
| 305. | Prolapse |
| 306. | ProlapsedLeaflets |
| 307. | ProlapseSeverity |
| 308. | MV ProlapsePhase |
| 309. | ProlapsedSegment |
| 310. | Flail |
| 311. | FlailLeaflets |
| 312. | FlailSeverity |
| 313. | FlailedSegment |
| 314. | RupturedChordae |
| 315. | RupturedChordaeLeaflets |
| 316. | ChordalShortening |
| 317. | ChordalFusion |
| 318. | LeafletEation |
| 319. | EatedLeaflet |
| 320. | LeafletEationSeverity |
| 321. | AnteriorLeafletMobility |
| 322. | PosteriorLeafletMobility |
| 323. | AnteriorLeafletThickeningPresent |
| 324. | AnteriorLeafletThickeningSeverity |
| 325. | PosteriorLeatletThickeningPresent |
| 326. | PosteriorLeafletThickeningSeverity |
| 327. | AnnularCalcificationPresent |
| 328. | AnnularCalcificationSeverity |
| 329. | SubvalvularCalcificationPresent |
| 330. | SubvalvularCalcificationSeverity |
| 331. | SubvalvularThickeningPresent |
| 332. | SubvalvularThickeningSeverity |
| 333. | AnnularDilatationPresent |
| 334. | AnnularDilatationSeverity |
| 335. | VegetationPresent |
| 336. | VegetationLocation |
| 337. | VegetationMobility |
| 338. | Vegetation Size |
| 339. | Vegetation Height |
| 340. | Vegetation Width |
| 341. | Abscess |
| 342. | Abscess Location |
| 343. | Abscess Size |
| 344. | Abscess Height |
| 345. | Abscess Width |
| 346. | Cleft |
| 347. | Cleft Leaflet |
| 348. | Cleft Severity |
| 349. | SAM |
| 350. | SAM Components |
| 351. | SAM Severity |
| 352. | DilatedAnnulus |
| 353. | DilatedAnnulusHeight |
| 354. | DilatedAnnulusWidth |
| 355. | IncreasedEPoSeptalSeperation |
| 356. | PreSystolicClosure |
| 357. | BNotch |
| 358. | Diastolic Fluttering |
| 359. | DiastolicFluttering Leaflet |
| 360. | Prosthetic Valve |
| 361. | Prosthetic Valve Material Type |
| 362. | Prosthetic Valve Functions Normally |
| 363. | Metallic Prosthetic Valve Type |
| 364. | BioProsthetic Valve Type |
| 365. | Valve Manufacturer |
| 366. | Prosthetic Valve Dysfunction Type |
| 367. | Ring |
| 368. | Commissurotomy |
| 369. | Stenosis |
| 370. | Stenosis Severity |
| 371. | Area ByPlanimetry(cm) |
| 372. | Area ByPressureHalfTime(cm) |
| 373. | Mean TransMitral Velocity(m/s) |
| 374. | Mean TransMitral Gradient(mm Hg) |
| 375. | Regurgitation |
| 376. | Regurgitation Severity |
| 377. | Regurgitation Jet Direction |
| 378. | Diastolic Regurgitation |
| 379. | MR Jet/LA area ratio |
| 380. | MVPulmonary Venous Flow Pattern |
| 381. | MR Volume Pulse Doppler Method(ml) |
| 382. | MR Volume Color Doppler Method(PISA)(ml) |
| 383. | MR Fraction Pulse Doppler Method(%) |
| 384. | MR Fraction Color Doppler Method(PISA)(%) |
| 385. | ERO Area Pulse Doppler Method(cm) |
| 386. | ERO Area Color Doppler Method(PISA)(cm) |
| 387. | Pressure Half Time (PHT) |
| 388. | Deceleration Time (DT) |
| 389. | E - Velocity (e) |
| 390. | A - Velocity (a) |
| 391. | Mitral Annular e' velocity |
| 392. | E/e' |
| 393. | Calcification |

Tricuspid Valve

| # | |
|---|---|
| 394. | NotVisualized |
| 395. | TVId |
| 396. | IsNormal |
| 397. | IsRheumatic |
| 398. | Prolapse |
| 399. | ProlapsedLeaflets |
| 400. | ProlapseSeverity |
| 401. | TV ProlapsePhase |
| 402. | RupturedChordae |
| 403. | RupturedChordaeFlailLeaflets |
| 404. | EbsteinsAnomaly |
| 405. | Atresia |
| 406. | VegetationPresent |
| 407. | VegetationLocation |
| 408. | VegetationMobility |
| 409. | Vegetation Size |
| 410. | Vegetation Height |
| 411. | Vegetation Width |
| 412. | DilatedAnnulus |
| 413. | DilatedAnnulus Size |
| 414. | Stenosis |
| 415. | Stenosis Severity |
| 416. | Peak Tricuspid Velocity(m/s) |
| 417. | Peak TransTricuspid Gradient(mm Hg) |
| 418. | Mean Tricuspid Velocity(m/s) |
| 419. | Mean TransTricuspid Gradient(mm Hg) |
| 420. | Area(cm) |
| 421. | Regurgitation |
| 422. | Regurgitation Severity |
| 423. | Regurgitation Jet Direction |
| 424. | Hepatic Venous Flow Pattern |
| 425. | Prosthetic Valve |
| 426. | Prosthetic Valve Material Type |
| 427. | Prosthetic Valve Functions Normally |
| 428. | Metallic Prosthetic Valve Type |
| 429. | BioProsthetic Valve Type |
| 430. | Valve Manufacturer |
| 431. | Prosthetic Valve Dysfunction Type |
| 432. | Calcification |
| 433. | NotVisualized |

Pulmonic Valve

| # | |
|---|---|
| 434. | IsNormal |
| 435. | Is Thickened |
| 436. | Doming |
| 437. | Excursion |

| # | |
|---|---|
| 438. | Dilated Annulus |
| 439. | VegetationPresent |
| 440. | VegetationMobility |
| 441. | Vegetation Size |
| 442. | Vegetation Height |
| 443. | Vegetation Width |
| 444. | Regurgitation |
| 445. | Regurgitation Severity |
| 446. | Stenosis |
| 447. | Stenosis Severity |
| 448. | Stenosis Level |
| 449. | Peak Velocity (m/s) |
| 450. | Peak TransPulmonic gradient(mm Hg) |
| 451. | Mean Velocity(m/s) |
| 452. | Mean TransPulmonic gradient(mm Hg) |
| 453. | Pulmonary Artery Diastolic Pressure(mm Hg) |
| 454. | Pulmonary Systolic Pressure(mm Hg) |
| 455. | Prosthetic Valve |
| 456. | Prosthetic Valve Material Type |
| 457. | Prosthetic Valve Functions Normally |
| 458. | Metallic Prosthetic Valve Type |
| 459. | BioProsthetic Valve Type |
| 460. | Valve Manufacturer |
| 461. | Prosthetic Valve Dysfunction Type |
| 462. | Calcification |
| 463. | NotVisualized |
| Pericardium | |
| 464. | IsNormal |
| 465. | PericardialThickening |
| 466. | PericardialMass |
| 467. | PericardialMassHeight |
| 468. | PericardialMassWidth |
| 469. | PericardialEffusion |
| 470. | PericardialEffusion Size |
| 471. | PericadialEffusionLength |
| 472. | PericardialEffusionLocation |
| 473. | Pericardial Effusion Content |
| 474. | Pleural Effusion |
| 475. | Pleural Effusion Size |
| 476. | Pleural Effusion Location |
| 477. | Pericardial Tamponade |
| 478. | Pericardial Constriction |
| 479. | Pericardial EffusoConstrictive |
| 480. | SeptalBounce |
| 481. | Excessive Respiratory Variation |
| 482. | Excessive Respiratory Variation Type |
| 483. | FatPad |
| 484. | Ascites |
| 485. | AscitesSeverity |
| 486. | NotVisualized |
| Aorta | |
| 487. | AorticRootDiameter |
| 488. | AscendingAortaDiameter |
| 489. | DescendingAortaDiameter |
| 490. | AorticArchDiameter |
| 491. | IsNormal |
| 492. | IsDilated |
| 493. | Dilatation Location |
| 494. | AorticAneurysm |
| 495. | AneurysmLocation |
| 496. | AorticAneurysmMaximumDiameter |
| 497. | AorticPlaque |
| 498. | PlaqueLocation |
| 499. | PlaqueCharacter |
| 500. | AorticPlaqueSize |
| 501. | AorticPlaqueMobile |
| 502. | AorticGraft |
| 503. | AorticGraftType |
| 504. | GraftLocation |
| 505. | AorticDissection |
| 506. | DissectionLocation |
| 507. | DissectionEntryPo |
| 508. | DissectionExitPo |
| 509. | False Lumen Has Thrombus |
| 510. | False Lumen Compresses SVC |
| 511. | False Lumen Compresses true lumen |
| 512. | False Lumen Thrombus and compresses true lumen |
| 513. | ramural Hematoma |
| 514. | ramural Hematoma Location |
| 515. | Aortic Dissection Classification |
| 516. | Aortic Coarctation |
| 517. | Aortic Coarctation minimum Diameter |
| 518. | Aortic Coarctation Peak Velocity |
| 519. | Aortic Coarctation Peak Gradient (mm hg) |
| 520. | Aorta TGA |
| 521. | Aorta Corrected TGA |
| 522. | NotVisualized |
| Ventricular Septum | |
| 523. | VSId |
| 524. | IsNormal |
| 525. | VSD |
| 526. | Location |
| 527. | VSDSize |
| 528. | VSDShunt |
| 529. | QpQsRatio |
| 530. | NotVisualized |
| Pulmonary Artery | |
| 531. | IsNormal |
| 532. | Is Dilated |
| 533. | DilatationSeverity |
| 534. | PulmonaryArterySystolicPressure(mm Hg) |
| 535. | SuspectPE |
| 536. | PELocation |
| 537. | PulmonaryHypertension |
| 538. | PulmonaryArteryHypoplasia |
| 539. | PulmonaryBranchStenosis |
| 540. | PatentDuctusArteriosus |
| 541. | RVOT Diameter |
| 542. | Main Pulmonary Artery Diameter |
| 543. | NotVisualized |
| Pulmonary Vein | |
| 544. | IsNormal |
| 545. | PulmonaryVenousFlowPattern |
| 546. | PulmonaryVehrombusPresent |
| 547. | PulmonaryVehrombusLocation |
| 548. | PulmonaryVeinMassPresent |
| 549. | PulmonaryVeinMassLocation |
| 550. | PulmonaryVeinLeftPartialAnomalousReturn |
| 551. | PulmonaryVeinRightPartialAnomalousReturn |
| 552. | PulmonaryVenousHypoplasia |
| 553. | Right Upper Pulmonary vein Diameter (RUPVD) |
| 554. | Right Lower Pulmonary vein Diameter (RLPVD) |
| 555. | Left Upper Pulmonary vein Diameter (LUPVD) |
| 556. | Left Lower Pulmonary vein Diameter (LLPVD) |
| 557. | Systolic Velocity (PVSV) |
| 558. | Diastolic Velocity (PVDV) |
| 559. | Pulmonary Vein Atrial Reversal Duration (PVARDUR) |
| 560. | NotVisualized |
| IVC/Hepatic Vein | |
| 561. | IsNormal |
| 562. | IVC Size |
| 563. | IvcRespiratoryChange |
| 564. | IVCFlowPattern |
| 565. | IVCMass |
| 566. | IVCMassSize |
| 567. | IVCMassHeight |
| 568. | IVCMassWidth |
| 569. | IVCArtifact |
| 570. | IVCCongenitalAnomaly |
| 571. | NotVisualized |
| Carotid artery ultrasound | |
| Common Carotid Artery (Right and Left) | |
| 572. | Segment |
| 573. | IsNormal |
| 574. | GSStenosisPresent |
| 575. | PriorCarotidEndarterectomy |
| 576. | IsPatent |
| 577. | GSStenosisSeverity |
| 578. | GSDissection |
| 579. | PeakSystolicVelocity |
| 580. | PeakDiastolicVelocity |
| 581. | SpectralBroadening |
| 582. | Stent |

-continued

| | |
|---|---|
| 583. | Origin |
| 584. | ExtendsTo |
| 585. | InstentRestenosisSeverity |
| 586. | InstentRestenosis |
| 587. | InstentRestenosisPercentage |
| 588. | RemarkId |

Internal Carotid Artery (Right and Left)

| | |
|---|---|
| 589. | Segment |
| 590. | IsNormal |
| 591. | GSStenosisPresent |
| 592. | PriorCarotidEndarterectomy |
| 593. | IsPatent |
| 594. | GSStenosisSeverity |
| 595. | GSDissection |
| 596. | PeakSystolicVelocity |
| 597. | PeakDiastolicVelocity |
| 598. | SpectralBroadening |
| 599. | Stent |
| 600. | Origin |
| 601. | ExtendsTo |
| 602. | InstentRestenosisSeverity |
| 603. | InstentRestenosis |
| 604. | InstentRestenosisPercentage |
| 605. | RemarkId |

External Carotid Artery (Right and Left)

| | |
|---|---|
| 606. | IsNormal |
| 607. | GSStenosisPresent |
| 608. | PriorCarotidEndarterectomy |
| 609. | IsPatent |
| 610. | GSStenosisSeverity |
| 611. | GSDissection |
| 612. | PeakSystolicVelocity |
| 613. | PeakDiastolicVelocity |
| 614. | SpectralBroadening |
| 615. | Stent |
| 616. | Origin |
| 617. | ExtendsTo |
| 618. | InstentRestenosisSeverity |
| 619. | InstentRestenosis |
| 620. | InstentRestenosisPercentage |

Vertebral Artery (Right and Left)

| | |
|---|---|
| 621. | VertebralArteryId |
| 622. | StudyId |
| 623. | PatientId |
| 624. | IsNormal |
| 625. | Stenosis |
| 626. | SegmentOfStenosis |
| 627. | Aneurysm |
| 628. | AneurysmalSegment |
| 629. | FlowDirection |
| 630. | Dissection |
| 631. | SegmentOfDissection |
| 632. | SubclavianStenosis |
| 633. | InnominateArteryStenosis |
| 634. | EvidenceOfHypoplasia |
| 635. | Diameter |
| 636. | Peak Systolic Velocity |
| 637. | Stent |
| 638. | Origin |
| 639. | ExtendsTo |
| 640. | InstentRestenosisSeverity |
| 641. | InstentRestenosis |
| 642. | InstentRestenosisPercentage |
| 643. | RemarkId |

Exercise Treadmill Test

| | |
|---|---|
| 644. | REKGId |
| 645. | StudyId |
| 646. | PatientId |
| 647. | IsNormal |
| 648. | HeartRate |
| 649. | Rhythm |
| 650. | SBP |
| 651. | DBP |
| 652. | Conduction |
| 653. | Arrhythmias |
| 654. | StudyIndication |
| 655. | Lead |
| 656. | Lead |
| 657. | Lead |
| 658. | AVR |
| 659. | AVL |
| 660. | AVF |
| 661. | V1 |
| 662. | V2 |
| 663. | V3 |
| 664. | V4 |
| 665. | V5 |
| 666. | V6 |

Stress EKG

| | |
|---|---|
| 667. | IsNormal |
| 668. | MaximumPredictedHR |
| 669. | MaximumAchievedHR |
| 670. | Protocols |
| 671. | Rhythm |
| 672. | STSegmentConfiguration |
| 673. | Conduction |
| 674. | Arrhythmias |
| 675. | ReasonForTermination |
| 676. | STSegmentLocation |
| 677. | STSegmentChange |
| 678. | STSegmentDepression |
| 679. | ComparisonStressSTChange |
| 680. | ComparisonETT |
| 681. | DukeTreadmillScore |
| 682. | DTScore |
| 683. | HeartRateRecovery |
| 684. | STDepressionAmount |
| 685. | Lead |
| 686. | Lead |
| 687. | Lead |
| 688. | AVR |
| 689. | AVL |
| 690. | AVF |
| 691. | V1 |
| 692. | V2 |
| 693. | V3 |
| 694. | V4 |
| 695. | V5 |
| 696. | V6 |
| 697. | ExerciseDuration |
| 698. | ExerciseMinutes |
| 699. | Time |
| 700. | HR |
| 701. | SBP |
| 702. | DBP |
| 703. | Comments |
| 704. | HRResponse |
| 705. | BPResponse |
| 706. | METS |
| 707. | MaximumSTDepressionChange |
| 708. | MaximumSTElevationChange |
| 709. | STElevationAmount |
| 710. | AnginalSymptoms |
| 711. | NonAnginalSymptoms |
| 712. | FunctionalCapacity |
| 713. | EKG Result |

Nuclear

| | |
|---|---|
| 714. | Resting EKG |
| 715. | REKGId |
| 716. | StudyId |
| 717. | PatientId |
| 718. | IsNormal |
| 719. | HeartRate |
| 720. | Rhythm |
| 721. | SBP |
| 722. | DBP |
| 723. | Conduction |
| 724. | Arrhythmias |
| 725. | Lead1 |
| 726. | Lead2 |
| 727. | Lead3 |
| 728. | AVR |
| 729. | AVL |
| 730. | AVF |

| | |
|---|---|
| 731. | V1 |
| 732. | V2 |
| 733. | V3 |
| 734. | V4 |
| 735. | V5 |
| 736. | V6 |

Stress EKG

| | |
|---|---|
| 737. | IsNormal |
| 738. | MaximumPredictedHR |
| 739. | MaximumAchievedHR |
| 740. | Protocols |
| 741. | Rhythm |
| 742. | STSegmentConfiguration |
| 743. | Conduction |
| 744. | Arrhythmias |
| 745. | ReasonForTermination |
| 746. | STSegmentLocation |
| 747. | STSegmentChange |
| 748. | STSegmentDepression |
| 749. | DukeTreadmillScore |
| 750. | DTScore |
| 751. | HeartRateRecovery |
| 752. | STDepressionAmount |
| 753. | Lead1 |
| 754. | Lead2 |
| 755. | Lead3 |
| 756. | AVR |
| 757. | AVL |
| 758. | AVF |
| 759. | V1 |
| 760. | V2 |
| 761. | V3 |
| 762. | V4 |
| 763. | V5 |
| 764. | V6 |
| 765. | ExerciseDuration |
| 766. | ExerciseMinutes |
| 767. | Time |
| 768. | HR |
| 769. | SBP |
| 770. | DBP |
| 771. | Comments |
| 772. | HRResponse |
| 773. | BPResponse |
| 774. | METS |
| 775. | MaximumSTDepressionChange |
| 776. | MaximumSTElevationChange |
| 777. | STElevationAmount |
| 778. | AnginalSymptoms |
| 779. | NonAnginalSymptoms |
| 780. | FunctionalCapacity |
| 781. | StressEKGResult |

Nuclear Rest Test

| | |
|---|---|
| 782. | IsNormal |
| 783. | IsLungUptake |
| 784. | IsRvUptake |
| 785. | SRS |
| 786. | PercentSRS |
| 787. | BasalAnterior |
| 788. | BasalAnteroseptal |
| 789. | BasalInferoseptal |
| 790. | BasalInferior |
| 791. | BasalInferolateral |
| 792. | BasalAnterolateral |
| 793. | MidAnterior |
| 794. | MidAnteroseptal |
| 795. | MidInferoseptal |
| 796. | MidInferior |
| 797. | MidInferolateral |
| 798. | MidAnterolateral |
| 799. | ApicalAnterior |
| 800. | ApicalSeptal |
| 801. | ApicalInferior |
| 802. | ApicalLateral |
| 803. | Apex |
| 804. | RemarkId |
| 805. | RestThickeningId |
| 806. | RestWallMotionId |

Nuclear Stress Test

| | |
|---|---|
| 807. | IsNormal |
| 808. | IsTidPresent |
| 809. | IsLungUptake |
| 810. | IsRvUptake |
| 811. | StressOnly |
| 812. | RestandStress |
| 813. | GatedStress |
| 814. | GatedRestandStress |
| 815. | Scatter |
| 816. | InjectDuration |
| 817. | RecoveryDuration |
| 818. | PreviousCardiacTests |
| 819. | RestDose |
| 820. | StressDose |
| 821. | PercentSSS |
| 822. | PercentSDS |
| 823. | TcdValue |
| 824. | RestDate |
| 825. | StressDate |
| 826. | StressInjectionTime |
| 827. | StressEndTime |
| 828. | SSS |
| 829. | SDS |
| 830. | LVEF |
| 831. | LVEDV |
| 832. | LVESV |
| 833. | RestLVEF |
| 834. | RestLVEDV |
| 835. | RestLVESV |
| 836. | AdenosineDose |
| 837. | RVEF |
| 838. | BasalAnterior |
| 839. | BasalAnteroseptal |
| 840. | BasalInferoseptal |
| 841. | BasalInferior |
| 842. | BasalInferolateral |
| 843. | BasalAnterolateral |
| 844. | MidAnterior |
| 845. | MidAnteroseptal |
| 846. | MidInferoseptal |
| 847. | MidInferior |
| 848. | MidInferolateral |
| 849. | MidAnterolateral |
| 850. | ApicalAnterior |
| 851. | ApicalSeptal |
| 852. | ApicalInferior |
| 853. | ApicalLateral |
| 854. | Apex |
| 855. | CardiacHistory |
| 856. | CardiacRiskFactors |
| 857. | ImagingProtocol |
| 858. | ImagingPosition |
| 859. | RestRadioPharmaceutical |
| 860. | RegionalWallMotion |
| 861. | RegionalWallMotionLocation |
| 862. | ScanSignificance |
| 863. | StressTestSummary |
| 864. | LVPerfusionSummary |
| 865. | DiseasedVessels |
| 866. | PharmacologicalStressAgent |
| 867. | ReasonofPharmacologicalAgent |
| 868. | StressRadioPharmaceutical |
| 869. | Medications |
| 870. | TestType |
| 871. | PerfusionDefectLocation |
| 872. | PerfusionDefectSize |
| 873. | PerfusionDefectSeverity |
| 874. | TypeofPerfusionDefect |
| 875. | RVMyocardialUptake |
| 876. | GlobalLVFunction |
| 877. | LVVolume |
| 878. | RegionalWallMotionSummary |
| 879. | Artifacts |
| 880. | ExtraCardiacActivity |
| 881. | RVUptake |
| 882. | GlobalRVfunction |
| 883. | RVVolume |
| 884. | NumberofDiseasedVessels |

-continued

| | |
|---|---|
| 885. | PreviousCardiacEvents |
| 886. | PreviousCardiacProcedure |
| 887. | ExtentofPerfusionDefect |
| 888. | RestGlobalLVfunction |
| 889. | RestLVVolume |
| 890. | RestRegionalWallMotionSummary |
| 891. | RemarkId |
| 892. | StressThickeningId |
| 893. | StressWallMotionId |
| | Nuclear Wall Motion (REST AND STRESS) |
| 894. | NWMId |
| 895. | StudyId |
| 896. | PatientId |
| 897. | IsNormal |
| 898. | BasalAnterior |
| 899. | BasalAnteroseptal |
| 900. | BasalInferoseptal |
| 901. | BasalInferior |
| 902. | BasalInferolateral |
| 903. | BasalAnterolateral |
| 904. | MidAnterior |
| 905. | MidAnteroseptal |
| 906. | MidInferoseptal |
| 907. | MidInferior |
| 908. | MidInferolateral |
| 909. | MidAnterolateral |
| 910. | ApicalAnterior |
| 911. | ApicalSeptal |
| 912. | ApicalInferior |
| 913. | ApicalLateral |
| 914. | Apex |
| | Nuclear Thickening (REST AND STRESS) |
| 915. | NFTId |
| 916. | StudyId |
| 917. | PatientId |
| 918. | IsNormal |
| 919. | BasalAnterior |
| 920. | BasalAnteroseptal |
| 921. | BasalInferoseptal |
| 922. | BasalInferior |
| 923. | BasalInferolateral |
| 924. | BasalAnterolateral |
| 925. | MidAnterior |
| 926. | MidAnteroseptal |
| 927. | MidInferoseptal |
| 928. | MidInferior |
| 929. | MidInferolateral |
| 930. | MidAnterolateral |
| 931. | ApicalAnterior |
| 932. | ApicalSeptal |
| 933. | ApicalInferior |
| 934. | ApicalLateral |
| 935. | Apex |
| | Stress Echocardiogram |
| 936. | Resting EKG |
| 937. | REKGId |
| 938. | StudyId |
| 939. | PatientId |
| 940. | IsNormal |
| 941. | HeartRate |
| 942. | Rhythm |
| 943. | SBP |
| 944. | DBP |
| 945. | Conduction |
| 946. | Arrhythmias |
| 947. | StudyIndication |
| 948. | Lead1 |
| 949. | Lead2 |
| 950. | Lead3 |
| 951. | AVR |
| 952. | AVL |
| 953. | AVF |
| 954. | V1 |
| 955. | V2 |
| 956. | V3 |
| 957. | V4 |

-continued

| | |
|---|---|
| 958. | V5 |
| 959. | V6 |
| | Stress EKG |
| 960. | StudyId |
| 961. | PatientId |
| 962. | IsNormal |
| 963. | MaximumPredictedHR |
| 964. | MaximumAchievedHR |
| 965. | Protocols |
| 966. | Rhythm |
| 967. | STSegmentConfiguration |
| 968. | Conduction |
| 969. | Arrhythmias |
| 970. | ReasonForTermination |
| 971. | STSegmentLocation |
| 972. | STSegmentChange |
| 973. | STSegmentDepression |
| 974. | DukeTreadmillScore |
| 975. | DTScore |
| 976. | METS |
| 977. | FunctionalCapacity |
| 978. | HeartRateRecovery |
| 979. | STDepressionAmount |
| 980. | Lead |
| 981. | Lead |
| 982. | Lead |
| 983. | AVR |
| 984. | AVL |
| 985. | AVF |
| 986. | V1 |
| 987. | V2 |
| 988. | V3 |
| 989. | V4 |
| 990. | V5 |
| 991. | V6 |
| 992. | ExerciseDuration |
| 993. | ExerciseMinutes |
| 994. | Time |
| 995. | HR |
| 996. | SBP |
| 997. | DBP |
| 998. | Comments |
| 999. | HRResponse |
| 1000. | BPResponse |
| 1001. | MaximumSTDepressionChange |
| 1002. | MaximumSTElevationChange |
| 1003. | STElevationAmount |
| 1004. | AnginalSymptoms |
| 1005. | NonAnginalSymptoms |
| 1006. | StressEKGResult |
| | Stress Echocardiogram & Rest Echocardiogram |
| 1007. | SEId |
| 1008. | StudyId |
| 1009. | PatientId |
| 1010. | IsStress |
| 1011. | WallMotionId |
| 1012. | ThickeningId |
| 1013. | LASizeOfChamber |
| 1014. | RASizeOfChamber |
| 1015. | LVSizeOfChamber |
| 1016. | LVGlobalFunction |
| 1017. | EjectionFraction |
| 1018. | LVHypertrophy |
| 1019. | RVSizeOfChamber |
| 1020. | RVGlobalFunction |
| 1021. | RVHypertrophy |
| 1022. | AVstenosis |
| 1023. | AVstenosisSeverity |
| 1024. | AVregurgitation |
| 1025. | AVRegurgitationSeverity |
| 1026. | AVPeakVelocity (m/s) |
| 1027. | AVMeanVelocity (m/s) |
| 1028. | AVMeanGradient (mmHg) |
| 1029. | AVPeakGradient (mmHg) |
| 1030. | MVregurgitation |
| 1031. | MVregurgitationSeverity |
| 1032. | MVregurgitationJetDirection |
| 1033. | MVdiastolicRegurgitation |

| | |
|---|---|
| 1034. | MVstenosis |
| 1035. | MVstenosisSeverity |
| 1036. | MVPeakVelocity (m/s) |
| 1037. | MVMeanVelocity (m/s) |
| 1038. | MVMeanGradient (mmHg) |
| 1039. | MVPeakGradient (mmHg) |
| 1040. | PVregurgitation |
| 1041. | PVregurgitationSeverity |
| 1042. | PVstenosis |
| 1043. | PVstenosisSeverity |
| 1044. | PVstenosisLevel |
| 1045. | PVPeakVelocity (m/s) |
| 1046. | PVMeanVelocity (m/s) |
| 1047. | PVMeanGradient (mmHg) |
| 1048. | PVPeakGradient (mmHg) |
| 1049. | TVstenosis |
| 1050. | TVstenosisSeverity |
| 1051. | TVregurgitation |
| 1052. | TVregurgitationSeverity |
| 1053. | TVregurgitationJetDirection |
| 1054. | PAsystolicPressure |
| 1055. | TVPeakVelocity (m/s) |
| 1056. | TVMeanVelocity (m/s) |
| 1057. | TVMeanGradient (mmHg) |
| 1058. | TVPeakGradient (mmHg) |
| 1059. | TissueHarmonicImaging |
| 1060. | ContrastStressEchocardiography |
| 1061. | RemarkId |
| Stress Echocardiogram Clinical Details | |
| 1062. | ClinicalId |
| 1063. | StudyId |
| 1064. | PatientId |
| 1065. | CardiacHistory |
| 1066. | CardiacRiskFactors |
| 1067. | Medications |
| 1068. | PreviousCardiacTests |
| 1069. | AtropineSulphateDose Wall Motion |
| 1070. | WallMotionId |
| 1071. | StudyId |
| 1072. | PatientId |
| 1073. | IsNormal |
| 1074. | BasalAnterior |
| 1075. | BasalAnteroseptal |
| 1076. | BasalInferoseptal |
| 1077. | BasalInferior |
| 1078. | BasalInferolateral |
| 1079. | BasalAnterolateral |
| 1080. | MidAnterior |
| 1081. | MidAnteroseptal |
| 1082. | MidInferoseptal |
| 1083. | MidInferior |
| 1084. | MidInferolateral |
| 1085. | MidAnterolateral |
| 1086. | ApicalAnterior |
| 1087. | ApicalSeptal |
| 1088. | ApicalInferior |
| 1089. | ApicalLateral |
| 1090. | Apex |
| 1091. | RemarkId |
| 1092. | Thickening |
| 1093. | IsNormal |
| 1094. | BasalAnterior |
| 1095. | BasalAnteroseptal |
| 1096. | BasalInferoseptal |
| 1097. | BasalInferior |
| 1098. | BasalInferolateral |
| 1099. | BasalAnterolateral |
| 1100. | MidAnterior |
| 1101. | MidAnteroseptal |
| 1102. | MidInferoseptal |
| 1103. | MidInferior |
| 1104. | MidInferolateral |
| 1105. | MidAnterolateral |
| 1106. | ApicalAnterior |
| 1107. | ApicalSeptal |
| 1108. | ApicalInferior |
| 1109. | ApicalLateral |
| 1110. | Apex |

| | |
|---|---|
| Angiogram | |
| 1111. | Consent |
| 1112. | ConsentId |
| 1113. | StudyId |
| 1114. | PatientId |
| 1115. | Obtained |
| 1116. | ObtainedText |
| 1117. | EmergencyNatureoftheProcedure |
| 1118. | PatientUnabletoGiveConsent |
| 1119. | LegalGuardianNotAvailable |
| 1120. | ObtainedFrom |
| 1121. | NotObtained |
| 1122. | Sedation |
| 1123. | SedationId |
| 1124. | SedationText |
| 1125. | StudyId |
| 1126. | PatientId |
| 1127. | Dose |
| 1128. | UnitofDose |
| 1129. | AdviserEvent |
| 1130. | AdviserEventText |
| Detail(ProcedureDetail) | |
| 1131. | ProcedureId |
| 1132. | CatheterId |
| 1133. | CatheterText |
| 1134. | StudyId |
| 1135. | PatientId |
| 1136. | BypassCatheterId |
| 1137. | BypassCatheterText |
| 1138. | LIMACatheterId |
| 1139. | LIMACatheterText |
| 1140. | RIMACatheterId |
| 1141. | RIMACatheterText |
| 1142. | SheathSize |
| 1143. | LHC |
| 1144. | LeftVentriculogram |
| 1145. | RHC |
| 1146. | BypassGraft |
| 1147. | Saphenous Venous |
| 1148. | LIMA |
| 1149. | RIMA |
| 1150. | AccessSiteDetail |
| 1151. | LocalAnestheticId |
| 1152. | LocalAnestheticText |
| 1153. | LeftCoronarycatheterId |
| 1154. | LeftCoronarycatheterText |
| 1155. | RightCoronarycatheterId |
| 1156. | RightCoronarycatheterText |
| 1157. | LeftCatheterSize |
| 1158. | RightCatheterSize |
| 1159. | LVCatheterSize |
| 1160. | CABG |
| 1161. | CABGText |
| 1162. | ValveSurgery |
| 1163. | ValveSurgeryText |
| Left Heart Catheterization | |
| 1164. | LhcId |
| 1165. | StudyId |
| 1166. | PatientId |
| 1167. | LVGramId |
| 1168. | LVGramText |
| 1169. | AorticValve |
| 1170. | LeftVentriculography |
| 1171. | LVPressure |
| 1172. | AorticDiastolicPressure |
| 1173. | TransAorticVelocity |
| 1174. | TransAorticGradient |
| 1175. | TransMitralGradient |
| 1176. | TransMitralVelocity |
| 1177. | LVDiastoilcPressure |
| 1178. | AorticSystolicPressure |
| Right Heart Catheterization | |
| 1179. | RhcId |
| 1180. | SheathId |
| 1181. | SheathText |
| 1182. | StudyId |

-continued

| | |
|---|---|
| 1183. | PatientId |
| 1184. | RHCCatheterId |
| 1185. | RHCCatheterText |
| 1186. | RHCSheathSize |
| 1187. | CatheterSize |
| 1188. | OxygenSaturation |
| 1189. | CardiacIO |
| 1190. | RightHeartPressure |
| 1191. | RhcFemoralVein |
| 1192. | Advance |
| 1193. | CardiaMethod |
| 1194. | CardiacOutput |
| 1195. | CardiacIndex |
| 1196. | PASystolicPressure |
| 1197. | PADiastolicPressure |
| 1198. | OxygenRA |
| 1199. | OxygenRV |
| 1200. | OxygenPA |
| 1201. | OxygenLV |
| 1202. | OxygenCA |
| 1203. | RAMeanPressure |
| 1204. | PAMeanPressure |
| 1205. | PulmonaryCapillaryMeanPressure |

Aortic Root Angiography

| | |
|---|---|
| 1206. | AorticRootId |
| 1207. | StudyId |
| 1208. | PatientId |
| 1209. | Size |
| 1210. | Regurgitation |
| 1211. | Aneursymal |
| 1212. | Ascending Aortic Angiography |
| 1213. | AscendingAorticId |
| 1214. | StudyId |
| 1215. | PatientId |
| 1216. | Size |
| 1217. | Aneursymal |
| 1218. | Lesion |
| 1219. | StenosisSeverity |
| 1220. | StentedSegment |
| 1221. | MultipleStents |
| 1222. | Tourtousity |
| 1223. | Bypass Graft |
| 1224. | BypassId |
| 1225. | StudyId |
| 1226. | PatientId |
| 1227. | DistalTargetNameId |
| 1228. | DistalTargetNameText |
| 1229. | GraftName |
| 1230. | GraftSegments |
| 1231. | StenosisPercent |
| 1232. | NumberOfBypassGrafts |
| 1233. | Stent |
| 1234. | Stenttype |
| 1235. | Stentname |
| 1236. | Stentdiameter |
| 1237. | Length |
| 1238. | Stenosisseverity |
| 1239. | Percentage |
| 1240. | Stenosisextend |
| 1241. | Stentyesno |
| 1242. | Dateofdeployment |
| 1243. | ManufacturerId |
| 1244. | ManufacturerName |
| 1245. | Coronaryervention |
| 1246. | CoronaryerventionId |
| 1247. | DimensionId |
| 1248. | Dimension |
| 1249. | InflationDuration |
| 1250. | DilatationPressure |
| 1251. | Numberofdilations |
| 1252. | Balloon |
| 1253. | BalloonId |
| 1254. | StudyId |
| 1255. | PatientId |
| 1256. | Diameter |
| 1257. | Length |
| 1258. | BalloonManufacturerNameId |
| 1259. | BalloonNameId |
| 1260. | BalloonNameText |

-continued

| | |
|---|---|
| 1261. | BalloonManufacturerNameText |
| 1262. | BalloonDilatationPressure |
| 1263. | Numberofdilatations |
| 1264. | BallooninflationDuration |
| 1265. | ManufacturerId |
| 1266. | ManufacturerName |
| 1267. | Coronaryervention |
| 1268. | CoronaryerventionId |
| 1269. | DimensionId |
| 1270. | Dimension |
| 1271. | ResidualStenosis |
| 1272. | Vessel |
| 1273. | VesselSize |
| 1274. | Diameter |
| 1275. | BloodFlow |
| 1276. | CalcificationSeverity |
| 1277. | CalcificationExtend |
| 1278. | StenosisSeverity |
| 1279. | StenosisPercentage |
| 1280. | OriginatingSegment |
| 1281. | EndingSegment |
| 1282. | StentedSegment |
| 1283. | MultipleStents |
| 1284. | Numberofstents |
| 1285. | Tourtousity |
| 1286. | Branches |
| 1287. | BranchName |
| 1288. | Angio Element |
| 1289. | AngioElementId |
| 1290. | AngioElementName |
| 1291. | AngioElementtype |
| 1292. | IsActive |
| 1293. | IsValid |
| 1294. | ValidationSummary |
| 1295. | Disposed |
| 1296. | Dimension |
| 1297. | Dimension |
| 1298. | IsActive |
| 1299. | Disposed |
| 1300. | CI Element |
| 1301. | CIElementId |
| 1302. | ManufacturerId |
| 1303. | ManufacturerName |
| 1304. | Coronaryervention |
| 1305. | CoronaryerventionId |
| 1306. | DimensionId |
| 1307. | Dimension |
| 1308. | CIElementtype |
| 1309. | IsActive |
| 1310. | IsValid |
| 1311. | ValidationSummary |
| 1312. | Disposed |
| 1313. | Coronary Inervention |
| 1314. | Name |
| 1315. | IsActive |
| 1316. | Disposed |
| 1317. | Manufacturer |
| 1318. | Id |
| 1319. | Name |
| 1320. | IsActive |
| 1321. | Disposed |

Peripheral Vascular Interventions

| | |
|---|---|
| 1322. | Consent |
| 1323. | ConsentId |
| 1324. | StudyId |
| 1325. | PatientId |
| 1326. | Obtained |
| 1327. | ObtainedText |
| 1328. | EmergencyNatureoftheProcedure |
| 1329. | PatientUnabletoGiveConsent |
| 1330. | LegalGuardianNotAvailable |
| 1331. | ObtainedFrom |
| 1332. | NotObtained |
| 1333. | Sedation |
| 1334. | SedationId |
| 1335. | SedationText |
| 1336. | StudyId |
| 1337. | PatientId |
| 1338. | Dose |

-continued

| | |
|---|---|
| 1339. | UnitofDose |
| 1340. | AdviserEvent |
| 1341. | AdviserEventText |
| 1342. | ProcedureDetails |
| 1343. | PciProcedureId |
| 1344. | StudyId |
| 1345. | PatientId |
| 1346. | LocalAnestheticId |
| 1347. | LocalAnestheticText |
| 1348. | AccessSiteDetail |
| 1349. | PeripherialAngiogramDetail |
| 1350. | GradeDetail |
| 1351. | IndicationsDetail |
| 1352. | Lesion |
| 1353. | StenosisDegree |
| 1354. | StenosisPercentage |
| 1355. | StenosisExtend |
| 1356. | Bypass Graft |
| 1357. | BypassId |
| 1358. | StudyId |
| 1359. | PatientId |
| 1360. | BypassName |
| 1361. | Stent |
| 1362. | StentType |
| 1363. | Stentname |
| 1364. | Stentdiameter |
| 1365. | Length |
| 1366. | SegmentStentOriginates |
| 1367. | SegmentStentends |
| 1368. | Percentage |
| 1369. | PostPercentage |
| 1370. | ManufacturerId |
| 1371. | ManufacturerName |
| 1372. | Coronaryervention |
| 1373. | CoronaryerventionId |
| 1374. | DimensionId |
| 1375. | Dimension |
| 1376. | InflationDuration |
| 1377. | DilatationPressure |
| 1378. | Numberofdilations |
| 1379. | InterventionsOutcome |
| 1380. | InterventionsOutcomeReason |
| 1381. | InterventionsComplication |
| 1382. | Balloon |
| 1383. | BalloonId |
| 1384. | StudyId |
| 1385. | PatientId |
| 1386. | Diameter |
| 1387. | Length |
| 1388. | BalloonManufacturerNameId |
| 1389. | BalloonNameId |
| 1390. | BalloonNameText |
| 1391. | BalloonManufacturerNameText |
| 1392. | BalloonDilatationPressure |
| 1393. | Numberofdilations |
| 1394. | BallooninflationDuration |
| 1395. | ManufacturerId |
| 1396. | ManufacturerName |
| 1397. | Coronaryervention |
| 1398. | CoronaryerventionId |
| 1399. | DimensionId |
| 1400. | Dimension |
| 1401. | ResidualStenosis |
| 1402. | TypeofBalloon |
| 1403. | InterventionsOutcome |
| 1404. | InterventionsOutcomeReason |
| 1405. | InterventionsComplication |
| 1406. | Vessel |
| 1407. | VesselSize |
| 1408. | Diameter |
| 1409. | Detail |
| 1410. | DetailsId |
| 1411. | StudyId |
| 1412. | PatientId |
| 1413. | Dilatation |
| 1414. | Calcification |
| 1415. | Tortousity |
| 1416. | AorticRegurgitation |
| 1417. | Dissection |
| 1418. | ByPassSurgery |

-continued

| | |
|---|---|
| 1419. | StenosisPercentage |
| 1420. | Diameter |
| 1421. | Report |

Venous Ultrasound

| | |
|---|---|
| 1422. | Segment |
| 1423. | LEVUId |
| 1424. | DetailsId |
| 1425. | SegmentName varchar(MAX) |
| 1426. | Visualized |
| 1427. | Compressibility |
| 1428. | Phasic |
| 1429. | Augmentation |
| 1430. | Thrombus |
| 1431. | HypoechoicDensity |
| 1432. | HyperechoicDensity |
| 1433. | SeverityOfOcclusion |
| 1434. | Reflux |
| 1435. | RemarkId |
| 1436. | SegmentDetails |
| 1437. | DetailsId |
| 1438. | StudyId |
| 1439. | PatientId |

Lipid Profile

| | |
|---|---|
| 1440. | Clinical History |
| 1441. | HistoryId |
| 1442. | PatientId |
| 1443. | CigaretteSmoking |
| 1444. | PatientAge |
| 1445. | Hypertension |
| 1446. | LowHDLCholesterol |
| 1447. | FamilyHistoryofPrematureCHD |
| 1448. | Diabetes |
| 1449. | Hypothyroidism |
| 1450. | NephroticSyndrome |
| 1451. | ObstructiveLiverDisease |
| 1452. | ChronicRenalFailure |
| 1453. | AcuteMyocardialInfarction |
| 1454. | SilentMyocardialInfarction |
| 1455. | HistoryofUnstableAngina |
| 1456. | StableAnginaPectoris |
| 1457. | HistoryofPCIorCABG |
| 1458. | SymptomaticCarotidArteryDisease |
| 1459. | PeripheralArterialDisease |
| 1460. | AbdominalAorticAneurysm |
| 1461. | TenYearRisk |
| 1462. | Cad |
| 1463. | AbdominalObesity |
| 1464. | TGgreaterthan |
| 1465. | HDLlessthan |
| 1466. | FBSgreaterthan |
| 1467. | Medications |

Lab Values

| | |
|---|---|
| 1468. | LipidId |
| 1469. | PatientId |
| 1470. | Received |
| 1471. | LDL |
| 1472. | HDL |
| 1473. | TC |
| 1474. | TG |
| 1475. | SGOT |
| 1476. | SGPT |
| 1477. | ALP |
| 1478. | TSH |
| 1479. | T4 |

Lab Values Details

| | |
|---|---|
| 1480. | LabDetailsId |
| 1481. | LipidId |
| 1482. | StudyId |
| 1483. | PatientId |
| 1484. | PhysicianId |

131
-continued

| | |
|---|---|
| 1485. TargetReason | |
| 1486. Allergies | |

Echocardiogram
Left Atrium
Size

| | |
|---|---|
| 1. Chamber Size | |
| 2. Dimension | |
| 3. Volume | Echocardiogram Measurements |
| 4. Volume Index | Formulas |

Thrombus

| | |
|---|---|
| 1. Size | Size |
| 2. Location | LAThrombusLocation |
| 3. Shape | EchoDensityShape |
| 4. Texture | EchoDensityTexture |
| 5. Mobility | EchoDensityMobility |
| 6. Height | Echocardiogram Measurements |
| 7. Width | Echocardiogram Measurements |

Mass

| | |
|---|---|
| 1. Size | Size |
| 2. Shape | EchoDensityShape |
| 3. Location | LAMassLocation |
| 4. Attachment Site | LA EchoDensityAttachmentSite |
| 5. Mobility | EchoDensityMobility |
| 6. Height | Echocardiogram Measurements |
| 7. Width | Echocardiogram Measurements |
| 8. Mass Type | EchoMassType |

Catheter

| | |
|---|---|
| 1. Location | AtrialArtifactLocation |

Spontaneous Echo Contrast

| | |
|---|---|
| 1. Location | AtrialSpontaneousEchoLocation |
| 2. Severity | Severity |

Miscellaneous

| | |
|---|---|
| 1. CorTriatriatum | |

Right Atrium
Size

| | |
|---|---|
| 1. Chamber Size | ChamberSize |
| 2. Dimension | Echocardiogram Measurements |

Thrombus

| | |
|---|---|
| 1. Size | Size |
| 2. Location | RAThrombusLocation |
| 3. Shape | EchoDensityShape |
| 4. Texture | EchoDensityTexture |
| 5. Mobility | EchoDensityMobility |
| 6. Height | Echocardiogram Measurements |
| 7. Width | Echocardiogram Measurements |

Mass

| | |
|---|---|
| 1. Size | Size |
| 2. Shape | EchoDensityShape |
| 3. Location | RAMassLocation |
| 4. Mobility | EchoDensityMobility |
| 5. Height | Echocardiogram Measurements |
| 6. Width | Echocardiogram Measurements |
| 7. Mass Type | EchoMassType |

Catheter

| | |
|---|---|
| 1. Location | AtrialArtifactLocation |

Pacemaker

| | |
|---|---|
| 1. Location | AtrialArtifactLocation |

Spontaneous Echo Contrast

| | |
|---|---|
| 1. Location | AtrialSpontaneousEchoLocation |
| 2. Severity | Severity |

132
-continued

Echocardiogram
Miscellaneous

1. Dilated Coronary Sinus
2. Dilated Hepatic Veins
3. Dilated IVC With Poor Inspiratory Collapse
4. Inter Atrial Septum Bowed Left
5. Pressure Elevated
6. Prominent Eustachian Valve
7. Prominent Chiari Network
8. Hyoplastic Right Atrium
9. Cardiac Transplant Appearance

Left Ventricle
Size

| | |
|---|---|
| 1. Chamber Size | ChamberSize |
| 2. End Diastolic Dimension | Echocardiogram Measurements |
| 3. End Systolic Dimension | Echocardiogram Measurements |
| 4. End Diastolic Septal Thickness | Echocardiogram Measurements |
| 5. End Diastolic posterobasal free wall thickness | Echocardiogram Measurements |
| 6. Left Ventricular Mass | Echocardiogram Measurements |
| 7. Left Ventricular Mass Index | Echocardiogram Measurements |

Systolic Function

| | |
|---|---|
| 1. Global Function | GlobalFunction |
| 2. Fractional Shortening | Formulas |
| 3. Ejection Fraction | Echocardiogram Measurements |

Diastolic Function

| | |
|---|---|
| 1. Deceleration Time | Echocardiogram Measurements |
| 2. E/A | |
| 3. E' Velocity | Echocardiogram Measurements |
| 4. E/E' | Echocardiogram Measurements |
| 5. Vp | Echocardiogram Measurements |
| 6. Valsalva | Valsalva |

Wall Motion Analysis

| | |
|---|---|
| 1. Abnormal Septal Motion | SeptalMotion |
| 2. SegmentBasalAS | WallMotionScoreIndex |
| 3. SegmentBasalAnt | WallMotionScoreIndex |
| 4. SegmentBasalAntLat | WallMotionScoreIndex |
| 5. SegmentBasalPostLat | WallMotionScoreIndex |
| 6. SegmentBasalInf | WallMotionScoreIndex |
| 7. SegmentBasalIS | WallMotionScoreIndex |
| 8. SegmentMidAS | WallMotionScoreIndex |
| 9. SegmentMidAnt | WallMotionScoreIndex |
| 10. SegmentMidAntLat | WallMotionScoreIndex |
| 11. SegmentMidPostLat | WallMotionScoreIndex |
| 12. SegmentMidInf | WallMotionScoreIndex |
| 13. SegmentMidIS | WallMotionScoreIndex |
| 14. SegmentApicalAS | WallMotionScoreIndex |
| 15. SegmentApicalAnt | WallMotionScoreIndex |
| 16. SegmentApicalAntLat | WallMotionScoreIndex |
| 17. SegmentApicalPostLat | WallMotionScoreIndex |
| 18. SegmentApicalInf | WallMotionScoreIndex |
| 19. SegmentApicalIS | WallMotionScoreIndex |

Hypertrophy

| | |
|---|---|
| 1. Severity | Severity |
| 2. Hypertrophy Type | HypertrophyType |

Thrombus

| | |
|---|---|
| 1. Size | Size |
| 2. Location | LVEchoDensityLocation |
| 3. Shape | EchoDensityShape |
| 4. Texture | EchoDensityTexture |
| 5. Mobility | EchoDensityMobility |
| 6. Height | |
| 7. Width | |

Mass

| | |
|---|---|
| 1. Size | Size |
| 2. Shape | EchoDensityShape |
| 3. Location | LVEchoDensityLocation |
| 4. Mobility | EchoDensityMobility |
| 5. Height | Echocardiogram Measurements |

Echocardiogram

| | |
|---|---|
| 6. Width | Echocardiogram Measurements |
| 7. Texture | EchoDensityTexture |

Pseudo Aneurysm

| | |
|---|---|
| 1. Type | PseudoAneurysmType |

Miscellaneous

| | |
|---|---|
| 1. LV Outflow Tract Diameter | Echocardiogram Measurements |
| 2. LV Outflow Tract VTI | Echocardiogram Measurements |
| 3. Peak Velocity | Echocardiogram Measurements |
| 4. Peak Gradient | Formulas |
| 5. Mean Velocity | Echocardiogram Measurements |
| 6. Mean Gradient | Formulas |
| 7. Cardiac Output | Echocardiogram Measurements |
| 8. Cardiac Index | Echocardiogram Measurements |

Right Ventricle
Size

| | |
|---|---|
| 1. Chamber Size | ChamberSize |

Systolic Function

| | |
|---|---|
| 1. Global Function | Global Function |
| 2. Freewall Segmental Abnormality | SegmentalMotionAbnormality |
| 3. Lateralwall Segmental Abnormality | SegmentalMotionAbnormality |
| 4. Septum Segmental Abnormality | SeptalMotion |

Hypertrophy

| | |
|---|---|
| 1. Severity | Severity |

Miscellaneous

| | |
|---|---|
| 1. Diastolic Dimension | Echocardiogram Measurements |
| 2. Systolic Pressure | Echocardiogram Measurements |
| 3. CorPulmonale | |
| 4. Dysplasia | |
| 5. Infarction | |

Atrial Septum
Atrial Septal Defect

| | |
|---|---|
| 1. Size | Size |
| 2. Location | ASDLocation |
| 3. Shunt Direction | ShuntDirection |
| 4. QpQs Ratio | Echocardiogram Measurements |

Patent Foramen Ovale

| | |
|---|---|
| 1. Shunt Direction | ShuntDirection |

Miscellaneous

| | |
|---|---|
| 1. Bowing of Atrial Septum to Left | |

Ventricular Septum
Ventricular Septal Defect

| | |
|---|---|
| 1. Size | Size |
| 2. Location | VSDLocation |
| 3. Shunt Direction | ShuntDirection |
| 4. QpQs Ratio | Echocardiogram Measurements |

Pulmonic Valve
Structure

| | |
|---|---|
| 1. Excursion | ValveExcursion |
| 2. Thickened | |
| 3. Doming | |
| 4. Dilated Annulus | |

Stenosis

| | |
|---|---|
| 1. Severity | Severity |
| 2. Level | PulmonaryStenosisLevel |

Regurgitation

| | |
|---|---|
| 1. Severity | Severity |

Doppler

| | |
|---|---|
| 1. Peak Velocity | Echocardiogram Measurements |
| 2. Mean Velocity | Echocardiogram Measurements |
| 3. Peak Trans Pulmonic gradient | Formulas |
| 4. Mean Trans Pulmonic gradient | Formulas |
| 5. Pulmonary Systolic Pressure | Echocardiogram Measurements |
| 6. Pulmonary Artery Diastolic Pressure | Echocardiogram Measurements |

Echocardiogram

Vegetation

| | |
|---|---|
| 1. Size | Size |
| 2. Mobility | VegetationMobility |
| 3. Height | Echocardiogram Measurements |
| 4. Width | Echocardiogram Measurements |

Prosthetic Valve

| | |
|---|---|
| 1. Prosthetic Valve Functions Normally | |
| 2. Prosthetic Valve Material Type | ProstheticValve MaterialType |
| 3. Valve Manufacturer | MetalicValveManufacturer |
| 4. Dysfunction Type | ProstheticValveDysfunction |

Valvular Calcification

| | |
|---|---|
| 1. Calcification | CalcificationSeverity |

Pulmonary Artery
Structure

| | |
|---|---|
| 1. RVOT Diameter | Echocardiogram Measurements |
| 2. Main Pulmonary Artery Diameter | Echocardiogram Measurements |

Dilatation

| | |
|---|---|
| 1. Severity | Severity |

Suspected Pulmonary Embolism

| | |
|---|---|
| 1. Location | PAComponents |

Pulmonary Artery Pressure

| | |
|---|---|
| 1. Pulmonary Artery Systolic Pressure | Echocardiogram Measurements |
| 2. Pulmonary Hypertension | |

Miscellaneous

| | |
|---|---|
| 1. Pulmonary Branch Stenosis | PAComponents |
| 2. Pulmonary Artery Hypoplasia | |
| 3. Patent Ductus Arteriosus | |

Pulmonary Vein
Structure

| | |
|---|---|
| 1. Right Upper Pulmonary vein Diameter | Echocardiogram Measurements |
| 2. Right Lower Pulmonary vein Diameter | Echocardiogram Measurements |
| 3. Left Upper Pulmonary vein Diameter | Echocardiogram Measurements |
| 4. Left Lower Pulmonary vein Diameter | Echocardiogram Measurements |
| 5. Systolic Velocity | Echocardiogram Measurements |
| 6. Diastolic Velocity | Echocardiogram Measurements |
| 7. Pulmonary Vein Atrial Reversal Duration | Echocardiogram Measurements |

Thrombus

| | |
|---|---|
| 1. Location | PulmonaryVeinComponents |

Mass

| | |
|---|---|
| 1. Location | PulmonaryVeinComponents |

Miscellaneous

| | |
|---|---|
| 1. Pulmonary Venous Flow Pattern | VenousFlowPattern |
| 2. Pulmonary Vein Left Partial Anomalous Return | |
| 3. Pulmonary Vein Right Partial Anomalous Return | |
| 4. Pulmonary Venous Hypoplasia | |

Mitral Valve
Structure

| | |
|---|---|
| 1. Anterior Leaflet Mobility | LeafletMobility |
| 2. Posterior Leaflet Mobility | LeafletMobility |
| 3. AnteriorLeafletThickeningSeverity | MitralValve Severity |
| 4. PosteriorLeafletThickeningSeverity | MitralValve Severity |
| 5. Elongated Leaflet | MitralLeaflets |
| 6. LeafletElongationSeverity | Severity |
| 7. AnnularCalcificationSeverity | Severity |
| 8. SubvalvularCalcificationSeverity | Severity |
| 9. SubvalvularThickeningSeverity | MitralValve Severity |
| 10. RupturedChordaeLeaflets | MitralLeaflets |

| Echocardiogram | |
|---|---|
| 11. Valvular Calcification | CalcificationSeverity |
| 12. Myxomatous | |
| 13. Rheumatic | |
| 14. ChordalShortening | |
| 15. ChordalFusion | |
| Stenosis | |
| 1. Stenosis Severity | Severity |
| 2. Area ByPlanimetry | Echocardiogram Measurements |
| 3. Area ByPressureHalfTime | Formulas |
| 4. Mean TransMitral Velocity | Echocardiogram Measurements |
| 5. Mean TransMitral Gradient | Formulas |
| 6. Evidence Of prior Commissurotomy | |
| Regurgitation | |
| 1. Regurgitation Severity | Severity |
| 2. Regurgitation Jet Direction | MRJetDirection |
| 3. Diastolic Regurgitation | |
| 4. MR Volume Color Doppler Method | Echocardiogram Measurements |
| 5. MR Volume Pulse Doppler Method | Echocardiogram Measurements |
| 6. MR Fraction Color Doppler Method | Echocardiogram Measurements |
| 7. MR Fraction Pulse Doppler Method | Echocardiogram Measurements |
| 8. ERO Area Color Doppler Method | Echocardiogram Measurements |
| 9. ERO Area Pulse Doppler Method | Echocardiogram Measurements |
| 10. MR Jet LA area ratio | Echocardiogram Measurements |
| Doppler | |
| 1. Pressure Half Time | Echocardiogram Measurements |
| 2. Deceleration Time | Echocardiogram Measurements |
| 3. E - Velocity | Echocardiogram Measurements |
| 4. A - Velocity | Echocardiogram Measurements |
| 5. Mitral Annular e' velocity | Echocardiogram Measurements |
| 6. E/e' | Echocardiogram Measurements |
| 7. Pulmonary Venous Flow Pattern | PulmonaryVenousFlowPattern |
| MMode Findings | |
| 1. DiastolicFluttering Leaflet | MitralLeaflets |
| 2. IncreasedEPointSeptalSeperation | |
| 3. PreSystolicClosure | |
| 4. BNotch | |
| Vegetation | |
| 1. Size | Size |
| 2. Location | MitralLeaflets |
| 3. Mobility | Vegetation Mobility |
| 4. Height | Echocardiogram Measurements |
| 5. Width | Echocardiogram Measurements |
| Abscess | |
| 1. Size | Size |
| 2. Location | MVAbscessLocation |
| 3. Height | Echocardiogram Measurements |
| 4. Width | Echocardiogram Measurements |
| Mitral Valve Annulus | |
| 1. AnnularDilatationSeverity | Severity |
| 2. DilatedAnnulusHeight | Echocardiogram Measurements |
| 3. DilatedAnnulusWidth | Echocardiogram Measurements |
| Mitral Valve Prolapse | |
| 1. Severity | Severity |
| 2. Leaflets | Mitral Leaflets |
| 3. ProlapsePhase | ProlapsePhase |
| 4. Segment | MitralLeafletSegment |
| Flail | |
| 1. Severity | Severity |
| 2. Leaflets | Mitral Leaflets |
| 3. Segment | MitralLeafletSegment |
| Cleft | |
| 1. Severity | Severity |
| 2. Leaflet | MitralLeaflets |
| Systolic Anterior Motion of Mitral Leaflets | |
| 1. SAM Severity | Severity |
| 2. SAM Components | SAMComponents |

| Echocardiogram | |
|---|---|
| Prosthetic Valve | |
| 1. Prosthetic Valve Functions Normally | |
| 2. Ring | |
| 3. Prosthetic Valve Dysfunction Type | ProstheticValveDysfunction |
| 4. Valve Manufacturer | MetalicValveManufacturer |
| 5. Dysfunction Type | ProstheticValveDysfunction |
| IVC/Hepatic Vein | |
| IVC Size | |
| 1. Chamber Size | Chamber Size |
| IVC Mass | |
| 1. IVCMassSize | Size |
| 2. Height | Echocardiogram Measurements |
| 3. Width | Echocardiogram Measurements |
| Miscellaneous | |
| 1. RespiratoryChange | IVCRespiratoryChange |
| 2. FlowPattern | VenousFlowPattern |
| 3. Artifact | VenousArtifact |
| 4. CongenitalAnomaly | IVCCongenitalAnomaly |
| Aorta | |
| Structure | |
| 1. Aortic Root Diameter | Echocardiogram Measurements |
| 2. Ascending Aorta Diameter | Echocardiogram Measurements |
| 3. Descending Aorta Diameter | Echocardiogram Measurements |
| 4. Aortic Arch Diameter | Echocardiogram Measurements |
| Dilatation | |
| 1. Dilatation Location | AorticDilatationLocations |
| Aortic Plaque | |
| 1. Aortic Plaque Size | Size |
| 2. PlaqueLocation | AorticPlaqueLocation |
| 3. PlaqueCharacter | AorticPlaqueCharacter |
| 4. PlaqueMobile | |
| Aortic Aneurysm | |
| 1. Aneurysm Location | AorticAneurysmLocation |
| 2. AneurysmMaximumDiameter | Echocardiogram Measurements |
| Aortic Dissection | |
| 1. DissectionLocation | AorticDissectionLocation |
| 2. Dissection Classification | AorticDissectionClass |
| 3. DissectionEntryPoint | AorticDissectionEntryPoint |
| 4. DissectionExitPoint | AorticDissectionExitPoint |
| Intramural Hematoma | |
| 1. Location | AorticDissectionLocation |
| False Lumen | |
| 1. False Lumen Has Thrombus | |
| 2. False Lumen Compresses SVC | |
| 3. False Lumen Compresses true lumen | |
| 4. False Lumen Thrombus and compresses true lumen | |
| Aortic Graft | |
| 1. GraftType | GraftType |
| 2. GraftLocation | AorticGraftLocation |
| Aortic Coarctation | |
| 1. Aortic Coarctation minimum Diameter | Echocardiogram Measurements |
| 2. Aortic Coarctation Peak Velocity | Echocardiogram Measurements |
| 3. Aortic Coarctation Peak Gradient | Formulas |
| Miscellaneous | |
| 1. Aorta TGA | |
| 2. Aorta Corrected TGA | |
| Aortic Valve | |
| Structure | |
| 1. Number Of Leaflets | NumberOfLeaflets |
| 2. Abnormal Leaflets | |
| 3. Aortic Cusp Seperation | |

Echocardiogram

Stenosis

| | |
|---|---|
| 1. Stenosis Severity | Severity |
| 2. Aortic Valve Area Planimetry | Echocardiogram Measurements |
| 3. Aortic Valve Area Continuity Equation | Echocardiogram Measurements |

Regurgitation

| | |
|---|---|
| 1. Regurgitation Severity | Severity |
| 2. Perforation | AVPerforation |

Doppler

| | |
|---|---|
| 1. Trans Aortic Peak Velocity | Echocardiogram Measurements |
| 2. Trans Aortic Peak gradient | Formulas |
| 3. Trans Aortic Mean Velocity | Echocardiogram Measurements |
| 4. Trans Aortic Mean Gradient | Formulas |
| 5. Aortic Regurgitation Deceleration Time | Echocardiogram Measurements |
| 6. Area By PHT | Echocardiogram Measurements |
| 7. Aortic Valve VTI | Echocardiogram Measurements |
| 8. Holodiastolic flow reversal | AVDiastolicFlowReversal |

Vegetation

| | |
|---|---|
| 1. Size | Size |
| 2. Location | AVVegetationLocation |
| 3. Mobility | Vegetation Mobility |
| 4. Height | Echocardiogram Measurements |
| 5. Width | Echocardiogram Measurements |

Abscess

| | |
|---|---|
| 1. Size | Size |
| 2. Location | AVAbscessLocation |
| 3. Height | Echocardiogram Measurements |
| 4. Width | Echocardiogram Measurements |

Mass

| | |
|---|---|
| 1. Size | Size |
| 2. Location | AVMassLocation |

Prosthetic Valve

| | |
|---|---|
| 1. Prosthetic Valve Functions Normally | |
| 2. Prosthetic Valve Material Type | Metallic ProstheticValveType |
| 3. Valve Manufacturer | MetallicValveManufacturer |
| 4. Dysfunction Type | ProstheticValveDysfunction |

Miscellaneous

| | |
|---|---|
| 1. LVOT Diameter | Echocardiogram Measurements |

Valvular Calcification

| | |
|---|---|
| 1. Calcification | CalcificationSeverity |

Pericardium
Pericardial Effusion

| | |
|---|---|
| 1. Size | Size |
| 2. Location | Pericardial Effusion Location |
| 3. Content | Pericardial Effusion Content |
| 4. Length | Echocardiogram Measurements |
| 5. Pericardial Tamponade | |

Pericardial Mass

| | |
|---|---|
| 1. Height | Echocardiogram Measurements |
| 2. Width | Echocardiogram Measurements |

Excessive Respiratory Variation

| | |
|---|---|
| 1. Type | RespiratoryVariation |

Miscellaneous

| | |
|---|---|
| 1. Pleural Effusion Size | Size |
| 2. Pleural Effusion Location | Pleural Effusion Location |
| 3. AscitesSeverity | Severity |
| 4. PericardialThickening | |
| 5. Pericardial Constriction | |
| 6. Pericardial EffusoConstrictive | |
| 7. FatPad | |
| 8. SeptalBounce | |

Echocardiogram

Tricuspid Valve
Structure

| | |
|---|---|
| 1. DilatedAnnulus Size | DilatedAnnulus Size |
| 2. Atresia | |
| 3. EbsteinsAnomaly | |
| 4. Rheumatic | |

Stenosis

| | |
|---|---|
| 1. Severity | Severity |

Regurgitation

| | |
|---|---|
| 1. Severity | Severity |
| 2. Jet Direction | TRJetDirection |

Prolapse

| | |
|---|---|
| 1. Severity | Severity |
| 2. Leaflets | Tricuspid Leaflets |
| 3. Prolapse Phase | ProlapsePhase |

Ruptured Chordae

| | |
|---|---|
| 1. Leaflets | TricuspidLeaflets |

Doppler

| | |
|---|---|
| 1. Peak Tricuspid Velocity | Echocardiogram Measurements |
| 2. Peak TransTricuspid Gradient | Formulas |
| 3. Mean Tricuspid Velocity | Echocardiogram Measurements |
| 4. Mean TransTricuspid Gradient | Formulas |
| 5. Hepatic Venous Flow Pattern | HepaticVenousFlowPattern |

Vegetation

| | |
|---|---|
| 1. Size | Size |
| 2. Location | TricuspidLeaflets |
| 3. Mobility | Vegetation Mobility |
| 4. Height | Echocardiogram Measurements |
| 5. Width | Echocardiogram Measurements |

Prosthetic Valve

| | |
|---|---|
| 1. Prosthetic Valve Functions Normally | |
| 2. Prosthetic Valve Material Type | ProstheticValve MaterialType |
| 3. Valve Manufacturer | MetalicValveManufacturer |
| 4. Dysfunction Type | ProstheticValveDysfunction |

Valvular Calcification

| | |
|---|---|
| 1. Calcification | CalcificationSeverity |

TEE

| | |
|---|---|
| 1. Study Position | Position |
| 2. IV Fluids | Echocardiogram Measurements |
| 3. Topical Anesthesia | text |
| 4. Consious Sedation | Sedation |
| 5. Study Difficulty | Difficulty |
| 6. Comments | text |
| 7. Complicated Study | Comlicated Study |
| 8. Comments | text |

Programming Elements

Enum's
Enum ChamberSize
 1. NotAssesed
 2. Normal
 3. MidlyIncreased
 4. ModeratelyIncreased
 5. SeverelyIncreased
 6. Decreased
Enum LAThrombusLocation
 1. LACavitySuperior
 2. LACavityInferior
 3. LACavityLateral
 4. LACavityAtrialSeptum 5. LACavityFossaOvalls
6. LACavityAppendage Enum LAEchopensityAttachmentSite
1. AtrialSeptum
2. FossaOvalls
3. Body
4. MitralValve Enum EchopensityShape
1. Flat
2. Protruding
3. Pedunculated
4. Papillary
5. Spherical
6. Regular
7. Irregular
8. Multilobular
9. Infilterating
10. Frondlike Enum EchopensityTexture
1. Solid
2. Layered
3. Hypoechoic
4. Echogenic
5. Calcified Enum EchoDensityMobility
1. Mobile
2. Fixed Enum LAMassLocation
1. LACavitySuperior
2. LACavityInferior
3. LACavityLateral
4. LAAtrialSeptum
5. LAFossaOvalis
6. LAAppendage Enum EchoMassType
1. SuggestiveOfMyxoma
2. SuggestiveOfPapilloma
3. SuggestiveOfFibroelastoma Enum AtrialArtifactLocation
1. Cavity
2. Appendage Enum AtrialSpontaneousEchoLocation
1. Cavity
2. Appendage
3. CavityAndAppendage Enum ASDLocation
1. Primum
2. Secondum
3. SinusVenosus Enum ShuntDirection
1. LeftToRight
2. RightToLeft
3. Bidirectional Enum RAThrombusLocation
1. Cavity
2. Appendage
3. ExtentingFromIVC Enum RAMassLocation
1. Cavity
2. Appendage
3. ExtentingFromIVC Enum Severity
1. Mild
2. MildtoModerate
3. Moderate
4. ModeratetoSevere
5. Severe Enum CalcificationSeverity
1. Mild
2. Moderate
3. Severe Enum GlobalFunction
1. Normal
2. Borderline
3. MildlyDecreased
4. ModeratelyDecreased
5. SeverelyDecreased
6. Hyperdynamic Enum SeptalMotion
1. ParadoxicalRVVolumeOrPressureOverload
2. ParadoxicalPostOperativeStatus
3. ParadoxicalLeftBundleBranchBlock
4. ParadoxicalRVPacemaker
5. ParadoxicalPreExcitation
6. FlattenedInDiastole
7. FlattenedInSystole
8. FlattenedInSystoleAndDiastole
9. SeptalBounce
10. ExcessiveRespiratoryChange Enum AbnormalDiastolicFilling
1. ImparedRelaxation
2. PseudoNormal
3. Restrictive Enum Size
1. Small
2. Moderate
3. Large Enum LVThrombusLocation
1. Apical
2. Basal
3. Lateral
4. Septal Enum HypertrophyType
1. ConcentricHypertrophy
2. AsymmetrkAnteriorHypertrophy
3. AsymmetricPosteriorHypertrophy
4. AsymmetricSeptalHypertrophy
5. AsymmetricLateralHypertrophy
6. AsymmetricApicalHypertrophy
7. AsymmetrkBasalHypertrophy
8. EccentricHypertrophy Enum PseudoAneurysmLocation
1. Anterior
2. Posterior
3. Inferior
4. Septal
5. Lateral
6. Apical
7. Basal Enum LVEchopensityLocation
1. Apical
2. Basal
3. Lateral
4. Septal Enum RAMassLocation
1. RACavity
2. RAAppendage
3. ExtendingFromIVC Enum RAThrombusLocation
1. RACavity
2. RAAppendage
3. ExtendingFromIVC Enum DiastolicFillingPattern
1. Normal
2. ImpairedRelaxation
3. Pseudonormal
4. Restrictive Enum LVDiastolicFillingPressure
1. Normal
2. ElevatedLaPressure
3. ElevatedLvedp
4. ElevatedLaPressureAndLvedp Enum SegmentalMotionAbnormality
1. MildHypokinesis
2. ModerateHypokinesis
3. SevereHypokinesis
4. Akinesis
5. Aneurysmal
6. Dyskinesis Enum NumberOfLeaflets
1. Unicuspid
2. Bicuspid
3. Tricuspid
4. Quadricuspid Enum AbnormalLeaflets
1. Doming
2. Focal Thickening
3. Diffuse thickening with normal excursion
4. Diffuse thickening with reduced excursion Enum Valsalva
1. No change in E and A
2. Decrease E and A Enum ProstheticValve_MaterialType
1. Bioprosthetic
2. Metallic Enum Metallic_ProstheticValve Type
1. TiltingDisk
2. Bileaflet
3. BallAndCage Enum MetallicValveManufacturer
1. StarrEdwards® (Ball Valve)
2. BjorkShiley® (Single Leaflet)
3. MedronicHall® (Single Leaflet)
4. Omniscience® (single Leaflet)
5. St. Jude® (Bileaflet)
6. Carbomedics (Bileaflet)
7. EdwardsDuromedics® (Bileaflet)

Enum ProstheticValveDysfunction
1. Rocking
2. Vegetation
3. Thrombus
4. Mass
5. DEHISCENCE
6. Stenosis
7. Physiologic Regurgitation
8. Prosthetic Regurgitation
9. PeriProsthetic Regurgitation
10. Abscess
11. Pannus
12. Fistula
13. Fracture
14. Perforation
1. Porcine
2. Homograft
3. Pericardial
4. NativePulmonic Enum AVVegetationLocation
1. RightCoronaryCusp
2. LeftCoronaryCusp
3. NonCoronaryCusp
4. RightCoronaryAndNonCoronaryCusp
5. RightCoronaryAndLeftCoronaryCusp
6. NonCoronaryAndLeftCoronaryCusp
7. RightLeftAndNonCoronaryCusp Enum Vegetation_Mobility
1. Mobile
2. Fixed
3. PedunculatedAndMobile Enum AVAbscessLocation
1. RightCoronaryCusp
2. LeftCoronaryCusp
3. NonCoronaryCusp
4. Annulus Enum AVPerforation
1. RightCoronaryCusp
2. LeftCoronaryCusp
3. NonCoronaryCusp
4. Annulus Enum AVMassLocation
1. RightCoronaryCusp
2. LeftCoronaryCusp
3. NonCoronaryCusp Enum AVBestWindowPeakVelocity
1. Apical
2. Suprasternal
3. RightParasternal
4. RightSupraclavicular Enum AVDiastolicFlowReversal
1. DescendingAorta
2. AbdominalAorta
3. Both Enum MitralLeaflets
1. Anterior
2. Posterior
3. Anterior and posterior //Should be able to choose multiple segments
Enum MitralLeafletSegments
1. AnteriorMedialSegment
2. AnteriorMiddleSegment
3. AnteriorLateralSegment
4. PosteriorMedialScallop
5. PosteriorMiddleScallop
6. PosteriorLateralScallop Enum LeafletMobility
1. Normal
2. MildlyDecreased
3. ModeratelyDecreased
4. Immobile Enum ProlapsePhase
1. Holosystolic
2. LateSystolic Enum MVAbscessLocation
1. AnteriorLeaflet
2. PosteriorLeaflet
3. AnteriorLeafletAndAnnulus
4. PosteriorLeafletAndAnnulus
S. IntravalvularFibrosa Enum SAM_Components
1. AnteriorLeaflet
2. Posteriorleaflet
3. Chordae Enum MRJetDirection
1. Anterior
2. Posterior
3. Central
4. ImpingingOnWall
5. ImpingIngOnPulmonaryVeins Enum TricuspidLeaflets
1. Anterior
2. Posterior
3. Septal
Enum PulmonaryVenousFlowPattern
1. Normal
2. BluntedSystolicFlow
3. SystolicFlowReversal
Enum TRJetDirection
1. Septum
2. RAFreeWall
3. Central
4. Eccentric
5. ImpingingOnTheWall
6. ExtendingToDome
Enum HepaticVenousFlowPattern
1. Normal
2. Blunted
3. Reversed
Enum ValveExcursion
1. Good
2. Mildly Decreased
3. ModeratelyDecreased
4. SeverelyDecreased
Enum PulmonaryStenosisLevel
1. Valvular
2. Infundibular
3. ValvularAndInfundibular
4. SupraValvular
5. LeftMainPulmonaryArtery
6. RightMainPulmonaryArtery
Enum Pericardial_Effusion_Location
1. Anterior
2. Posterior
3. AnteriorAndPosterior
Enum Pericardial_Effusion_Content
1. Fluid
2. Fibrinous
3. FocalStrands
4. EffusiveConstrictive
Enum Pleural_Effusion_Location
1. Right
2. Left
3. RightAndLeft
Enum RespiratoryVariation
1. Ventricles
2. MitralValveSlope
3. MitralDopplerFlowVelocities
4. TricuspidDopplerFlowVelocities
5. AorticDopplerFlowVelocities
6. PulmonicDopplerFlowVelocities
7. Hepatic DopplerFlowVelocities
Enum AorticDilatationLocations
1. Aortic Root
2. AorticRootAndAscendingAorta
3. AorticRootLimitedToSinusOfValsalva
4. AorticRootAscendingAndDescendingAorta
5. AorticRootSinusAndAscendingAorta
6. AorticRootAscendingAndTransverseAorta
7. AorticRootTransverseDescendingAndAscendingAorta
8. AorticRootSinusAscendingAndTransverseAorta
9. AscendingAorta
10. AscendingAndDescendingAorta
11. AscendingAndTransverseAorta
12. AscendingAortaAndSinus
13. AscendingTransverseAndDescendingAorta
14. DescendingAorta Enum AorticAneurysmLocation
1. AscendingAorta
2. TransverseAorta
3. DescendingAorta
4. AscendingAndTransverseAorta
5. AscendingTransverseAndDescendingAorta
6. AscendingAndDescendingAorta
7. TransverseAnddescendingAorta
Enum AorticPlaqueLocation
1. AscendingAorta
2. TransverseAorta
3. DescendingAorta
4. AscendingAndTransverseAorta
5. AscendingTransverseAndDescendingAorta
6. AscendingAndDescendingAorta
7. TransverseAndDescendingAorta
Enum AorticPlaqueCharacter
1. Layered
2. Protruding
3. LayeredAndProtruding
4. Multilobular
5. EcholucentCenter
Enum GraftType
1. Prosthetic
2. Homograft
Enum AorticGraftLocation
1. AscendingAorta
2. AscendingAndTransverseAorta
3. DescendingAorta
4. TransverseAortaAndDescendingAorta
5. AscendingTransverseAndDescendingaorta
Enum AorticDissectionLocation
1. AorticRootToArch
2. AorticRootToAscendingAorta
3. AorticRootToDescendingAorta
4. AscendingAortaToAorticArch
5. AscendingAortaToDescendingAorta
6. AorticArchToDescendingAorta
7. DescendingAorta
Enum AorticDissectionEntryPoint
1. AorticRoot
2. AorticArch
3. AscendingAorta
4. DescendingAorta

| Enum AorticDissectionExitPoint | |
|---|---|
| 1. AorticRoot | |
| 2. AorticArch | |
| 3. AscendingAorta | |
| 4. DescendingAorta | |
| 5. Multiple | //May have to describe - free text |

Enum AorticDissectionClass
1. StanfordTypeA
2. StanfordTypeB
3. DebakeyType1
4. DebakeyType2
5. DebakeyType3
Enum VSDLocation
1. Membraneous
2. Infundlbular
3. Inlet
4. Muscular Enum PAComponents
  1. MainPulmonaryArtery
  2. LeftPulmonaryArtery
  3. RightPulmonaryArtery
Enum VenousFlowPattern
  1. Normal
  2. SystolicBlunting
  3. SystolicFlowReversal
Enum PulmonaryVeinComponents
  1. LeftUpper
  2. LeftLower
  3. RightUpper
  4. RightLower
  S. LeftUpperAndLeftLower
  6. RightUpperAndRightLower
  7. LeftUpperAndRightLower
  8. RightUpperAndLeftLower
  9. ThreePulmonaryVeins
  10. FourPulmonaryVeins
Enum IVCRespiratoryChange
  1. <50%
  2. >50%
  3. Plethora
  4. DilatedIVCAndPoorInspiratoryCollapse
Enum IVCCongenitalAnomaly
  1. AzygosContinuationToLeftSVC
  2. AzygosContinuationToRightSVC
Enum PseudoAneurysmType
  1. Anterior
  2. Posterior
  3. Inferior
  4. Septal
  5. Lateral
  6. Apical
  7. Basal
Enum VenousArtifact
  1. PacerWIre
  2. VenousCatheter
Enum DilatedAnnulusSize
  1. Mild
  2. Moderate
  3. Severe
Enum MitralValveSeverity
  1. Mild
  2. Moderate
  3. Moderately Severe
  4. Severe
Enum WallMotionScoreIndex
  1. Normal
  2. Hypokinesis
  3. Akinesis
  4. Dyskinesis
Enum StudyPosition
  1. Leftlateral
  2. RightLateral
  3. Supine
Enum ConsiousSedation
  1. Attained
  2. NotAttained
Enum ComplicatedStudy
  1. Yes
  2. No
Enum Difficulty
  1. WithDifficulty
  2. WithoutDifficulty Formulas
Volume Index
Volume Index=LAVolume/BSA
Fractional Shortening
FS=(LvEdd LvEsd)/LvEdd
  LvEdd—LeftVentricle end diastolic dimension
  LvEsd—LeftVentricle end systolic dimension
Gradient
Gradient=4 Velocity*Velocity)
PHT
MV Area by PHT=220/MV PHT; PHT—Pressure Half Time Echocardiogram Measurements:

| Findings | Minimum | Maximum | Incremental | Unit |
|---|---|---|---|---|
| Left Atrium | | | | |
| Diameter | 1 | 10 | 0.1 | Cm(s) |
| Volume | 20 | 100 | 1 | ml |
| Mass Height and Width | 0.1 | 5 | 0.1 | Cm(s) |
| Thrombus Height and Width | 0.1 | 5 | 0.1 | Cm(s) |
| Right Atrium | | | | |
| Thrombus Height and Width | 0.1 | 5 | 0.1 | Cm(s) |
| Mass Height and Width | 0.1 | 5 | 0.1 | Cm(s) |
| Diameter | 1 | 10 | 0.1 | Cm(s) |
| Left Ventricle | | | | |
| End Diastolic Diameter | 1 | 10 | 0.1 | Cm(s) |
| End Systolic Diameter | 1 | 10 | 0.1 | Cm(s) |
| PosteriorBasal Free Wall Thickness | 0.5 | 3 | 0.1 | Cm(s) |
| End Diastolic Septal Thickness | 0.5 | 3 | 0.1 | Cm(s) |
| Ejection Fraction | 10 | 100 | 5 | % |
| Deceleration Time | 100 | 400 | 10 | ms |
| E' Velocity | 0.1 | 2 | 0.1 | m/s |
| E/E' | 2 | 10 | 0.1 | |
| Cardiac Output | 1 | 10 | 0.1 | L/Mins |
| Cardiac Index | 1 | 5 | 0.1 | L/Min/M$^2$ |
| Mass Height and Width | 0.1 | 5 | 0.1 | Cm(s) |
| Thrombus Height and Width | 0.1 | 5 | 0.1 | Cm(s) |
| Vp | 1 | 200 | 1 | m/s |
| Left Ventricle Mass | 50 | 350 | 1 | gm |
| Left Ventricle Mass Index | 30 | 300 | 1 | gm/m$^2$ |
| Lv Out Flow Tract Diameter | 0.5 | 3 | 0.1 | cm |
| Lv Out Flow Tract VTI | 1 | 100 | 1 | cm |
| Peak Velocity | 0.5 | 10 | 0.1 | m/s |
| Mean Velocity | 0.5 | 10 | 0.1 | m/s |
| Right Ventricle | | | | |
| Diastolic Diameter | 1 | 10 | 0.1 | Cm(s) |
| Systolic Pressure | 10 | 150 | 1 | mmHg |
| Ventricular Septum | | | | |
| QpQsRatio | 0.1 | 5 | 0.1 | |
| Pericardium | | | | |
| Pericardial Effusion Length | 0.1 | 5 | 0.1 | Cm(s) |
| Mass Height and Width | 0.1 | 5 | 0.1 | Cm(s) |
| Mitral Valve | | | | |
| Pressure Half Time | 100 | 700 | 10 | ms |
| Deceleration Time | 100 | 400 | 10 | ms |
| E Velocity | 0.1 | 5 | 0.1 | m/s |

Echocardiogram Measurements:

| Findings | Minimum | Maximum | Incremental | Unit |
|---|---|---|---|---|
| A Velocity | 0.1 | 5 | 0.1 | m/s |
| Mitral Annular e' Velocity | 0.1 | 2 | 0.1 | m/s |
| E/e' | 2 | 10 | 0.1 | |
| Mean Trans Mitral Velocity | 1 | 10 | 0.1 | m/s |
| Area By Planimetry | 0.1 | 5 | 0.1 | $cm^2$ |
| MR Volume Color Doppler Method | 10 | 100 | 1 | ml/beat |
| MR Volume Pulse Doppler Method | 10 | 100 | 1 | ml/beat |
| MR Fraction Color Doppler Method | 1 | 100 | 1 | ml/beat |
| MR Fraction Pulse Doppler Method | 1 | 100 | 1 | ml/beat |
| MR jet LA Area Ratio | 1 | 100 | 1 | |
| ERO Area Color Doppler Method | 0.1 | 1 | 0.1 | $cm^2$ |
| ERO Area Pulse Doppler Method | 0.1 | 1 | 0.1 | $cm^2$ |
| Abscess Height and Width | 0.1 | 5 | 0.1 | Cm(s) |
| Dilated Annulus Height and Width | 0.1 | 5 | 0.1 | Cm(s) |
| Vegetation Height and Width | 0.1 | 5 | 0.1 | Cm(s) |
| Atrial Septum | | | | |
| QpQsRatio | 0.1 | 5 | 0.1 | |
| Aorta | | | | |
| Aorta Ascending Diameter | 2 | 10 | 0.1 | Cm(s) |
| Aorta Descending Diameter | 1 | 10 | 0.1 | Cm(s) |
| Aortic Arch Diameter | 1 | 10 | 0.1 | Cm(s) |
| Aortic Root Diameter | 2 | 10 | 0.1 | Cm(s) |
| Aneursym Maximum Diameter | 1 | 10 | 0.1 | Cm(s) |
| Aortic Coarctation Diameter | 1 | 10 | 0.1 | Cm(s) |
| Aortic Coarctation Peak Velocity | 0.5 | 10 | 0.1 | m/s |
| Aortic Valve | | | | |
| Trans Aortic Peak Velocity | 1 | 10 | 0.1 | m/s |
| Trans Aortic Mean Velocity | 1 | 10 | 0.1 | m/s |
| Area By PHT | 0.1 | 5 | 0.1 | $cm^2$ |
| Area By Planimetry | 0.1 | 5 | 0.1 | $cm^2$ |
| Area By Continuity Equation | 0.1 | 5 | 0.1 | $cm^2$ |
| Aortic Valve VTI | 1 | 10 | 0.1 | Cm(s) |
| Aortic Regurgitation Deceleration Time | 50 | 400 | 10 | m/s |
| LVOT Diameter | 0.5 | 5 | 0.1 | Cm(s) |
| Vegetation Height and Width | 0.1 | 5 | 0.1 | Cm(s) |
| Abscess Height and Width | 0.1 | 5 | 0.1 | Cm(s) |
| Aortic Cusp Seperation | 0.1 | 4 | 0.1 | Cm(s) |
| Tricuspid Valve | | | | |
| Peak Velocity | 0.5 | 10 | 0.1 | m/s |
| Mean Velocity | 0.5 | 10 | 0.1 | m/s |
| Vegetation Height and Width | 0.1 | 5 | 0.1 | Cm(s) |
| Pulmonic Valve | | | | |
| Peak Velocity | 0.5 | 10 | 0.1 | m/s |
| Mean Velocity | 0.5 | 10 | 0.1 | m/s |
| Pulmonary Systolic Pressure | 10 | 150 | 5 | mmHg |
| Pulmonary Artery Diastolic pressure | 10 | 100 | 5 | mmHg |
| Vegetation Height and Width | 0.1 | 5 | 0.1 | Cm(s) |
| Pulmonary Artery | | | | |
| RVOT Diameter | 0.5 | 3 | 0.1 | Cm(s) |
| Main Pulmonary Artery Diameter | 0.5 | 10 | 0.1 | Cm(s) |
| Pulmonary Artery Pressure | 10 | 200 | 1 | mmHg |
| Pulmonary Vein | | | | |
| Right Upper Diameter | 1 | 10 | 1 | Cm(s) |
| Right Lower Diameter | 1 | 10 | 1 | Cm(s) |
| Left Upper Diameter | 1 | 10 | 1 | Cm(s) |
| Left Lower Diameter | 1 | 10 | 1 | Cm(s) |
| Systolic Velocity | 0.5 | 10 | 1 | m/s |
| Diastolic Velocity | 0.5 | 10 | 1 | m/s |
| PV Atrial Reversal Duration | 1 | 300 | 1 | ms |
| IVC | | | | |
| Mass Height | 0.1 | 5 | 0.1 | Cm(s) |
| Mass Width | 0.1 | 5 | 0.1 | Cm(s) |
| TEE | | | | |
| IV Fluids | 10 | 100 | 1 | Cc/hr |

EXERCISE TREADMILL TEST

Resting EKG:

| | |
|---|---|
| 1. HeartRate | ETTMeasurements |
| 2. SBP | ETTMeasurements |
| 3. DBP | ETTMeasurements |
| 4. Rhythm | Rhythm |
| 5. Lead1 | Repolarization |
| 6. Lead2 | Repolarization |
| 7. Lead3 | Repolarization |
| 8. AVR | Repolarization |
| 9. AVL | Repolarization |
| 10. AVF | Repolarization |
| 11. V1 | Repolarization |
| 12. V2 | Repolarization |
| 13. V3 | Repolarization |
| 14. V4 | Repolarization |
| 15. V5 | Repolarization |
| 16. V6 | Repolarization |
| 17. Conduction | RestingConduction |
| 18. Arrhythmias | RestingArrhythmias |
| 19. Remarks | |

Stress EKG

| | |
|---|---|
| 1. Protocols | Protocols |
| 2. MaximumPredictedHR | MaxHR |
| 3. MaximumAchievedHR | |
| 4. Exercise Time Measurements Table | |
| 5. Lead1 | Repolarization |
| 6. Lead2 | Repolarization |
| 7. Lead3 | Repolarization |
| 8. AVR | Repolarization |
| 9. AVL | Repolarization |
| 10. AVF | Repolarization |
| 11. V1 | Repolarization |
| 12. V2 | Repolarization |
| 13. V3 | Repolarization |

| EXERCISE TREADMILL TEST | |
|---|---|
| 14. V4 | Repolarization |
| 15. V5 | Repolarization |
| 16. V6 | Repolarization |
| 17. Rhythm | Rhythm |
| 18. STSegmentDepression | STSegmentDepression |
| 19. FunctionalCapacity | FunctionalCapacity |
| 20. STSegmentLocation | STSegmentLocation |
| 21. BPResponse | BPResponse |
| 22. ReasonForTermination | ReasonForTermination |
| 23. HRResponse | HRResponse |
| 24. DukeTreadmillScore | DukeTreadmillScore |
| 25. DTScore | DTS |
| 26. AnginalSymptoms | AnginalSymptoms |
| 27. HeartRateRecovery | HeartRateRecovery |
| 28. NonAnginalSymptoms | NonAnginalSymptoms |
| 29. STChangeComparison | ComparisonStressSTChange |
| 30. METS | |
| 31. ComparisonETT | ComparisonETT |
| 32. StressEKGResult | StressEKGResult |
| 33. Conduction | StressConduction |
| 34. Arrhythmias | StressArrhythmias |
| 35. Remarks | |
| Exercise Time Measurements | |
| 1. Time | |
| 2. ExerciseDuration | |
| 3. ExerciseMinutes | |
| 4. HR | ETTMeasurements |
| 5. SBP | ETTMeasurements |
| 6. DBP | ETTMeasurements |
| 7. Comments | CommentsSymptoms |
| ST Depression | |
| 1. STDepressionAmount | |
| 2. STSegmentConfiguration | STSegmentConfiguration |
| 3. STSegmentChange | STSegmentChange |
| 4. MaximumSTDepressionChange | |

ST Elevation
   1. STElevationAmount
   2. MaximumSTElevationChange
Enums:
Rhythm
   1. SinusRhythm,
   2. SinusBradycardia,
   3. SinusTachycardia,
   4. JunctionalRhythm,
   5. SVT,
   6. EctopicAtrialRhythm,
   7. AtrialFibrillation,
   8. AtrialPaced,
   9. VentricularPaced,
   10. AVSequentialPaced
RestingConduction
   1. Normal,
   2. IVCD,
   3. LBBB,
   4. RBBB,
   5. IncompleteRBBB,
   6. IncompleteLBBB,
   7. LAFB,
   8. LPFB,
   9. FirstDegreeAVBlock,
   10. SecondDegreeAVBlock,
   11. ThirdDegreeAVBlock,
   12. PreExcitation
RestingArrhythmias
   1. APC,
   2. VPC,
   3. AtrialFibrillation,
   4. SVT,
   5. NSVT
StressEKGResult
   1. Normal,
   2. Abnormal,
   3. Indeterminate
StudyIndication
   1. PreoperativeEvaluation,
   2. CAD,
   3. HeartFailure,
   4. CoronaryRiskFactors,
   5. Dyspnea,
   6. HistoryofPTCA,
   7. HistoryofCABG,
   8. AbnormalStressTest,
   9. AbnormalElectrocardiogram,
   10. Arrhythmia,
   11. AnginaPectoris,
   12. Hypertension,
   13. Palpitations,
   14. SVT,
   15. Syncope
Repolarization
   1. Normal,
   2. EarlyRepolarization,
   3. NonspecificSTandTChanges,
   4. STDepression,
   5. STElevation,
   6. SecondarySTandTChanges
Protocols
   1. Bruce,
   2. Modified Bruce,
   3. Naughton
STSegmentConfiguration
   1. Upsloping,
   2. Downsloping,
   3. Elevation
StressConduction
   1. Normal,
   2. IVCD,
   3. LBBB,
   4. RBBB,
   5. IncompleteRBBB,
   6. IncompleteLBBB,
   7. BifascicularBlock
   8. LAFB,
   9. LPFB,
   10. FirstDegreeAVBlock,
   11. SecondDegreeAVBlock,
   12. ThirdDegreeAVBlock
StressArrhythmias
   1. APC,
   2. VPC,
   3. AtrialFibrillation,
   4. VentricularTachycardia,
   5. SVT,
   6. NSVT,
   7. VentricularFibrillation
ReasonForTermination
   1. ChestPain,
   2. ECGChanges,
   3. Fatigue,
   4. Dyspnea,
   5. AchievementOfTargetHR,
   6. Hypotensionwithevidenceofischemia,
   7. Hypotensionwithoutevidenceofischemia,
   8. Hypertension, 9. Claudication,
10. EndOfProtocol,
11. ModeratetoSevereAngina,
12. Ataxia,
13. Dizziness,
14. NearSyncope,
15. CyanosisandPallor,
16. UnabletomonitorBPorHR,
17. Patientsdesiretostop,
18. SVT,
19. STelevationgreaterthanonemm,
20. ExcessiveSTorTwavechanges,
21. ExcessiveAxisChange,
22. ShortnessofBreath,
23. NewBundleBranchBlock,
24. VT,
25. NSVT,
26. AtrialFibrillation,
27. AtrialFlutter STSegmentLocation
1. Anterior,
2. Inferior,
3. Lateral,
4. Inferolateral,
5. Anteriorlateral,
6. Septal STSegmentChange
1. NondiagnosticLowHeartRate,
2. NondiagnosticVPacing,
3. LBBB,
4. MildlyPositive,
5. ModeratelyPositive,
6. StronglyPositive,
7. StronglyPositiveSTElevation STSegmentDepression
1. StressOnly,
2. StressandRecovery,
3. RecoveryOnly ComparisonStressSTChange
1. Lower,
2. Higher ComparisonETT
1. NoChange,
2. NewIschemia,
3. ResolutionOfIschemia,
4. MoreIschemiaThanPrior DukeTredmillScore
1. Low Risk,
2. Moderate Risk,
3. High Risk HeartRateRecovery
1. Normal,
2. Abnormal,
3. MarkedlyAbnormal HRResponse
1. Normal,
2. Blunted,
3. Accentuated BPResponse
1. Normal,
2. Hypotensive,
3. Hypertensive,
4. Blunted AnginalSymptoms
1. Atypical angina,
2. Nonanginal chest pain,
3. Anginal equivalent,
4. No chest pain NonAnginalSymptoms
1. Dyspnea,
2. Claudication,
3. Syncope,
4. Flushing,
5. Nausea,
6. Dizziness,
7. Fatigue FunctionalCapacity
1. Average,
2. Below average,
3. Above average CommentsSymptoms
1. No chest pain
2. Chest pain
3. Nonanginal chest pain,
4. Atypical chest pain
5. Typical Chest Pain for ischemia
6. Syncope
7. Dyspnea
8. Fatigue
9. Dizziness
10. Nausea
11. Flushing
12. Claudication
13. Anginal Equivalent Formulas

DTS $$DTS = \text{Exercise time} - (5 * ST \text{ deviation}) - (4 * \text{Treadmill angina})$$

MaxPredictedHR $$MaxPredictedHR = 220 \text{ Patient Age}$$

| ETTMeasurements: | | | | |
|---|---|---|---|---|
| Findings | Minimum | Maximum | Incremental | Unit |
| Resting EKG | | | | |
| Heart Rate | 30 | 250 | 1 | beats/min |
| SBP | 50 | 300 | 1 | mmHg |
| DBP | 20 | 200 | 1 | mmHg |
| Stress EKG | | | | |
| ST Depression Amount | 0.5 | 10 | 0.5 | mm |
| ST Elevation Amount | 0.5 | 10 | 0.5 | mm |
| Maximum ST Depression Change | 0.5 | 10 | 0.5 | mm |
| Maximum ST Elevation Change | 0.5 | 10 | 0.5 | mm |
| METS | 1 | 25 | 0.1 | |

Holter Monitoring

Holter Monitoring
1. Days
2. Hrs
3. Mins
4. Rhythm
5. MaxHeartRate
6. Occurred At
7. MinHeartRate 8. Occurred At
9. EpisodesofPauses
10. MaxPauseDuration
11. Conduction
12. Arrhythmias
  a. APC
  b. VPC
  c. Atrialfibrillation
  d. Atrialflutter
  e. SVT
  f. VT
  g. Bigemini
  h. Trigemini
  i. Couplets
13. Remarks
Enum's
Rhythm
  1. Sinus Rhythm
  2. Sinus Bradycardia
  3. Sinus Tachycardia
  4. Junctional Rhythm
  5. SVT
  6. Ectopic Atrial Rhythm
  7. Atrial Fibrillation
  8. Atrial Paced
  9. Ventricular Paced
  10. AV Sequential Paced
RestingConduction
  1. Normal
  2. Intra ventricular conduction defect
  3. Left bundle branch block
  4. Right bundle branch block
  5. Incomplete right bundle branch block
  6. Incomplete left bundle branch block
  7. Left anterior fassicular block
  8. Left posterior fassicular block
  9. First degree atrio ventricular block
  10. Second degree atrio ventricular block
  11. Third degree atrio ventricular block
  12. Pre excitation
ArrhythmiaFrequency
  1. Rare
  2. Frequent
  3. Occasional

| HolterMeasurements: | | | | |
|---|---|---|---|---|
| Findings | Minimum | Maximum | Incremental | Unit |
| Days | 1 | 31 | 1 | |
| Hrs | 1 | 12 | 1 | |
| Mins | 1 | 60 | 1 | |
| MaxHR | 30 | 250 | 1 | |
| MinHR | 30 | 250 | 1 | |
| EpisodesofPauses | 1 | 100 | 1 | |
| MaxiumPauseDuration | 1 | 60 | 0.5 | |

| EXERCISE NUCLEAR MYOCARDIAL PERFUSION IMAGING | |
|---|---|
| Resting EKG : | |
| 1. HeartRate | |
| 2. SBP | NuclearMeasurements |
| 3. DBP | NuclearMeasurements |
| 4. Rhythm | Rhythm |
| 5. Lead1 | |
| 6. Lead2 | |
| 7. Lead3 | |
| 8. AVR | |
| 9. AVL | |
| 10. AVF | |
| 11. V1 | |
| 12. V2 | |
| 13. V3 | |
| 14. V4 | |
| 15. V5 | |
| 16. V6 | |
| 17. Conduction | RestingConduction |
| 18. Arrhythmias | RestingArrhythmias |
| 19. Remarks | |
| Stress EKG | |
| 1. Protocols | Protocols |
| 2. MaximumPredictedHR | Formulas |
| 3. MaximumAchievedHR | |
| 4. Exercise Time Measurements Table | |
| 5. Lead1 | |
| 6. Lead2 | |
| 7. Lead3 | |
| 8. AVR | |
| 9. AVL | |
| 10. AVF | |
| 11. V1 | |
| 12. V2 | |
| 13. V3 | |
| 14. V4 | |
| 15. V5 | |
| 16. V6 | |

17. Rhythm
  18. STSegmentDepression
  19. FunctionalCapacity
  20. STSegmentLocation
  21. BPResponse
  22. ReasonForTermination
  23. HRResponse
  24. DukeTreadmillScore
  25. DTScore
  26. AnginalSymptoms
  27. HeartRateRecovery
  28. NonAnginalSymptoms
  29. STChangeComparison
  30. METS
  31. ComparisonETT
  32. StressEKGResult
  33. Conduction
  34. Arrhythmias
  35. Remarks
Exercise Time Measurements
  1. Time
  2. Exercise Duration
  3. ExerciseMinutes
  4. HR
  5. SBP
  6. DBP
  7. Comments
ST Depression
  1. STDepressionAmount
  2. STSegmentConfiguration
  3. STSegmentChange
  4. MaximumSTDepressionChange ST Elevation
1. STElevationAmount
2. MaximumSTElevationChange Clinical History
1. CardiacHistory
2. PreviousCardiacTests
3. PreviousCardiacEvents
4. PreviousCardiacProcedure
5. CardiacRiskFactors
6. Medications Study Details
1. StudyQuality
2. StudyType
3. ImagingProtocol
4. ImagingPosition
5. PharmacologicalStressAgent
6. ReasonforPharmacologicalStudy
7. RestRadioPharmaceutical
8. StressRadioPharmaceutical
9. RestDose
10. StressDose
11. RestDate
12. StressDate Image Acquisition
1. Scatter Correction
2. GatedStress
3. GatedRestandStress Perfusion Imaging
1. ScanSignificance
2. StressTestSummary
3. NumberofDiseasedVessels
4. Diseased Vessels
5. TcdValue
6. SSS
7. SRS
8. SDS
9. % MyoStress
10. % MyoFixed
11. % Myoischemic
12. LVPerfusionSummary LV Functional Analysis
1. StressGlobalFunction
2. StressLVVolume
3. RegionalWallMotionSummary
4. StressEjectionFraction
5. StressEndSystolicVolume
6. StressEndDiastolicVolume LungUptake
1. StressOnly
2. RestandStress RV Myocardial Uptake
1. StressOnly
2. RestandStress Artifacts
1. StudyArtifacts
2. ExtraCardiacActivity RVPerfusionAndFunction
1. GlobalRVfunction
2. RVVolume
3. StressEjectionFraction Remarks
1. FreeText Nuclear Rest and Stress MPI
1. BasalAnterior
2. BasalAnteroseptal
3. BasalInferoseptal
4. Basalinferior
5. BasalInferolateral
6. BasalAnterolateral
7. MidAnterior
8. MidAnteroseptal
9. MidInferoseptal
10. Midinferior
11. MidInferolateral
12. MidAnterolateral
13. ApicalAnteriori
14. ApicalSeptal
15. ApicalInferior
16. ApicalLateral
17. Apex Nuclear Wall Motion (REST AND STRESS)
1. BasalAnterior
2. BasalAnteroseptal
3. BasalInferoseptal
4. Basalinferior
5. BasalInferolateral
6. BasalAnterolateral
7. MidAnterior
8. MidAnteroseptal
9. MidInferoseptal
10. MidInferior
11. MidInferolateral
12. MidAnterolateral
13. ApicalAnterior
14. ApicalSeptal
15. ApicalInferior
16. ApicalLateral
17. Apex
18. Remarks Nuclear Thickening (REST AND STRESS)
1. BasalAnterior
2. BasalAnteroseptal
3. BasalInferoseptal
4. BasalInferior
5. BasalInferolateral
6. BasalAnterolateral
7. MidAnterior
8. MidAnteroseptal
9. MidInferoseptal
10. MidInferior
11. MidInferolateral
12. MidAnterolateral
13. ApicalAnterior
14. ApicalSeptal
15. ApicalInferior
16. ApicalLateral
19. Apex
20. Remarks Enums
Rhythm
1. SinusRhythm,
2. SinusBradycardia,
3. SinusTachycardia,
4. JunctionalRhythm,
5. SVT,
6. EctopicAtrialRhythm,
7. AtrialFibrillation,
8. AtrialPaced,
9. VentricularPaced,
10. AVSequentialPaced RestingConduction
1. Normal,
2. IVCD,
3. LBBB, 4. RBBB,
  5. IncompleteRBBB,
  6. IncompleteLBBB,
  7. LAFB,
  8. LPFB,
  9. FirstDegreeAVBlock,
  10. SecondDegreeAVBlock,
  11. ThirdDegreeAVBlock,
  12. PreExcitation
RestingArrhythmias
  1. Atrial Fibrillation,
  2. APC,
  3. VPC,
  4. SVT,
  5. NSVT
  1. Normal,
  2. Early,
  3. NonspecificSTandTChanges,
  4. STDepression,
  5. STElevation,
  6. SecondarySTandTChanges
Protocols
  1. Bruce,
  2. ModifiedBruce,
  3. Naughton
STSegmentConfiguration
  1. Upsloping,
  2. Downsloping,
  3. Elevation
StressConduction
  1. Normal,
  2. IVCD,
  3. LBBB,
  4. RBBB,
  5. IncompleteRBBB,
  6. IncompleteLBBB,
  7. LAFB,
  8. LPFB,
  9. FirstDegreeAVBlock,
  10. SecondDegreeAVBlock,
  11. ThirdDegreeAVBlock,
  12. BifascicularBlock
StressArrhythmias
  1. APC,
  2. VPC,
  3. AtrialFibrillation,
  4. VentricularTachycardia,
  5. SVT,
  6. NSVT,
  7. VentricularFibrillation
ReasonForTermination
  1. ChestPain,
  2. ECGChanges,
  3. Fatigue,
  4. Dyspnea,
  5. AchievementOfTargetHR,
  6. Hypotensionwithevidenceofischemia,
  7. Hypotensionwithoutevidenceofischemia,
  8. Hypertension,
  9. Claudication,
  10. EndOfProtocol,
  11. ModeratetoSevereAngina,
  12. Ataxia,
  13. Dizziness,
  14. NearSyncope,
  15. CyanosisandPallor,
  16. UnabletomonitorBPorHR,
  17. Patientsdesiretostop,
  18. SVT,
  19. STelevationgreaterthanonemm,
  20. ExcessiveSTorTwavechanges,
  21. ExcessiveAxisChange,
  22. ShortnessofBreath,
  23. NewBundleBranchBlock,
  24. VT,
  25. NSVT,
  26. AtrialFibrillation,
  27. AtrialFlutter
STSegmentLocation
  1. Anterior,
  2. Inferior,
  3. Lateral,
  4. Inferolateral,
  5. Anteriorlateral,
  6. Septal
STSegmentChange
  1. NondiagnosticLowHeartRate,
  2. NondiagnosticVPacing,
  3. LBBB,
  4. MildlyPositive,
  5. ModeratelyPositive,
  6. StronglyPositive,
  7. StronglyPositiveSTElevation
STSegmentDepression
  1. StressOnly,
  2. StressandRecovery,
  3. RecoveryOnly
DukeTredmillScore
  1. Low Risk,
  2. Moderate Risk,
  3. High Risk
HeartRateRecovery
  1. Normal,
  2. Abnormal,
  3. MarkedlyAbnormal
HRResponse
  1. Normal,
  2. Blunted,
  3. Accentuated
BPResponse
  1. Normal,
  2. Hypotensive,
  3. Hypertensive,
  4. Blunted
AnginalSymptoms
  1. Atypical angina,
  2. Nonanginal chest pain,
  3. Anginal equivalent,
  4. No chest pain
NonAnginalSymptoms
  1. Dyspnea,
  2. Claudication,
  3. Syncope,
  4. Flushing,
  5. Nausea,
  6. Dizziness,
  7. Fatigue
FunctionalCapacity
  1. Average,
  2. Below average,
  3. Above average
EKGResult
  1. Normal
  2. Abnormal
  3. Inderminate TypeofDefect
1. Normal,
2. Mild Defect,
3. Moderate Defect,
4. SevereDefect,
5. AbsentUptake PreviousCardiacTests
1. ExerciseTreadmillTest,
2. ExerciseMyocardialPerfusionImaging,
3. Echocardiogram,
4. StressEchocardiogram,
5. CoronaryAngiogram,
6. HolterMonitor CardiacHistory
1. S/p PTCA/stent,
2. S/p CABG,
3. S/p MI,
4. Historyofperipheralvascular,
5. Disease,
6. PerfusionImaging,
7. StressEcho,
8. Catheterization,
9. MRI,
10. CT CardiacRiskFactors
1. Diabetes,
2. Hypercholesterolemia,
3. FamilyHistory,
4. Smoking,
5. Obesity,
6. MetabolicSyndrome,
7. PeripheralVascularDisease ImagingProtocol
1. StressThallium,
2. RestThallium/StressTechnetium,
3. RestTechnetium/StressTechnetium 1 day,
4. RestTechnetium/StressTechnetium 2 day,
5. StressTechnetium/RestTechnetium 1 day,
6. ViabilityStudy ImagingPosition
1. Supine,
2. Prone,
3. SupineandProne OverallStudyQuality
1. Poor,
2. Fair,
3. Good,
4. Excellent StudyType
1. Exercise,
2. Pharmacologic,
3. Pharmacologic/Exercise RestRadioPharmaceutical
4. Thallium,
5. Tc99 mSestamibi,
6. Tc99 mTetrofosmin RegionalWallMotion
1. Normal,
2. MildHypokinesis,
3. ModerateHypokinesis,
4. SevereHypokinesis,
5. Akinesis,
6. Dyskinesis RegionalWallMotionLocation
1. BasalAnterior,
2. BasalInferior,
3. BasalAnteroSeptal,
4. BasalInferoSeptal,
5. BasalInferoLateral,
6. BasalAnterolateral,
7. MidAnterior,
8. MidAnteroSeptal,
9. MidInferoSeptal,
10. MidInferior,
11. MidInferolateral,
12. MidAnterolateral,
13. ApicalAnterior,
14. ApicalSeptal,
15. ApicalInferior,
16. ApicalLateral,
17. Apex ScanSignificance
1. Normal,
2. LowRisk,
3. LowtoModerateRisk,
4. ModerateRisk,
5. ModeratetoHighRisk,
6. HighRisk,
7. UncertainRisk StressTestSummary
1. Normal,
2. AbNormal,
3. NonDiagnostic LVPerfusionSummary
1. Normal,
2. Equivocal,
3. Abnormal,
4. Ischemia,
5. Infarction,
6. NegativeforIschemia DiseasedVessels
1. LeftAnteriorDescending,
2. RightCoronary,
3. LeftCircumflex,
4. LeftMain PharmacologicalStressAgent
1. Dipyridamole,
2. Dobutamine,
3. Adenosine,
4. Atropine ReasonofPharmacologicalAgent
1. LBBB,
2. Pacemaker,
3. InabilitytoExercise StressRadioPharmaceutical
1. Thallium,
2. Tc99 mSestamibi,
3. Tc99 mTetrofosmin Medications
1. CaChannelblocker,
2. Beta Blockers,
3. Nitrates,
4. Digoxin,
5. ACE/ARB,
6. Diuretics TestType
1. Exercise,
2. Pharmacologic,
3. PharmacologicExercise PerfusionDefectLocation
1. BasalAnterior,
2. BasalInferior,
3. BasalAnteroseptal, 4. BasalInferoseptal,
   5. BasalInferolateral,
   6. BasalAnterolateral,
   7. MidAnterior,
   8. MidAnteroseptal,
   9. MidInferoseptal,
   10. Midinferior,
   11. MidInferolateral,
   12. MidAnterolateral,
   13. ApicalAnterior,
   14. ApicalSeptal,
   15. ApicalInferior,
   16. ApicalLateral,
   17. Apex
PerfusionDefectSize
   1. Small,
   2. Medium,
   3. Large
PerfusionDefectSeverity
   1. Mild,
   2. Moderate,
   3. Severe
TypeofPerfusionDefect
   1. Reversible,
   2. Fixed,
   3. Mixed
RVMyocardialUptake
   1. Normal,
   2. Increased
GlobalLVFunction
   1. Normal,
   2. MildlyReduced,
   3. Moderately Reduced,
   4. SeverelyReduced,
   5. Hyperkinetic
LVVolume
   1. Normal,
   2. MildlyEnlarged,
   3. ModeratelyEnlarged,
   4. MarkedlyEnlarged
RegionalWallMotionSummary
   1. ConsistentwithPerfusion,
   2. InconsistentwithPerfusion
Artifacts
   1. PatientMotion,
   2. BreastAttenuation,
   3. DiaphragmaticAttenuation,
   4. SubdiaphragmaticActivity
ExtraCardiacActivity
   1. Normal,
   2. IncreasedLungUptake,
   3. InsufficientMyocardialActivity
RVUptake
   1. Normal,
   2. Increased
GlobalRVfunction
   1. Normal,
   2. Hyperkinetic
   3. MildlyReduced,
   4. ModeratelyReduced,
   5. Severely Reduced
RVVolume
   1. Normal,
   2. MildlyEnlarged,
   3. ModeratelyEnlarged,
   4. SeverelyEnlarged NumberofDiseasedVessels
   1. One,
   2. Two,
   3. Three
PreviousCardiacEvents
   1. MyocardialInfarction,
   2. Angina,
   3. Arrhythmias,
   4. CardioMyopathy
PreviousCardiacProcedure
   1. CoronaryAngioplasty,
   2. CoronaryStenting,
   3. CoronaryAtherectomy,
   4. CoronaryArteryBypassSurgery
ExtentofPerfusionDefect
   1. Small,
   2. Moderate,
   3. LargeAreaofIschemia,
   4. Infarction

| RestGlobalLVfunction | |
|---|---|
| 1. Normal | EF >55-65% |
| 2. Mildly reduced | EF 45-55% |
| 3. Moderately reduced | EF 35-44% |
| 4. Severely reduced | EF <35% |
| 5. Hyperkinetic | EF = >65 |

RestLVVolume
   1. Normal,
   2. Mildly enlarged,
   3. Moderately enlarged,
   4. Severely enlarged
RestRegionalWallMotion
   1. Normal,
   2. Mild hypokinesis,
   3. Moderate hypokinesis,
   4. Severe hypokinesis,
   5. Akinesis,
   6. Dyskinesis
RestRegionalWallMotionLocation
   1. Basal anterior
   2. Basal anteroseptal
   3. Basal inferoseptal
   4. Basal inferior
   5. Basal inferolateral
   6. Basal anterolateral
   7. Mid anterior
   8. Mid anteroseptal
   9. Mid inferoseptal
   10. Mid inferior
   11. Mid inferolateral
   12. Mid anterolateral
   13. Apical anterior
   14. Apical septal
   15. Apical inferior
   16. Apical lateral
   17. Apex
RestRegionalWallMotionSummary
   1. Consistent with perfusion,
   2. Inconsistent with perfusion
NuclearThickening
   1. Normal,
   2. EquivocalReduction,
   3. DefiniteReduction,
   4. NoThickening Formulas
DTS $$DTS = \text{Exercise time} - (5 * ST \text{ deviation}) - (4 * \text{Treadmill angina})$$

MaxPredictedHR $$\text{MaxPredicted}HR = 220 \text{ Patient Age}$$

17segment

% of myoStress = $SSS/68 \times 100\%$

% of myoFixed = $SRS/68 \times 100\%$

% of myoIschemic = $SDS/68 \times 100$ $SSS$ = sum of 17 segment stress score $SRS$ = sum of 17 segment rest score $SDS = SSS - SRS$

| NuclearMeasurements: | | | | |
|---|---|---|---|---|
| Findings | Minimum | Maximum | Incremental | Unit |
| Resting EKG | | | | |
| Heart Rate | 30 | 250 | 1 | beats/min |
| SBP | 50 | 300 | 1 | mmHg |
| DBP | 20 | 200 | 1 | mmHg |
| Stress EKG | | | | |
| ST Depression Amount | 0.5 | 10 | 0.5 | mm |
| ST Elevation Amount | 0.5 | 10 | 0.5 | mm |
| Maximum ST Depression Change | 0.5 | 10 | 0.5 | mm |
| Maximum ST Elevation Change | 0.5 | 10 | 0.5 | mm |
| METS | 1 | 25 | 0.1 | |
| Nuclear Perfusion Imaging | | | | |
| Adenosine Dose | 10 | 70 | 1 | |
| Rest Dose | 7 | 15 | 0.1 | mCi |
| Stress Dose | 25 | 35 | 1 | mCi |
| TCD/TID Value | 0.5 | 3 | 0.1 | |
| Left Ventricle | | | | |
| Ejection Fraction | 10 | 100 | 1 | |
| End Diastolic Volume | 10 | 300 | 1 | |
| End Systolic Volume | 10 | 300 | 1 | |
| Right Ventricle | | | | |
| Ejection Fraction | 10 | 100 | 1 | |

Stress Echocardiogram

Resting EKG:
1. HeartRate
2. SBP
3. DBP
4. Rhythm
5. Lead1
6. Lead2
7. Lead3
8. AVR
9. AVL
10. AVF
11. V1
12. V2
13. V3
14. V4
15. V5
16. V6
17. Conduction
18. Arrhythmias
19. Remarks Stress EKG
1. Protocols
2. MaximumPredictedHR
3. MaximumAchievedHR
4. Exercise Time Measurements Table
5. Lead1
6. Lead2
7. Lead3
8. AVR
9. AVL
10. AVF
11. V1
12. V2
13. V3
14. V4
15. V5
16. V6
17. Rhythm
18. STSegmentDepression
19. FunctionalCapacity
20. STSegmentLocation
21. BPResponse
22. ReasonForTermination
23. HRResponse
24. DukeTreadmillScore
25. DTScore
26. AnginalSymptoms
27. HeartRateRecovery
28. NonAnginalSymptoms
29. STChangeComparison
30. METS
31. ComparisonETT
32. StressEKGResult
33. Conduction
34. Arrhythmias
35. Remarks Exercise Time Measurements
1. Time
2. ExerciseDuration
3. ExerciseMinutes
4. HR
5. SBP
6. DBP
7. Comments ST Depression
1. STDepressionAmount
2. STSegmentConfiguration
3. STSegmentChange
4. MaximumSTDepressionChange ST Elevation
1. STElevationAmount
2. MaximumSTElevationChange Clinical History
1. CardiacHistory
2. PreviousCardiacTests
3. CardiacRiskFactors
4. Medications Miscelleneous
1. TissueHarmonicimaging
2. ContrastStressEchocardiography Stress Echocardiogram & Rest Echocardiogram
Left Atrium
   1. ChamberSize
Right Atrium
   1. ChamberSize
Left Ventricle
   1. ChamberSize
   2. Global Function
   3. Ejection Fraction
   4. Hypertrophy
Right Ventricle
   1. ChamberSize
   2. Global Function
   3. Hypertrophy
Mitral Valve
   1. RegurgitationSeverity
   2. RegurgitationJetDirection
   3. StenosisSeverity
   4. PeakVelocity
   5. MeanVelocity
   6. MeanGradient
   7. PeakGradient
Aortic Valve
   1. RegurgitationSeverity
   2. StenosisSeverity
   3. PeakVelocity
   4. MeanVelocity
   5. MeanGradient
   6. PeakGradient
Tricuspid Valve
   1. StenosisSeverity
   2. RegurgitationSeverity
   3. RegurgitationJetDirection
   4. PAsystolicPressure
   5. PeakVelocity
   6. MeanVelocity
   7. MeanGradient
   8. PeakGradient
Pulmonic Valve
   1. StenosisSeverity
   2. StenosisLevel
   3. RegurgitationSeverity
   4. PeakVelocity
   5. MeanVelocity
   6. MeanGradient
   7. PeakGradient
Remarks
   1. Free Text
Stress Echo Wall Motion (REST AND STRESS)
   1. BasalAnterior
   2. BasalAnteroseptal
   3. BasalInferoseptal
   4. BasalInferior
   5. BasalInferolateral
   6. BasalAnterolateral
   7. MidAnterior
   8. MidAnteroseptal
   9. MidInferoseptal
   10. MidInferior
   11. MidInferolateral
   12. MidAnterolateral
   13. ApicalAnterior
   14. ApicalSeptal
   15. ApicalInferior
   16. ApicalLateral
   17. Apex
   18. Remarks
Stress Echo (REST AND STRESS)
   1. BasalAnterior
   2. BasalAnteroseptal
   3. BasalInferoseptal
   4. BasalInferior
   5. BasalInferolateral
   6. BasalAnterolateral
   7. MidAnterior
   8. MidAnteroseptal
   9. MidInferoseptal
   10. MidInferior
   11. MidInferolateral
   12. MidAnterolateral
   13. ApicalAnterior
   14. ApicalSeptal
   15. ApicalInferior
   16. ApicalLateral
   19. Apex
   20. Remarks
Enums
Rhythm
   1. SinusRhythm,
   2. SinusBradycardia,
   3. SinusTachycardia,
   4. JunctionalRhythm,
   5. SVT,
   6. EctopicAtrialRhythm,
   7. AtrialFibrillation,
   8. AtrialPaced,
   9. VentricularPaced,
   10. AVSequentialPaced
RestingConduction
   1. Normal,
   2. IVCD,
   3. LBBB,
   4. RBBB,
   5. IncompleteRBBB,
   6. IncompleteLBBB,
   7. LAFB,
   8. LPFB,
   9. FirstDegreeAVBlock,
   10. SecondDegreeAVBlock,
   11. ThirdDegreeAVBlock,
   12. Pre Excitation
RestingArrhythmias
   1. APC,
   2. VPC,
   3. AtrialFibrillation,
   4. SVT,
   5. NSVT
StudyIndication
   1. PreoperativeEvaluation,
   2. CAD,
   3. HeartFailure,
   4. CoronaryRiskFactors,
   5. Dyspnea,
   6. HistoryofPTCA,
   7. HistoryofCABG,
   8. AbnormalStressTest,
   9. AbnormalElectrocardiogram,
   10. Arrhythmia,
   11. AnginaPectoris,
   12. Hypertension,
   13. Palpitations,
   14. SVT,
   15. Syncope 1. Normal,
2. Early,
3. NonspecificSTandTChanges,
4. STDepression,
5. STElevation,
6. SecondarySTandTChanges Protocols
   1. Bruce (Exercise Stress Echocardiogram),
   2. Bicycle Upright Ergometer (Exercise Stress Echocardiogram),
   3. Bicycle Supine Ergometer (Exercise Stress Echocardiogram),
   4. Dobutamine (Chemical Stress Echocardiogram)

STSegmentConfiguration
   1. Upsloping,
   2. Downsloping,
   3. Elevation

StressConduction
   1. Normal,
   2. IVCD,
   3. LBBB,
   4. RBBB,
   5. IncompleteRBBB,
   6. IncompleteLBBB,
   7. LAFB,
   8. LPFB,
   9. FirstDegreeAVBlock,
   10. SecondDegreeAVBlock,
   11. ThirdDegreeAVBlock,
   12. BifascicularBlock StressArrhythmias
   1. APC,
   2. VPC,
   3. Atrial Fibrillation,
   4. VentricularTachycardia,
   5. SVT,
   6. NSVT,
   7. VentricularFibrillation ReasonForTermination
   1. ChestPain,
   2. ECGChanges,
   3. Fatigue,
   4. Dyspnea,
   5. AchievementOfTargetHR,
   6. Hypotensionwithevidenceofischemia,
   7. Hypotensionwithoutevidenceofischemia,
   8. Hypertension,
   9. Claudication,
   10. EndOfProtocol,
   11. ModeratetoSevereAngina,
   12. Ataxia,
   13. Dizziness,
   14. NearSyncope,
   15. CyanosisandPallor,
   16. UnabletomonitorBPorHR,
   17. Patientsdesiretostop,
   18. SVT,
   19. STelevationgreaterthanonemm,
   20. ExcessiveSTorTwavechanges,
   21. ExcessiveAxisChange,
   22. ShortnessofBreath,
   23. NewBundleBranchBlock,
   24. VT,
   25. NSVT,
   26. AtrialFibrillation,
   27. AtrialFlutter STSegmentLocation
   1. Anterior,
   2. Inferior,
   3. Lateral,
   4. Inferolateral,
   5. Anteriorlateral,
   6. Septal STSegmentChange
   1. NondiagnosticLowHeartRate,
   2. NondiagnosticVPacing,
   3. LBBB,
   4. MildlyPositive,
   5. ModeratelyPositive,
   6. StronglyPositive,
   7. StronglyPositiveSTElevation STSegmentDepression
   1. StressOnly,
   2. StressandRecovery,
   3. RecoveryOnly DukeTredmillScore
   1. Low Risk,
   2. Moderate Risk,
   3. High Risk HeartRateRecovery
   1. Normal,
   2. Abnormal,
   3. MarkedlyAbnormal HRResponse
   1. Normal,
   2. Blunted,
   3. Accentuated BPResponse
   1. Normal,
   2. Hypotensive,
   3. Hypertensive,
   4. Blunted AnginalSymptoms
   1. Atypical angina,
   2. Nonanginal chest pain,
   3. Anginal equivalent,
   4. No chest pain NonAnginalSymptoms
   1. Dyspnea,
   2. Claudication,
   3. Syncope,
   4. Flushing,
   5. Nausea,
   6. Dizziness,
   7. Fatigue FunctionalCapacity
   1. Average,
   2. Below average,
   3. Above average TypeofDefect
   1. Normal,
   2. Mild Defect,
   3. ModerateDefect,
   4. SevereDefect,
   5. AbsentUptake PreviousCardiacTests
   1. ExerciseTreadmillTest,
   2. ExerciseMyocardialPerfusionImaging,
   3. Echocardiogram,
   4. StressEchocardiogram,
   5. CoronaryAngiogram,
   6. HolterMonitor CardiacHistory
 1. S/p PTCA/stent,
 2. S/p CABG,
 3. S/p MI,
 4. HistoryofperipheralvascuIar,
 5. Disease,
 6. PerfusionImaging,
 7. StressEcho,
 8. Catheterization,
 9. MRI,
 10. CT
Medications
 1. CaChannelblocker,
 2. Beta Blockers,
 3. Nitrates,
 4. Digoxin,
 5. ACEARB,
 6. Diuretics
CardiacRiskFactors
 1. Diabetes,
 2. Hypercholesterolemia,
 3. FamilyHistory,
 4. Smoking,
 5. Obesity,
 6. MetabolicSyndrome,
 7. PeripheralVascularDisease
Size
 1. NotAssesed,
 2. Normal,
 3. MidlyIncreased,
 4. Moderately Increased,
 5. SeverelyIncreased,
 6. Decreased
GlobalFunction
 1. Normal,
 2. Borderline,
 3. MildlyDecreased,
 4. ModeratelyDecreased,
 5. Severely Decreased,
 6. Hyperdynamic
Severity
 1. Mild,
 2. MildtoModerate,
 3. Moderate,
 4. ModeratetoSevere,
 5. Severe
MVRegurgitationJetDirection
 1. Anterior,
 2. Posterior,
 3. Central,
 4. ImpingingOnWall,
 5. ImpingingOnPulmonaryVeins
StenosisLevel
 1. Valvular,
 2. Infundibular,
 3. ValvularAndInfundibular,
 4. SupraValvular,
 5. LeftMainPulmonaryArtery,
 6. RightMainPulmonaryArtery
TVRegurgitationJetDirection
 1. Septum,
 2. RAFreeWall,
 3. Central,
 4. Eccentric,
 5. ImpingingOnTheWall,
 6. ExtendingToDome EKGResult
 1. Normal
 2. Abnormal
 3. Inderminate
 1. Normal
 2. Hyperdynamic
 3. Hypokinesis
 4. Akinesis
 5. Dyskinesis
 1. Normal
 2. Thinning
PASystolicPressure
 1. Less than 35 Normal
 2. 3545 mmHg Mild
 3. 4555 mmHg Moderate
 4. >55 mmHg Severe
Formulas
DTS $$DTS = \text{Exercise time} - (5*\text{ST deviation}) - (4*\text{Treadmill angina})$$

MaxPredictedHR $$\text{MaxPredicted}HR = 220 \text{ Patient Age}$$

Gradient $$\text{Gradient} = 4*(\text{Velocity}*\text{Velocity})$$

StressEchocardiogramMeasurements:

| Findings | Minimum | Maximum | Incremental | Unit |
|---|---|---|---|---|
| Resting EKG | | | | |
| Heart Rate | 30 | 250 | 1 | beats/min |
| SBP | 50 | 300 | 1 | mmHg |
| DBP | 20 | 200 | 1 | mmHg |
| Stress EKG | | | | |
| ST Depression Amount | 0.5 | 10 | 0.5 | mm |
| ST Elevation Amount | 0.5 | 10 | 0.5 | mm |
| Maximum ST Depression Change | 0.5 | 10 | 0.5 | mm |
| Maximum ST Elevation Change | 0.5 | 10 | 0.5 | mm |
| METS | 1 | 25 | 0.1 | |
| Echocardiogram | | | | |
| Ejection Fraction | 10 | 100 | 5 | % |
| PA Systolic Pressure | 1 | 100 | 1 | mmHg |
| Peak Velocity | 0.5 | 10 | 0.1 | m/s |
| Mean Velocity | 0.5 | 10 | 0.1 | m/s |

Ultrasound Modules

Carotid Artery Ultrasound

Common Carotid Artery (Right and Left)
 Segments: Proximal, Mid, Distal, Bifurcation (Both Right and Left)
Grayscale:
 1. StenosisSeverity
 2. PriorCarotidEndarterectomy
 3. PriorCarotidEndarterectomy with patent
 4. Dissection
Duplex Parameter:
 1. PeakSystolicVelocity
 2. PeakDiastolicVelocity
 3. SpectralBroadening Stent:
   1. Origin
   2. Extends To
   3. InstentRestenosisSeverity
   4. InstentRestenosisPercentage
   5. Remarks:
   1. Free Text
Internal Carotid Artery (Right and Left)
   Segments: Proximal, Mid, Distal (Both Right and Left)
Grayscale:
   1. StenosisSeverity
   2. PriorCarotidEndarterectomy
   3. PriorCarotidEndarterectomy with patent
   4. Dissection
Duplex Parameter:
   1. PeakSystolicVelocity
   2. PeakDiastolicVelocity
   3. SpectralBroadening
Stent:
   1. Origin
   2. Extends To
   3. InstentRestenosisSeverity
   4. InstentRestenosisPercentage
Remarks:
   1. Free Text
External Carotid Artery (Right and Left)
   Grayscale:
   1. StenosisSeverity
   2. PriorCarotidEndarterectomy
   3. PriorCarotidEndarterectomy with patent
   4. Dissection
Duplex Parameter:
   1. PeakSystolicVelocity
   2. PeakDiastolicVelocity
   3. SpectralBroadening
Stent:
   1. Origin
   2. Extends To
   3. InstentRestenosisSeverity
   4. InstentRestenosisPercentage
Remarks:
   1. Free Text
Vertebral Artery (Right and Left)
   Doppler:
   1. Flow Direction
   2. PeakSystolicVelocity
Stenosis:
   1. SegmentStenosed
   2. SubclavianStenosis (For Left VA)
   3. InnominateArteryStenosis (For Right VA)
Stent:
   1. Origin
   2. InstentRestenosisSeverity
   3. InstentRestenosisPercentage
Miscellaneous:
   1. Diameter
   2. SegmentofAneurysma
   3. SegmentOfDissection
   4. EvidenceOfHypoplasia
Remarks:
   1. Free Text
Enum's:
VertebralArterySegments
   1. V1
   2. V2
   3. V3
   4. V4

VertebralArteryFlowDirection
   1. Antegrade
   2. Bidirectional
   3. Retrograde
StenosisSeverity
   1. Mild
   2. Mild to Moderate
   3. Moderate
   4. Moderate to Severe
   5. Severe
   6. Totally Occluded
Severity
   1. Mild
   2. Mild to Moderate
   3. Moderate
   4. Moderate to Severe
   5. Severe
CarotidArterySegment
   1. Proximal Common Carotid Artery
   2. Mid Common Carotid Artery
   3. Distal Common Carotid Artery
   4. Bifurcation Common Carotid Artery
   5. Proximal Internal Carotid Artery
   6. Mid Internal Carotid Artery
   7. Distal Internal Carotid Artery
   8. External Carotid Artery

| Findings | Minimum | Maximum | Incremental | Unit |
|---|---|---|---|---|
| PeakSystolic Velocity | 0 | 1000 | 10 | Cm/sec |
| PeakDiastolic Velocity | 0 | 1000 | 10 | Cm/sec |
| Instent Restenosis Percentage | 10 | 100 | 10 | % |
| Vertebral Artery | | | | |
| PeakSystolic Velocity | 20 | 100 | 10 | Cm/sec |
| Instent Restenosis Percentage | 10 | 100 | 10 | % |
| Diameter | 0.5 | 10 | 0.1 | Cm |

Renal Artery Ultrasound

Intra Renal Evaluation (Right and Left)
   Region: Upper, Middle, Lower (Both Right and Left)
   1. Peak systolic velocity
   2. Peak diastolic velocity
   3. AccelerationTime
   4. NormalSystolicUpstroke
   5. EarlySystolicCompliancePeak
   6. TardusParvusWaveform
   7. ResistiveIndex
   8. RenalArteryToAortaRatio
   9. Stenosis
   10. RenalAneursym
   11. RenalAneursymHeight
   12. RenalAneursymWidth
   13. CalcificationOfTheWall
   14. Thrombus
   15. ThrombusDetails
   16. AVMalformationAndFistula
   17. AVMalformationAndFistulaDetails
Extra Renal Evaluation (Right and Left)
   Segment: Ostium, Mid, Distal (Both Right and Left)
   1. Peak systolic velocity
   2. Peak diastolic velocity 3. Turbulence
4. ResistiveIndex
5. RenalArteryToAortaRatio
6. Stenosis Renal Vascular
Grayscale:
1. RightKidneyVisualized
2. RightPoleLength
3. LeftKidneyVisualized
4. LeftPoleLength Mid Aorta:
1. PeakSystolicVelocity Remarks:
1. Free Text

| RenalMeasurements: | | | | |
|---|---|---|---|---|
| Findings | Minimum | Maximum | Incremental | Unit |
| PeakSystolicVelocity | | | | Cm/sec |
| PeakDiastolic Velocity | | | | Cm/sec |
| AccelerationTime | | | | ms |
| RenalAneursymHeight | | | | mm |
| RenalAneursymWidth | | | | mm |
| LeftPoleLength | | | | cm |
| RightPoleLength | | | | cm |

Formula's:
Resistive Index (RI):

(Peak systolic velocity–end diastolic velocity)/peak systolic velocity

Renal Artery to Aorta Ratio (RAR):
Peak systolic velocity in the renal artery/peak systolic velocity in the mid aorta at the level of the renal artery

| Stenosis: | |
|---|---|
| 059% | RAR <3.5 without significant turbulent flow |
| 6099% | PSV >200 cm/sec; RAR >3.5 with significant turbulent flow. |
| >80% | EDV >150 cm/sec. |

Low Extremity Venous Ultrasound

Segments of interest: one for each side.
1. Common femoral Artery
2. Profunda femoral Artery
3. Superficial femoral Artery
  a. Proximal
  b. Mid
  c. Distal
4. Popliteal artery
5. Anterior tibial artery
6. Posterior tibial artery
7. Peroneal artery
For each segments:

| Segment Details: |
|---|
| 1. Visualized |
| 2. Compressibility |
| 3. Phasic |
| 4. Augmentation |

| -continued | |
|---|---|
| Segment Details: | |
| 5. Thrombus | |
| 6. Hypoechoic density | |
| 7. Hyperechoic density | |
| 8. Severity of occlusion | –Enum SeverityOfOcclusion |
| 9. Reflux | (Value 1-60) |
| 10. Remarks | |

Enum's:
Enum SeverityOfOcclusion
1. Occlusive Thrombus (Vein is fully occluded with thrombus)
2. Partially Occlusive Thrombus (Vein is partially occluded with thrombus)

Lower Extremity Arterial Duplex

Segments of Interest
1. Common femoral Artery
2. Profunda femoral Artery
3. Superficial femoral Artery
  a. Proximal
  b. Mid
  c. Distal
4. Popliteal artery
5. Anterior tibial artery
6. Posterior tibial artery
7. Peroneal artery
For Each Segments:
Details:
1. SpectralBroadening
2. Peaksystolicvelocity
3. Peakdiastolicvelocity
4. Stenosis
Bypass:
1. GraftName
Proximal
1. SpectralBroadening
2. Peaksystolicvelocity
3. Peakdiastolicvelocity
4. Stenosis
Mid
1. SpectralBroadening
2. Peaksystolicvelocity
3. Peakdiastolicvelocity
4. Stenosis
Distal
1. SpectralBroadening
2. Peaksystolicvelocity
3. Peakdiastolicvelocity
4. Stenosis
Enum's:
Spectral Broadening
1. None
2. Minimal
3. Prominent
4. Extensive
GraftName
1. LeftAxilloFemoralBypass
2. AortoLeftFemoralArtery
3. LeftFemeroPoplitealBypass
4. LeftFemeroBelowKneeBypass
5. RightAxilloFemoralBypass
6. AortoRightFemoralArtery
7. RightFemeroPoplitealBypass
8. RightFemeroBelowKneeBypass Stenosis
  1. Normal
  2. 10% 29%
  3. 30% 49%
  4. 50% 75%
  5. >75%
  6. Occlusion

| Arterial Measurements: | | | | |
|---|---|---|---|---|
| Findings | Minimum | Maximum | Incremental | Unit |
| PeakSystolic Velocity | | | | Cm/sec |
| PeakDiastolic Velocity | | | | Cm/sec |

The invention claimed is:

1. A method of enabling a physician to evaluate the health of the heart of a patient, comprising the steps of:
   a) providing a computer having a data base, the database including a first set of cardiology guidelines;
   b) providing a user interface connected to the computer that includes a display screen, and the computer receiving test data from testing of a patient for one or more cardiac testing modalities;
   c) simultaneously displaying multiple icons on the display screen that are each designations of different anatomical portions of a human heart;
   d) enabling the physician to select one of the icons displayed and automatically displaying both an anatomical representation of a portion of the patient's heart and patient data relating to the selected portion of the patient's heart responsive to a selection of an icon;
   e) wherein in step "d" the automatically displayed data corresponds to at least one of the portions of the human heart that is represented by the icon selected and that is displayed as the anatomical representation of that portion of the human heart; and
   f) wherein in step "d" the automatically displayed data includes one or more menus that provide selections of data input which are selectable by the physician;
   g) based at least in part on the test data received in step "b", the computer determining a second set of cardiology guidelines which are applicable to the patient which second set cardiology guidelines are a subset of the first set of cardiology guidelines, and providing an option to the physician of displaying on the display screen the text of one or more of the cardiology guidelines contained in the second set of cardiology guidelines;
   h) based on the second set of cardiology guidelines of step "g", the computer requesting guideline specific input from the physician;
   i) based on the input from the physician in step "h", the computer determining a third set of cardiology guidelines which third set is a subset of the second set of cardiology guidelines;
   j) automatically generating a report that is visible on the display screen and responsive to the input by the physician in steps "d" and "i".

2. The method of claim 1, wherein the physician is provided the option of displaying one or more of the guidelines identified in steps "g" or "i", and displaying on the display screen one or more of the cardiology guidelines identified in steps "g" or "i".

3. The method of claim 1, wherein the first set of cardiology guidelines of step "a" are periodically updated, and the data of steps "d" and "e" includes study parameters.

4. The method of claim 1, wherein the data of steps "d" and "e" includes a collection of various studies relating to the patient.

5. The method of claim 1, wherein a physician reading reported data on the display can add an interpretation of the data by selecting one of multiple displayed options.

\* \* \* \* \*